(12) United States Patent
Habib

(10) Patent No.: US 11,672,801 B2
(45) Date of Patent: Jun. 13, 2023

(54) COMPOSITIONS AND METHODS FOR TREATING CANCER

(71) Applicant: UNITED STATES GOVERNMENT AS REPRESENTED BY THE DEPARTMENT OF VETERANS AFFAIRS, Washington, DC (US)

(72) Inventor: Amyn Aziz Habib, Washington, DC (US)

(73) Assignee: United States Government as represented by the Department of Veterans Affairs, Washington, DC (US)

( * ) Notice: Subject to any disclaimer, the term of this patent is extended or adjusted under 35 U.S.C. 154(b) by 0 days.

(21) Appl. No.: 16/342,142

(22) PCT Filed: Oct. 19, 2017

(86) PCT No.: PCT/US2017/057477
§ 371 (c)(1),
(2) Date: Apr. 15, 2019

(87) PCT Pub. No.: WO2018/075823
PCT Pub. Date: Apr. 26, 2018

(65) Prior Publication Data
US 2019/0255050 A1    Aug. 22, 2019

Related U.S. Application Data

(60) Provisional application No. 62/410,323, filed on Oct. 19, 2016, provisional application No. 62/410,799, filed on Oct. 20, 2016.

(51) Int. Cl.
*A61K 31/517*    (2006.01)
*A61K 31/573*    (2006.01)
(Continued)

(52) U.S. Cl.
CPC .......... *A61K 31/517* (2013.01); *A61K 31/454* (2013.01); *A61K 31/573* (2013.01);
(Continued)

(58) Field of Classification Search
CPC ........................... A61K 31/517; A61K 31/573
(Continued)

(56) References Cited

U.S. PATENT DOCUMENTS 7,947,653 B1    5/2011 Sordella et al.
8,946,235 B2 *  2/2015 Butterworth ......... C07D 487/10
                                                        514/256

(Continued)

FOREIGN PATENT DOCUMENTS

CN    101669941 A  *  3/2010
CN    102389424 B     11/2013
(Continued)

OTHER PUBLICATIONS

Sausville et al. (Cancer Research, 2006,vol. 66, pp. 3351-3354) (Year: 2006).*

(Continued)

*Primary Examiner* — Shengjun Wang
(74) *Attorney, Agent, or Firm* — Ballard Spahr LLP

(57) ABSTRACT

Provided herein are methods and pharmaceutical compositions for treating cancer, in a patient in need thereof, said method comprising administering to said patient an effective amount of an EGFR inhibitor and a TNF inhibitor.

9 Claims, 99 Drawing Sheets

(51) Int. Cl.
        *A61P 35/00*          (2006.01)
        *A61K 31/454*         (2006.01)
        *A61K 38/17*          (2006.01)
        *A61K 39/395*         (2006.01)
(52) U.S. Cl.
        CPC ........ *A61K 38/1793* (2013.01); *A61K 39/395* (2013.01); *A61P 35/00* (2018.01)
(58) Field of Classification Search
        USPC .................. 514/171, 178, 266.4, 266.24
        See application file for complete search history.

(56)                References Cited

U.S. PATENT DOCUMENTS

| 2004/0147428 | A1* | 7/2004  | Pluenneke ............ A61K 31/00 514/1 |
|---|---|---|---|
| 2011/0301194 | A1  | 12/2011 | Chan et al. |
| 2011/0313010 | A1  | 12/2011 | Recinos et al. |
| 2012/0022098 | A1  | 1/2012  | Ibrahim et al. |
| 2012/0141479 | A1  | 6/2012  | Witta et al. |
| 2016/0136284 | A1  | 5/2016  | Gill et al. |
| 2017/0027951 | A1  | 2/2017  | Lidija |
| 2017/0106059 | A1  | 4/2017  | Modiano et al. |
| 2017/0107577 | A1  | 4/2017  | Al-Ejeh |
| 2018/0057606 | A1  | 3/2018  | Old et al. |
| 2018/0264129 | A1  | 9/2018  | Chang et al. |
| 2019/0016808 | A1  | 1/2019  | Li et al. |
| 2019/0231778 | A1  | 8/2019  | Habib |

FOREIGN PATENT DOCUMENTS

| EP | 3528798 A1 | 8/2019 |
|---|---|---|
| WO | WO-2001/027268 A2 | 4/2001 |
| WO | WO 2011/014872 A2 | 2/2011 |
| WO | WO 2013/152313 A1 | 10/2013 |
| WO | WO 2016/191471 A1 | 12/2016 |
| WO | WO-2017/037579 A1 | 3/2017 |
| WO | WO 2017/106189 | 6/2017 |
| WO | WO-2018/075823 A1 | 4/2018 |
| WO | WO-2018/183762 A1 | 10/2018 |
| WO | WO 2020/227676 A1 | 11/2020 |

OTHER PUBLICATIONS

Johnson et al. (British J. of Cancer, 2001, 84(10):1424-1431) (Year: 2001).*
Chen et al (PLoS ONE, 2011, 6(6) ):e21428) (Year: 2011).*
Augustin et al (Mol Cancer Ther; 12(4) Apr. 2013) (Year: 2013).*
Barnes "Anti-inflammatory action of glucocorticoids: molecular mechanisms," Clinical Science, 1998, vol. 94, pp. 557-572 (Year: 1998).*
Yu et al. "Afatinib-new therapy option for EGFR-mutant lung cancer," Nature Reviews/Clinical Oncology, Oct. 2013, vol. 10, pp. 551-552 (Year: 2013).*
Cancer Network "FDA grants Osimertinib accelerated approval for T790M-positive NSCLC" Nov. 16, 2015, https://www.cancernetwork.com/view/fda-grants-osimertinib-accelerated-approval-t790m-positive-nsclc (Year: 2015).*
International Search Report and Written Opinion dated Mar. 5, 2018 by the International Searching Authority for International Application No. PCT/US17/57477, filed on Oct. 19, 2017 and published as WO 2018/075823 on Apr. 26, 2018 (Applicant—United States Department of Veteran's Affairs) (8 Pages).
International Preliminary Report on Patentability dated Apr. 23, 2019 by the International Searching Authority for International Application No. PCT/US17/57477, filed on Oct. 19, 2017 and published as WO 2018/075823 on Apr. 26, 2018 (Applicant—United States Department of Veteran's Affairs) (5 Pages).
International Search Report and Written Opinion dated Aug. 30, 2018 by the International Searching Authority for International Application No. PCT/US18/25278, filed on Mar. 29, 2018 and published as WO 2018/183762 on Oct. 4, 2018 (Applicant—United States Department of Veteran's Affairs) (11 Pages).
International Preliminary Report on Patentability dated Oct. 1, 2019 by the International Searching Authority for International Application No. PCT/US18/25278, filed on Mar. 29, 2018 and published as WO 2018/183762 on Oct. 4, 2018 (Applicant—United States Department of Veteran's Affairs) (7 Pages).
Requirement for Restriction/Election dated Nov. 4, 2019 by the USPTO for U.S. Appl. No. 15/940,802, filed Mar. 29, 2018 and published as US 2019-0231778 on Aug. 1, 2019 (Inventor—A. Habib) (10 Pages).
Acquaviva, et al. (2011) "Chronic activation of wild-type epidermal growth factor receptor and loss of Cdkn2a cause mouse glioblastoma formation" *Cancer Res* 71: 7198-7206.
Aggarwal, et al. (2013) "Curcumin: an orally bioavailable blocker of TNF and other pro-inflammatory biomarkers" *British Journal of Pharmacology* 169(8): 1672-1692.
Ahmad, et al. (2016) "Nrf2-driven TERT regulates pentose phosphate pathway in glioblastoma" *Cell Death Dis* 7: e2213.
Akbay al. (2013) "Activation of the PD-1 pathway contributes to immune escape in EGFR-driven lung tumors" *Cancer Discov* 3: 1355-1363.
Akhavan, et al. (2013) "De-repression of PDGFRbeta transcription promotes acquired resistance to EGFR tyrosine kinase inhibitors in glioblastoma patients" *Cancer Discov* 3: 534-547.
Almeida, et al. (2009) Paradoxical effect of isoniazid on the activity of rifampin-pyrazinamide combination in a mouse model of tuberculosis, *Antimicrob Agents Chemother* 53, 4178-4184.
Altieri, et al. (2015) Glioma Surgery: Technological Advances to Achieve a Maximal Safe Resection, *Surg Technol Int* 27, 297-302.
An, et al. (2018) "Epidermal growth factor receptor and EGFRvIII in glioblastoma: signaling pathways and targeted therapies" *Oncogene* 37: 1561-1575.
Armento, et al. (2017) Molecular Mechanisms of Glioma Cell Motility, In *Glioblastoma* (De Vleeschouwer, S., Ed.), Brisbane (AU).
Au, et al. (1995) "Identification of a member of the interferon regulatory factor family that binds to the interferon-stimulated response element and activates expression of interferon-induced genes" *Proc Natl Acad Sci U S A* 92: 11657-11661.
Ausubel, F. M. (1987) *Current protocols in molecular biology*, Published by Greene Pub. Associates and Wiley-Interscience : J. Wiley, New York.
Bachoo, et al. (2002) Epidermal growth factor receptor and Ink4a/Arf: convergent mechanisms governing terminal differentiation and transformation along the neural stem cell to astrocyte axis, *Cancer Cell* 1, 269-277.
Bae, et al. (2013) Sestrins activate Nrf2 by promoting p62-dependent autophagic degradation of Keap1 and prevent oxidative liver damage, *Cell Metab* 17, 73-84.
Bai, et al. (2016) "Emerging role of NRF2 in chemoresistance by regulating drug-metabolizing enzymes and efflux transporters" *Drug Metab Rev* 48: 541-567.
Bald, et al. (2014) "Immune cell-poor melanomas benefit from PD-1 blockade after targeted type I IFN activation" *Cancer Discov* 4: 674-687.
Bansal, et al. (2012) The transcription factor Wilms tumor 1 confers resistance in myeloid leukemia cells against the proapoptotic therapeutic agent TRAIL (tumor necrosis factor alpha-related apoptosis-inducing ligand) by regulating the antiapoptotic protein Bcl-xL, *J Biol Chem* 287, 32875-32880.
Bansal, A., and Simon, M. C. (2018) Glutathione metabolism in cancer progression and treatment resistance, *J Cell Biol* 217, 2291-2298.
Bardella, et al. (2012) Cells lacking the fumarase tumor suppressor are protected from apoptosis through a hypoxia-inducible factor-independent, AMPK-dependent mechanism, *Mol Cell Biol* 32, 3081-3094.
Batra, et al. (1995) Epidermal growth factor ligand-independent, unregulated, cell-transforming potential of a naturally occurring human mutant EGFRvIII gene, *Cell Growth Differ* 6, 1251-1259.
Best, S. A., and Sutherland, K. D. (2018) "Keaping" a lid on lung cancer: the Keap1-Nrf2 pathway, *Cell Cycle* 17, 1696-1707.

(56) References Cited

OTHER PUBLICATIONS

Bhatt, et al. (2014) Pharmacokinetics of rifampin and isoniazid in tuberculosis-HIV-coinfected patients receiving nevirapine- or efavirenz-based antiretroviral treatment, *Antimicrob Agents Chemother* 58, 3182-3190.

Biernat, et al. (2004) Predominant expression of mutant EGFR (EGFRvIII) is rare in primary glioblastomas, *Brain pathology* 14, 131-136.

Birnbaum, et al. (2003) Chromosome arm 8p and cancer: a fragile hypothesis, *The lancet oncology* 4, 639-642.

Blakely, C. M. et al. NF-kappaB-activating complex engaged in response to EGFR oncogene inhibition drives tumor cell survival and residual disease in lung cancer. *Cell Rep* 11, 98-110, doi:10.1016/j.celrep.2015.03.012 (2015).

Bronger, et al. (2005) ABCC drug efflux pumps and organic anion uptake transporters in human gliomas and the blood-tumor barrier, *Cancer Res* 65, 11419-11428.

Brown, et al. (2008) Phase I/II trial of erlotinib and temozolomide with radiation therapy in the treatment of newly diagnosed glioblastoma multiforme: North Central Cancer Treatment Group Study N0177, *J Clin Oncol* 26, 5603-5609.

Bryan, et al. (2013) The Nrf2 cell defence pathway: Keap1-dependent and -independent mechanisms of regulation, *Biochem Pharmacol* 85, 705-717.

Budhwani, et al. Plasticity of Type I Interferon-Mediated Responses in Cancer Therapy: From Anti-tumor Immunity to Resistance. *Front Oncol* 8, 322, doi:10.3389/fonc.2018.00322 (2018).

Camp, et al. (2012) Wilms tumor gene on X chromosome (WTX) inhibits degradation of NRF2 protein through competitive binding to KEAP1 protein, *J Biol Chem* 287, 6539-6550.

Carlson, et al. (2011) Establishment, maintenance and in vitro and in vivo applications of primary human glioblastoma multiforme (GBM) xenograft models for translational biology studies and drug discovery, *Curr Protoc Pharmacol* Chapter 14, Unit 14 16.

Chakraborty, et al. (2013) Cytoplasmic TRADD Confers a Worse Prognosis in Glioblastoma, *Neoplasia* 15, 888-897.

Chakraborty, S. et al. Constitutive and ligand-induced EGFR signalling triggers distinct and mutually exclusive downstream signalling networks. *Nat Commun* 5, 5811, doi:10.1038/ncomms6811 (2014).

Chandarlapaty, S. et al. AKT inhibition relieves feedback suppression of receptor tyrosine kinase expression and activity. *Cancer Cell* 19, 58-71, doi:10.1016/j.ccr.2010.10.031 (2011).

Chang, et al. (2007) Integration of somatic deletion analysis of prostate cancers and germline linkage analysis of prostate cancer families reveals two small consensus regions for prostate cancer genes at 8p, *Cancer Res* 67, 4098-4103.

Chatterjee, A., and Gupta, S. (2018) The multifaceted role of glutathione S-transferases in cancer, *Cancer Lett* 433, 33-42.

Chaudiere, et al. (1984) Mechanism of selenium-glutathione peroxidase and its inhibition by mercaptocarboxylic acids and other mercaptans, *J Biol Chem* 259, 1043-1050.

Chen, et al. (2009) Direct interaction between Nrf2 and p21(Cip1/WAF1) upregulates the Nrf2-mediated antioxidant response, *Mol Cell* 34, 663-673.

Chen, H. H., and Kuo, M. T. (2010) Role of glutathione in the regulation of Cisplatin resistance in cancer chemotherapy, *Met Based Drugs* 2010.

Chen, et al. (2013) Isoniazid suppresses antioxidant response element activities and impairs adipogenesis in mouse and human preadipocytes, *Toxicology and applied pharmacology* 273, 435-441.

Chen, et al. (2015) Erastin sensitizes glioblastoma cells to temozolomide by restraining xCT and cystathionine-gamma-lyase function, *Oncology reports* 33, 1465-1474.

Chen, et al. (2016) Mammalian drug efflux transporters of the ATP binding cassette (ABC) family in multidrug resistance: A review of the past decade, *Cancer Lett* 370, 153-164.

Cheon, H. et al. IFNbeta-dependent increases in STAT1, STAT2, and IRF9 mediate resistance to viruses and DNA damage. *EMBO J* 32, 2751-2763, doi:10.1038/emboj.2013.203 (2013).

Chong, C. R. & Janne, P. A. The quest to overcome resistance to EGFR-targeted therapies in cancer. *Nature medicine* 19, 1389-1400, doi:10.1038/nm.3388 (2013).

Chow, et al. RIG-I and Other RNA Sensors in Antiviral Immunity. *Annu Rev Immunol* 36, 667-694, doi: 10.1146/annurev-immunol-042617-053309 (2018).

Chung, et al. (2005) Inhibition of cystine uptake disrupts the growth of primary brain tumors, *J Neurosci* 25, 7101-7110.

Chung, W. J., and Sontheimer, H. (2009) Sulfasalazine inhibits the growth of primary brain tumors independent of nuclear factor-kappaB, *J Neurochem* 110, 182-193.

Coll, et al. (2007) Hob3p, the fission yeast ortholog of human BIN3, localizes Cdc42p to the division site and regulates cytokinesis, *EMBO J* 26, 1865-1877.

Cong, et al. (2013) ERK and PI3K signaling cascades induce Nrf2 activation and regulate cell viability partly through Nrf2 in human glioblastoma cells, *Oncology reports* 30, 715-722.

Corcoran, R. B. et al. EGFR-mediated re-activation of MAPK signaling contributes to insensitivity of BRAF mutant colorectal cancers to RAF inhibition with vemurafenib. *Cancer Discov* 2, 227-235, doi:10.1158/2159-8290.CD-11-0341 (2012).

Cui, et al. (2018) Modulating ROS to overcome multidrug resistance in cancer, *Drug Resist Updat* 41, 1-25.

de Kreuk, B. J., and Hordijk, P. L. (2012) Control of Rho GTPase function by BAR-domains, *Small GTPases* 3, 45-52.

Dhruv, et al. (2013) Reciprocal activation of transcription factors underlies the dichotomy between proliferation and invasion of glioma cells, *PLoS One* 8, e72134.

Di Fiore, et al. (1987) Overexpression of the human EGF receptor confers an EGF-dependent transformed phenotype to NIH 3T3 cells, *Cell* 51, 1063-1070.

Dickinson, et al. (1992) Bioavailability of rifampin in experimental murine tuberculosis, *Antimicrob Agents Chemother* 36, 2066-2067.

Ding, et al. (2018) A Novel Signaling Complex between TROY and EGFR Mediates Glioblastoma Cell Invasion, *Mol Cancer Res* 16, 322-332.

Dinkova-Kostova, et al. (2002) Direct evidence that sulfhydryl groups of Keap1 are the sensors regulating induction of phase 2 enzymes that protect against carcinogens and oxidants, *Proc Natl Acad Sci U S A* 99, 11908-11913.

Dinkova-Kostova, A. T., and Talalay, P. (2010) NAD(P)H:quinone acceptor oxidoreductase 1 (NQO1), a multifunctional antioxidant enzyme and exceptionally versatile cytoprotector, *Arch Biochem Biophys* 501, 116-123.

Duarte, C. W. et al. Expression signature of IFN/STAT1 signaling genes predicts poor survival outcome in glioblastoma multiforme in a subtype-specific manner. *PLoS One* 7, e29653, doi:10.1371/journal.pone.0029653 (2012).

Duncan, J. S. et al. Dynamic reprogramming of the kinome in response to targeted MEK inhibition in triple-negative breast cancer. *Cell* 149, 307-321, doi:10.1016/j.cell.2012.02.053 (2012).

Dunn, G. P. et al. A critical function for type I interferons in cancer immunoediting. *Nat Immunol* 6, 722-729, doi:10.1038/ni1213 (2005).

Dutu, T. et al. Differential expression of biomarkers in lung adenocarcinoma: a comparative study between smokers and never-smokers. *Ann Oncol* 16, 1906-1914, doi:10.1093/annonc/mdi408 (2005).

Ekstrand, et al. (1991) Genes for epidermal growth factor receptor, transforming growth factor alpha, and epidermal growth factor and their expression in human gliomas in vivo, *Cancer Res* 51, 2164-2172.

Endres, N. F. et al. (2013) Conformational coupling across the plasma membrane in activation of the EGF receptor. *Cell* 152, 543-556.

Engelman, J. A. et al. MET amplification leads to gefitinib resistance in lung cancer by activating ERBB3 signaling. *Science* 316, 1039-1043, doi:1141478 [pii] 10.1126/science.1141478 (2007).

Estrada-Bernal, et al. (2011) The role of sphingosine kinase-1 in EGFRvIII-regulated growth and survival of glioblastoma cells, *J Neurooncol* 102, 353-366.

(56) References Cited

OTHER PUBLICATIONS

Fallahi-Sichani, M. et al. Systematic analysis of BRAF(V600E) melanomas reveals a role for JNK/c-Jun pathway in adaptive resistance to drug-induced apoptosis. *Mol Syst Biol* 11, 797, doi:10.15252/msb.20145877 (2015).
Fan, et al. (2003) Combinatorial efficacy achieved through two-point blockade within a signaling pathway—a chemical genetic approach, *Cancer Res* 63, 8930-8938.
Fan, et al. (2006) A dual PI3 kinase/mTOR inhibitor reveals emergent efficacy in glioma, *Cancer Cell* 9, 341-349.
Fan, et al. (2013) EGFR Phosphorylates Tumor-Derived EGFRvIII Driving STAT3/5 and Progression in Glioblastoma, *Cancer Cell* 24, 438-449.
Fan, Z., et al. (2017) Nrf2-Keap1 pathway promotes cell proliferation and diminishes ferroptosis, *Oncogenesis* 6, e371.
Fitzgerald, K. A. et al. IKKepsilon and TBK1 are essential components of the IRF3 signaling pathway. *Nat Immunol* 4, 491-496, doi:10.1038/ni921 [pii] (2003).
Fletcher, et al. (2016) ABC transporters as mediators of drug resistance and contributors to cancer cell biology, *Drug Resist Updat* 26, 1-9.
Fortin Ensign, et al. (2013) Implications of Rho GTPase Signaling in Glioma Cell Invasion and Tumor Progression, *Front Oncol* 3, 241.
Fourquet, et al. (2010) Activation of NRF2 by nitrosative agents and H2O2 involves KEAP1 disulfide formation, *J Biol Chem* 285, 8463-8471.
Frank, et al. (2006) Gene expression signature of primary imatinib-resistant chronic myeloid leukemia patients, *Leukemia* 20, 1400-1407.
Frederick, et al. (2000) Diversity and frequency of epidermal growth factor receptor mutations in human glioblastomas, *Cancer Res* 60, 1383-1387.
Fruh, M., and Pless, M. (2012) EGFR IHC score for selection of cetuximab treatment: Ready for clinical practice?, *Transl Lung Cancer Res* 1, 145-146.
Furie, R. et al. Anifrolumab, an Anti-Interferon-alpha Receptor Monoclonal Antibody, in Moderate-to-Severe Systemic Lupus Erythematosus. *Arthritis Rheumatol* 69, 376-386, doi:10.1002/art.39962 (2017).
Furnari, et al. (2007) Malignant astrocytic glioma: genetics, biology, and paths to treatment, *Genes Dev* 21, 2683-2710.
Gadea, G., and Blangy, A. (2014) Dock-family exchange factors in cell migration and disease, *Eur J Cell Biol* 93, 466-477.
Gadgeel, et al. (2009) "Retracted: Genistein enhances the effect of epidermal growth factor receptor tyrosine kinase inhibitors and inhibits nuclear factor kappa B in nonsmall cell lung cancer cell lines" *Cancer* 115(10): 2165-2176.
Gainor, J. F. et al. EGFR Mutations and ALK Rearrangements Are Associated with Low Response Rates to PD-1 Pathway Blockade in Non-Small Cell Lung Cancer: A Retrospective Analysis. *Clin Cancer Res* 22, 4585-4593, doi:10.1158/1078-0432.CCR-15-3101 (2016).
Galan-Cobo, et al. (2019) LKB1 and KEAP1/NRF2 Pathways Cooperatively Promote Metabolic Reprogramming with Enhanced Glutamine Dependence in KRAS-Mutant Lung Adenocarcinoma, *Cancer Res* 79, 3251-3267.
Gao, et al. (2005) Proliferation and invasion: plasticity in tumor cells, *Proc Natl Acad Sci U S A* 102, 10528-10533.
Giese, et al. (1996) Dichotomy of astrocytoma migration and proliferation, *Int J Cancer* 67, 275-282.
Gonzalez-Juarrero, et al. (2012) Mouse model for efficacy testing of antituberculosis agents via intrapulmonary delivery, *Antimicrob Agents Chemother* 56, 3957-3959.
Gorrini, et al. (2013) BRCA1 interacts with Nrf2 to regulate antioxidant signaling and cell survival, *J Exp Med* 210, 1529-1544.
Gu, et al. (2011) Determination of sulphasalazine and its main metabolite sulphapyridine and 5-aminosalicylic acid in human plasma by liquid chromatography/tandem mass spectrometry and its application to a pharmacokinetic study, *Journal of chromatography. B, Analytical technologies in the biomedical and life sciences* 879, 449-456.
Guo, et al. (2009) EGFR signaling through an Akt-SREBP-1-dependent, rapamycin-resistant pathway sensitizes glioblastomas to antilipogenic therapy, *Sci Signal* 2, ra82.
Guo, G. et al. Ligand-Independent EGFR Signaling. *Cancer Res* 75, 3436-3441, doi: 10.1158/0008-5472.CAN-15-0989 (2015).
Guo, G. et al. A TNF-JNK-Axl-ERK signaling axis mediates primary resistance to EGFR inhibition in glioblastoma. *Nat Neurosci* 20, 1074-1084, doi:10.1038/nn.4584 (2017).
Guo, et al. (2019) Efficacy of EGFR plus TNF inhibition in a preclinical model of temozolomide-resistant glioblastoma, *Neuro Oncol.* Jul. 31, 2019. pii: noz127. doi:10.1093/neuonc/noz127. [Epub ahead of print].
Gupta, et al. (2016) Delineation of MGMT Hypermethylation as a Biomarker for Veliparib-Mediated Temozolomide-Sensitizing Therapy of Glioblastoma, *Journal of the National Cancer Institute* 108.
Habermann, B. (2004) The BAR-domain family of proteins: a case of bending and binding?, *EMBO reports* 5, 250-255.
Hall, et al. (2014) Inhibition of glutathione peroxidase mediates the collateral sensitivity of multidrug-resistant cells to tiopronin, *J Biol Chem* 289, 21473-21489.
Hammond, et al. (2010) American society of clinical oncology/college of american pathologists guideline recommendations for immunohistochemical testing of estrogen and progesterone receptors in breast cancer, *J Oncol Pract* 6, 195-197.
Hast, et al. (2013) Proteomic analysis of ubiquitin ligase KEAP1 reveals associated proteins that inhibit NRF2 ubiquitination, *Cancer Res* 73, 2199-2210.
Hatanpaa, et al. (2010) Epidermal growth factor receptor (EGFR) in glioma: Signal transduction, neuropathology, imaging and radioresistance *Neoplasia* 12, 675-684.
Hatzikirou, et al. (2012) 'Go or grow': the key to the emergence of invasion in tumour progression?, *Math Med Biol* 29, 49-65.
Hayes, J. D., and McMahon, M. (2009) NRF2 and KEAP1 mutations: permanent activation of an adaptive response in cancer, *Trends in biochemical sciences* 34, 176-188.
Hedditch, et al. (2014) ABCA transporter gene expression and poor outcome in epithelial ovarian cancer, *Journal of the National Cancer Institute* 106.
Hegi, et al. (2005) MGMT gene silencing and benefit from temozolomide in glioblastoma, *N Engl J Med* 352, 997-1003.
Hirst, et al. (2013) Systematic review and meta-analysis of temozolomide in animal models of glioma: was clinical efficacy predicted?, *Br J Cancer* 108, 64-71.
Honda, K. & Taniguchi, T. IRFs: master regulators of signalling by Toll-like receptors and cytosolic pattern-recognition receptors. *Nat Rev Immunol* 6, 644-658, doi:nri1900 [pii] 10.1038/nri1900 (2006).
Horing, et al. (2012) The "go or grow" potential of gliomas is linked to the neuropeptide processing enzyme carboxypeptidase E and mediated by metabolic stress, *Acta neuropathologica* 124, 83-97.
Hsieh, et al. Co-expression of epidermal growth factor receptor and transforming growth factor-alpha is independent of ras mutations in lung adenocarcinoma. *Lung cancer* 29, 151-157 (2000).
Huang, et al. (2009) Oncogenic EGFR signaling networks in glioma, *Sci Signal* 2, re6.
Hundsberger, et al. (2017) Angiogenesis inhibitors in tackling recurrent glioblastoma, *Expert Rev Anticancer Ther* 17, 507-515.
Huo, et al. (2016) Erastin Disrupts Mitochondrial Permeability Transition Pore (mPTP) and Induces Apoptotic Death of Colorectal Cancer Cells, *PLoS One* 11, e0154605.
Hutchinson, et al. (2015) Epidermal growth factor receptor immunohistochemistry: new opportunities in metastatic colorectal cancer, *J Transl Med* 13, 217.
Ichimura, et al. (2013) Phosphorylation of p62 activates the Keap1-Nrf2 pathway during selective autophagy, *Mol Cell* 51, 618-631.
Inda, et al. (2010) Tumor heterogeneity is an active process maintained by a mutant EGFR-induced cytokine circuit in glioblastoma, *Genes Dev* 24, 1731-1745.
Ivashkiv, L. B. & Donlin, L. T. Regulation of type I interferon responses. *Nat Rev Immunol* 14, 36-49, doi:10.1038/nri3581 (2014).

(56) References Cited

OTHER PUBLICATIONS

Jackson, et al. (2019) Mechanisms of immunotherapy resistance: lessons from glioblastoma, *Nat Immunol* 20, 1100-1109.
Jahangiri, et al. (2017) Cross-activating c-Met/beta1 integrin complex drives metastasis and invasive resistance in cancer, *Proc Natl Acad Sci U S A* 114, E8685-E8694.
Jaramillo, M. C., and Zhang, D. D. (2013) The emerging role of the Nrf2-Keap1 signaling pathway in cancer, *Genes Dev* 27, 2179-2191.
Jen-Yi, et al. (2011) "Curcumin Induces EGFR Degradation in Lung Adenocarcinoma and Modulates p38 Activation in Intestine: The Versatile Adjuvant for Gefitinib Therapy" *PLoS One* 6(8): e23756.
Jeong, et al. (2017) Role of KEAP1/NRF2 and TP53 Mutations in Lung Squamous Cell Carcinoma Development and Radiation Resistance, *Cancer Discov* 7, 86-101.
Ji, et al. (2018) xCT (SLC7A11)-mediated metabolic reprogramming promotes non-small cell lung cancer progression, *Oncogene* 37, 5007-5019.
Jia, et al. (2012) Inhibition of glutathione synthesis reverses Kruppel-like factor 4-mediated cisplatin resistance, *Cancer Chemother Pharmacol* 69, 377-385.
Jia, et al. (2015) Micheliolide overcomes KLF4-mediated cisplatin resistance in breast cancer cells by downregulating glutathione, *Onco Targets Ther* 8, 2319-2327.
Jiang, et al. (2014) PKM2 phosphorylates MLC2 and regulates cytokinesis of tumour cells, *Nat Commun* 5, 5566.
Johannessen, T. A., and Bjerkvig, R. (2019) A new chance for EGFR inhibition in glioblastoma?, *Neuro Oncol.* 21(12): 1487-1488.
Kanamori, et al. (2015) Activation of the NRF2 pathway and its impact on the prognosis of anaplastic glioma patients, *Neuro Oncol* 17, 555-565.
Kansanen, et al. (2013) The Keap1-Nrf2 pathway: Mechanisms of activation and dysregulation in cancer, *Redox Biol* 1, 45-49.
Karapetian, et al. (2005) Nuclear oncoprotein prothymosin alpha is a partner of Keap1: implications for expression of oxidative stress-protecting genes, *Mol Cell Biol* 25, 1089-1099.
Karpel-Massler, et al. (2009) Therapeutic inhibition of the epidermal growth factor receptor in high-grade gliomas: where do we stand?, *Mol Cancer Res* 7, 1000-1012.
Kathagen-Buhmann, et al. (2016) Glycolysis and the pentose phosphate pathway are differentially associated with the dichotomous regulation of glioblastoma cell migration versus proliferation, *Neuro Oncol* 18, 1219-1229.
Kerins, M. J., and Ooi, A. (2018) A catalogue of somatic NRF2 gain-of-function mutations in cancer, *Sci Rep* 8, 12846.
Khodarev, N. N. et al. Signal transducer and activator of transcription 1 regulates both cytotoxic and prosurvival functions in tumor cells. *Cancer Res* 67, 9214-9220, doi:10.1158/0008-5472.CAN-07-1019 (2007).
Khodarev, N. N. et al. STAT1 is overexpressed in tumors selected for radioresistance and confers protection from radiation in transduced sensitive cells. *Proc Natl Acad Sci U S A* 101, 1714-1719, doi:10.1073/pnas.0308102100 (2004).
Kim, et al. (2010) Oncogenic NRF2 mutations in squamous cell carcinomas of oesophagus and skin, *The Journal of pathology* 220, 446-451.
Kitajima, S. et al. Suppression of STING Associated with LKB1 Loss in KRAS-Driven Lung Cancer. *Cancer Discov* 9, 34-45, doi: 10.1158/2159-8290.CD-18-0689 (2019).
Knobbe-Thomsen, et al. (2013) EGFR Phosphorylates Tumor-Derived EGFRvIII Driving STAT3/5 and Progression in Glioblastoma, *Cancer Cell* 24, 438-449.
Komatsu, et al. (2010) The selective autophagy substrate p62 activates the stress responsive transcription factor Nrf2 through inactivation of Keap1, *Nat Cell Biol* 12, 213-223.
Konstantinopoulos, et al. (2011) Keap1 mutations and Nrf2 pathway activation in epithelial ovarian cancer, *Cancer Res* 71, 5081-5089.
Krall, et al. (2017) KEAP1 loss modulates sensitivity to kinase targeted therapy in lung cancer, *Elife* 6.

Kruspig, B. et al. The ERBB network facilitates KRAS-driven lung tumorigenesis. *Sci Transl Med* 10, doi:10.1126/scitranslmed.aao2565 (2018).
Lazzari, E. & Meroni, G. TRIM32 ubiquitin E3 ligase, one enzyme for several pathologies: From muscular dystrophy to tumours. *Int J Biochem Cell Biol* 79, 469-477, doi:10.1016/j.biocel.2016.07.023 (2016).
Le, et al. (2018) Landscape of EGFR-Dependent and -Independent Resistance Mechanisms to Osimertinib and Continuation Therapy Beyond Progression in EGFR-Mutant NSCLC, *Clin Cancer Res* 24, 6195-6203.
Lee, H. J. et al. Drug resistance via feedback activation of Stat3 in oncogene-addicted cancer cells. *Cancer Cell* 26, 207-221, doi:10.1016/j.ccr.2014.05.019 (2014).
Li, et al. (2011) KEAP1 gene mutations and NRF2 activation are common in pulmonary papillary adenocarcinoma, *J Hum Genet* 56, 230-234.
Li, et al. (2014) An EGFR wild type-EGFRvIII-HB-EGF feed-forward loop regulates the activation of EGFRvIII, *Oncogene* 33, 4253-4264.
Li, et al. (2016) beta-elemene sensitizes hepatocellular carcinoma cells to oxaliplatin by preventing oxaliplatin-induced degradation of copper transporter 1, *Sci Rep* 6, 21010.
Lim, et al. (2018) Current state of immunotherapy for glioblastoma, *Nat Rev Clin Oncol* 15, 422-442.
Liou, G. Y., and Storz, P. (2010) Reactive oxygen species in cancer, *Free Radic Res* 44, 479-496.
Liou, G. Y., and Storz, P. (2015) Detecting reactive oxygen species by immunohistochemistry, *Methods Mol Biol* 1292, 97-104.
Liu, et al. (2015) APR-246 potently inhibits tumour growth and overcomes chemoresistance in preclinical models of oesophageal adenocarcinoma, *Gut* 64, 1506-1516.
Liu, S. et al. Phosphorylation of innate immune adaptor proteins MAVS, STING, and TRIF induces IRF3 activation. *Science* 347, aaa2630, doi:10.1126/science.aaa2630 (2015).
Liu, Q. et al. EGFR-TKIs resistance via EGFR-independent signaling pathways. *Mol Cancer* 17, 53, doi:10.1186/s12943-018-0793-1 (2018).
Liu, Y. et al. Tumor-Repopulating Cells Induce PD-1 Expression in CD8(+) T Cells by Transferring Kynurenine and AhR Activation. *Cancer Cell* 33, 480-494 e487, doi:10.1016/j.ccell.2018.02.005 (2018).
Lopez-Bertoni, et al. (2016) Epigenetic modulation of a miR-296-5p:HMGA1 axis regulates Sox2 expression and glioblastoma stem cells, *Oncogene* 35, 4903-4913.
Lu, et al. (2009) Fyn and SRC are effectors of oncogenic epidermal growth factor receptor signaling in glioblastoma patients, *Cancer Res* 69, 6889-6898.
Lu, et al. (2017) NRF2 Induction Supporting Breast Cancer Cell Survival Is Enabled by Oxidative Stress-Induced DPP3-KEAP1 Interaction, *Cancer Res* 77, 2881-2892.
Lu, K. V., and Bergers, G. (2013) Mechanisms of evasive resistance to anti-VEGF therapy in glioblastoma, *CNS Oncol* 2, 49-65.
Luo, et al. (2009) Principles of cancer therapy: oncogene and non-oncogene addiction, *Cell* 136, 823-837.
Lynch, et al. (2004) Activating mutations in the epidermal growth factor receptor underlying responsiveness of non-small-cell lung cancer to gefitinib, *N Engl J Med* 350, 2129-2139.
Ma, et al. (2012) PALB2 interacts with KEAP1 to promote NRF2 nuclear accumulation and function, *Mol Cell Biol* 32, 1506-1517.
Ma, et al. (2019) TNFalpha inhibitor C87 sensitizes EGFRvIII transfected glioblastoma cells to gefitinib by a concurrent blockade of TNFalpha signaling, *Cancer Biol Med* 16, 606-617.
Mai, et al. (2017) Cytoplasmic p53 couples oncogene-driven glucose metabolism to apoptosis and is a therapeutic target in glioblastoma, *Nature medicine* 23, 1342-1351.
Majd, et al. (2019) The path forward for anti-programmed death-1 therapy in gliomas, *Curr Opin Neurol*.
Matsuda, et al. (2012) "Targeting JNK for therapeutic depletion of stem-like glioblastoma cells" *Sci Rep* 2: 516.
McDonald, et al. (2010) Ionizing radiation activates the Nrf2 antioxidant response, *Cancer Res* 70, 8886-8895.

(56) References Cited

OTHER PUBLICATIONS

McNeill, et al. (2015) Contemporary murine models in preclinical astrocytoma drug development, *Neuro Oncol* 17, 12-28.

Meissl, et al. The good and the bad faces of STAT1 in solid tumours. *Cytokine* 89, 12-20, doi:10.1016/j.cyto.2015.11.011 (2017).

Misek, et al. (2017) EGFR Signals through a DOCK180-MLK3 Axis to Drive Glioblastoma Cell Invasion, *Mol Cancer Res* 15, 1085-1095.

Mishima, et al. (1998) Heparin-binding epidermal growth factor-like growth factor stimulates mitogenic signaling and is highly expressed in human malignant gliomas, *Acta Neuropathol (Berl)* 96, 322-328.

Mohell, et al. (2015) APR-246 overcomes resistance to cisplatin and doxorubicin in ovarian cancer cells, *Cell Death Dis* 6, e1794.

Moll, H. P. et al. Afatinib restrains K-RAS-driven lung tumorigenesis. *Sci Transl Med* 10, doi:10.1126/scitranslmed.aao2301 (2018).

Muhlbauer, M. et al. PD-L1 is induced in hepatocytes by viral infection and by interferon-alpha and -gamma and mediates T cell apoptosis. *J Hepatol* 45, 520-528, doi:10.1016/j.jhep.2006.05.007 (2006).

Murray, et al. (2014) Guanine nucleotide exchange factor Dock7 mediates HGF-induced glioblastoma cell invasion via Rac activation, *Br J Cancer* 110, 1307-1315.

Nair, A. B., and Jacob, S. (2016) A simple practice guide for dose conversion between animals and human, *J Basic Clin Pharm* 7, 27-31.

Nakamuta, et al. (2017) Dual role for DOCK7 in tangential migration of interneuron precursors in the postnatal forebrain, *J Cell Biol* 216, 4313-4330.

Nathanson, et al. (2014) Targeted therapy resistance mediated by dynamic regulation of extrachromosomal mutant EGFR DNA, *Science* 343, 72-76.

Nau, et al. (2010) Penetration of drugs through the blood-cerebrospinal fluid/blood-brain barrier for treatment of central nervous system infections, *Clin Microbiol Rev* 23, 858-883.

Negishi, et al. The Interferon (IFN) Class of Cytokines and the IFN Regulatory Factor (IRF) Transcription Factor Family. *Cold Spring Harb Perspect Biol* 10, doi:10.1101/cshperspect.a028423 (2018).

Newman, et al. (2017) Interleukin-13 receptor alpha 2 cooperates with EGFRvIII signaling to promote glioblastoma multiforme, *Nat Commun* 8, 1913.

Nishikawa, et al. (1994) A mutant epidermal growth factor receptor common in human glioma confers enhanced tumorigenicity, *Proc Natl Acad Sci U S A* 91, 7727-7731.

Nishikawa, et al. (2004) Immunohistochemical analysis of the mutant epidermal growth factor, deltaEGFR, in glioblastoma, *Brain Tumor Pathol* 21, 53-56.

O'Reilly, M. A. (2005) Redox activation of p21Cip1/WAF1/Sdi1: a multifunctional regulator of cell survival and death, *Antioxid Redox Signal* 7, 108-118.

Ooi, et al. (2013) CUL3 and NRF2 mutations confer an NRF2 activation phenotype in a sporadic form of papillary renal cell carcinoma, *Cancer Res* 73, 2044-2051.

Orcutt, et al. (2011) Erlotinib-mediated inhibition of EGFR signaling induces metabolic oxidative stress through NOX4, *Cancer Res* 71, 3932-3940.

Padmanabhan, et al. (2006) Structural basis for defects of Keap1 activity provoked by its point mutations in lung cancer, *Mol Cell* 21, 689-700.

Padmanabhan, et al. (2008) Structural analysis of the complex of Keap1 with a prothymosin alpha peptide, *Acta Crystallogr Sect F Struct Biol Cryst Commun* 64, 233-238.

Paez, et al. (2004) EGFR mutations in lung cancer: correlation with clinical response to gefitinib therapy, *Science* 304, 1497-1500.

Park, et al. (2009) The receptor interacting protein 1 inhibits p53 induction through NF-kappaB activation and confers a worse prognosis in glioblastoma, *Cancer Res* 69, 2809-2816.

Park, et al. (2018) Resistance to gefitinib and cross-resistance to irreversible EGFR-TKIs mediated by disruption of the Keap1-Nrf2 pathway in human lung cancer cells, *FASEB J*, fj201800011R.

Pathania, et al. (2018) Drug metabolizing enzymes and their inhibitors' role in cancer resistance, *Biomed Pharmacother* 105, 53-65.

Peereboom, et al. (2010) Phase II trial of erlotinib with temozolomide and radiation in patients with newly diagnosed glioblastoma multiforme, *J Neurooncol* 98, 93-99.

Pelosof, et al. (2017) GPX3 promoter methylation predicts platinum sensitivity in colorectal cancer, *Epigenetics* 12, 540-550.

Peng, et al. (2016) Suppression of NRF2-ARE activity sensitizes chemotherapeutic agent-induced cytotoxicity in human acute monocytic leukemia cells, *Toxicology and applied pharmacology* 292, 1-7.

Peter, et al. (2004) BAR domains as sensors of membrane curvature: the amphiphysin BAR structure, *Science* 303, 495-499.

Polewski, et al. (2016) Increased Expression of System xc—in Glioblastoma Confers an Altered Metabolic State and Temozolomide Resistance, *Mol Cancer Res* 14, 1229-1242.

Polewski, et al. (2017) SLC7A11 Overexpression in Glioblastoma Is Associated with Increased Cancer Stem Cell-Like Properties, *Stem Cells Dev* 26, 1236-1246.

Polonen, et al. (2019) Nrf2 and SQSTM1/p62 jointly contribute to mesenchymal transition and invasion in glioblastoma, *Oncogene*.

Prahallad, A. et al. Unresponsiveness of colon cancer to BRAF(V600E) inhibition through feedback activation of EGFR. *Nature* 483, 100-103, doi:10.1038/nature10868 (2012).

Prendergast, et al. (2009) BAR the door: cancer suppression by amphiphysin-like genes, *Biochim Biophys Acta* 1795, 25-36.

Puchalski, et al. (2018) An anatomic transcriptional atlas of human glioblastoma, *Science* 360, 660-663.

Puliyappadamba V.T. et al. Opposing effect of EGFRwt on EGFRvIII mediated NF-kappaB activation with RIP1 as a cell death switch. *Cell Reports* 4, 764-775. 2013.

Qian, et al. (2009) Erlotinib activates mitochondrial death pathways related to the production of reactive oxygen species in the human non-small cell lung cancer cell line A549, *Clin Exp Pharmacol Physiol* 36, 487-494.

Raizer, et al. (2010) A phase II trial of erlotinib in patients with recurrent malignant gliomas and nonprogressive glioblastoma multiforme postradiation therapy, *Neuro Oncol* 12, 95-103.

Ramalingam, et al. (2008) Bin3 deletion causes cataracts and increased susceptibility to lymphoma during aging, *Cancer Res* 68, 1683-1690.

Ramnarain, et al. (2006) Differential gene expression analysis reveals generation of an autocrine loop by a mutant epidermal growth factor receptor in glioma cells, *Cancer Res* 66, 867-874.

Rasmussen, et al. (2016) BRCA1-regulated RRM2 expression protects glioblastoma cells from endogenous replication stress and promotes tumorigenicity, *Nat Commun* 7, 13398.

Reardon, et al. (2010) Phase 2 trial of erlotinib plus sirolimus in adults with recurrent glioblastoma, *J Neurooncol* 96, 219-230.

Rich, et al. (2004) Phase II trial of gefitinib in recurrent glioblastoma, *J Clin Oncol* 22, 133-142.

Rickardson, L. et al. Identification of molecular mechanisms for cellular drug resistance by combining drug activity and gene expression profiles. *Br J Cancer* 93, 483-492, doi:10.1038/sj.bjc.6602699 (2005).

Robert, et al. (2015) SLC7A11 expression is associated with seizures and predicts poor survival in patients with malignant glioma, *Sci Transl Med* 7, 289ra286.

Rocha, et al. (2016) NRF2 and glutathione are key resistance mediators to temozolomide in glioma and melanoma cells, *Oncotarget* 7, 48081-48092.

Rojo de la Vega, et al. (2018) NRF2 and the Hallmarks of Cancer, *Cancer Cell*.

Romero, et al. (2017) Keap1 loss promotes Kras-driven lung cancer and results in dependence on glutaminolysis, *Nature medicine* 23, 1362-1368.

Roos, et al. (2018) EGFRvIII-Stat5 Signaling Enhances Glioblastoma Cell Migration and Survival, *Mol Cancer Res* 16, 1185-1195.

Roth, P., and Weller, M. (2014) Challenges to targeting epidermal growth factor receptor in glioblastoma: escape mechanisms and combinatorial treatment strategies, *Neuro Oncol 16 Suppl* 8, viii14-19.

(56) References Cited

OTHER PUBLICATIONS

Rubio-Moscardo, et al. (2005) Characterization of 8p21.3 chromosomal deletions in B-cell lymphoma: TRAIL-R1 and TRAIL-R2 as candidate dosage-dependent tumor suppressor genes, *Blood* 106, 3214-3222.
Rusch, V. et al. Differential expression of the epidermal growth factor receptor and its ligands in primary non-small cell lung cancers and adjacent benign lung. *Cancer Res* 53, 2379-2385 (1993).
Russell, et al. (2017) Sex as a biological variable in response to temozolomide, *Neuro Oncol*.
Russell, et al. (2018) PTEN expression by an oncolytic herpesvirus directs T-cell mediated tumor clearance, *Nat Commun* 9, 5006.
Rusthoven, et al. (2016) Combined-Modality Therapy With Radiation and Chemotherapy for Elderly Patients With Glioblastoma in the Temozolomide Era: A National Cancer Database Analysis, *JAMA Neurol* 73, 821-828.
Sabharwal, S. S., and Schumacker, P. T. (2014) Mitochondrial ROS in cancer: initiators, amplifiers or an Achilles' heel?, *Nat Rev Cancer* 14, 709-721.
Santosh, V., and Sravya, P. (2017) Glioma, glutamate (SLC7A11) and seizures—a commentary, *Ann Transl Med* 5, 214.
Sarkaria, et al. (2006) Use of an orthotopic xenograft model for assessing the effect of epidermal growth factor receptor amplification on glioblastoma radiation response, *Clin Cancer Res* 12, 2264-2271.
Sathornsumetee, et al. (2010) Phase II trial of bevacizumab and erlotinib in patients with recurrent malignant glioma, *Neuro Oncol* 12, 1300-1310.
Sato, et al. (2018) The ferroptosis inducer erastin irreversibly inhibits system xc- and synergizes with cisplatin to increase cisplatin's cytotoxicity in cancer cells, *Sci Rep* 8, 968.
Schnell, et al. (2014) Pharmacokinetics of afatinib in subjects with mild or moderate hepatic impairment, *Cancer Chemother Pharmacol* 74, 267-275.
Shah, et al. (2016) Survival Trends in Elderly Patients with Glioblastoma in the United States: a Population-based Study, *Anticancer Res* 36, 4883-4886.
Sharma, et al. Epidermal growth factor receptor mutations in lung cancer. *Nat Rev Cancer* 7, 169-181, doi:10.1038/nrc2088 (2007).
Shi, et al. (2017) All-trans retinoic acid enhances temozolomide-induced autophagy in human glioma cells U251 via targeting Keap1/Nrf2/ARE signaling pathway, *Oncol Lett* 14, 2709-2714.
Shibata, et al. (2008) Cancer related mutations in NRF2 impair its recognition by Keap1-Cul3 E3 ligase and promote malignancy, *Proc Natl Acad Sci U S A* 105, 13568-13573.
Shukla, et al. (2011) Inhibition of xc(-) transporter-mediated cystine uptake by sulfasalazine analogs, *Bioorg Med Chem Lett* 21, 6184-6187.
Silva-Islas, C. A., and Maldonado, P. D. (2018) Canonical and non-canonical mechanisms of Nrf2 activation, *Pharmacol Res* 134, 92-99.
Simionescu-Bankston, et al. (2013) The N-BAR domain protein, Bin3, regulates Rac1- and Cdc42-dependent processes in myogenesis, *Dev Biol* 382, 160-171.
Singh, et al. (2006) Dysfunctional KEAP1-NRF2 interaction in non-small-cell lung cancer, *PLoS Med* 3, e420.
Singh, et al. (2016) Small Molecule Inhibitor of NRF2 Selectively Intervenes Therapeutic Resistance in KEAP1-Deficient NSCLC Tumors, *ACS chemical biology* 11, 3214-3225.
Sivanand, et al. (2012) A validated tumorgraft model reveals activity of dovitinib against renal cell carcinoma, *Sci Transl Med* 4, 137ra175.
Sleire, et al. (2015) Drug repurposing: sulfasalazine sensitizes gliomas to gamma knife radiosurgery by blocking cystine uptake through system Xc-, leading to glutathione depletion, *Oncogene* 34, 5951-5959.
Snell, et al. Type I Interferon in Chronic Virus Infection and Cancer. *Trends Immunol* 38, 542-557, doi:10.1016/j.it.2017.05.005 (2017).

Solis, et al. (2010) Nrf2 and Keap1 abnormalities in non-small cell lung carcinoma and association with clinicopathologic features, *Clin Cancer Res* 16, 3743-3753.
Song, G. et al. E3 ubiquitin ligase RNF128 promotes innate antiviral immunity through K63-linked ubiquitination of TBK1. *Nat Immunol* 17, 1342-1351, doi:10.1038/ni.3588 (2016).
Sontheimer, H., and Bridges, R. J. (2012) Sulfasalazine for brain cancer fits, *Expert Opin Investig Drugs* 21, 575-578.
Sorensen, et al. (2018) High expression of cystine-glutamate antiporter xCT (SLC7A11) is an independent biomarker for epileptic seizures at diagnosis in glioma, *J Neurooncol* 138, 49-53.
Starheim, et al. (2016) Intracellular glutathione determines bortezomib cytotoxicity in multiple myeloma cells, *Blood Cancer J* 6, e446.
Stupp, et al. (2005) Radiotherapy plus concomitant and adjuvant temozolomide for glioblastoma, *N Engl J Med* 352, 987-996.
Sullins, A. K., and Abdel-Rahman, S. M. (2013) Pharmacokinetics of antibacterial agents in the CSF of children and adolescents, *Paediatr Drugs* 15, 93-117.
Sun, C. & Bernards, R. Feedback and redundancy in receptor tyrosine kinase signaling: relevance to cancer therapies. *Trends in biochemical sciences* 39, 465-474, doi:10.1016/j.tibs.2014.08.010 (2014).
Sun, C. et al. Intrinsic resistance to MEK inhibition in KRAS mutant lung and colon cancer through transcriptional induction of ERBB3. *Cell Rep* 7, 86-93, doi:10.1016/j.celrep.2014.02.045 (2014).
Talasila, et al. (2013) EGFR wild-type amplification and activation promote invasion and development of glioblastoma independent of angiogenesis, *Acta neuropathologica* 125, 683-698.
Tamura, et al. (2017) Bevacizumab for malignant gliomas: current indications, mechanisms of action and resistance, and markers of response, *Brain Tumor Pathol* 34, 62-77.
Tan, et al. (2016) Stress-Induced EGFR Trafficking: Mechanisms, Functions, and Therapeutic Implications, *Trends Cell Biol* 26, 352-366.
Tang, et al. (1997) The autocrine loop of TGF-alpha/EGFR and brain tumors, *J Neurooncol* 35, 303-314.
Tang, et al. (2014) Cdk5-dependent Mst3 phosphorylation and activity regulate neuronal migration through RhoA inhibition, *J Neurosci* 34, 7425-7436.
Terai, H. et al. ER Stress Signaling Promotes the Survival of Cancer "Persister Cells" Tolerant to EGFR Tyrosine Kinase Inhibitors. *Cancer Res* 78, 1044-1057, doi:10.1158/0008-5472.CAN-17-1904 (2018).
The Cancer Genome Atlas Research Network (2008) Comprehensive genomic characterization defines human glioblastoma genes and core pathways, *Nature* 455, 1061-1068.
Thungappa, S. et al. Immune checkpoint inhibitors in lung cancer: the holy grail has not yet been found. *ESMO Open* 2, e000162, doi:10.1136/esmoopen-2017-000162 (2017).
Trinchieri, G. Type I interferon: friend or foe? *J Exp Med* 207, 2053-2063, doi:10.1084/jem.20101664 (2010).
Trudgian, D. C. et al. Comparative evaluation of label-free SINQ normalized spectral index quantitation in the central proteomics facilities pipeline. *Proteomics* 11, 2790-2797 (2011).
Tsai, M. H. et al. Gene expression profiling of breast, prostate, and glioma cells following single versus fractionated doses of radiation. *Cancer Res* 67, 3845-3852, doi:10.1158/0008-5472.CAN-06-4250 (2007).
Tu, D. et al. Structure and ubiquitination-dependent activation of TANK-binding kinase 1. *Cell Rep* 3, 747-758, doi:10.1016/j.celrep.2013.01.033 (2013).
Velu, et al. (1987) Epidermal-growth-factor-dependent transformation by a human EGF receptor proto-oncogene, *Science* 238, 1408-1410.
Venere, et al. (2015) The mitotic kinesin KIF11 is a driver of invasion, proliferation, and self-renewal in glioblastoma, *Sci Transl Med* 7, 304ra143.
Verhaak, et al. (2010) Integrated genomic analysis identifies clinically relevant subtypes of glioblastoma characterized by abnormalities in PDGFRA, IDH1, EGFR, and NF1, *Cancer Cell* 17, 98-110.
Verma, et al. (2015) Isoniazid prevents Nrf2 translocation by inhibiting ERK1 phosphorylation and induces oxidative stress and apoptosis, *Redox Biol* 6, 80-92.

(56) References Cited

OTHER PUBLICATIONS

Volante, M. et al. Epidermal growth factor ligand/receptor loop and downstream signaling activation pattern in completely resected nonsmall cell lung cancer. Cancer 110, 1321-1328, doi:10.1002/cncr.22903 (2007).
Wainwright, et al. (2014) Durable therapeutic efficacy utilizing combinatorial blockade against IDO, CTLA-4 and PD-L1 in mice with brain tumors, Clin Cancer Res.
Wang, et al. (2015) Identification of proteins responsible for adriamycin resistance in breast cancer cells using proteomics analysis, Sci Rep 5, 9301.
Wang, et al. (2016) Anti-Tumor Pharmacey Jun. 28, 2016 Editorial Department of Anti-Tumor Pharmacy CHN, 6(3): 193-197.
Wang, et al. (2017) Pathology—Research and Practice 214(2): 263-267.
Wang, L., Li, S. & Dorf, M. E. NEMO binds ubiquitinated TANK-binding kinase 1 (TBK1) to regulate innate immune responses to RNA viruses. PLoS One 7, e43756, doi:10.1371/journal.pone.0043756 (2012).
Warta, R., and Herold-Mende, C. (2017) Helping EGFR inhibition to block cancer, Nat Neurosci 20, 1035-1037.
Weichselbaum, R. R. et al. An interferon-related gene signature for DNA damage resistance is a predictive marker for chemotherapy and radiation for breast cancer. Proc Natl Acad Sci U S A 105, 18490-18495, doi:10.1073/pnas.0809242105 (2008).
Weller, et al. (2017) Rindopepimut with temozolomide for patients with newly diagnosed, EGFRvIII-expressing glioblastoma (ACT IV): a randomised, double-blind, international phase 3 trial, The lancet oncology 18, 1373-1385.
Wind, et al. (2017) Clinical Pharmacokinetics and Pharmacodynamics of Afatinib, Clin Pharmacokinet 56, 235-250.
Wolff, et al. (2007) American Society of Clinical Oncology/College of American Pathologists guideline recommendations for human epidermal growth factor receptor 2 testing in breast cancer, J Clin Oncol 25, 118-145.
Wong, et al. (1992) Structural alterations of the epidermal growth factor receptor gene in human gliomas, Proc Natl Acad Sci U S A 89, 2965-2969.
Worley, et al. (2018) GPx3 supports ovarian cancer progression by manipulating the extracellular redox environment, Redox Biol.
Wykosky, et al. (2015) A urokinase receptor-Bim signaling axis emerges during EGFR inhibitor resistance in mutant EGFR glioblastoma, Cancer Res 75, 394-404.
Xie, et al. (2014) Targeting adaptive glioblastoma: an overview of proliferation and invasion, Neuro Oncol 16, 1575-1584.
Xie, et alD. (2017) The Tumor Suppressor p53 Limits Ferroptosis by Blocking DPP4 Activity, Cell Rep 20, 1692-1704.
Yamada, et al. (2013) High expression of ATP-binding cassette transporter ABCC11 in breast tumors is associated with aggressive subtypes and low disease-free survival, Breast cancer research and treatment 137, 773-782.
Yamamoto, et al. (2013) DOCK7 is a critical regulator of the RAGE-Cdc42 signaling axis that induces formation of dendritic pseudopodia in human cancer cells, Oncology reports 29, 1073-1079.
Ye, et al. (2007) Genomic assessments of the frequent loss of heterozygosity region on 8p21.3-p22 in head and neck squamous cell carcinoma, Cancer Genet Cytogenet 176, 100-106.
Ye, M. et al. Activation of the Aryl Hydrocarbon Receptor Leads to Resistance to EGFR TKIs in Non-Small Cell Lung Cancer by Activating Src-mediated Bypass Signaling. Clin Cancer Res 24, 1227-1239, doi:10.1158/1078-0432.CCR-17-0396 (2017).
Ye, Z. et al. Prevalent Homozygous Deletions of Type I Interferon and Defensin Genes in Human Cancers Associate with Immunotherapy Resistance. Clin Cancer Res 24, 3299-3308, doi:10.1158/1078-0432.CCR-17-3008 (2018).
Yoneyama, et al. Control of IRF-3 activation by phosphorylation. J Interferon Cytokine Res 22, 73-76, doi:10.1089/107999002753452674 (2002).
Yoshida, T. et al. Tyrosine phosphoproteomics identifies both codrivers and cotargeting strategies for T790M-related EGFR-TKI resistance in non-small cell lung cancer. Clin Cancer Res 20, 4059-4074, doi:10.1158/1078-0432.CCR-13-1559 (2014).
Yu, H. A. et al. Analysis of tumor specimens at the time of acquired resistance to EGFR-TKI therapy in 155 patients with EGFR-mutant lung cancers. Clin Cancer Res 19, 2240-2247, doi:10.1158/1078-0432.CCR-12-2246 (2013).
Yuan, et al. (2012) A positive/negative ion-switching, targeted mass spectrometry-based metabolomics platform for bodily fluids, cells, and fresh and fixed tissue, Nat Protoc 7, 872-881.
Zanca, et al. (2017) Glioblastoma cellular cross-talk converges on NF-kappaB to attenuate EGFR inhibitor sensitivity, Genes Dev 31, 1212-1227.
Zhang, et al. TRIM32 protein modulates type I interferon induction and cellular antiviral response by targeting MITA/STING protein for K63-linked ubiquitination. J Biol Chem 287, 28646-28655, doi:10.1074/jbc.M112.362608 (2012).
Zhang, Z. et al. Activation of the AXL kinase causes resistance to EGFR-targeted therapy in lung cancer. Nat Genet 44, 852-860, doi:10.1038/ng.2330 (2012).
Zhang, et al. (2016) ROS and ROS-Mediated Cellular Signaling, Oxid Med Cell Longev 2016, 4350965.
Zhang, et al. (2017) Efficacy of afatinib, an irreversible ErbB family blocker, in the treatment of intracerebral metastases of non-small cell lung cancer in mice, Acta Pharmacol Sin 38, 233-240.
Zhang, L., and Wang, H. (2017) FTY720 inhibits the Nrf2/ARE pathway in human glioblastoma cell lines and sensitizes glioblastoma cells to temozolomide, Pharmacol Rep 69, 1186-1193.
Zheng, et al. (1993) Toxicokinetics of sulfasalazine (salicylazosulfapyridine) and its metabolites in B6C3F1 mice, Drug Metab Dispos 21, 1091-1097.
Zhou, et al. (2009) Dynamic near-infrared optical imaging of 2-deoxyglucose uptake by intracranial glioma of athymic mice, PLoS One 4, e8051.
Zhu, et al. (2013) Nrf2 is required to maintain the self-renewal of glioma stem cells, BMC Cancer 13, 380.
Zhu, M., and Fahl, W. E. (2001) Functional characterization of transcription regulators that interact with the electrophile response element, Biochem Biophys Res Commun 289, 212-219.
Zitka, et al. (2012) Redox status expressed as GSH:GSSG ratio as a marker for oxidative stress in paediatric tumour patients, Oncol Lett 4, 1247-1253.
Zitvogel, et al. Type I interferons in anticancer immunity. Nat Rev Immunol 15, 405-414, doi:10.1038/nri3845 (2015).
Response to Requirement for Restriction filed on Jan. 30, 2020 with the USPTO for U.S. Appl. No. 15/940,802, filed Mar. 29, 2018 and published as US 2019-0231778 on Aug. 1, 2019 (Inventor—A. Habib) (9 Pages).
Non-final Office Action dated May 18, 2020 by the USPTO for U.S. Appl. No. 15/940,802, filed Mar. 29, 2018 and published as US 2019-0231778 on Aug. 1, 2019 (Inventor—A. Habib) (17 Pages).
Response to Office Action filed on Jul. 28, 2020 with the USPTO for U.S. Appl. No. 15/940,802, filed Mar. 29, 2018 and published as US 2019-0231778 on Aug. 1, 2019 (Inventor—A. Habib) (19 Pages).
European Search Report dated Jun. 8, 2020 by the European Search Authority for EP Application No. 17862082.9, filed on Oct. 19, 2017 and published as EP 3528798 on Aug. 28, 2019 (Inventor—A. Habib) (19 Pages).
Extended European Search Report dated Sep. 16, 2020 by the European Patent Office for EP Application No. 17862082.9, filed on Oct. 19, 2016 and published as EP 3528798 on Aug. 28, 2019 (Applicant—United States Government as Represented by the Department of Veterans Affairs) (16 pages).
Ju-Hwa, et al. (2013) "SP600125 overcomes antimitotic drug-resistance in cancer cells by increasing apoptosis with independence of P-gp inhibition," European Journal of Pharmacology, 732: 141-147.
Shingu, et al. (2015) "Abstract 3483: Synergistic combination therapy with molecular targeted drugs in glioma stem-like cells," Cancer Research. AACR 106th Annual Meeting, 2015, Philadelphia, PA.

(56) References Cited

OTHER PUBLICATIONS

Supplementary European Search Report dated Dec. 2, 2020 by the European Patent Office for EP Application No. 18775555.8, filed on Mar. 29, 2018 and published as EP 3600302 on Feb. 5, 2020 (Applicant—United States Government as Represented by the Department of Veterans Affairs) (7 pages).
International Search Report and Written Opinion dated Oct. 9, 2020 by the International Searching Authority for International Application No. PCT/US2020/032203, filed on May 8, 2020 and published as WO 2020/227676 on Nov. 12, 2020 (Applicant—United States Government as Represented by the Department of Veterans Affairs) (18 pages).
Im et al., Immune-Modulation by Epidermal Growth Factor Receptor Inhibitors: Implication on Anti-Tumor Immunity in Lung Cancer. PLOS One. Jul. 28, 2016, vol. 11, No. 7, pp. 1-20.
Cui et al. Low BIN3 Expression is an Independent Predictor of Unfavorable Survival in Patients With Primary Colorectal Cancer, Technol Cancer Res Treat. Dec. 26, 2017, vol. 16, No. 6, pp. 1244-1251.
Tang et al. Jak/Stat3 signaling promotes somatic cell reprogramming by epigenetic regulation. Stem Cells, Dec. 2012, vol. 30, No. 12, pp. 2645-2656.
Banks (2015) "Peptides and the blood-brain barrier" *Peptides* 72: 16-19.
Fortin (2012) "The blood-brain barrier: its influence in the treatment of brain tumors metastases" *Current Cancer Drug Targets* 12: 247-259.
Holzberg et al. (2003) "Disruption of the c-JUN-JNK complex by a cell-permeable peptide containing the c-JUN delta domain induces apoptosis and affects a distinct set of interleukin-1-induced inflammatory genes" *Journal of Biological Chemistry* 278: 40213-40223.
Lampson (2011) "Monoclonal antibodies in neuro-oncology: Getting past the blood-brain barrier" *mAbs* 3: 153-160.
Pardrige (2015) "Targeted delivery of protein and gene medicines through the blood-brain barrier" *Clinical Pharmacology & Therapeutics* 97: 347-361.
Taylor, Te et al. "Targeting EGFR for Treatment of Glioblastoma: Molecular Basis to Overcome Resistance," *Current Cancer Drug Targets*. Mar. 2021, 12, No. 3.
Yan, Y et al. "Targeting autophagy to sensitive glioma to temozolomide treatment," *Journal of Experimental and Clinical Cancer Research*. Feb. 2, 2016, 35, No. 23.
Akbay, E. A. & Kim, J. (2018) "Autochthonous murine models for the study of smoker and never-smoker associated lung cancers" Transl Lung Cancer Res 7: 464-486.
Alcazar, et al. "Augmented HR Repair Mediates Acquired Temorozolomide Resistance in Glioblastoma," *Mol Cancer Res*, 23, 928-940.
Awad, et al. (2014) "Targeting MET for Glioma Therapy" *Neurosurgical Focus*, 37, E10zhu.
Balkwill, et al. (2009), "Tumour Necrosis Factor and Cancer," *Nat. Rev. Cancer* 9, 361-371.
Balkwill, et al. (2006) " TNF-alpha in Promotion and Progression of Cancer," *Cancer Metastasis Reviews* 25, 409-416.
Barkovich, et al. (2012) "Kinetics of Inhibitor Cycling Underlie Therapeutic Disparities Between EGFR-Driven Lung and Brain Cancers," *Cancer Discov*, 2, 450-457.
Barnett, et al., "Anti-inflammatory Effects of mi-21 in the Macrophage Response to Peritonitis," *J Leukoc Biol*, 99, 361-371.
Bartel, (2009) "MicroRNAs: Target Recognition and Regulatory Functions," *Cell*, 136, 215-233.
Belda-Iniesta, et al. (2006) "Long Term Responses with Cetuximab Therapy in Glioblastoma Multiforme" Cancer Biol. & Ther; 5:8 pp. 912-914.
Ben-Neriah, et al. "Inflammation Meets Cancer, with NF-kappaB as the Matchmaker," *Nat. Immunol*, 12, 715-723.
Bivona, et al. "FAS and NF-kappaB Signaling Modulate Dependence of Lung Cancers on Mutant EGFR" *Nature*, 471, 523-526.
Brenner, et al. Regulation of Tumour Necrosis Factor Signaling: Live or Let Die, *Nat Rev Immunol*, 15, 362-374.

Burger, et al. (2001) "Small Cell Architecture—a Histological Equivalent of EGFR Amplification in Glioblastoma Multiforme" *J. Neuropathol Exp Neurol*, 60, 1099-1104.
Ciardiello, et al EGFR Antagonists in Cancer Treatment, *N. Engl. J. Med*. 358, 1160-1174.
Das, et al. (2014) Engulfment of Apoptotic Cells by Macrophages: a role of micro-RNA-21 in the Resolution of Wound Inflammation, *j. Immunol*, 192, 1120-1129.
Davis (2000) "Signal Transduction by JNK Group of MAP Kinases" *Cell*, 103, 239-252.
Deng, et al. (2003) "Thalidomide Inhibits Tumor Necrosis Factor-Alpha Production and Antigen Prosentation by Langerhans Cells," *The Journal of Investigative Dermatology*, 121, 1050-1065.
De la Iglesia, et al. (2008)"Identification of a PTEN-Regulated STAT3 Brain Tumor Suppressor Pathway," *Genes Dev*, 22, 449-462.
Ebelt, et al. (2017) "A c-Jun-N-terminal Kinase Inhibitor, JNK-IN-8, Sensitttizer Triple Negative Breast Cancer Cells to Lapatinib;" Oncotarget, Vo. 8: 62, pp. 104894-104912.
Fan, et al. (2011) "MET-independent Lung Cancer Cells Evading EGFR Kinase Inhibitors are Therapeutically Susceptible to BH3 Mimetic Agents," *Cancer Res*. 71, 4494-4505.
Faustman, (2010) "*TNF Receptor 2 Pathway: Drug Target for Autoimmune Diseases,"Nat Rev Drug Discov*, 9, 482-493.
Furnari, et al. (2015) "Heterogeneity of Epidermal Growth Factor Receptor Signalling Networks in Glioblastoma," *Nat Rev Cancer*, 15, 302-310.
Gong, K. et al. TNF-driven adaptive response mediates resistance to EGFR inhibition in lung cancer. J Clin Invest 128, 2500-2518, doi:10.1172/JCI96148 (2018).
Greenall, et al. (2015) "EGFvIII-Mediated Transactivation of Receptor Tyrosine Kinases in Glioma: Mechanism and Therapeutic Implications," *Oncogene*, 34, 5277-5287.
Greulich, et al. (2005) "Oncogenic Transformation by Inhibitor-Sensitive and -resistant EGFR Mutants." *PLos Med*, 2, e313.
Gross, et al. (2007) "Inhibition of Jun NH2-Terminal Kinases Suppresses the Growth of Experimental Head and Neck Squamous Cell Carcinoma" *Clin Cancer Res* 13, 5910-5917.
Groves, et al. (2007) "A North American Brain Tumor Consortium (NABTC 99-04) Phase II Trial of Temozolomide Plus Thalidomide for Recurrent Glioblastoma Multiforme," *J. Neurooncol*, 81, 271-277.
Gullick, (1991) "Prevalence of Aberrant Expression of the Epidermal Growth Factor Receptor in Human Cancers," *Br Med Bull*, 47, 87-98.
Guo, et al. "Signaling Networks Assembled by Oncogenic EGFR and c-Met" *Proc Natl Acad Sci U*, 105, 692-697.
Habib, et al. (2001) The Epidermal Growth Factor Receptor Engages Receptor Interacting Protein and Nuclear Factor-Kappa B (NF-Kappa B)-Inducing Kinase to Activate NF-kappa B, Identification of Novel Receptor-Tyrosine Kinase Signalosome, *J. Biol Chem*, 276,8865-8874.
Higuchi, (1994) "TNF Induces Internalization of the p60 Receptor and Shedding of the p80 Receptor," *J. Immunol*, 152, 3550-3558.
Hirsch, et al. "Epidermal Growth Factor Receptor in Non-Small-Cell Lung Carcinomas: Correlation Between Gene Copy Number and Protein Expression and Impact on Prognosis," *J. Clin Onc.*, 21, 3798-3807.
Holland, et al. (1998) "A Constitutively Active Epidermal Growth Factor Receptor Cooperates with Disruption of G1 Cell-Cycle Arrest Pathways to Induce Glioma-like Lesions in Mice," *Genes Dev*, 12, 3675-3685.
Huang, et al. (2007) "Quantitative Analysis of EGFRvIII Cellular Signaling Networks Reveals a Combinatorial Therapeutic Stragegy for Gioblastoma," *Proc Natl Acad Sci USA*, 104, 12867-12872.
Jahani-Asl, et al. (2016) "Control of Glioblastoma Tumorigenesis by Feed-Forward Cytokine Signaling," *Nat. Neurosci*, 19, 798-806.
Kiefer, et al. "Inhibition of NF-kappa B Activity by Thalidomide Through Suppression of IkappaB Kinase Activity," *J Biol Chem*, 276, 22382-22387.
Hsieh, et al. (2000) "Co-Expression of Epidermal Growth Factor Receptor and Transforming Growth Factor-α is Independent of ras Mutations in Lung Adenocarcinoma" Lung Cancer 29:151-157.

(56) References Cited

OTHER PUBLICATIONS

Lin (2015) "MicroRNA Biogenesis Pathways in Cancer," *Nat Rev Cancer*, 15, 321-333.
Lu, et al. (2005) "MicroRNA Expression Profiles Classify Human Cancers," *Nature*, 435, 834-838.
Moreira, (1993) Thalidomide Exerts its Inhibitory Action on Tumor Necrosis Factor Alpha by Enhancing MRNA Degradation, *J Exp Med*, 177, 1675-1680.
Mulloy, et al. (2007) "Epidermal Growth Factor Receptor Mutants from Human Lung Cancers Exhibit Enhanced Catalytic Activity and Increased Sensitivity to Gefitinib," *Cancer Res*, 67, 2325-2330.
Nelson, et al. (2013) "Afatinib: Emerging Next-Generation Tyrosine Kinase Inhibitor for NSCLC" OncoTargets and Therapy 2013:6 pp. 135-143.
Nelson, et al., (2006) "Protocol for the Fast Chromatin Immunoprecipitation," (ChOP) Method, *Nat Protoc*, 1, 179-185.
Ohashi, et al. (2013) "Epidermal Growth Factor Receptor Tyrosine Kinase Inhibitor-Resistant Disease." *J Clin Oncol*, 31, 1070-1080.
Ohgaki, et al. (2007) "Genetic Pathways to Primary and Secondary Gioblastoma," *Am J. Pathol*, 170, 1445-1453.
Pao, et al. (2004) "EGF Receptor Gene Mutations are Common in Lung Cancers from "Never Smokers" and are associated with Sensitivity of Tumors to Gefitinib and Erlotinib," *Proc Natl Acad Sci USA*, 1010, 13306-13311.
Pillay, et al. (2009) "The Plasticity of Oncogene Addiction : Implications for Targeted Therapies Directed to Receptor Tyrosine Kinases,"*Neoplasia*, 11, 448-458.
Pingle, et al. "In Silico Modeling Predicts Drug Sensitivity of Patient-Derived Cancer Cells," *J. Transl Med*, 12, 128.
Schuster, et al. (2015) "A Phase II, Multicenter rial of rindopepimut (CDX-110) in Newly Diagnoses Glioblastoma: the Act III Study," *Neuro Oncol*, 17, 854-861.
Sedger, et al. (2014) TNF and TNF-receptors: From Mediators of Cell Death and Inflammation to Therapeutic Giants—Past, Present, and Future, *Cytokine Growth Factor Rev*, 25, 453-472.
Seike, et al. (2009) MiR-21 is an EGFR-Regulated Anti-Apoptopic Factor in Lung Cancer in Never-Smokers, *Prc Natl Acad Sci USA*, 106, 12085-12090.
Sethi, et al. (2008) "Tnf: A Master Switch for Inflammation to Cancer." *Frontiers in Bioscience: a Journal and Virtual Library* 13, 5094-5107.
Sordella, et al. (2004) "Gefitinib-Sensitizing EGFR Mutations in Lung Cancer Activate Anti-Apoptotic Pathways." *Science*, 305, 1163-1167.
Strommel, et al. (2007) "Coactivation of Receptor Tyrosine Kinases Affects the Response of Tumor Cells to Targeted Therapies," *Science*, 318, 287-290.
Sun, et al. (1998) Epidermal Growth Factor Activation of NF-kappaB is Mediated Through IkappaBalpha Degradation and Intracellular Free Calcium, *Oncogene*, 16, 2095-2102.
Tsao, et al. "Erlotinib in Lung Cancer—Molecular and Clinical Predictors of Outcome," *N Engl J Med*, 353, 133-144.
Tsuchihashi, et al. (2016) The EGF Receptor Promotes the Malignant Potential of Glioma by Regulating Amino Acid Transport System xc(-), Cancer Res 76, 2954-2963.
Tsunoda, et al. (1999) "Estimating Transcription Factor Bindability on DNA," *Bioinformatics*, 15, 622-630.
Wajant, et al. (2003) "Tumor Necrosis Factor Signaling," *Cell Death Differ*, 10, 45-65.
Weinstein, (2002) Cancer. Addition to Oncogenes—the Achilles Heel of Cancer, *Science* 297, 63-64.
Westpal (2017) "EGFR as a Target for Glioblastoma Treatment: An Unfulfilled Promise"DNS Drugs 31:723-735.
Yanaihara, et al. (2006) Unique MicroRNA Molecular Profiles in Lung Cancer Diagnosis and Prognosis, *Cancer Cell*, 9, 189-198.
Yun, et al. (2007) Structures of Lung Cancer-Derived EGFR Mutants and Inhibitor Complexes: mechanism of Activation and Insights into Differential Inhibitor Sensitivity, Cancer Cell, 11, 217-227.
Zhang, et al. (2012) "MicroRNA 21 Modulates the Levels of Reactive Oxygen Species by Targeting SOD3 and TNFalpha," *Cancer Res*, 72, 4707-4713.
Zhu, et al. (2018) Glutathione reductase mediates drug resistance in glioblastoma cells by regulating redox homeostasis, *J Neurochem* 144, 93-104.
Zhu, et al. (2014) "Multiple Lesions in Receptor Tyrosine Kinase Pathway Determine Glioblastoma Response to Pan-ERBB Inhibitor PF-00299804 and P13K/mTOR Dual Inhibitor PF-05212384" *Cancer Biol Ther*, 15, 815-822.

* cited by examiner

COMPOSITIONS AND METHODS FOR TREATING CANCER

CROSS REFERENCE TO RELATED APPLICATIONS

This application is a U.S. National Phase Application of International Application No. PCT/US2017/057477, filed Oct. 19, 2017, which claims the benefit of U.S. Provisional Patent Application No. 62/410,323, filed on Oct. 19, 2016, and U.S. Provisional Patent Application No. 62/410,799, filed Oct. 20, 2016, which are both incorporated herein by reference in their entirety.

This invention was made with Government support under NIH grants R01 NS062080; under NCI Lung Cancer SPORE (P50CA70907), U01CA176284, and CPRIT (RP110708); and NIH grant 1R01CA194578 and, in part by a National Cancer Institute (NCI) grant K24CA201543-01. The Government has certain rights in the invention.

FIELD OF THE INVENTION

The present invention is related to pharmaceutical compositions and methods for treating cancer.

BACKGROUND OF THE INVENTION

Oncogene addiction has been described primarily in cancers that express oncogenes rendered constitutively active by mutation. Constitutive activation results in a continuous and unattenuated signaling that may result in a widespread activation of intracellular pathways and reliance of the cell on such pathways for survival. A subset of NSCLCs harbor EGFR activating mutations that render the receptor constitutively active and oncogene addicted. Lung cancers with activating EGFR mutations exhibit a dramatic initial clinical response to treatment with EGFR tyrosine kinase inhibitors (TKIs), but this is followed by the inevitable development of secondary resistance spurring intensive investigation into resistance mechanisms. Major TKI resistance mechanisms identified in EGFR mutant lung cancer include the emergence of other EGFR mutations such as the T790M mutation that prevent TKI enzyme interaction and activation of other receptor tyrosine kinases such as Met or Axl providing a signaling bypass to EGFR TKI mediated inhibition. Rapid feedback loops with activation of STAT3 have also been invoked to mediated EGFR TKI resistance in lung cancer cells with EGFR activating. However, the STAT3 resistance loop was not found in lung cancer cells with EGFR wild type (EGFRwt) and primary resistance to EGFR TKIs. Multiple additional mechanisms and distinct evolutionary pathways have been invoked to explain secondary resistance to EGFR inhibition in lung cancer. In addition, a subset of patients with EGFR activating mutations do not respond to EGFR inhibition, exhibiting a primary or intrinsic resistance, and various mechanisms have been proposed to account for such resistance.

The most common type of EGFR expressed in lung cancer is EGFRwt (EGFR wild type). EGFRwt expressing tumor cells are not oncogene addicted and are usually resistant to EGFR inhibition. The differential responsiveness of cells with EGFR activating mutations may result from altered downstream signal transduction. EGFR activating mutations result in constitutive signaling and have been shown to be transforming. Compared to EGFRwt, EGFR activating mutations lead to activation of extensive networks of signal transduction that, in turn, lead to dependence of tumor cells on continuous EGFR signaling for survival. This is likely the reason that EGFR inhibition is effective in NSCLC patients with EGFR activating mutations despite the well documented generation of early adaptive survival responses such as STAT3 in EGFR mutant cells. Increased affinity of mutant EGFR for tyrosine kinase inhibitors has also been reported.

TNF (tumor necrosis factor) is a key mediator of the inflammatory response. Depending on the cellular context, it may play a role in cell death or in cell survival and inflammation induced cancer. TNF is produced by a variety of tissues and is inducibly expressed in response to inflammatory stimuli such as LPS. TNF binds to its cognate receptors TNFR1 or TNFR2 and activates a number of inflammatory signaling networks. Interestingly, malignant cells are known to produce TNF, as are cells in the microenvironment of tumors and there is experimental evidence from a variety of models that TNF can promote the growth of tumors.

MicroRNAs (miRNAs) are small noncoding RNAs that target coding RNAs and regulate the translation and degradation of mRNAs and may play an important role in cancer. Expression levels of miRNAs are altered in various types of cancer, including lung cancer. EGFR activity can regulate miRNA levels in lung cancer. The expression of five microRNAs (hsa-mir-155, hsa-mir-17-3p, hsa-let-7a-2, hsa-mir-145, and hsa-mir-21) were altered in lung cancer from smokers compared to uninvolved lung tissue and there is evidence from examination of archival tissue and cell culture studies that EGFR activity upregulates the expression of mir-21 while inhibition of EGFR activity downregulates miR-21. Both EGFRwt and mutant activity may regulate miR-21 in lung cancer, although EGFR activating mutants appear to have a stronger effect.

Accordingly, improved methods and compositions for treating cancer are needed.

SUMMARY OF THE INVENTION

Provided herein are methods for treating cancer, in a patient in need thereof, said method comprising administering to said patient an effective amount of an EGFR inhibitor and a TNF inhibitor.

The EGFR inhibitor can be selected from the group consisting of: erlotinib, afatinib, Cetuximab, panitumumab, Erlotinib HCl, Gefitinib, Lapatinib, Neratinib, Lifirafenib, HER2-nhibitor-1, Nazartinib, Naquotinib, Canertinib, Lapatinib, AG-490, CP-724714, Dacomitinib, WZ4002, Sapitinib, CUDC-101, AG-1478, PD153035 HCL, pelitinib, AC480, AEE788, AP26113-analog, OSI-420, WZ3146, WZ8040, AST-1306, Rociletinib, Genisten, Varlitinib, Icotinib, TAK-285, WHI-P154, Daphnetin, PD168393, Tyrphostin9, CNX-2006, AG-18, AZ5104, Osimertinib, CL-387785, Olmutinib, AZD3759, Poziotinib, vandetanib, necitumumab, The TNF inhibitor is selected from the group consisting of: thalidomide, prednisone, etanercept, adalimumab, certolizumab pegol, golimumab, infliximab, efalizumab, ustekinumab, beclomethasone, betamethasone, cortisone, dexamethasone, hydrocortisone, methylprednisolone, and prednisolone. In particular embodiments, the EGFR inhibitor and TNF inhibitor can combinations selected from the group consisting of:

erlotinib and thalidomide; erlotinib and prednisone; afatinib and thalidomide; afatinib and prednisone; erlotinib and etanercept; and afatinib and etanercept.

In the particular cancers treated herein, the EGFR is either EGFR wild type or contains at least one EGFR activating mutation. In some embodiments, the particular cancer being treated can be selected from the group consisting of: lung cancer, cervical cancer, ovarian cancer, cancer of CNS, skin cancer, prostate cancer, sarcoma, breast cancer, leukemia, colorectal cancer, colon cancer, head cancer, neck cancer, endometrial and kidney cancer. In a particular embodiment, the lung cancer is non-small cell lung cancer. In other embodiments, the cancer is a human epithelial carcinoma, which can be selected from the group consisting of: basal cell carcinoma, squamous cell carcinoma, renal cell carcinoma (RCC), ductal carcinoma in situ (DCIS), and invasive ductal carcinoma.

In a particular embodiment, the particular cancer being treated is resistant to EGFR inhibition; or has previously been determined to have been resistant to EGFR inhibition. The cancer resistant to EGFR inhibition can be non-small cell lung cancer.

Also provided is a method of treating a tumor resistant to EGFR inhibition, in a patient in need thereof, comprising administering an agent that inhibits TNF activity in combination with an agent that inhibits EGFR activity.

Also provided herein are pharmaceutical compositions comprising a therapeutically effective amount of an EGFR inhibitor and a TNF inhibitor. The EGFR inhibitor can be selected from the group consisting of: erlotinib, afatinib, Cetuximab, panitumumab, Erlotinib HCl, Gefitinib, Lapatinib, Neratinib, Lifirafenib, HER2-nhibitor-1, Nazartinib, Naquotinib, Canertinib, Lapatinib, AG-490, CP-724714, Dacomitinib, WZ4002, Sapitinib, CUDC-101, AG-1478, PD153035 HCL, pelitinib, AC480, AEE788, AP26113-analog, OSI-420, WZ3146, WZ8040, AST-1306, Rociletinib, Genisten, Varlitinib, Icotinib, TAK-285, WHI-P154, Daphnetin, PD168393, Tyrphostin9, CNX-2006, AG-18, AZ5104, Osimertinib, CL-387785, Olmutinib, AZD3759, Poziotinib, vandetanib, necitumumab, The TNF inhibitor is selected from the group consisting of: thalidomide, prednisone, etanercept, adalimumab, certolizumab pegol, golimumab, infliximab, efalizumab, ustekinumab, beclomethasone, betamethasone, cortisone, dexamethasone, hydrocortisone, methylprednisolone, and prednisolone, In particular embodiments, the EGFR inhibitor and TNF inhibitor are combinations selected from the group consisting of:

erlotinib and thalidomide; erlotinib and prednisone; afatinib and thalidomide; afatinib and prednisone; erlotinib and etanercept; and afatinib and etanercept.

Although aberrant EGFR signaling is widespread in human cancer, EGFR inhibition is primarily effective only in a subset of NSCLC (non-small cell lung cancer) that harbor EGFR activating mutations. A majority of NSCLCs express EGFR wild type (EGFRwt) and do not respond to EGFR inhibition. Tumor necrosis factor (TNF) is a major mediator of inflammation induced cancer. In accordance with the present invention, it has been demonstrated that a rapid increase in TNF level is a universal adaptive response to inhibition of EGFR signaling in lung cancer cells regardless of whether EGFR is mutant or wild type. EGFR inhibition upregulates TNF by a dual mechanism. First, EGFR signaling actively suppresses TNF mRNA levels by inducing expression of microRNA-21 resulting in decreased TNF mRNA stability. Conversely, inhibition of EGFR activity results in loss of miR-21 and increase in TNF mRNA stability. As a second mechanism, activation of TNF-induced NF-κB activation leads to increased TNF transcription in a feedforward loop. Increased TNF mediates intrinsic resistance to EGFR inhibition, while exogenous TNF can protect oncogene addicted lung cancer cells from a loss of EGFR signaling. Biological or chemical inhibition of TNF signaling renders EGFRwt expressing NSCLC cell lines and an EGFRwt PDX model highly sensitive to EGFR inhibition. In oncogene addicted cells, blocking TNF enhances the effectiveness of EGFR inhibition. In accordance with the present invention, there are provided methods for the combined inhibition of EGFR and TNF as a treatment approach useful for treating human cancers, such as lung cancer (e.g., NSCLC, and the like) patients.

Figure 1A:
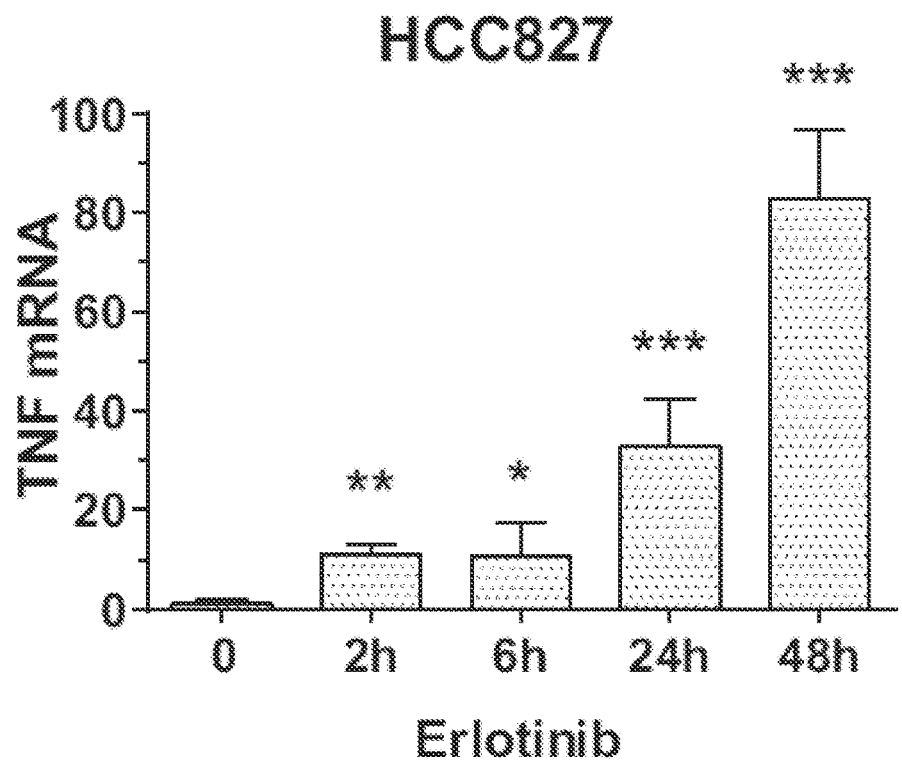
FIG. 1 Upregulation of TNF signaling by EGFR inhibition
Figure 1B:
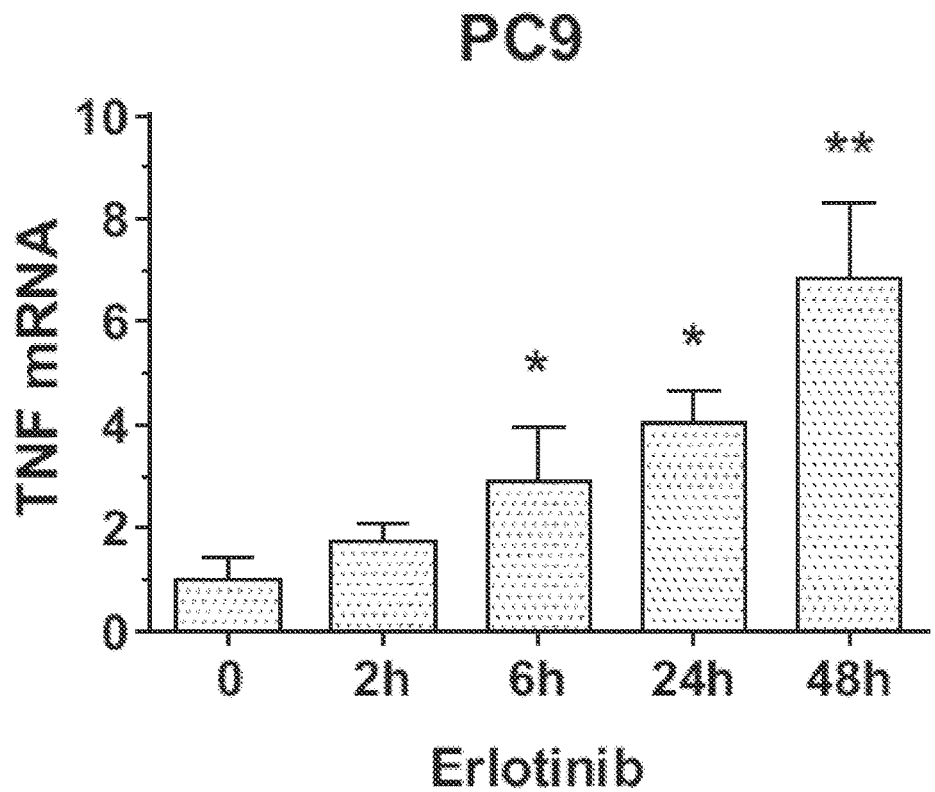
Figure 1C:
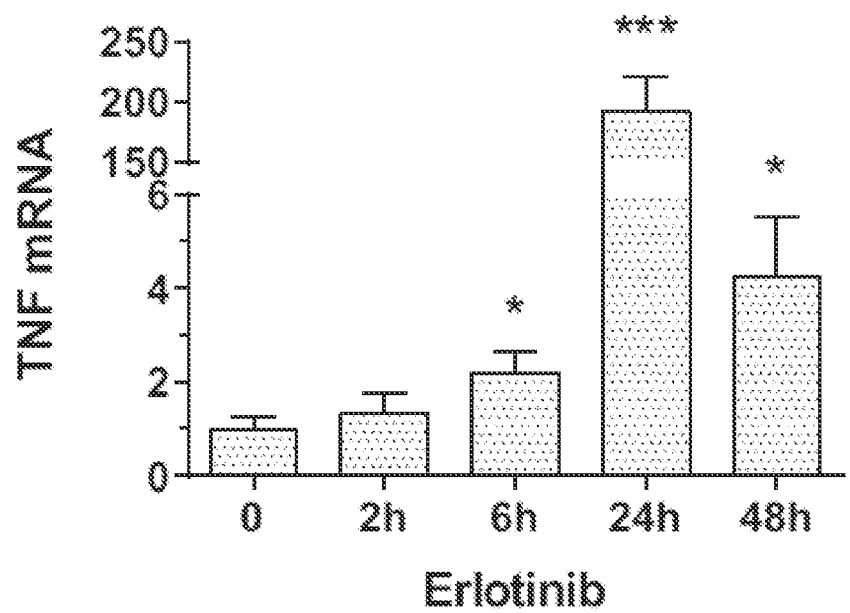
Figure 1D:
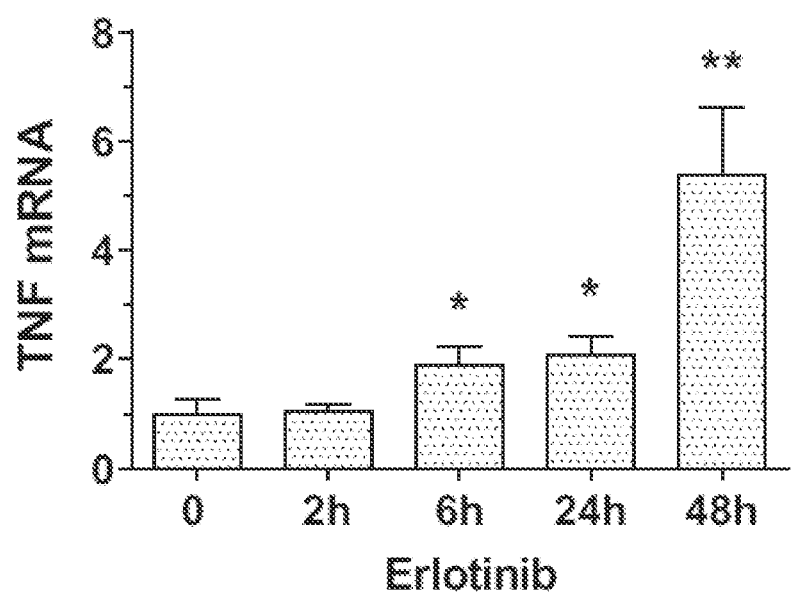
Figure 1E:
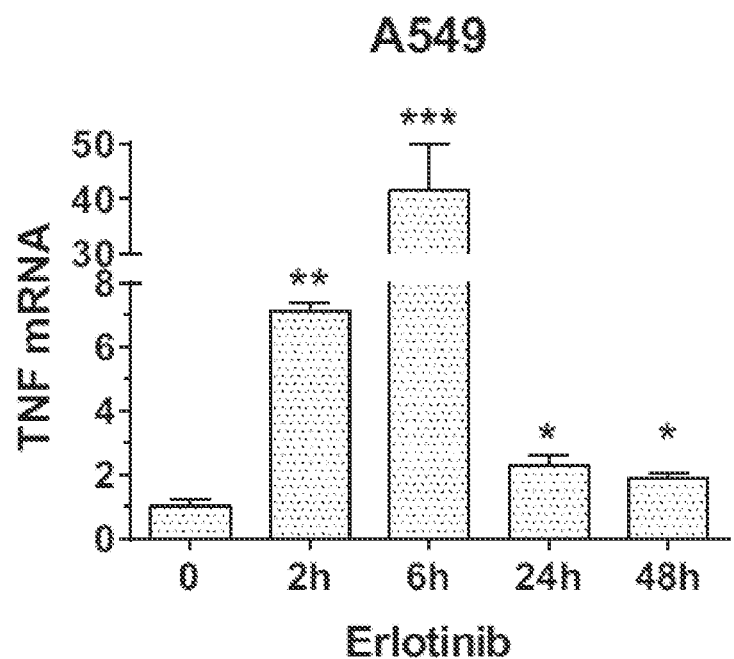
Figure 1F:
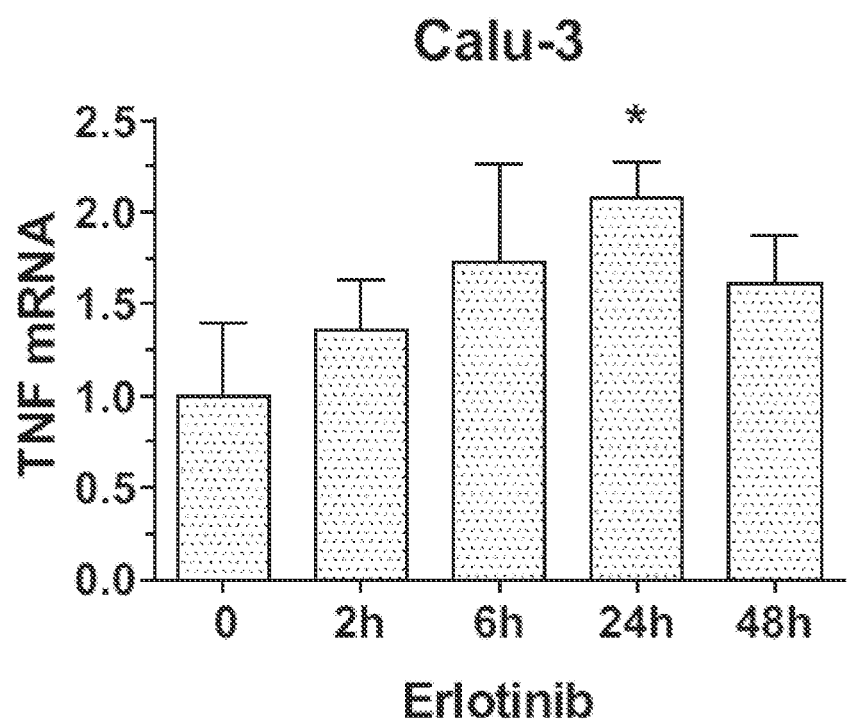

A-F NSCLC cell lines were cultured in RPMI-1640 in 5% FBS and were treated with Erlotinib for the times indicated followed by RNA extraction and quantitative real time PCR for TNF. G-H Cells were treated with Erlotinib and the TNF level was measured in the supernatant by ELISA. In kJ, athymic mice were injected subcutaneously with HCC827 cells. After formation of tumors, Erlotinib at the dose of 50 mg/kg body weight was administered for the times indicated followed by removal of tumor and quantitation of TNF mRNA by qRT-PCR or protein by ELISA. K-L. Athymic mice were injected subcutaneously with A549 cells. After formation of tumors, Erlotinib of 100 mg/kg body weight was administered for the times indicated followed by removal of tumor and quantitation of TNF mRNA by qRT-PCR or protein by ELISA. Since the TNF level remained high at 7 days in these cells, an additional time point was added at 14 days. M-N. NOD SCID mice were implanted subcutaneously with HCC4087 PDX tumor tissues. After formation of tumors, Erlotinib of 100 mg/kg body weight was given to the mice for 0, 1, 2, 4, 7, and 14 days, then mice were sacrificed and tumors were removed for quantitation of TNF mRNA by qRT-PCR or protein by ELISA.

FIG. 2 EGFR activity regulates TNF mRNA stability mediated by upregulation of miR-21

A-D NSCLC cell lines were exposed to EGF (50 ng/ml) for the indicated time points followed by qRT-PCR for TNF mRNA. E. HCC827 Cells were treated with Actinomycin D (5 µg/ml) and erlotinib (100 nM) for the indicated time points followed by RNA extraction and qRT-PCR for TNF mRNA. F. A similar experiment was done in A549 cells using an erlotinib concentration of 1 µM. G-H miR-21 expression was examined in HCC827 and A549 cells following exposure to EGF for the indicated time points followed by qRT-PCR using a TaqMan Human MicroRNA Assay kit. I-J HCC827 or A549 cells were exposed to Erlotinib (100 nM or 1 uM) for the indicated time points followed by qRT-PCR for miR-21 using a TaqMan Human MicroRNA Assay kit. K-L HCC827 or A549 cells were transfected with a control antisense oligonucleotide (C-AS) or a miR-21 antisense oligonucleotide (miR-21 AS) for 48 h followed by exposure of cells to EGF for 1 h and qRT-PCR for TNF. In M-N the downregulation of miR-21 by the miR-21 antisense oligonucleotide was confirmed. In all experiments involving the use of EGF, cells were serum starved overnight.

FIG. 3 EGFR inhibition induces a TNF-dependent activation of NF-κB

A. HCC827, H3255, A549 and H441 cells were exposed to erlotinib (100 nM for EGFR mutant and 1 uM for EGFRwt cells) for 24 h followed by a dual luciferase reporter assay. Renilla luciferase was used as an internal control. B. Cells were treated with erlotinib for various time points followed by preparation of cell lysates and Western blot with an IkBα antibody. C. siRNA knockdown of TNFR1 was performed in HCC827 cells followed by transfection of cells with an NF-κB luciferase reporter and exposure of cells to erlotinib following by a reporter assay. Silencing of TNFR1 was confirmed with a Western blot. D. A similar experiment was undertaken in A549 cells and TNFR1 silencing was confirmed with a Western blot. E. A TNF blocking drug Etanercept (Enbrel) was used at a concentration of 100 µg/ml along with erlotinib for 48 h followed by a reporter assay in HCC827 cells. F. A similar experiment was conducted in A549 cells. G-H. Reporter assay for NF-κB in cells treated with Erlotinib in the presence or absence of Thalidomide (5 µg/ml). I-J HCC827 and A549 cells were treated with exogenous TNF (10 ng/ml) with or without thalidomide followed by a reporter assay for NF-κB transcriptional activity.

FIG. 4 An NF-κB-TNF feedforward loop regulates the expression of TNF in response to EGFR inhibition A. Inhibition of NF-κB using various chemical inhibitors (BMS-345541 conc 10 µM, QNZ: 6 amino-4-(4-phenoxyphenylethylamino) quinazoline (1 µM), or Sodium Salicylate, 5 mM) inhibited erlotinib (100 nM, 24 h) induced upregulation of TNF in HCC827 cells, as determined by real time qRT-PCR for TNF mRNA. Cells were pretreated with NF-κB inhibitors for 1 h and then erlotinib was added for an additional 24 h. B. Expression of a dominant negative IkBα super repressor mutant also blocks erlotinib-induced upregulation of TNF. C. Mithramycin (1 uM), an inhibitor of Sp1, failed to inhibit erlotinib-induced TNF upregulation. Cells were pretreated with Mithramycin for 1 h followed by erlotinib addition for 24 h. D. Inhibition of NF-κB by various chemical inhibitors abolishes erlotinib (1 µM) induced upregulation of TNF mRNA in A549 cells, as determined by qRT-PCR for TNF mRNA. E. Expression of a dominant negative IkBα super repressor mutant also blocks erlotinib-induced upregulation of TNF in A549 cells. F. Expression of the dominant negative IkBα super repressor mutant was detected by Western blot in HCC827 and A549 cells. The mutant protein migrates slower on electrophoretic gels. G-I. siRNA knockdown of TNFR1 in HCC827, H441 and A549 cells inhibits erlotinib induced upregulation of TNF mRNA as detected by real time qRT-PCR. Silencing of TNFR1 was confirmed with a Western blot. J,K. Inhibition of TNFR signaling using Enbrel (100 ug/ml) results in a block of erlotinib induced TNF upregulation in HCC827 and A549 cells. L. ChIP was carried out to assess the recruitment of the NF-κB p65 subunit onto the TNF promoter. The extent of recruitment was assessed by qPCR using primers specific to NF-κB binding region 1 on TNF promoter. There are increased p65 antibody enrichment (percentage of input, compared to rabbit IgG) on TNF promoter in both HCC827 and A549 cells, which can be further enhanced after 1 µM erlotinib treatment for 24 hours.

FIG. 5 Inhibition of TNF induces or sensitivity of EGFRwt expressing NSCLC cells to EGFR inhibition A-B. AlamarBlue cell viability assay in H441 or A549 cells. TNFR1 was silenced using siRNA and cells were exposed to erlotinib for 72 h in RPMI-1640 with 5% FBS. C. Silencing of TNFR1 was confirmed by Western blot. D-E. Thalidomide sensitizes H441 and A549 cells to EGFR inhibition with erlotinib. Thalidomide (5 ug/ml) and erlotinib were added to H441 and A549 cells concurrently and AlamarBlue assay was done after 72 h. F-G. A similar experiment was done using Enbrel (100 µg/ml) and erlotinib in H441 and A549 cells. H. H441 cells were treated with afatinib in the presence or absence of enbrel. AlamarBlue assay was conducted after 72 hours. I. H441 cells were treated with afatinib and thalidomide for 72 hours, followed by AlamarBlue assay. J-K. Similar experiments were done as described in H and I in A549 cells. The concentration of erlotinib and afatinib was 1 µM in all experiments shown in this figure.

FIG. 6 Inhibition of TNF enhances sensitivity of NSCLC cells with EGFR activating mutations to EGFR inhibition A-B. AlamarBlue assay in HCC827 or H3255 cells. TNFR1 was silenced using siRNA and cells were exposed to Erlotinib for 72 h in RPMI-1640 with 5% FBS. C. Silencing of TNFR1 was confirmed by Western blot. D-E. Thalidomide sensitizes HCC827 and H3255 cells to EGFR inhibition with erlotinib. Thalidomide (5 ug/ml) and erlotinib were added concurrently and AlamarBlue assay was done after 72 h. F-G. Similar experiments were done using Enbrel (100 µg/ml) and erlotinib in HCC827 and H3255 cells. H, I. HCC827 and H3255 Cells were treated with afatinib with or without thalidomide for 72 hours, following exposure AlamarBlue assay was performed to test cell viability. J, K. Similar experiments were performed in HCC827 and H3255 cells with afatinib and enbrel. The concentration of erlotinib or afatinib was 10 nM in A-K. L-M. Exogenous TNF protects H3255 and HCC827 from all erlotinib induced cell death. Cells were exposed to erlotinib (100 nM) with or without TNF (1 ng/ml). Cell viability was determined 72 hours later using AlamarBlue assay.

FIG. 7 Inhibition of NF-κB sensitizes EGFRwt and EGFR mutant NSCLC to EGFR inhibition A-B. A549 cells were exposed to erlotinib with our without NF-κB inhibitor BMS-345541 or QNZ: 6 amino-4-(4-phenoxyphenylethylamino) quinazoline (100 nM) for 72 h followed by an AlamarBlue assay. C-H Same experiments as described in A,B were performed in multiple NSCLC cells. Inhibition of NF-κB using inhibitors results in enhanced sensitivity to erlotinib in H3255 and HCC827 cells. I-J HCC827 and H3255 cells were transiently transfected with NF-κB p65 plasmid, 48 hours later cells were treated with erlotinib for 72 hours, followed by AlamarBlue assay. Increased expression of the p65 subunit of NF-κB protects EGFR inhibition sensitive HCC827 and H3255 cells from erlotinib induced cell death in an AlamarBlue assay. K. Overexpression of p65 in cells was confirmed by Western blot. The erlotinib concentration used was 10 nM for EGFR mutant cell lines and 1 µM for EGFR wild type cell lines in FIG. A-H. The erlotinib concentration used was 100 nM in I-J.

FIG. 8 Combined inhibition of EGFR and TNF in a mouse model

A. Treatment of subcutaneous tumor models with a combination of erlotinib and thalidomide. Athymic mice were subcutaneously injected with 1×106 A549 cells. When palpable tumor formed, mice were randomly divided into four groups (control group, erlotinib group, thalidomide group and erlotinib plus thalidomide group, n=8). The mice were treated with Erlotinib 100 mg/kg by oral gavage and/or intraperitoneal (i.p.) injection of 150 mg/kg thalidomide for 10 consecutive days. Tumors were measured every 2 days and tumor volume was calculated using the following formula: (Length×Width×Width)/2. Thalidomide or erlotinib alone did not have a significant effect on tumor growth, whereas the combination of erlotinib and thalidomide was found to reduce tumor growth significantly (p=0.00078). B. A similar experiment was a PDX model derived from a patient with NSCLC expressing EGFR without activating mutations. HCC4087 PDX tumor tissues were implanted subcutaneously in NOD-SCID mice. When palpable tumor formed mice were divided into 4 groups (n=12) and treated with erlotinib at the dose of 100 mg/kg body weight by oral gavage or thalidomide of 150 mg/kg body weight by intraperitoneal injection for 28 days. The combination of erlotinib+thalidomide inhibited the growth of tumors significantly in this PDX model (p=0.00068). C. This experiment was conducted with HCC827 cells (n=8). Erlotinib (10 mg/kg/day) was provided by oral gavage and thalidomide was provided by i.p. injection. There is a significant decrease in tumor size with combined treatment with erlotinib and thalidomide (p=0.0067). D. Stable silencing of TNF in A549 cells was determined by ELISA with isolation of two clones with low basal and LPS induced TNF (#16 and #23). E. A549 cells with stably silenced TNF (clone 16) or with control shRNA were implanted in flanks of athymic mice. When palpable tumors formed mice were grouped into control shRNA, TNF shRNA, control shRNA+afatinib and TNF shRNA+afatinib (n=6). Afatinib (25 mg/kg) or control vehicle were provided by oral gavage. Afatinib had a greater effect in suppressing tumor growth in cells with stably silenced TNF (p=0.00020). F. Athymic mice were injected subcutaneously with 1×106 A549 cells. When palpable tumor formed, mice were randomly divided into four groups (control group, afatinib group, thalidomide group afatinib plus enbrel group, n=6). The mice were treated by oral gavage of 25 mg/kg afatinib or/and with intraperitoneal (i.p.) injection of 3 mg/kg Enbrel. The combination of afatinib and enbrel was found to further reduce tumor growth significantly (p=0.0093). Each data point represents the mean tumor volume±S.E.M. Statistical significance was defined as p<0.05 (ratio paired Student's t-test by GraphPad Prism 7.0) *<0.05,<0.01,*<0.001.

Figure 9A:
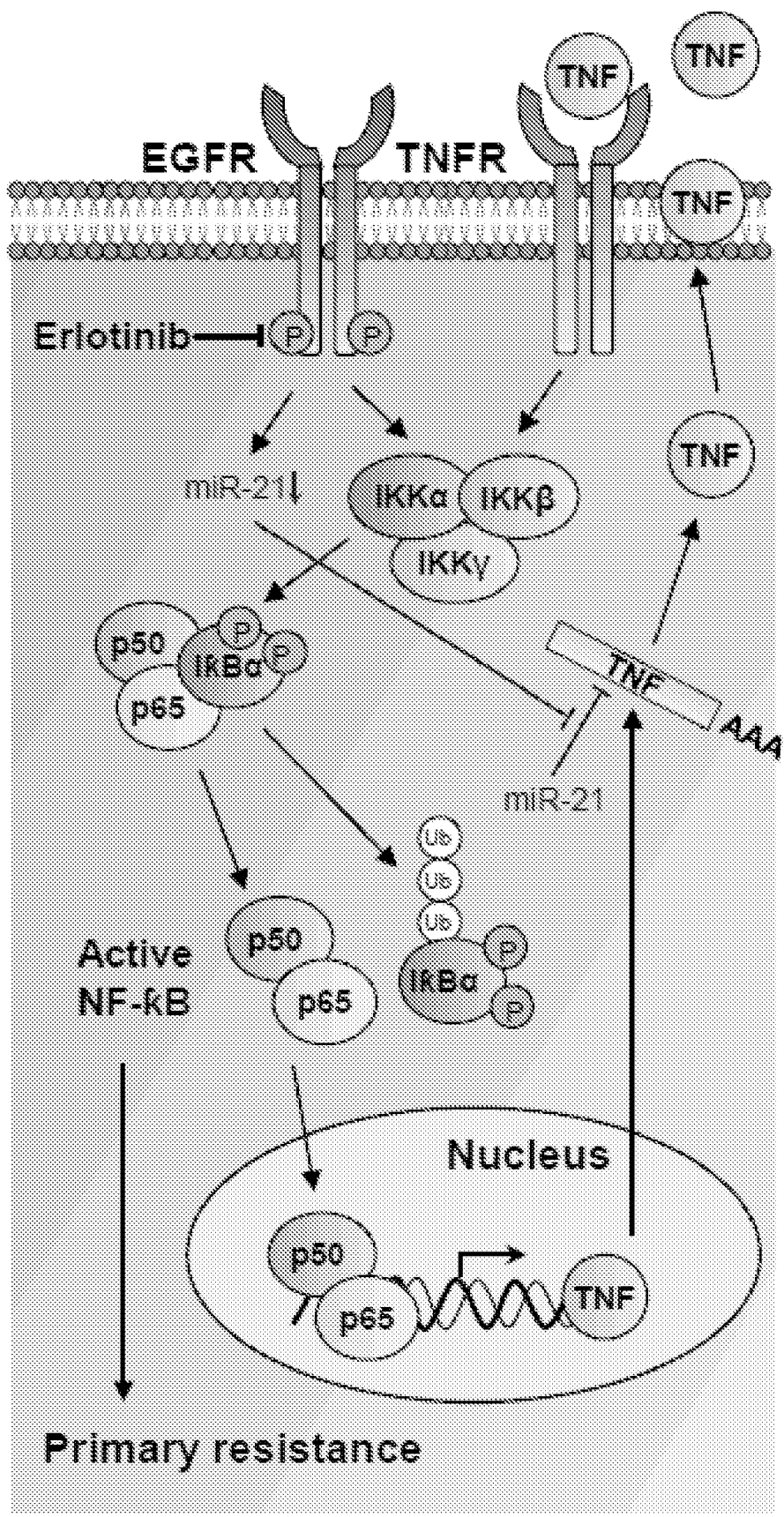
Figure 9B:
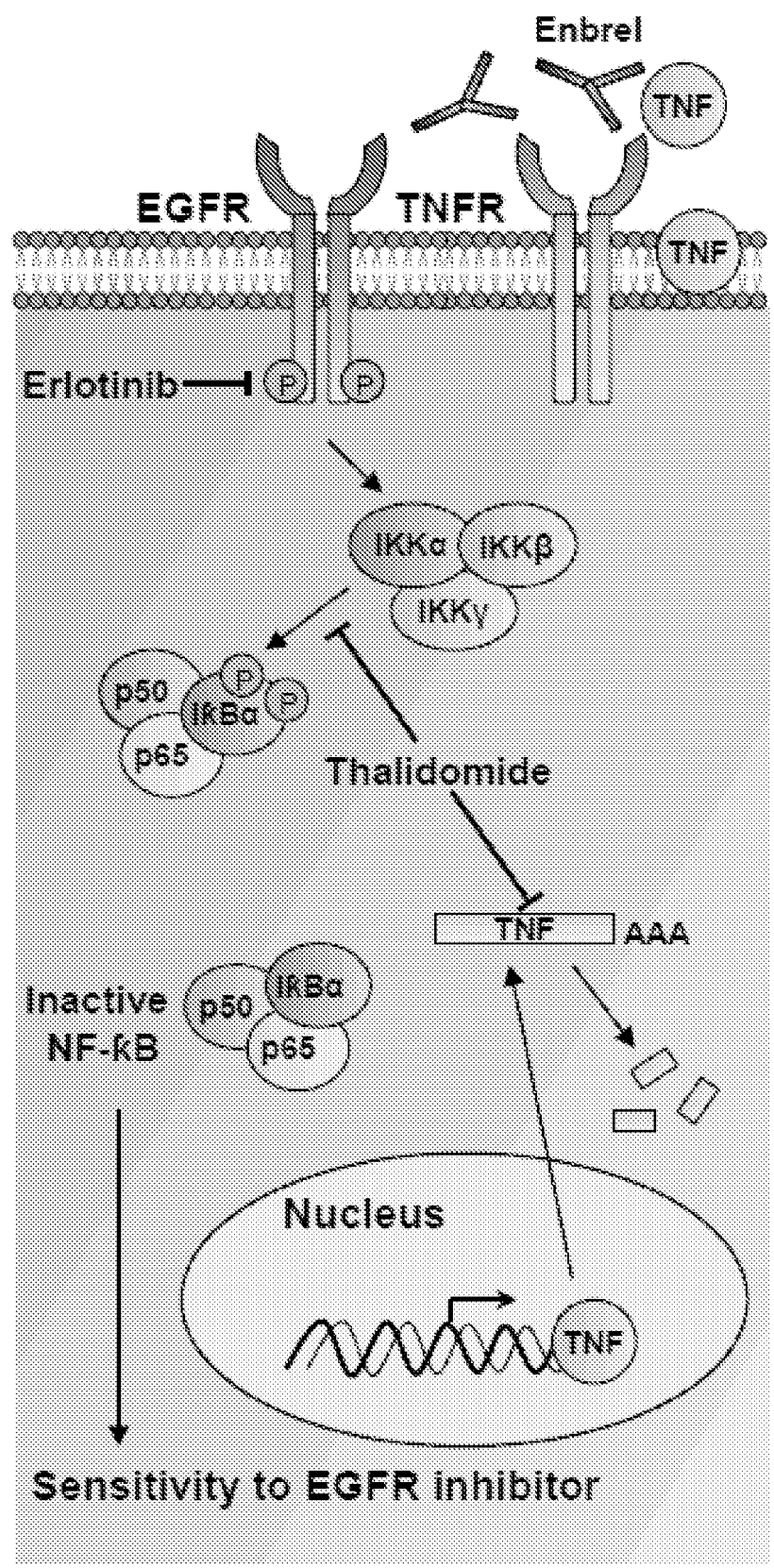
Figure 9C:
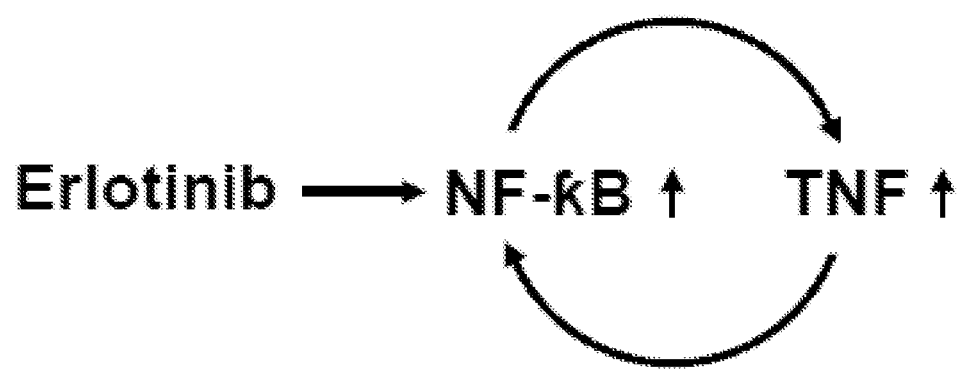
Figure 10A:
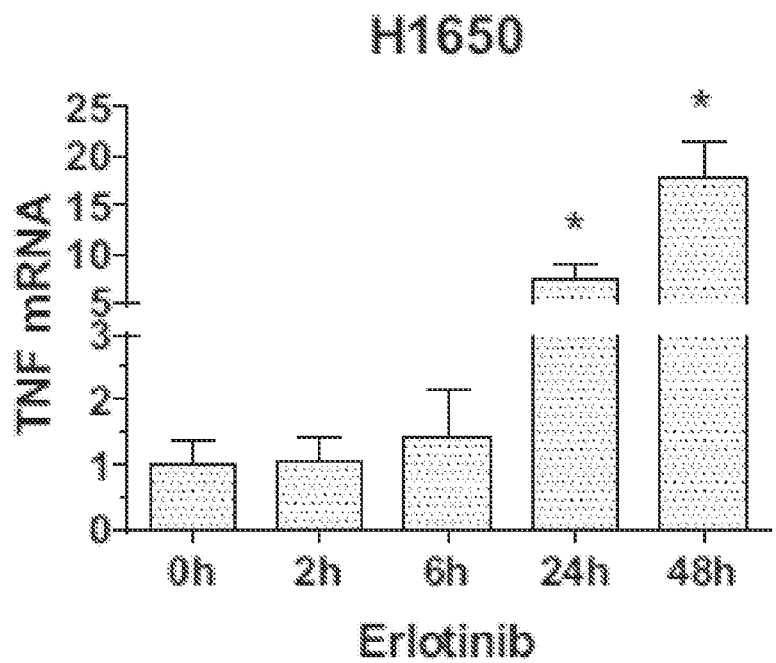
Figure 10B:
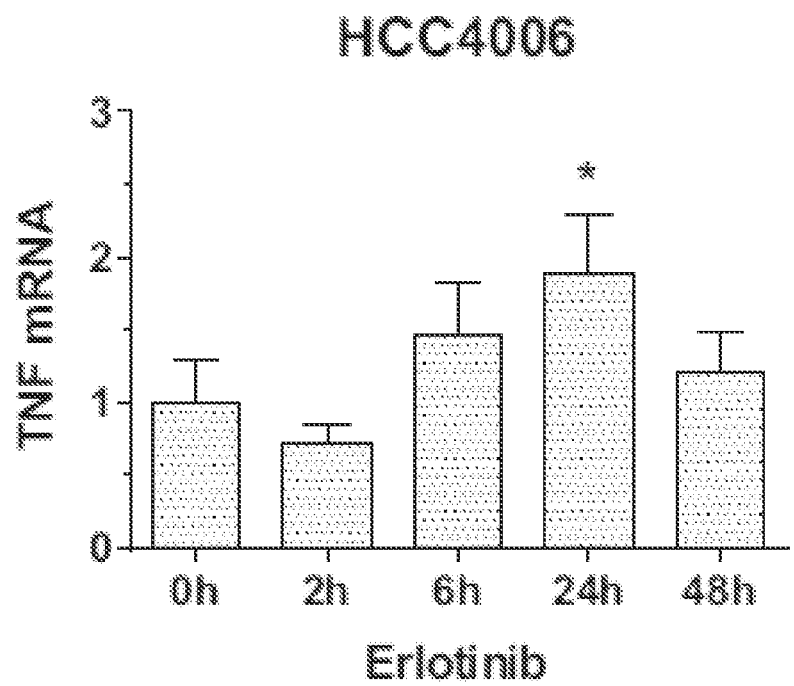
Figure 10C:
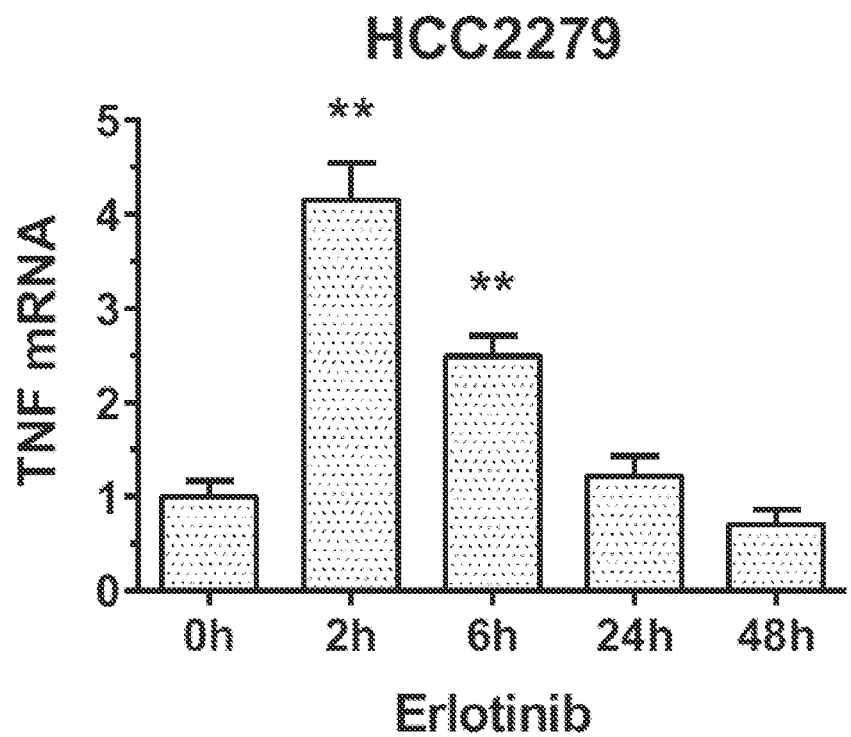
Figure 10D:
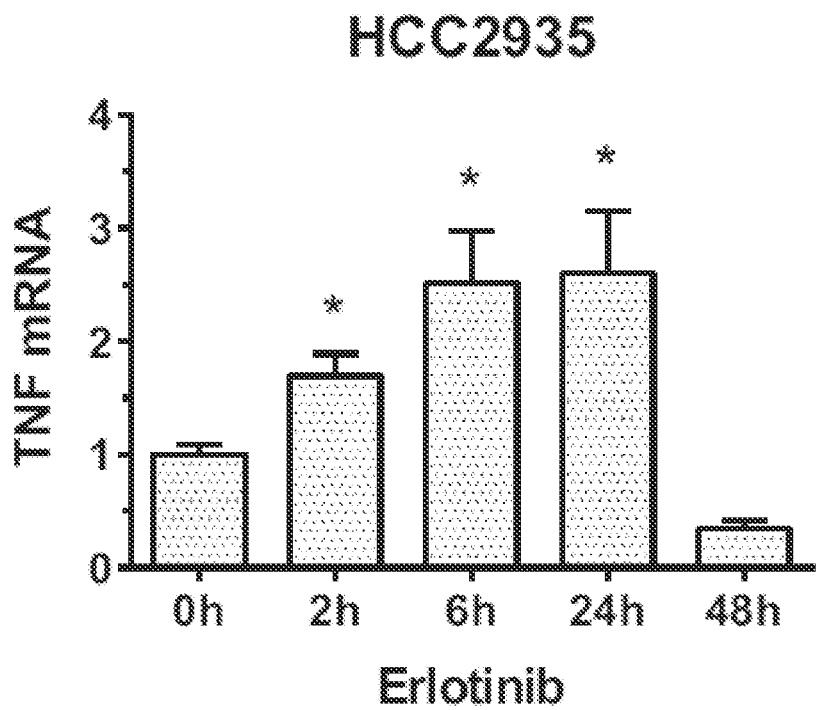
Figure 10E:
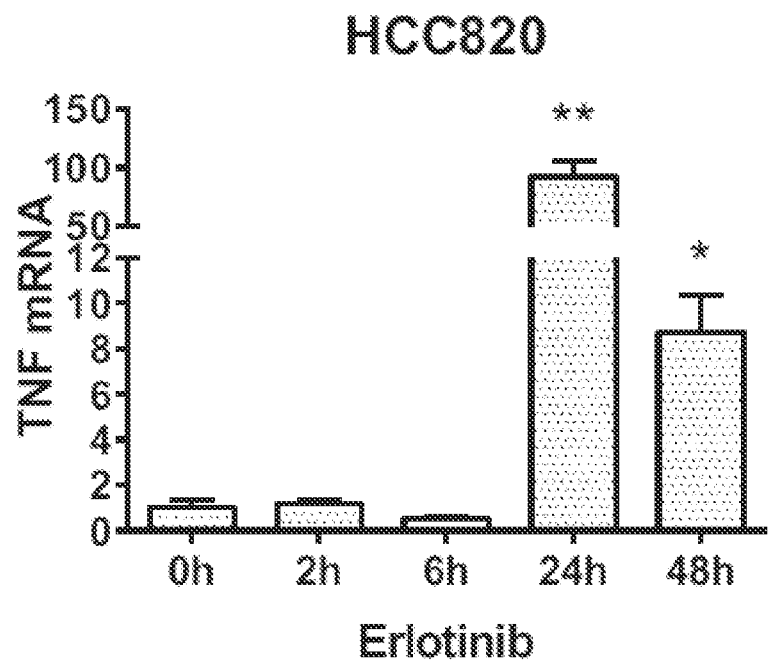
Figure 10F:
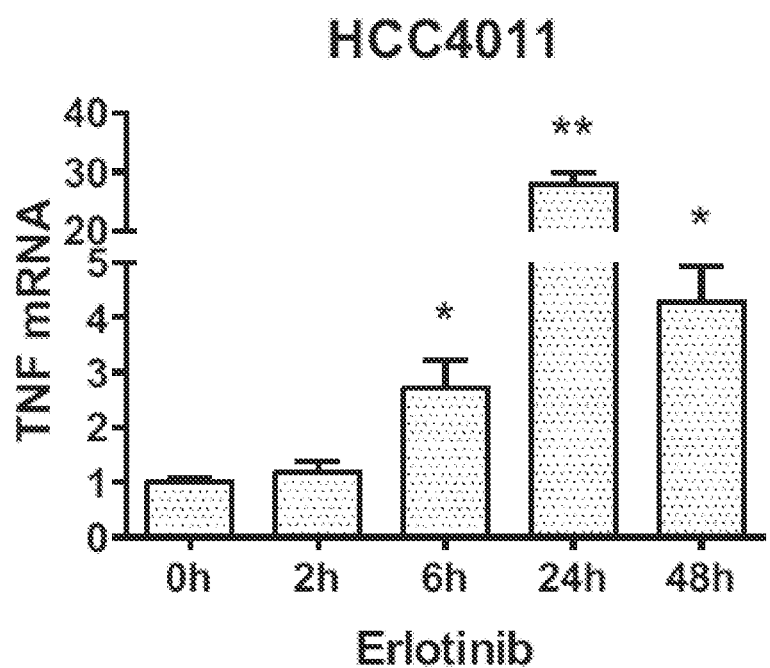
Figure 10G:
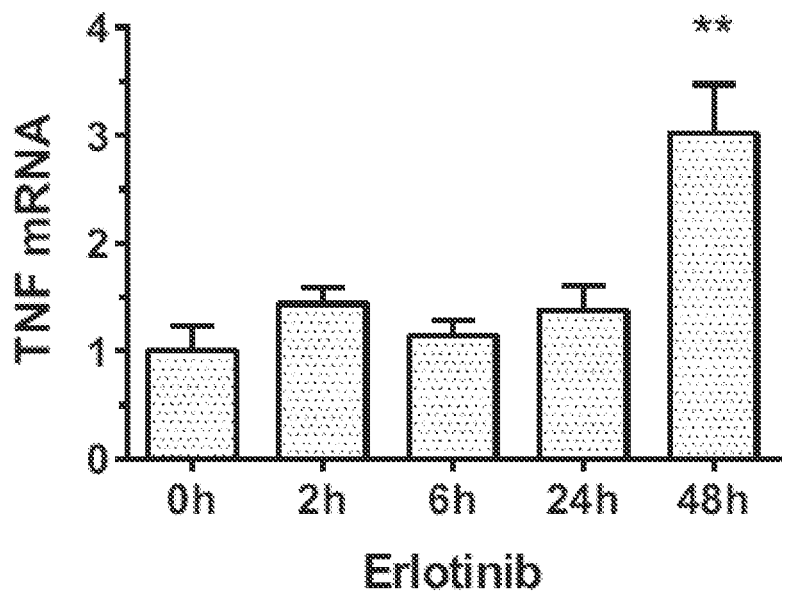
Figure 10H:
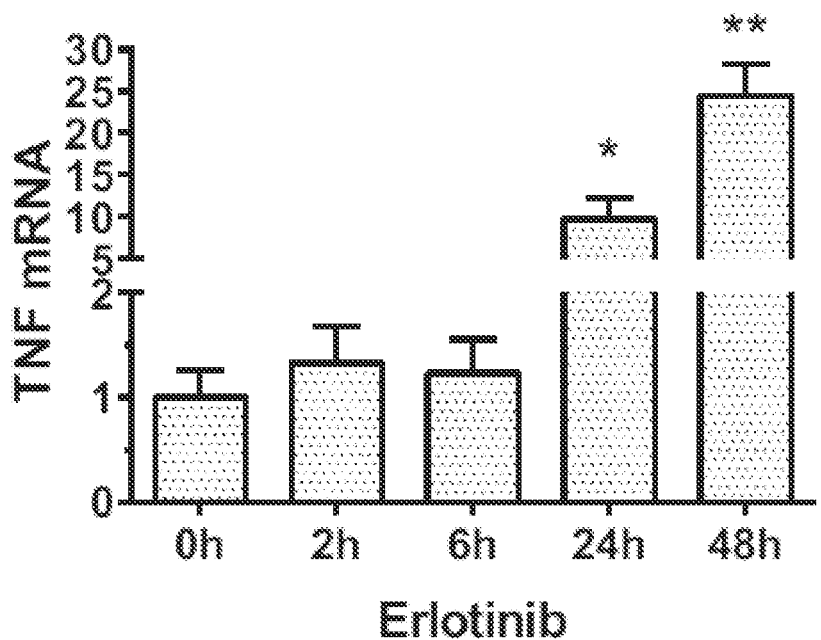
Figure 10I:
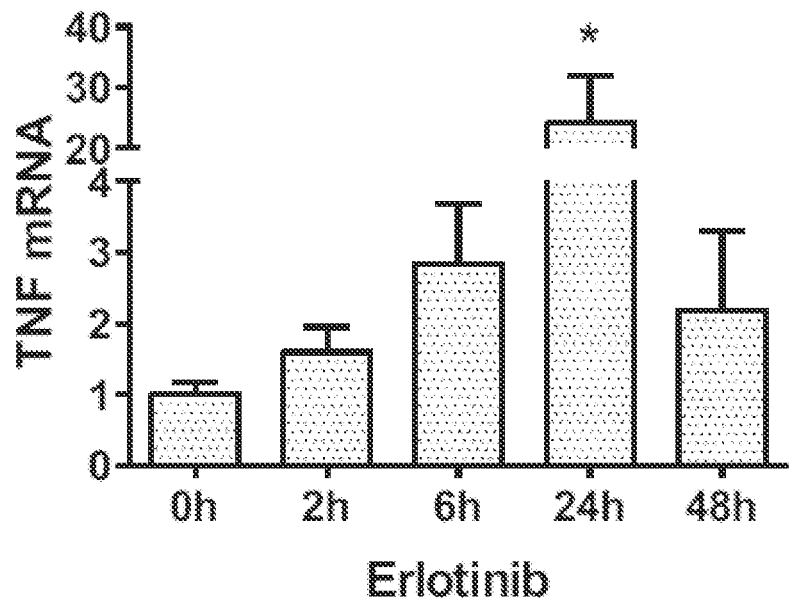
Figure 10J:
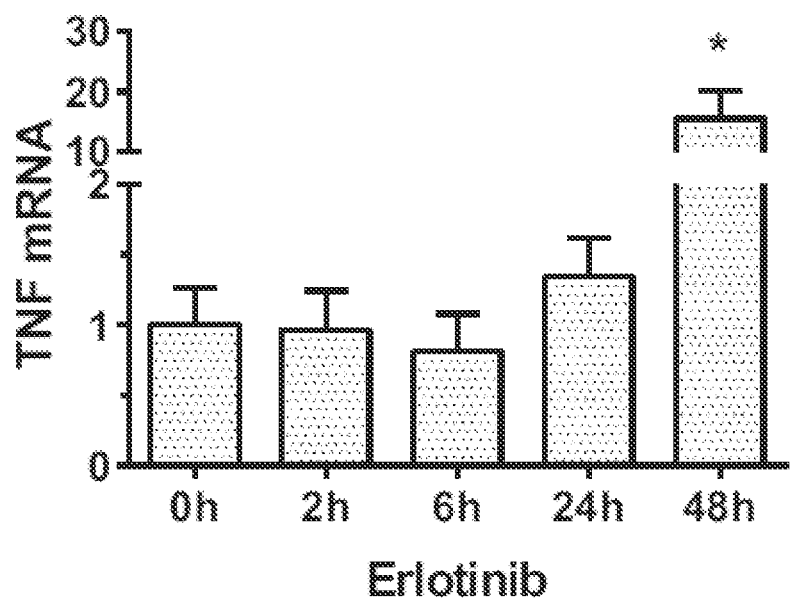
Figure 10K:
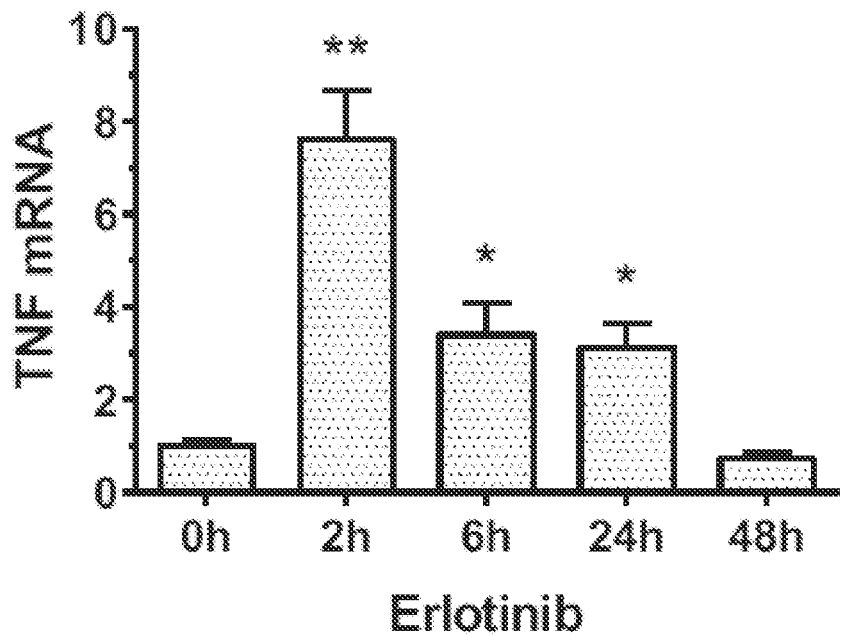
Figure 10L:
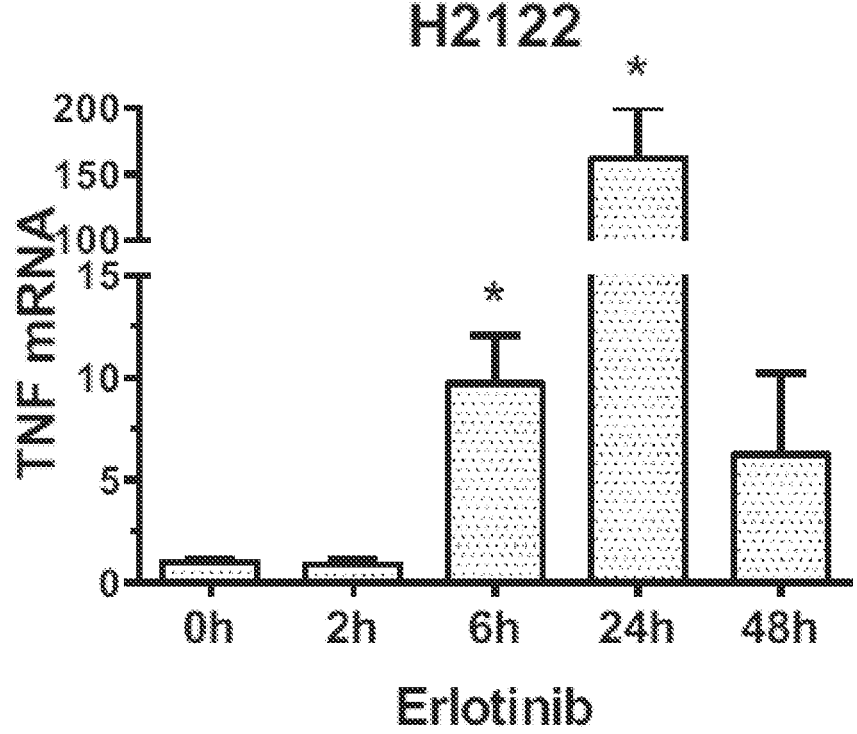

FIG. 9: A schematic of TNF signaling triggered by EGFR inhibition:

Depicting the adaptive response triggered by EGFR inhibition in our model. A. The left panel indicates that inhibition of EGFR leads to increased TNF mRNA via increased stability of TNF mRNA and increased NF-κB mediated transcription of TNF. Increased TNF leads to NF-κB activation in a feed-forward loop. Activation of NF-κB leads to resistance to EGFR inhibition induced cell death. B. The right panel shows that blocking the TNF-NF-κB adaptive response renders lung cancer cells sensitive to EGFR inhibition. Etanercept (Enbrel) inhibits TNF signaling at the receptor level while thalidomide inhibits both NF-κB activation and upregulation of TNF. C. Upon EGFR inhibition, NF-κB activation and accumulation of TNF form a feedforward loop to enhance each other.

FIG. 10: EGFR inhibition induced upregulation of TNF mRNA

A-L NSCLC cell lines were cultured in RPMI-1640 in 5% FBS and were treated with erlotinib (100 nM for EGFR mutant cell lines and 1 μM for EGFR wild type cell lines) for the times indicated followed by RNA extraction and quantitative real time PCR for TNF.

FIG. 11 EGFR inhibition induced TNF unregulation at a protein level

A-C. NSCLC cells were cultured in serum free medium and exposed to erlotinib for 48 hours followed by preparation of cell lysates and level of TNF protein was measured by ELISA. D. PC9 or H1373 cells were treated with erlotinib and the TNF level was measured in the supernatant by ELISA. E-F. H2122 cells were exposed to erlotinib for 48 hours, followed by preparation of cell lysates and supernatant, TNF level in cell lysates and supernatant was measured by ELISA. G. H1975 cells were exposed to afatinib (100 nM) for 48 hours followed by preparation of cell lysates and supernatant, TNF level in cell lysates or supernatant was measured by ELISA. The erlotinib concentration used was 100 nM for EGFR mutant cell lines and 1 μM for EGFR wild type cell lines.

FIG. 12: Afatinib induces upregulation of TNF in lung cancer cell lines

A-F: NSCLC cell lines were cultured in RPMI-1640 in 5% FBS and were treated with afatinib (100 nM) for the times indicated followed by RNA extraction and quantitative real time PCR for TNF. G-H: A549 or HCC827 cells were treated with afatinib (1 uM or 100 nM) and the TNF level was measured in the supernatant by ELISA.

FIG. 13: EGFR activity regulates miR-21

A-D NSCLC cell lines were exposed to EGF (50 ng/ml) for the indicated time points followed by qRT-PCR for TNF mRNA. E. Regulation of TNF level in multiple cell lines by EGF treatment detected by ELISA. F. H3255 Cells were treated with Actinomycin D (5 μg/ml) and erlotinib (100 nM) for the indicated time points followed by RNA extraction and qRT-PCR for TNF mRNA. G. A similar experiment was done in H441 cells using an erlotinib concentration of 1 μM. H-I miR-21 expression was examined in H3255 and H441 cells following exposure to EGF for the indicated time points followed by qRT-PCR using a TaqMan Human MicroRNA Assay kit. J-K HCC827 or A549 cells were exposed to Erlotinib (100 nM or 1 uM) for the indicated time points followed by qRT-PCR for miR-21 using a TaqMan Human MicroRNA Assay kit.

FIG. 14: EGFR activity regulates TNF mRNA stability mediated by upregulation of miR-21

A-D H3255, PC9, H441 or H322 cells were transfected with a control antisense oligonucleotide (C-AS) or a miR-21 antisense oligonucleotide (miR-21 AS) for 48 h followed by exposure of cells to EGF for 1 h and qRT-PCR for TNF. In E-H, the downregulation of miR-21 by the miR-21 antisense oligonucleotide was confirmed. In all experiments involving the use of EGF, cells were serum starved overnight.

FIG. 15: EGFR inhibition induces a TNF-dependent activation of NF-κB

A-B. siRNA knockdown of TNFR1 was performed in H3255 or H441 cells followed by transfection of cells with an NF-κB luciferase reporter and exposure of cells to erlotinib following by a reporter assay. Silencing of TNFR1 was confirmed with a Western blot. C. A TNF blocking drug Etanercept (Enbrel) was used at a concentration of 100 μg/ml along with erlotinib for 48 h followed by a reporter assay in H3255 cells. D. A similar experiment was conducted in H441 cells. E-F. Reporter assay for NF-κB in H3255 or H442 cells treated with erlotinib in the presence or absence of thalidomide (5 μg/ml).

FIG. 16 Thalidomide blocks upregulation of TNF in response to EGFR inhibition.

A-C. Cells were pretreated with thalidomide (5 ug/ml) for 1 hour, followed by addition of erlotinib (HCC827 and H3255 100 nM, A549 1 uM). 24 hours later mRNA was isolated from untreated or treated cells. TNF mRNA was measured by qRT-PCR. Erlotinib induced TNF mRNA levels was significantly decreased by thalidomide. D-E. Cells were cultured in serum free medium and pretreated with thalidomide (10 uM) for 1 hour, followed by addition of erlotinib (HCC827,H3255 100 nM, H441, A549 1 uM). After 48 hours supernatant was collected and concentrated. The levels of TNF protein in supernatant were measured by ELISA. Erlotinib increases levels of TNF protein, which was significantly reduced by thalidomide.

FIG. 17: Erlotinib does not induce feedback activation of ERK and JNK in HCC827 and H441 cells.

HCC827 and H441 cells were treated with 100 nM and 1 µM erlotinib respetively. Protein samples were collected at indicated time point. pEGFR, pERK and pJNK were detected by western blot. Actin was used as a loading control. The blots are representative of three independent experiments.

Figure 18:
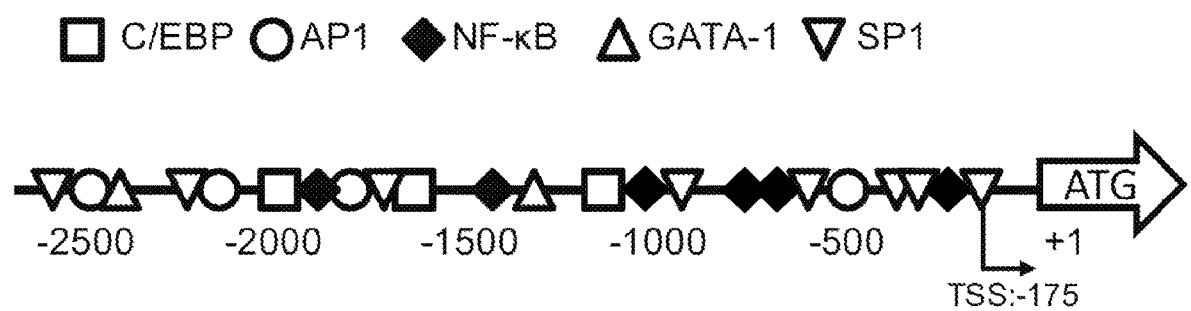

FIG. 18: Transcriptional sites in the TNF promoter.

A schematic of the TNF promoter showing sites for major transcription factors.

Figure 19A:
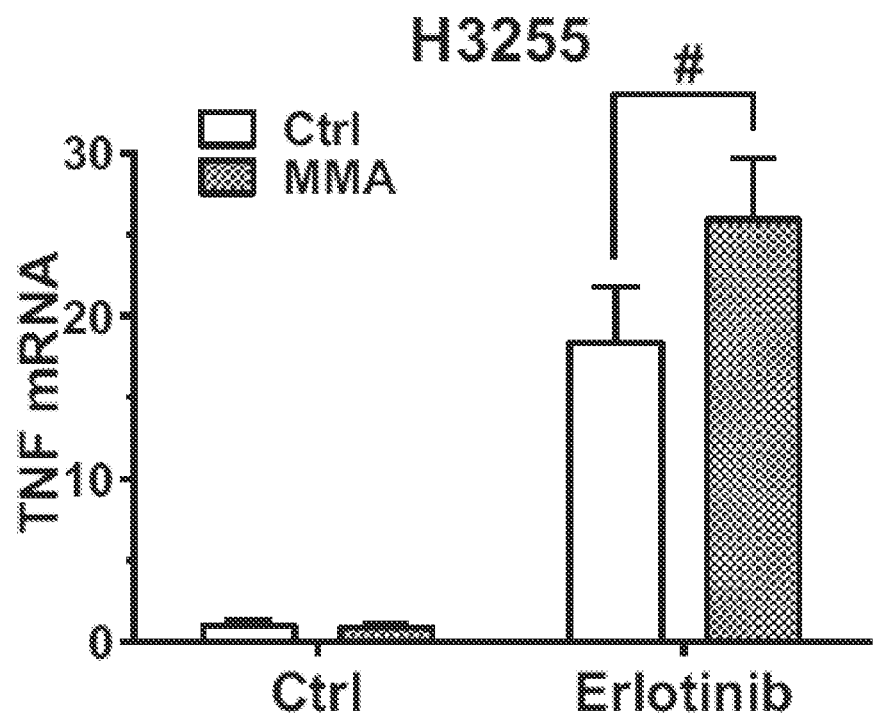
Figure 19B:
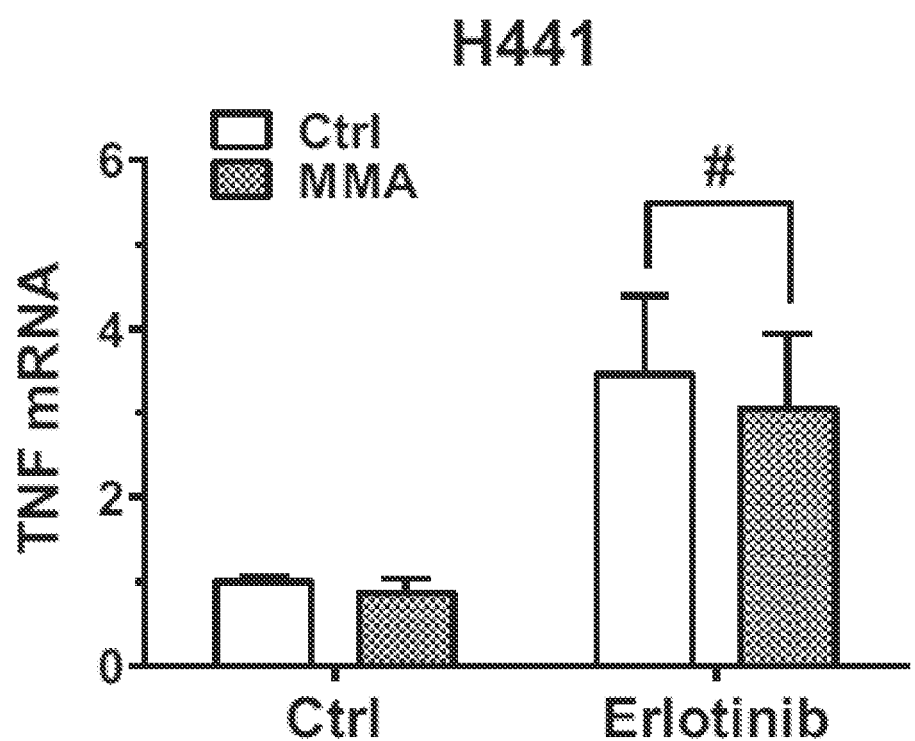
Figure 19C:
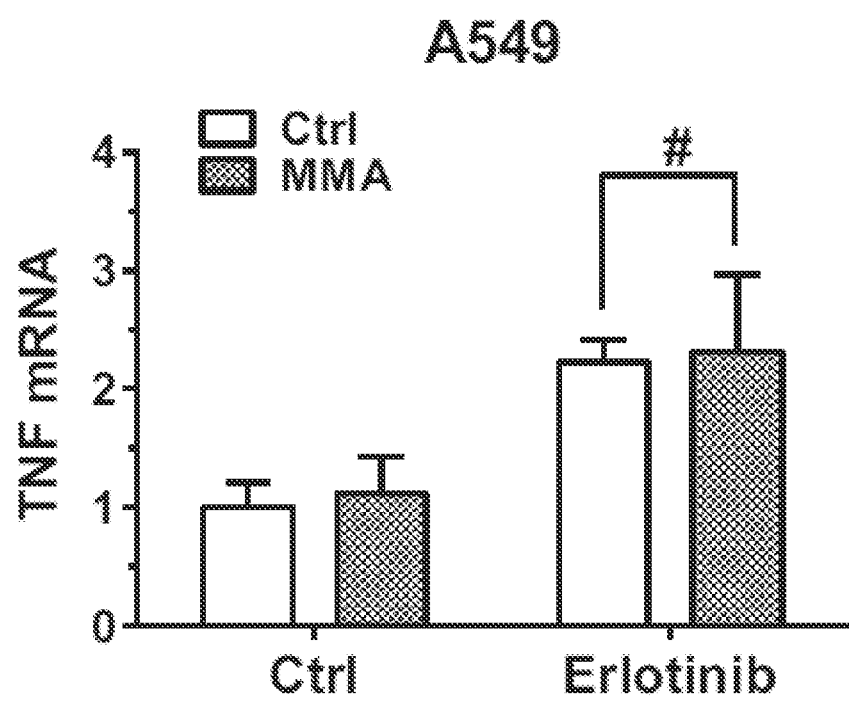

FIG. 19: Sp1 inhibition fails to inhibit erlotinib-induced upregulation of TNF mRNA.

A-C: Inhibition of Sp1, using Mithramycin (1 uM), fails to inhibit erlotinib-induced TNF upregulation in various cell lines. Cells were pretreated with Mithramycin for 1 h followed by erlotinib addition for 24 h, followed by qRT-PCR for TNF mRNA. # indicates not statistically significant.

Figure 20A:
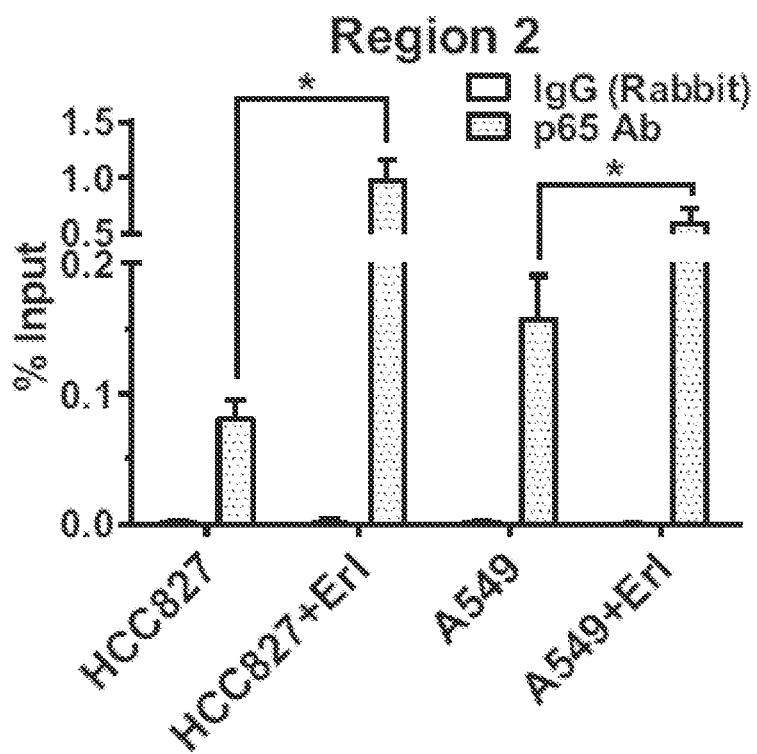
Figure 20B:
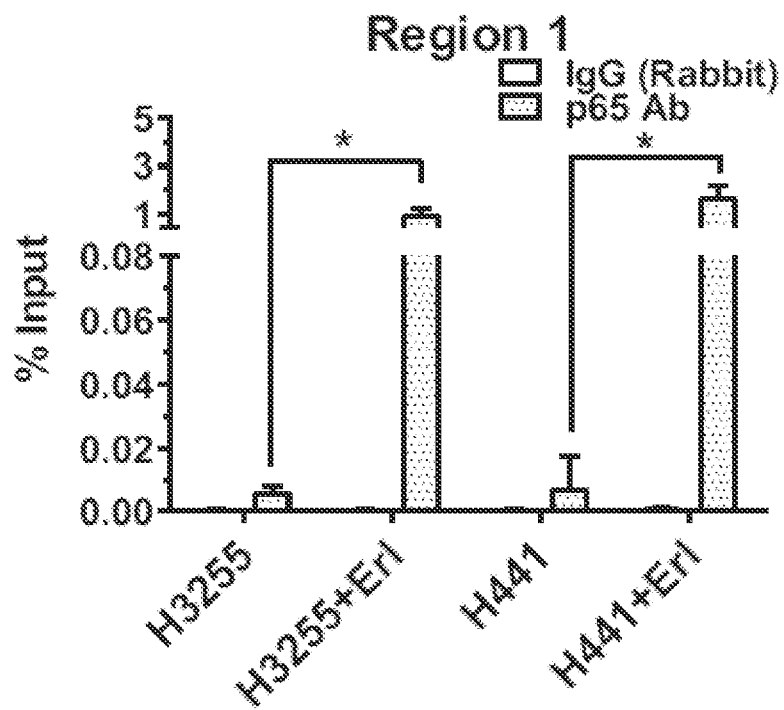
Figure 20C:
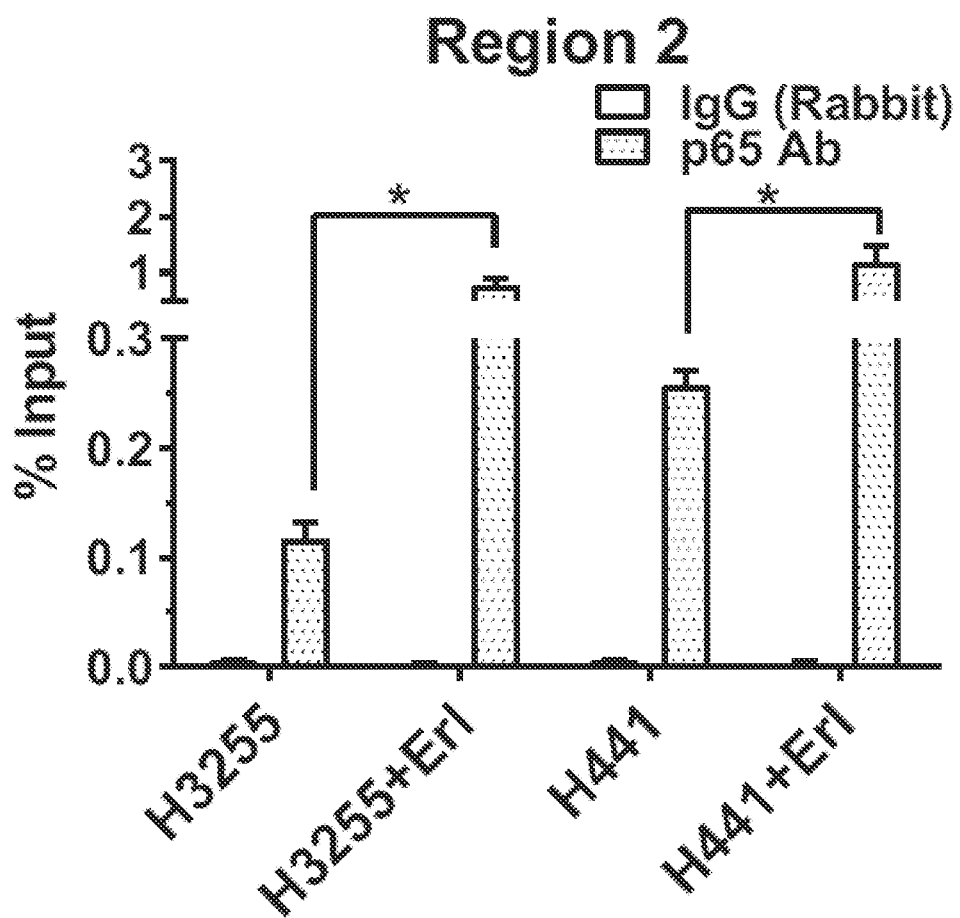
Figure 21A:
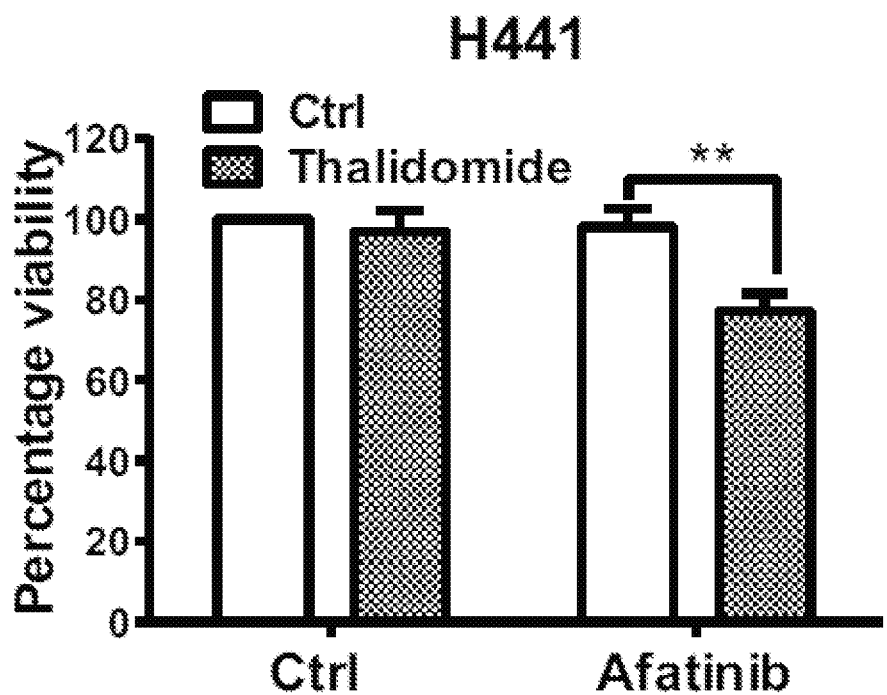
Figure 21B:
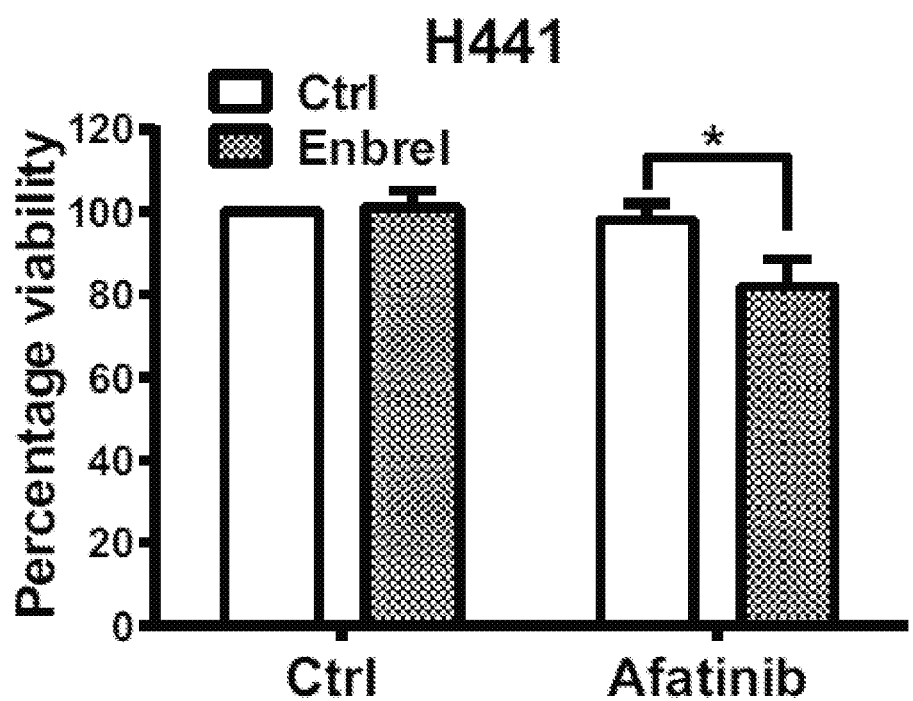
Figure 21C:
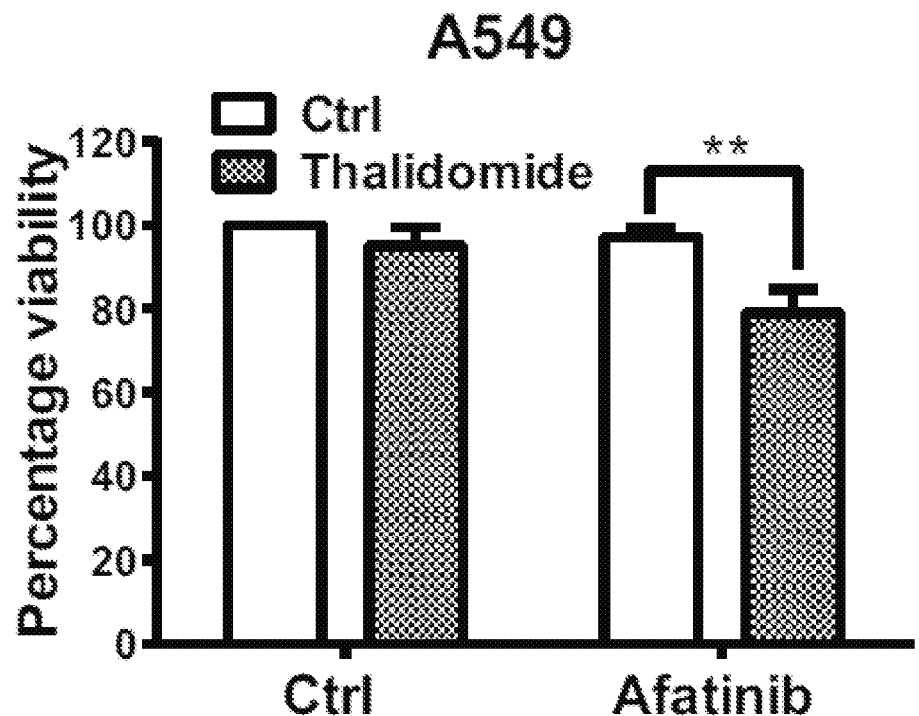
Figure 21D:
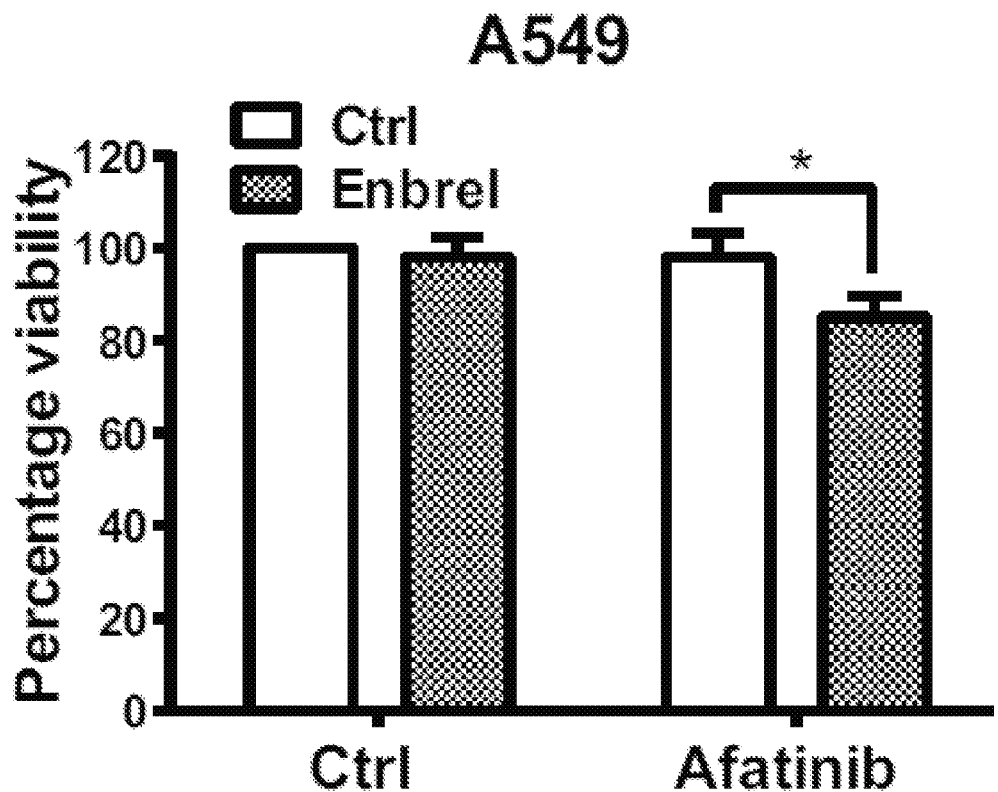

FIG. 20: Increased NF-κB at the TNF gene promoter in response to EGFR inhibition A-C ChIP-qPCR shows p65 NF-κB antibody enrichment (percentage of input, comparing to rabbit IgG) over putative NF-κB binding region 2 on TNF promoter in HCC827 and A549 cells, as well as both region 1 and 2 in H3255 and H441 cells, which can be further enhanced after 1 µM Erlotinib treatment for 24 hours.

FIG. 21: TNF inhibition sensitizes EGFR wt expressing lung cancer cell lines to a a lower concentration of EGFR inhibitor:

A. AlamarBlue assay in H441 cells. Thalidomide (5 ug/ml) and afatinib were added concurrently and Alamar-Blue assay was done after 72 h. B. A similar experiment was done using Enbrel (100 µg/ml) and afatinib in H441 cells. C. A similar AlamarBlue assay was conducted in A549 cells with afatinib and thalidomide. D. A similar AlamarBlue assay was conducted in A549 cells with afatinib and Enbrel. The afatinib concentration in these experiments was 100 nM.

FIG. 22: Biological effects of a combined EGFR and TNF inhibition in additional lung cancer cell lines:

A-B Calu-3 and H1373 cells were cultured in RPMI-1640 with 5% FBS and treated with erlotinib (1 µM) or thalidomide (5 µg/ml) or a combination for 72 h followed by an AlamarBlue assay. C. H1975 cells were cultured in RPMI-1640 with 5% FBS and treated with afatinib (100 nM) or thalidomide or a combination for 72 h followed by an AlamarBlue assay. D. H1975 cells were cultured in RPMI-1640 with 5% FBS and treated with afatinib (100 nM) or Enbrel (100 ug/ml) or a combination for 72 h followed by an AlamarBlue assay. D. AlamarBlue assay in H1975 cells. TNFR1 was silenced using siRNA and cells were exposed to afatinib for 72 h in RPMI-1640 with 5% FBS. Silencing of TNFR1 was confirmed by Western blot.

FIG. 23: Biological and signaling consequences of TNF silencing in A549 cells:

A. Stable silencing of TNF in A549 cells was done with isolation of two clones with low basal and LPS induced TNF (#16 and #23) as determined by qRT-PCR. B-C. A549 cells with stable silencing of TNF (clones 16 and 23) or control shRNA were exposed to erlotinib or afatinib (1 µM) for 72 h followed by an AlamarBlue cell viability assay. D. HCC827, A549 xenografts and HCC4087 PDX bearing mice were given erlotinib by oral gavage once daily as described in FIG. 1 for the indicated time points followed by Western blot with the indicated antibodies.

Figure 24:
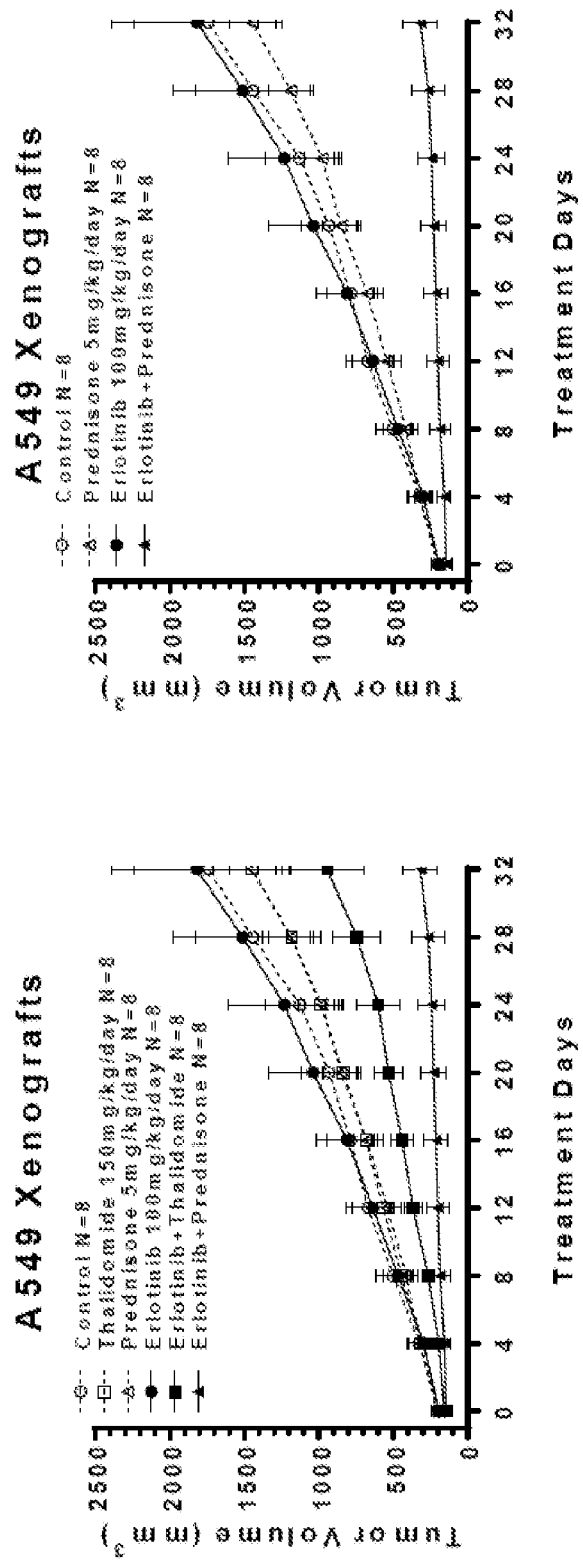

FIG. 24: A549 EGFR wt Xenograft: Combination Therapy Erlotinib+Thalidomide/Prednisone.

Figure 25:
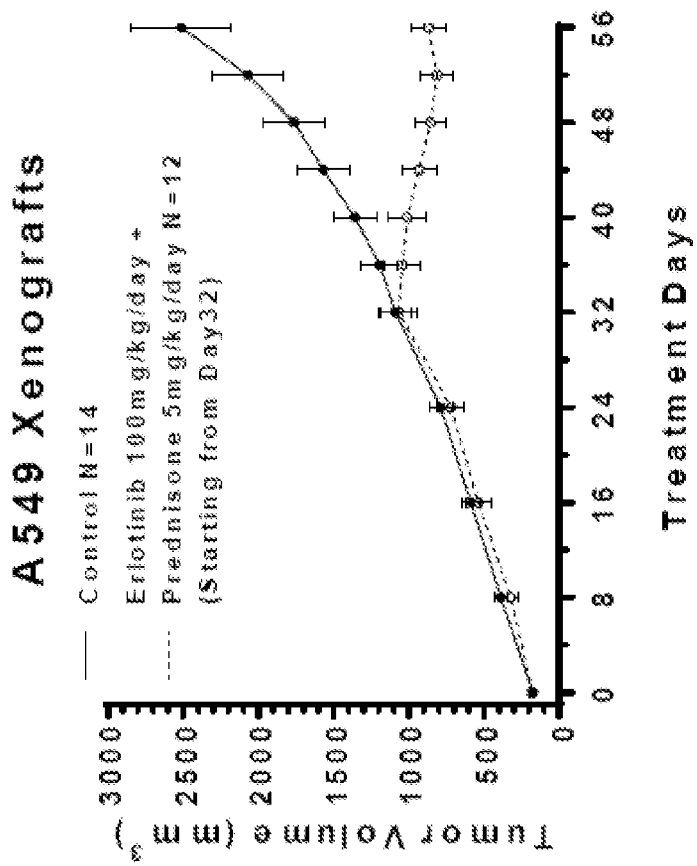

FIG. 25: A549 Xenograft: Shrinking Tumors Erlotinib+Prednisone.

Figure 26:
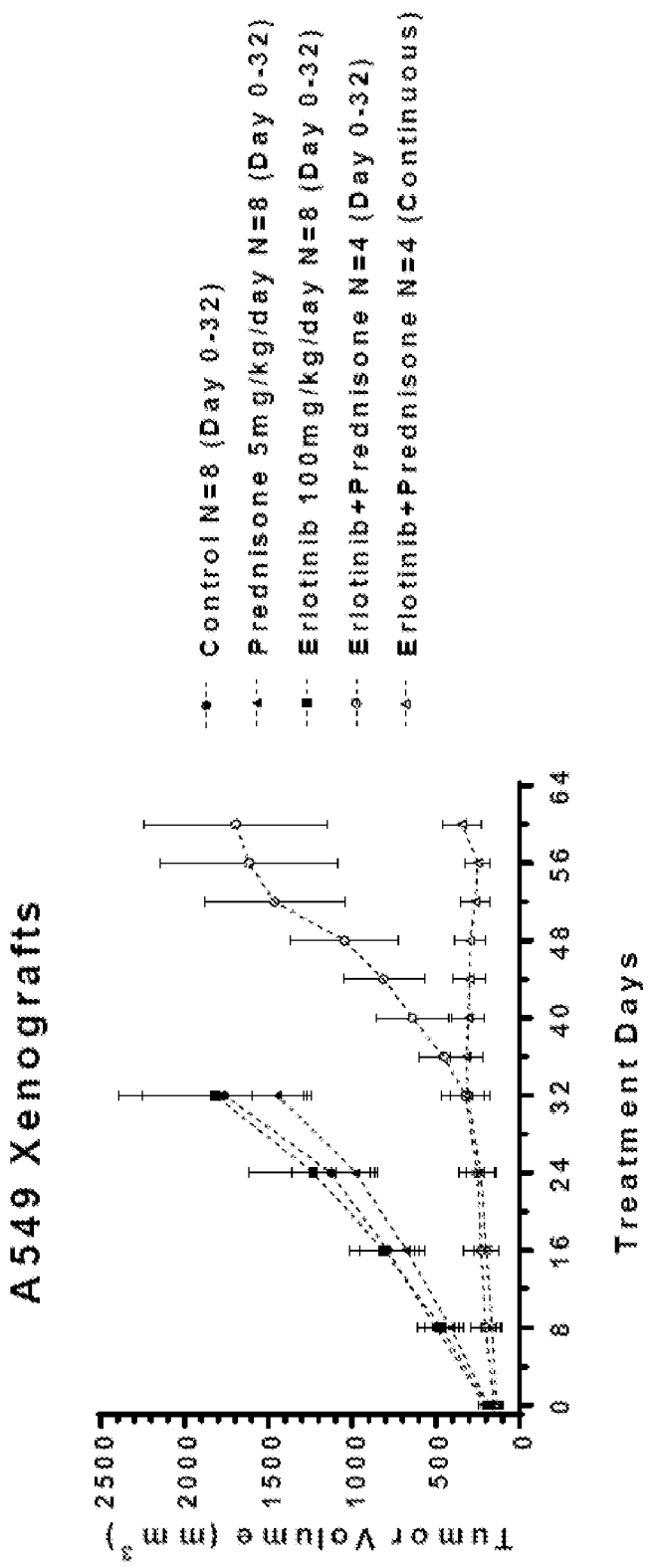

FIG. 26: A549 Xenograft: Drug Withdrawal Erlotinib+Prednisone.

Figure 27:
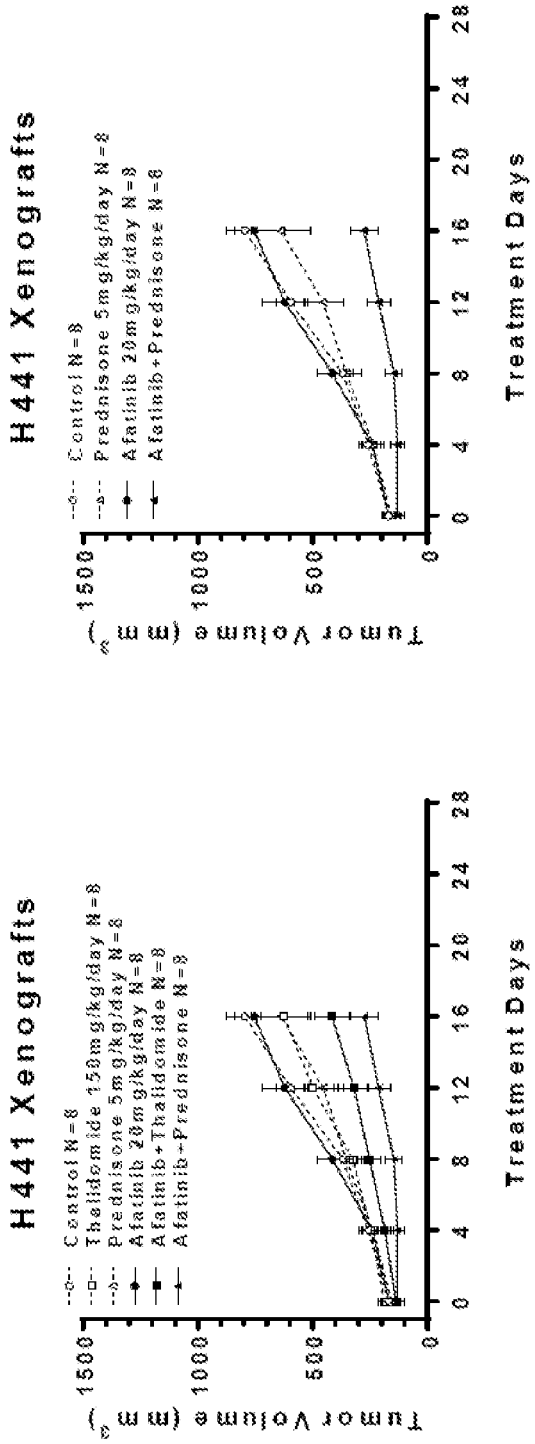

FIG. 27: H441 EGFR wt Xenograft: Combination Therapy Afatinib+Thalidomide/Prednisone.

Figure 28:
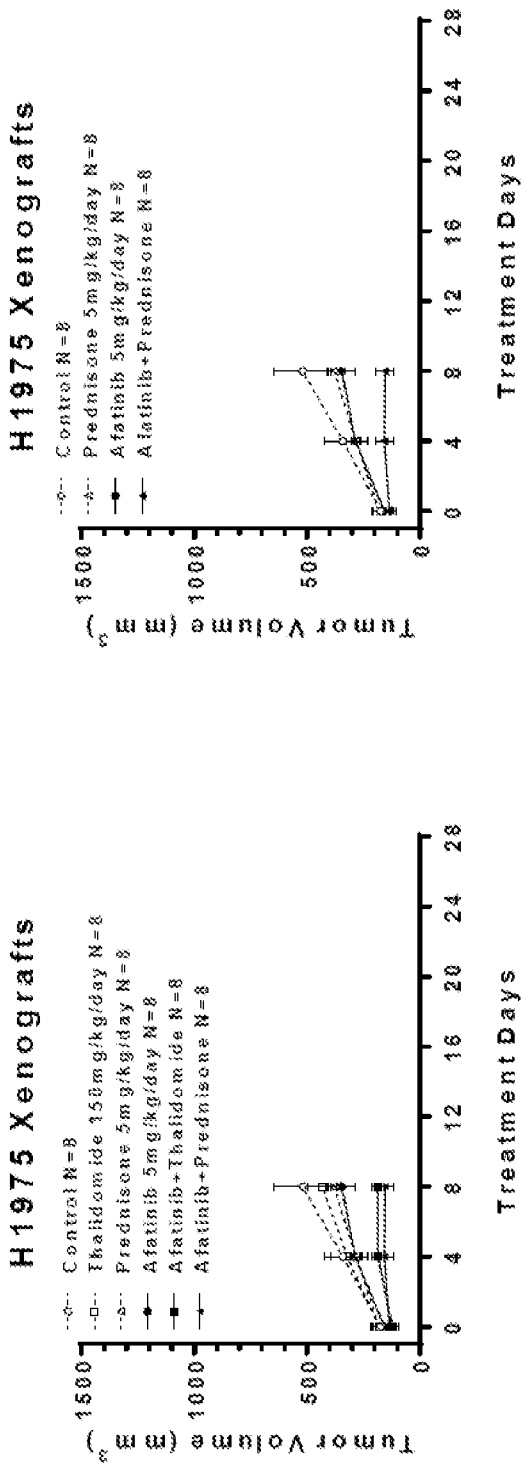

FIG. 28: H1975 EGFR L858R/T790M Xenograft: Combination Therapy Afatinib+Thalidomide/Prednisone.

Figure 29:
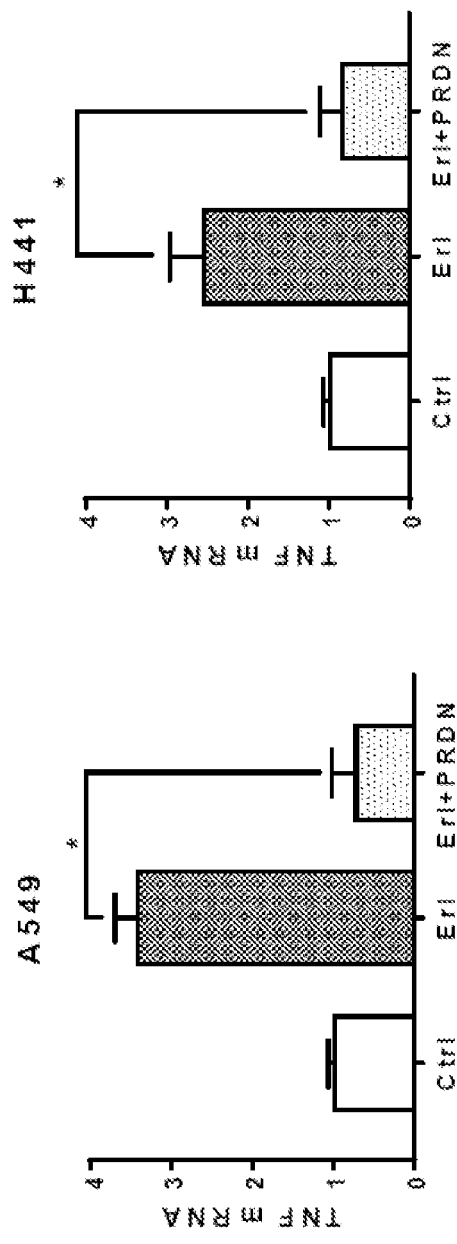

FIG. 29: Prednisone blocks EGFR inhibition induced TNF upregulation.

DETAILED DESCRIPTION

Provided herein are methods for treating cancer, in a patient in need thereof, said method comprising administering to said patient an effective amount of an EGFR inhibitor and a TNF inhibitor.

The EGFR inhibitor can be selected from the group consisting of: erlotinib, afatinib, Cetuximab, panitumumab, Erlotinib HCl, Gefitinib, Lapatinib, Neratinib, Lifirafenib, HER2-nhibitor-1, Nazartinib, Naquotinib, Canertinib, Lapatinib, AG-490, CP-724714, Dacomitinib, WZ4002, Sapitinib, CUDC-101, AG-1478, PD153035 HCL, pelitinib, AC480, AEE788, AP26113-analog, OSI-420, WZ3146, WZ8040, AST-1306, Rociletinib, Genisten, Varlitinib, Icotinib, TAK-285, WHI-P154, Daphnetin, PD168393, Tyrphostin9, CNX-2006, AG-18, AZ5104, Osimertinib, CL-387785, Olmutinib, AZD3759, Poziotinib, vandetanib, necitumumab, The TNF inhibitor is selected from the group consisting of: thalidomide, prednisone, etanercept, adalimumab, certolizumab pegol, golimumab, infliximab, efalizumab, ustekinumab, beclomethasone, betamethasone, cortisone, dexamethasone, hydrocortisone, methylprednisolone, and prednisolone. In particular embodiments, the EGFR inhibitor and TNF inhibitor can combinations selected from the group consisting of: erlotinib and thalidomide; erlotinib and prednisone; afatinib and thalidomide; afatinib and prednisone; erlotinib and etanercept; and afatinib and etanercept.

In the particular cancers treated herein, the EGFR is either EGFR wild type or contains at least one EGFR activating mutation. In some embodiments, the particular cancer being treated can be selected from the group consisting of: lung cancer, cervical cancer, ovarian cancer, cancer of CNS, skin cancer, prostate cancer, sarcoma, breast cancer, leukemia, colorectal cancer, colon cancer, head cancer, neck cancer, endometrial and kidney cancer. In a particular embodiment, the lung cancer is non-small cell lung cancer. In other embodiments, the cancer is a human epithelial carcinoma, which can be selected from the group consisting of: basal cell carcinoma, squamous cell carcinoma, renal cell carcinoma (RCC), ductal carcinoma in situ (DCIS), and invasive ductal carcinoma.

In a particular embodiment, the particular cancer being treated is resistant to EGFR inhibition; or has previously been determined to have been resistant to EGFR inhibition. The cancer resistant to EGFR inhibition can be non-small cell lung cancer.

Also provided is a method of treating a tumor resistant to EGFR inhibition, in a patient in need thereof, comprising administering an agent that inhibits TNF activity in combination with an agent that inhibits EGFR activity.

Also provided herein are pharmaceutical compositions, said compositions comprising a therapeutically effective amount of an EGFR inhibitor and a TNF inhibitor. The EGFR inhibitor can be selected from the group consisting of: erlotinib, afatinib, Cetuximab, panitumumab, Erlotinib HCl, Gefitinib, Lapatinib, Neratinib, Lifirafenib, HER2-nhibitor-1, Nazartinib, Naquotinib, Canertinib, Lapatinib, AG-490, CP-724714, Dacomitinib, WZ4002, Sapitinib, CUDC-101, AG-1478, PD153035 HCL, pelitinib, AC480, AEE788, AP26113-analog, OSI-420, WZ3146, WZ8040, AST-1306, Rociletinib, Genisten, Varlitinib, Icotinib, TAK-285, WHI-P154, Daphnetin, PD168393, Tyrphostin9, CNX-2006, AG-18, AZ5104, Osimertinib, CL-387785, Olmutinib, AZD3759, Poziotinib, vandetanib, necitumumab, The TNF inhibitor is selected from the group consisting of: thalidomide, prednisone, etanercept, adalimumab, certolizumab pegol, golimumab, infliximab, efalizumab, ustekinumab, beclomethasone, betamethasone, cortisone, dexamethasone, hydrocortisone, methylprednisolone, and prednisolone, In particular embodiments, the EGFR inhibitor and TNF inhibitor are combinations selected from the group consisting of: erlotinib and thalidomide; erlotinib and prednisone; afatinib and thalidomide; afatinib and prednisone; erlotinib and etanercept; and afatinib and etanercept.

As used herein, the phrase "EGFR inhibitor" (also referred to as EGFR TKI) or an "agent that inhibits EGFR activity" refers to any agent (molecule) that functions to reduce or inactivate the biological activity of epidermal growth factor receptpr (EGFR). Exemplary EGFR inhibitors include erlotinib, afatinib, Cetuximab, panitumumab, Erlotinib HCl, Gefitinib, Lapatinib, Neratinib, Lifirafenib, HER2-nhibitor-1, Nazartinib, Naquotinib, Canertinib, Lapatinib, AG-490, CP-724714, Dacomitinib, WZ4002, Sapitinib, CUDC-101, AG-1478, PD153035 HCL, pelitinib, AC480, AEE788, AP26113-analog, OSI-420, WZ3146, WZ8040, AST-1306, Rociletinib, Genisten, Varlitinib, Icotinib, TAK-285, WHI-P154, Daphnetin, PD168393, Tyrphostin9, CNX-2006, AG-18, AZ5104, Osimertinib, CL-387785, Olmutinib, AZD3759, Poziotinib, vandetanib, necitumumab, and the like.

As used herein, the phrase "TNF inhibitor" or an "agent that inhibits TNF activity" refers to any of the well-known agents (molecules/compounds) that function to reduce or inactivate the biological activity of Tumor Necrosis Factor (TNF). Exemplary TNF inhibitors include thalidomide, prednisone, Enbrel® (etanercept), etanercept-szzs, adalimumab, adalimumab-atto, certolizumab pegol, golimumab, infliximab, infliximab-dyyb, efalizumab, ustekinumab, beclomethasone, betamethasone, cortisone, dexamethasone, hydrocortisone, methylprednisolone, prednisolone and the like.

Exemplary cancers contemplated for treatment herein can be selected from the group consisting of lung cancer, cervical cancer, ovarian cancer, cancer of CNS, skin cancer, prostate cancer, sarcoma, breast cancer, leukemia, colorectal cancer, colon cancer, head cancer, neck cancer, endometrial and kidney cancer. In another aspect, the cancer is selected from the group consisting of non-small cell lung cancer (NSCLC), small cell lung cancer, breast cancer, acute leukemia, chronic leukemia, colorectal cancer, colon cancer, brain cancer, carcinoma, ovarian cancer, or endometrial cancer, carcinoid tumors, metastatic colorectal cancer, islet cell carcinoma, metastatic renal cell carcinoma, adenocarcinomas, glioblastoma multiforme, bronchoalveolar lung cancers, non-Hodgkin's lymphoma, neuroendocrine tumors, and neuroblastoma. In another aspect, the cancer is ovarian, colon, colorectal or endometrial cancer.

The terms "treatment" or "treating" of a subject includes the application or administration of a compound of the invention to a subject (or application or administration of a compound or pharmaceutical composition of the invention to a cell or tissue from a subject) with the purpose of stabilizing, curing, healing, alleviating, relieving, altering, remedying, less worsening, ameliorating, improving, or affecting the disease or condition, the symptom of the disease or condition, or the risk of (or susceptibility to) the disease or condition. The term "treating" refers to any indicia of success in the treatment or amelioration of an injury, pathology or condition, including any objective or subjective parameter such as abatement; remission; lessening of the rate of worsening; stabilization, diminishing of symptoms or making the injury, pathology or condition more tolerable to the subject; slowing in the rate of degeneration or decline; making the final point of degeneration less debilitating; or improving a subject's physical or mental well-being. In an embodiment, the term "treating" can include increasing a subject's life expectancy.

The term "in combination with" refers to the concurrent administration of a combination of EGFR and TNF inhibitor compounds; or the administration of either one of the compounds prior to the administration of the other inhibitory compound.

As used herein an "effective amount" of a compound or composition for treating a particular disease, such as cancer, is an amount that is sufficient to ameliorate, or in some manner reduce the symptoms associated with the disease. Such amount can be administered as a single dosage or can be administered according to a regimen, whereby it is effective. The amount can cure the disease but, in certain embodiments, is administered in order to ameliorate the symptoms of the disease. In particular embodiments, repeated administration is required to achieve a desired amelioration of symptoms. A "therapeutically effective amount" or "therapeutically effective dose" can refer to an agent, compound, material, or composition containing a compound that is at least sufficient to produce a therapeutic effect. An effective amount is the quantity of a therapeutic agent necessary for preventing, curing, ameliorating, arresting or partially arresting a symptom of a disease or disorder.

As used herein, "patient" or "subject" to be treated includes humans and or non-human animals, including mammals. Mammals include primates, such as humans, chimpanzees, gorillas and monkeys; and domesticated animals.

As used herein, the phrase "EGFR activating mutation(s)" refers to at least one mutation within the protein sequence of EGFR that results in constitutive signaling, which signaling and has been shown to be transforming. Compared to EGFRwt, it is well-known that EGFR activating mutations lead to activation of extensive networks of signal transduction that, in turn, lead to dependence of tumor cells on continuous EGFR signaling for survival.

As used herein, the phrase "EGFR wild type" or EGFRwt refers to epidermal growth factor receptor in its native un-mutated form.

As used herein, the phrase "cancer is resistant to EGFR inhibition" or variations thereof, refers to the well-known mechanism whereby cancer or tumor cells are initially resistant to EGFR inhibition; or have acquired such resistance after initially being susceptible to treatment by a well-known EGFR inhibitor. For example, numerous cancers with activating EGFR mutations, such as non-small cell lung cancers, exhibit a dramatic initial clinical response to treatment with EGFR tyrosine kinase inhibitors (TKIs), but it is well known that this is followed by the inevitable development of secondary resistance to effective treatment with the particular EGFR inhibitor. As another example well known in the art, resistance to EGFR inhibition can include the emergence of other EGFR mutations such as the T790M mutation that prevent TKI enzyme interaction; as well as activation of other receptor tyrosine kinases such as Met or Axl providing a signaling bypass to EGFR TKI mediated inhibition.

As used herein, a combination refers to any association between two or among more items. The association can be spatial or refer to the use of the two or more items for a common purpose.

As used herein, a pharmaceutical composition refers to any mixture of two or more products or compounds (e.g., agents, modulators, regulators, etc.). It can be a solution, a suspension, liquid, powder, a paste, aqueous or non-aqueous formulations or any combination thereof.

Pharmaceutical compositions containing the invention EGFR and TNF inhibitors, either as separate agents or in combination in a single composition mixture can be formulated in any conventional manner by mixing a selected amount of the respective inhibitor with one or more physiologically acceptable carriers or excipients. Selection of the carrier or excipient is within the skill of the administering profession and can depend upon a number of parameters. These include, for example, the mode of administration (i.e., systemic, oral, nasal, pulmonary, local, topical, or any other mode) and disorder treated. The pharmaceutical compositions provided herein can be formulated for single dosage (direct) administration or for dilution or other modification. The concentrations of the compounds in the formulations are effective for delivery of an amount, upon administration, that is effective for the intended treatment. Typically, the compositions are formulated for single dosage administration. To formulate a composition, the weight fraction of a compound or mixture thereof is dissolved, suspended, dispersed, or otherwise mixed in a selected vehicle at an effective concentration such that the treated condition is relieved or ameliorated.

Generally, pharmaceutically acceptable compositions are prepared in view of approvals for a regulatory agency or other prepared in accordance with generally recognized pharmacopeia for use in animals and in humans. Pharmaceutical compositions can include carriers such as a diluent, adjuvant, excipient, or vehicle with which an isoform is administered. Such pharmaceutical carriers can be sterile liquids, such as water and oils, including those of petroleum, animal, vegetable or synthetic origin, such as peanut oil, soybean oil, mineral oil, and sesame oil. Water is a typical carrier when the pharmaceutical composition is administered intravenously. Saline solutions and aqueous dextrose and glycerol solutions also can be employed as liquid carriers, particularly for injectable solutions.

It is understood that appropriate doses depend upon a number of factors within the level of the ordinarily skilled physician, veterinarian, or researcher. The dose(s) of the small molecule will vary, for example, depending upon the identity, size, and condition of the subject or sample being treated, further depending upon the route by which the composition is to be administered, if applicable, and the effect which the practitioner desires the therapeutic agent to have upon the subject. Exemplary doses include milligram or microgram amounts of the therapeutic agent per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram). It is furthermore understood that appropriate doses depend upon the potency. Such appropriate doses may be determined using the assays known in the art. When one or more of these compounds is to be administered to an animal (e.g., a human), a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, and any drug combination.

Parenteral compositions may be formulated in dosage unit form for ease of administration and uniformity of dosage. Dosage unit form as used herein refers to physically discrete units suited as unitary dosages for the subjects to be treated; each unit containing a predetermined quantity of compound of the invention calculated to produce the desired therapeutic effect in association with the required pharmaceutical vehicle. The specification for the dosage unit forms of the invention are dictated by and directly dependent on (a) the unique characteristics of the therapeutic agent and the particular therapeutic effect to be achieved, and (b) the limitations inherent in the art of compounding such a compound of the invention for the treatment of the disease.

In accordance with the present invention, it has been demonstrated that a rapid increase in TNF levels is a universal response to inhibition of EGFR signaling in lung cancer cells, regardless of whether EGFR is mutant or wild type; and this rapid increase in TNF levels is even detected in cells expressing the T790M mutation. EGFR normally suppresses TNF levels by induction of miR-21 that negatively regulates TNF mRNA stability. It has now been found that inhibition of EGFR signaling results in decreased miR-21 and a rapid upregulation of TNF. TNF then activates NF-κB, which in turn leads to a further increase in TNF transcription, generating a feedforward loop. The biological effect of this TNF driven adaptive response is tumor cell survival despite cessation of EGFR signaling. Of great clinical translational importance in accordance with the present invention, it has been found that Inhibition of the TNF adaptive response renders previously EGFR TKI resistant EGFRwt tumor cells sensitive to EGFR inhibition, suggesting that such resistant cells are still potentially "oncogene addicted" but protected from EGFR TKI induced cell death by this adaptive response. Biological inhibition of TNF signaling or treatment with the clinically available agents Etanercept (Enbrel® or thalidomide results in lung cancer sensitivity to EGFR TKI's in previously EGFR TKI resistant cells. As noted, NSCLCs with EGFR activating mutations respond clinically to EGFR inhibition despite the well documented adaptive survival responses such as STAT3 activation triggered in these cells by EGFR inhibition. Similarly, increased TNF secretion in response to EGFR inhibition, fails to completely protect EGFR mutant oncogene addicted cancers. However, TNF inhibition enhances the effectiveness of EGFR inhibition in oncogene addicted lung cancers. Importantly, exogenous TNF also protects oncogene addicted tumor cells from loss of EGFR signaling. Our data suggest a key role for TNF signaling in inducing primary resistance to EGFR inhibition in lung cancer.

The epidermal growth factor receptor (EGFR) is widely expressed in lung cancer and represents an important therapeutic target. However, EGFR inhibition using tyrosine kinase inhibitors is effective only in the 10-15 percent of cases that harbor activating EGFR activating mutations. For the remainder of cases—of which the majority express wild type EGFR—EGFR inhibition has minimal efficacy and is no longer an approved therapy. In accordance with the present invention, it has been found that a combined inhibition of EGFR and TNF renders previously EGFR TKI resistant EGFRwt tumor cells sensitive to EGFR inhibition, indicating that such resistant cells are still potentially "oncogene addicted" but protected from EGFR TKI induced cell death by a TNF driven adaptive survival response. Thus, a combined inhibition of EGFR and TNF in accordance with the present invention is believed to greatly expand the reach and impact of EGFR targeted treatment in NSCLC.

An important finding provided herein is the identification of an early and widespread mechanism that mediates primary resistance to EGFR inhibition in lung cancer cells, regardless of whether EGFR is wild type or mutant. NSCLC cells respond to EGFR inhibition with a rapid increase in TNF levels and the TNF upregulation was detected in all NSCLC cell lines examined, in animal tumors derived from NSCLC cell lines, and in a direct xenograft model. In the case of EGFR wild type expressing NSCLCs the increase in TNF appears sufficient to protect cells from loss of EGFR signaling. Since the majority of NSCLC express EGFR, this adaptive mechanism is likely triggered in the majority of NSCLC treated with EGFR inhibition. The TNF driven adaptive response is also detected in lung cancer cells with EGFR activating mutations and seemingly conflicts with the proven initial effectiveness of EGFR inhibition in such patients. This is likely because the EGFR activating mutations in oncogene addicted cells lead to activation of extensive signaling networks resulting in an exquisite reliance on EGFR signaling. Thus, the TNF upregulation triggered by EGFR inhibition in these cells is only partially protective and the protection is detected only at low concentrations of EGFR inhibitors. STAT3 is also rapidly activated upon EGFR inhibition in NSCLCs with EGFR activating mutations and does not seem to inhibit the clinical response in patients. Thus EGFR inhibited in oncogene addicted cells in the clinical setting may trigger adaptive responses that are ineffective or partially effective. Interestingly, a biologically significant TNF upregulation can also be detected in cells harboring the T790M mutation. The T790M mutation is a frequent mechanism for secondary resistance in tumors that are initially sensitive to EGFR inhibition. Thus, the upregulation of TNF in response to EGFR inhibition appears to be a universal feature of EGFR expressing NSCLCs. The upregulation of TNF in our animal models is rapid and peaks around 2-7 days, receding in 7-14 days which makes it difficult to document the TNF upregulation in archival patient tumor specimens, since tissue is rarely resampled at such early times after EGFR inhibition.

EGFR expression is common in NSCLC and intermediate or high levels of EGFR have been detected in 57 to 62% of NSCLCs by immunohistochemistry. EGFR mutations are detected in 10-15% of patients in Caucasians and are found in a higher percentage of Asian populations. The clinical response to EGFR inhibition in tumors with EGFR activating mutations illustrates both the promise and the difficulties of targeted treatment. It became apparent that patients who clearly responded to EGFR inhibition inevitably developed a secondary resistance to this treatment. Thus, overcoming mechanisms of resistance to targeted treatment is critical to the success of targeted treatment and some insights have emerged into mechanisms of secondary resistance to EGFR inhibition in lung cancer. The emergence of secondary resistance implies the persistence of subsets of cancer cells that are not eliminated during the initial exposure of cells to targeted treatment. Thus, a more effective elimination of cancer cells during the initial exposure to targeted treatment may delay or abrogate the emergence of secondary resistance. In addition, it may be possible to overcome the secondary resistance of human epithelial cancers, such as NSCLC and the like, with appropriately targeted treatments such as the methods provided herein.

Primary or intrinsic resistance to EGFRwt inhibition could occur because the EGFRwt does not drive the survival/proliferation of these cells. The alternative possibility is that an adaptive response prevents cell death in response to EGFR inhibition. Currently most of the attention is focused on the subset of cancers with EGFR activating mutations and the general assumption may be that EGFRwt is not a useful target for treatment, because, although EGFRwt expression is common, EGFR inhibition is ineffective in EGFRwt expressing NSCLC. Furthermore, EGFR mutants are constitutively active and more oncogenic compared to EGFRwt, and engage more signaling networks in cancer cells resulting in a state of dependence or oncogene addiction in EGFR mutant expressing cells. However, the presence of EGFR ligand is common and well documented in lung cancer. Furthermore, a constitutive overexpression induced EGFRwt signaling has also been reported. Thus, it seems likely that EGFRwt expressing cells are also activated in lung cancer. The data provided herein indicate that EGFRwt expressing lung cancer cells can also be rendered sensitive to EGFR inhibition if the TNF adaptive response is inhibited. This finding, in combination with the therapeutic methods provided herein, is believed broaden the use of EGFR inhibition as an effective treatment in epithelial cancers, such as lung cancer, to include EGFRwt expressing cancers if combined with a TNF inhibitor.

It is contemplated that EGFR inhibition results in an increase in TNF levels via a dual mechanism (as shown in the schematic in FIG. 9). First, it has been demonstrated that activation of EGFR signaling results in a rapid downregulation of TNF mRNA. This temporal profile suggests an effect on RNA stability. Indeed, it has been found that inhibition of EGFR results in increased TNF mRNA stability. It is contemplated that EGFR signaling actively suppresses TNF Levels by inducing specific microRNAs that inhibit TNF mRNA stability. MiR-21 was identified as a plausible candidate, because it is both rapidly induced by EGFR signaling in lung cancer cells and also reported to negatively regulate TNF mRNA. It has been confirmed that miR-21 is rapidly upregulated in lung cancer cell lines when EGFR is activated and also that inhibition of miR-21 inhibits EGFR induced TNF upregulation. A second mechanism that also operates early involves the transcription factor NF-κB. TNF activates NF-κB, which in turn, increases the transcription of TNF mRNA in a feedforward loop. Inhibition of NF-κB also blocks the erlotinib induced upregulation of TNF levels. In addition, inhibition of TNFR1 also blocks erlotinib induced upregulation of TNF, confirming the existence of a feed forward loop. The TNF-mediated activation of NF-κB is likely to be a major mechanism of resistance to EGFR inhibition.

The biological effect of increased TNF signaling is protection from cell death mediated by a loss of EGFR signaling. When the TNF mediated adaptive response is blocked, there is an enhanced sensitivity to EGFR inhibition. Conversely, exogenous TNF protects lung cancer cells with EGFR activating mutations from cell death resulting from EGFR inhibition. Inhibition of TNF signaling in sensitive cells with EGFR activating mutations results in an increased sensitivity to EGFR inhibition. Surprisingly, it has been found that TNF inhibition results in rendering EGFRwt expressing cells sensitive to EGFR inhibition. The combined effect of TNF and EGFR inhibition in a resistant EGFRwt cell line A549 cells was examined in a mouse model using multiple approaches to inhibit TNF. A combination of EGFR TKI plus thalidomide was highly effective in inhibiting tumor growth, while EGFR inhibition or thalidomide alone was ineffective. Thalidomide is a known inhibitor of TNF and may regulate TNF transcription and/or stability. A substantial reduction in tumor growth was also noted in A549 cells with stably silencing of TNF, and with Etanercept, a specific inhibitor of TNF signaling, with a greater than 50% reduction of tumor growth, while inhibition of TNF alone had no significant effect. Using a low concentration of erlotinib, a significant reduction was noted in tumor growth with a combined inhibition of TNF and EGFR using the oncogene addicted cell line, HCC827 cells compared to EGFR inhibition alone, although the tumors were sensitive to EGFR inhibition alone. Thalidomide alone had no effect.

A biologically significant upregulation of TNF upon EGFR inhibition may have enormous implications for the treatment of lung cancer. Lung cancer is the most common cancer worldwide, with NSCLC comprising about 85% of all lung cancer. A majority of NSCLC express EGFRwt with a smaller subset expressing EGFR activating mutations. The therapeutic approach provided herein is applicable to the majority of NSCLC including EGFRwt expressing cancers, and include the subset with EGFR activating mutations. In accordance with the present invention, it is believed that inhibiting the EGFR with a combination of TKI plus a TNF inhibitor such as thalidomide or Enbrel is effective in the treatment of human epithelial cancers, such as NSCLCs, and the like, that express EGFRwt. In the subset of tumors with EGFR activating mutations, a combined treatment with EGFR and TNF inhibition is believed to result in a more effective elimination of tumor cells during the initial treatment and perhaps eliminate or delay secondary resistance. A number of TNF inhibiting drugs and antibodies are safe and currently in use in various rheumatologic and immune diseases, making it easy to test this approach in patients. TNF upregulation has also been found in H1975 cells, which harbor a T790M mutation, and it has been found that combined TNF and EGFR inhibition overcomes resistance to EGFR inhibition in these cells, indicating that this approach can be effective in tumors with secondary resistance. EGFR expression is widespread in other types of human cancer, and it is contemplated herein that a biologically significant upregulation of TNF in response to EGFR inhibition is widespread feature of human epithelial cancer, such that the invention methods and compositions provided herein will be effective for treating human epithelial cancers generally.

The above description of the disclosed embodiments is provided to enable any person skilled in the art to make or use the invention. Various modifications to these embodiments will be readily apparent to those skilled in the art, and the generic principles described herein can be applied to other embodiments without departing from the spirit or scope of the invention. Thus, it is to be understood that the description and drawings presented herein represent a presently preferred embodiment of the invention and are therefore representative of the subject matter which is broadly contemplated by the present invention. It is further understood that the scope of the present invention fully encompasses other embodiments that may become obvious to those skilled in the art and that the scope of the present invention is accordingly not limited.

EXAMPLES

Materials & Methods

Plasmids, transfection and Generation of Cell Lines

Calu-3 and A549 cells were obtained from ATCC. All other cell lines were obtained from the Hamon Center for Therapeutic Oncology Research at the University of Texas Southwestern Medical Center (and deposited at the ATCC). Cells were cultured in RPMI-1640 in 5% FBS for all experiments except for experiments involving the use of EGF. Cell lines were DNA fingerprinted using Promega StemElite ID system which is an STR based assay at UT Southwestern genomics core and mycoplasma tested using an e-Myco kit (Boca Scientific). p65 expression plasmid was obtained from Stratagene (La Jolla, Calif.). NF-κB-LUC plasmid was provided by Dr. Ezra Burstein (UT Southwestern). At least 3 independent experiments were performed unless otherwise indicated.

Luciferase Assays

Cells were plated in 48 well dishes followed by transfection with NF-κB-LUC plasmid using lipofectamine 2000. A dual-luciferase reporter assay system was used according to the instructions of the manufacturer (Promega, Madison Wis.). Firefly luciferase activity was measured in a luminometer and normalized on the basis of Renilla luciferase activity. Experiments were done in triplicate and 3 independent experiments were done.

RNA Interference

For transient silencing, a pool was used of siRNA sequences directed against human TNFR1 or control (scrambled) siRNA all obtained from Santa Cruz Biotechnology (Dallas, Tex.). siRNA knockdown was performed according to the manufacturer's protocol using Lipofectamine 2000 reagent (Invitrogen Carlsbad, Calif.). Experiments were conducted 48 h after siRNA transfection.

Antibodies, Reagents and Western Blotting

Western blot and immunoprecipitation were performed according to standard protocols. In all experiments involving use of EGF, cells were cultured overnight in serum free RPMI-1640 and EGF was added to serum free medium. In such experiments, cells not treated with EGF were also serum starved. Erlotinib was purchased from SelleckChem (Houston, Tex.). pEGFR(2236), pERK (4376), ERK (4695), pJNK (9251), JNK (9252), NF-κB p65 (8242), IKBα (4814) antibodies were from Cell Signaling Technology (Danvers, Mass.); TNFR1 (sc-8436), and β-Actin (sc-47778) were from Santa Cruz Biotechnology (Dallas, Tex.); EGFR (06-847) was from EMD Millipore (Billerica, Mass.).

Reagents: Recombinant human TNF and EGF was obtained from Peprotech (Rocky Hill, N.J.). Erlotinib was purchased from SelleckChem (Houston, Tex.). Afatinib was bought from AstaTech, Inc. (Bristol, Pa.). Thalidomide and Mithramycin (MMA) were from Cayman Chemical (Ann Arbor, Mich.). Enbrel (Etanercept) was purchased from Mckesson Medical Supply (San Francisco Calif.). The NF-κB inhibitors, BMS-345541, QNZ (EVP4593), and sodium salicylate were obtained from EMD Millipore (Billerica, Mass.).

Chromatin Immunoprecipitation Assay

HCC827, H3255, H441, or A549 cells were plated in 15 cm plates per reaction for ChIP assay (2×106 cells). The ChIP assay was carried out by using Chromatin Immunoprecipitation (ChIP) Assay Kit (Millipore) according to standard protocols (Nelson et al., 2006). For qPCR 2 μl of DNA from each reaction was mixed with SYBR Green Master Mix (Applied Biosystems, Calif.) and carried out in ViiA 7 Real-Time PCR System (Applied Biosystems). The data are expressed as percentage of input. Putative NF-κB binding sites on TNF promoter were predicted by running AliBaba 2.1 program, and two sites were examined. The following 2 primer pairs were used: Region 1 (−1909/−1636) covering putative NF-κB binding site (−1812/−1801): (SEQ ID NO:1) 5'-CCGGAGCTTTCAAAGAAGGAAT-TCT-3' (forward) and (SEQ ID NO:2) 5'-CCCCTCTCTC-CATCCTCCATAAA-3' (reverse); Region 2 (−1559/−1241) covering putative NF-κB binding site (−1513/−1503): (SEQ ID NO:3) 5'-ACCAAGAGAGAAAGAAGTAGGCATG-3' (forward) and (SEQ ID NO:4) 5'-AGCAGTCTGGCGGCCTCACCTGG-3' (reverse).

cDNA Synthesis and Real Time PCR

Total RNA was isolated by TRIzol Reagent (Ambion). cDNA Reverse Transcription was performed by using High-Capacity cDNA Reverse Transcription Kit (Applied Biosystems). PCR primers were synthesized by IDT (Coralville, Iowa). Each PCR was carried out in triplicate in a 20 μl volume using SYBR Green Master Mix (Applied Biosystems) for 15 minutes at 95° C. for initial denaturing, followed by 40 cycles of 95° C. for 15 s and 60° C. for 60 s in ViiA 7 Real-Time PCR System (Applied Biosystems). At least three independent experiments were done. Values for each gene were normalized to expression levels of GAPDH mRNA. Primer sequences were as below. TNF: (SEQ ID NO:5) 5'-CCCAGGGACCTCTCTCTAATCA-3' (forward) and (SEQ ID NO:6) 5'-GCTACAGGCTTGT-CACTCGG-3' (reverse); GAPDH: (SEQ ID NO:7) 5'-GT-GAAGGTCGGAGTCAACGG-3' (forward) and (SEQ ID NO:8) 5'-TGATGACAAGCTTCCCGTTCTC-3' (reverse).

MicroRNA Studies

For microRNA quantitation, mirVana miRNA Isolation Kit (Ambion) was used to isolate the high-quality small RNAs. TaqMan MicroRNA Reverse Transcription Kit (Applied Biosystems) was used for converting miRNA to cDNA. The RT primers were within the Taqman MicroRNA Assay hsa-miR-21-5p and hsa-miR-423-5p (ThermoFisher). hsa-miR-423-5p was used as the endogenous control. PCR reactions were performed in triplicate by TaqMan® Universal Master Mix II (Applied Biosystems), using the same PCR program as SYBR Green Master Mix. PCR primers of hsa-miR-21-5p and hsa-miR-423-5p were from Taqman MicroRNA Assay (ThermoFisher). Each experiment was carried out independently at least twice. The miR-21 expression levels were normalized to miR-423.

For microRNA inhibition, miRNA inhibitors were obtained from IDT (Coralville, Iowa). The mature sequence of hsa-miR-21-5p was achieved from www.mirbase.org as (SEQ ID NO:9) uagcuuaucagacugauguuga; The human negative control miRNA inihibitor sequence was proposed by IDT as (SEQ ID NO:10) ucguuaaucggcuauaauacgc. miRNA inhibitors were transfected into cultured cells by a method similar to siRNA transfection, using Lipofectamine 2000 reagent.

ELISA

To detect TNF levels in medium, cells were cultured in serum free medium and treated with indicated drugs for 48 hours. Supernatant was then collected and concentrated using a Pierce protein concentrator (Thermo-Fisher). To test TNF in lysates, cell and tumor lysates were extracted following standard protocols used for Western blot. Total protein concentrations were determined by Pierce BCA Protein Assay Kit (Fisher Scientific). Then, the levels of TNF protein were measured by ELISA using a commercial TNF detection kit (Fisher Scientific) according to the manufacturer's instruction.

Virus Infection

Adenovirus-GFP or IkBα adenovirus were obtained from Vector Biolabs (Malvern, Pa.). An MOI of 10 was used in the experiments. Cells were exposed to adenovirus in the presence or absence of Erlotinib for 72 h followed by Cell viability assay or Western blotting.

Human shTNF Lentiviral Particles and Control shRNA Lentiviral Particles-A were purchased from Santa Cruz Biotechnology (Dallas, Tex.). Cells were infected with shRNA lentiviral particles following the manufacturer's protocol and 0.6 μg/mL puromycin was added for selecting stable clones.

Cell Viability Assay

Cell viability assay was conducted using AlamarBlue cell viability assay from Thermo-Fisher, according to the manufacturer's protocol. Cells were treated by indicated drugs for 72 h before detection. In AlamarBlue cell viability assay, cells were cultured at Corning 96-well black plates with clear bottom, and the detection was carried out under the fluorimeter (excitation at 544 nm and emission at 590 nm) using POLARstar Omega Microplate Reader (BMG LABTECH, Germany).

Animal Studies 4 to 6 weeks old female athymic mice were purchased from Charles River Laboratories. 1×10⁶ A549 or 2×10⁶ HCC827 cells were subcutaneously injected into the flanks of athymic mice. After about 10 days post injection, all mice had developed subcutaneous tumors. The mice were randomly divided into control and treatment groups, mice were treated with drugs using the doses described in the figure legends for 10 days. For combination treatment, both drugs were given concurrently for indicated periods. Tumor dimensions were measured every two days and tumor volumes calculated by the formula: volume=length×length×width/2. Mice were sacrificed when tumors reached over 2000 m3 or after 24 days.

HCC4087 PDX model was established at UT Southwestern. The NSCLC specimen (P0) was surgically resected from a patient diagnosed with adenocarcinoma/squamous cell carcinoma, IIB, T3, at UT Southwestern, after obtaining Institutional Review Board approval and informed consent. It has KRAS G13C mutation but no EGFR activating mutations in the normal lung or lung tumor detected by Exome sequencing. 4 to 6 weeks old female NOD SCID mice were purchased from Charles River Laboratories. The PDX tumor tissues were cut into small pieces (~20 mm3) and subcutaneously implanted in NOD SCID mice of serial generations (P1, P2, etc.). P4 tumor bearing SCID mice were used in this study.

All animal studies were done under Institutional Animal Care and Use Committee-approved protocols at the University of Texas Southwestern Medical Center and North Texas VA Medical Center.

Statistical Analysis

Error bars represent the means±SEM of three independent experiments. All data were analyzed for significance with Student's t-test using GraphPad Prism 7.0 software, where $P<0.05$ was considered statistically significant. * means that $P<0.05$,  means that $P<0.01$, and * indicates any p value less than 0.001. # indicates not statistically significant.

Results

EGFR Inhibition Leads to Upregulation of TNF Expression in Lung Cancer Cell Lines and Xenograft Tumors Previous studies have shown that exposure of lung cancer cells to EGFR tyrosine kinase inhibitors such as erlotinib results in a rapid activation of NF-κB in EGFR mutant NSCLC cells. The activation of NF-κB is biologically significant and appears to protect cancer cells from cell death resulting from EGFR inhibition. TNF is a key activator of NF-κB, and the possibility that TNF may mediate the NF-κB activation triggered by EGFR inhibition was evaluated. First, whether erlotinib induced an increase in TNF levels in lung cancer cell lines was investigate. It was found that exposure of lung cancer cell lines to erlotinib resulted in increased TNF mRNA levels in all 18 cell lines examined (Table 1) as determined by real time quantitative PCR as shown in FIG. 1A-F and FIG. 10.

TABLE 1

|   | Cell Lines | EGFR Status |
|---|---|---|
| 1 | H3255 | Mutant(L858R) |
| 2 | PG9 | Mutant(ex19del) |
| 3 | HCC827 | Mutant(ex19del) |
| 4 | HCC4006 | Mutant(ex19del) |
| 5 | H1373 | Wild type |
| 6 | H1975 | Mutant(L858R/T790M) |
| 7 | H1650 | Mutant(ex19del) |
| 8 | H322 | Wild type |
| 9 | H441 | Wild type |
| 10 | H1666 | Wild type |
| 11 | A549 | Wild type |
| 12 | Calu-3 | Wild type |
| 13 | HCC2279 | Mutant(ex19del) |
| 14 | HCC4011 | Mutant(L858R) |
| 15 | HCC820 | Mutant(ex19del/T790M) |
| 16 | HCC2935 | Mutant(ex19del) |
| 17 | H1573 | Wild type |
| 18 | H2122 | Wild type |

Lists the cell lines used in this study with EGFR mutation status.

Figure 1G:
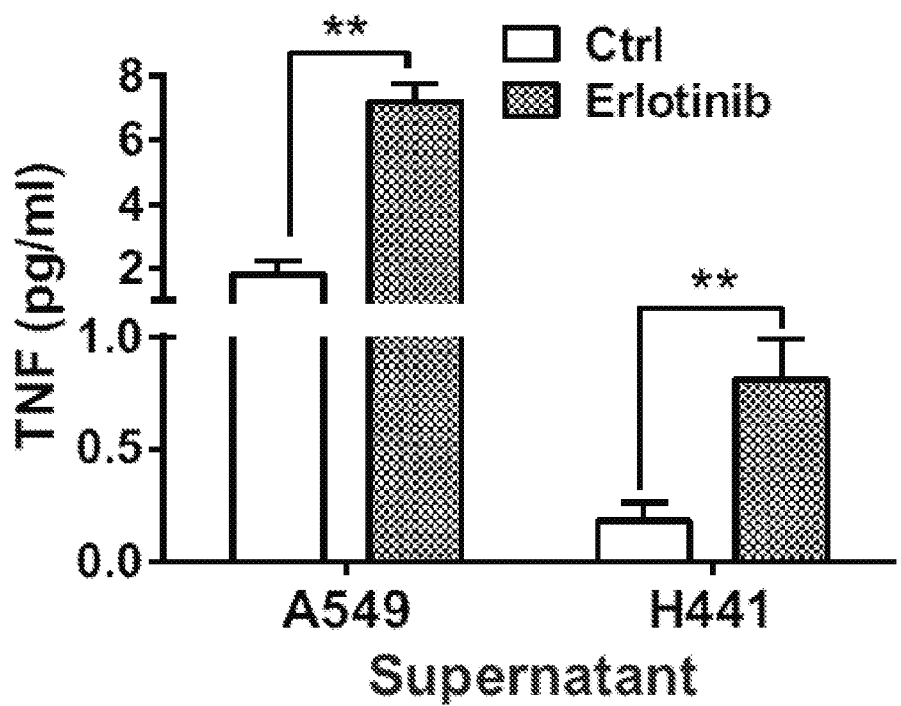
Figure 1H:
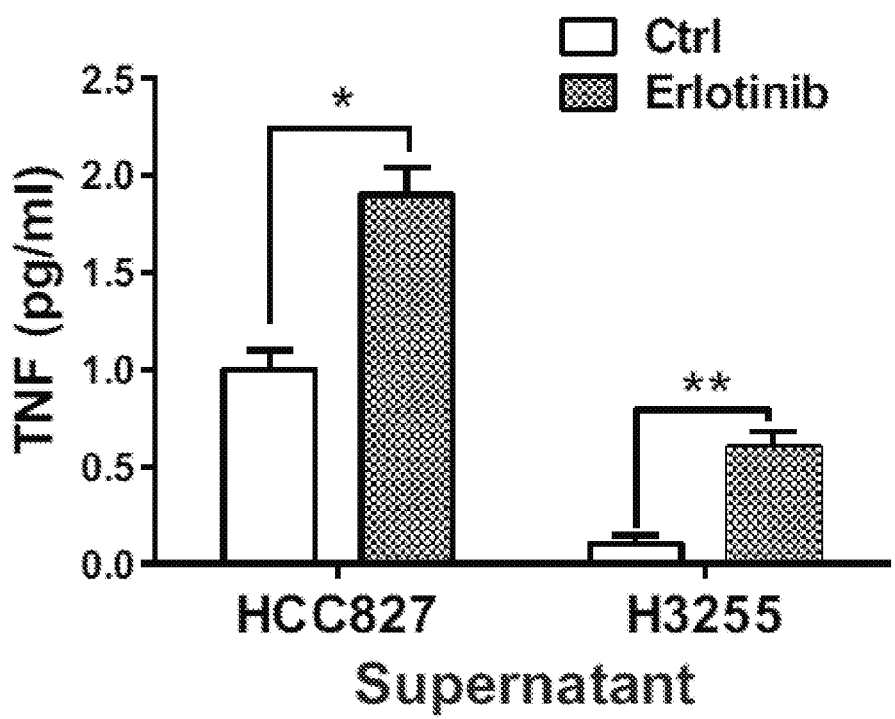
Figure 1I:
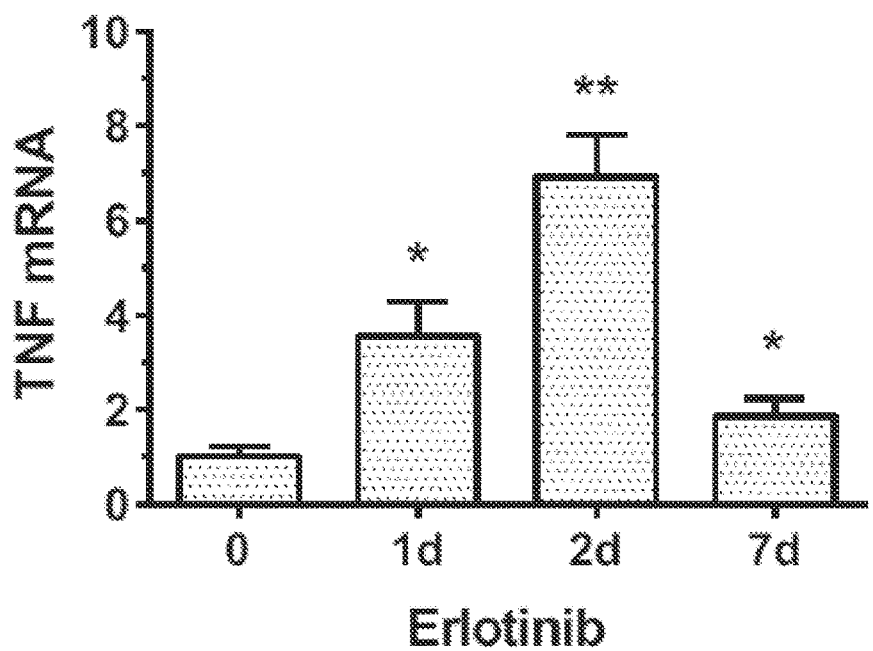
Figure 1J:
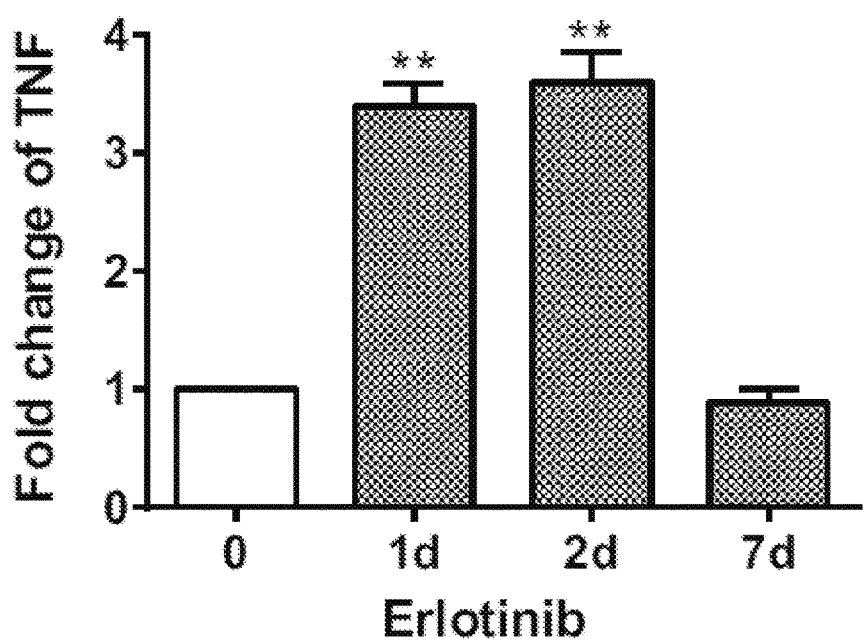
Figure 1K:
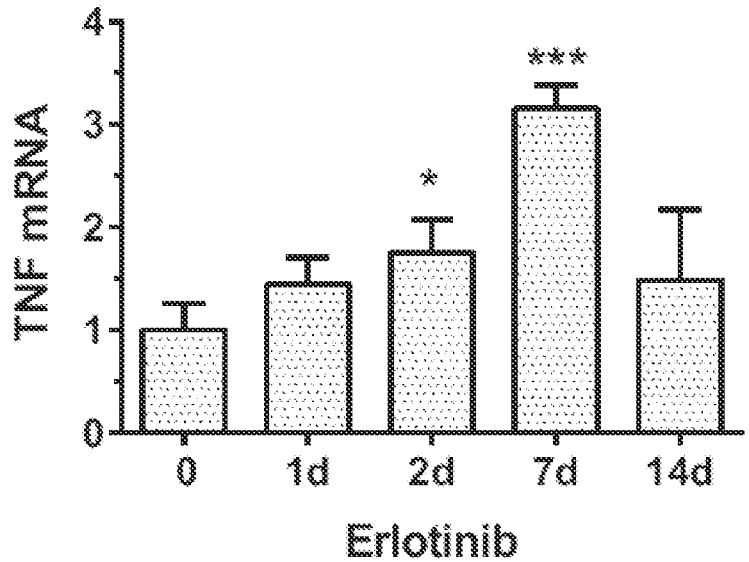
Figure 1L:
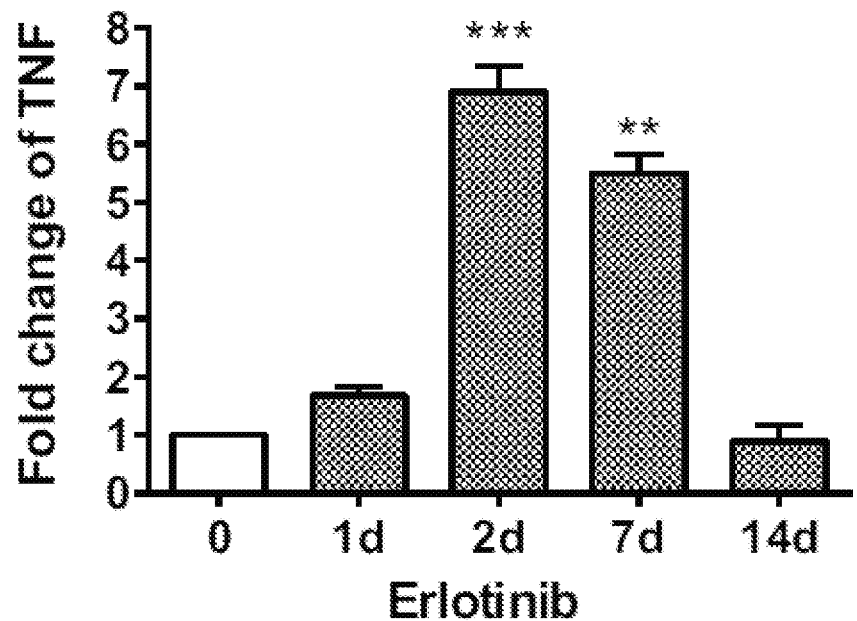
Figure 11A:
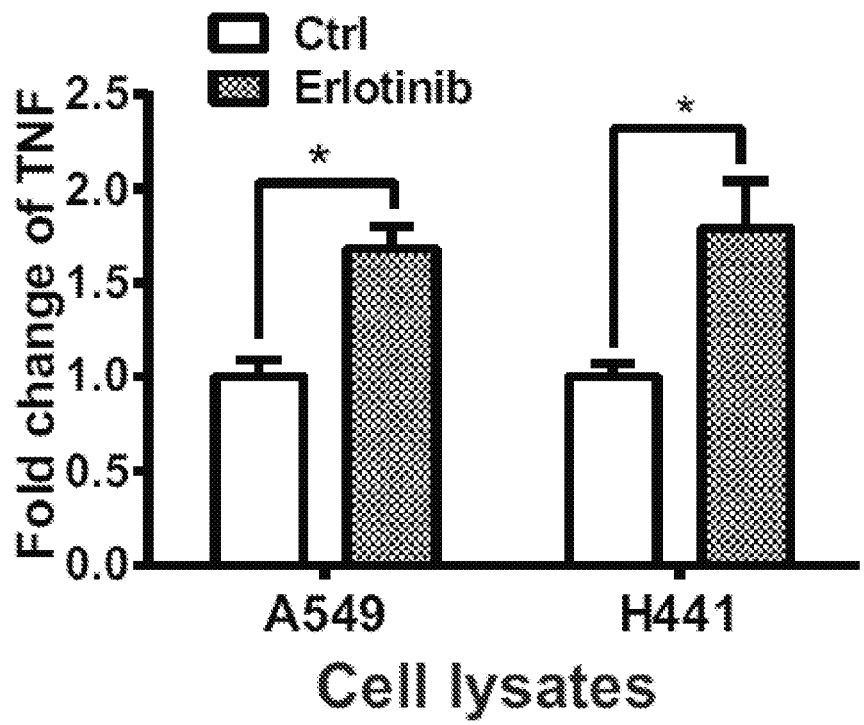
Figure 11B:
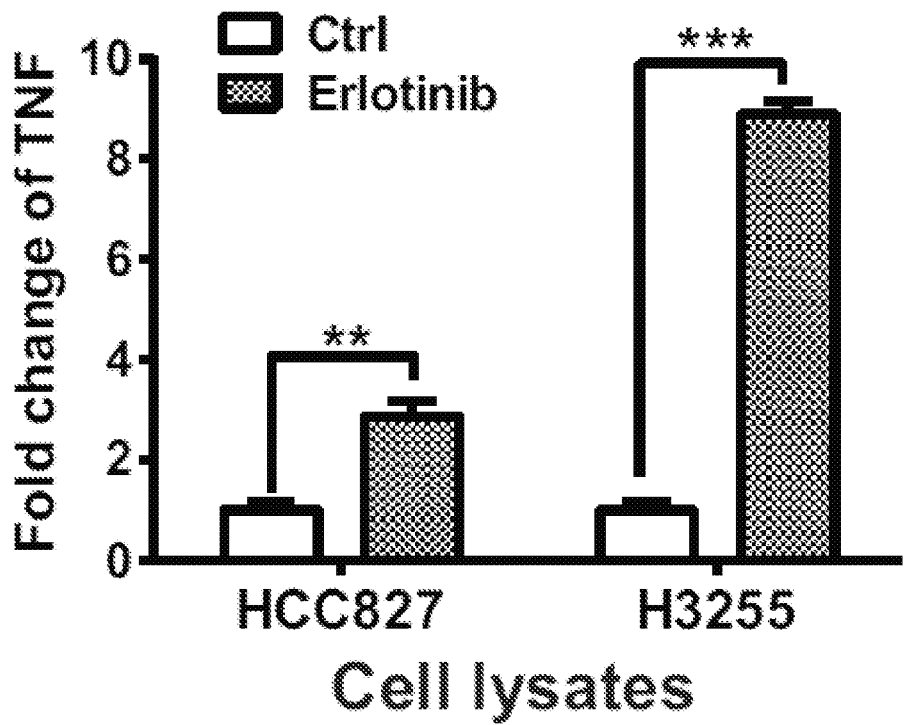
Figure 11C:
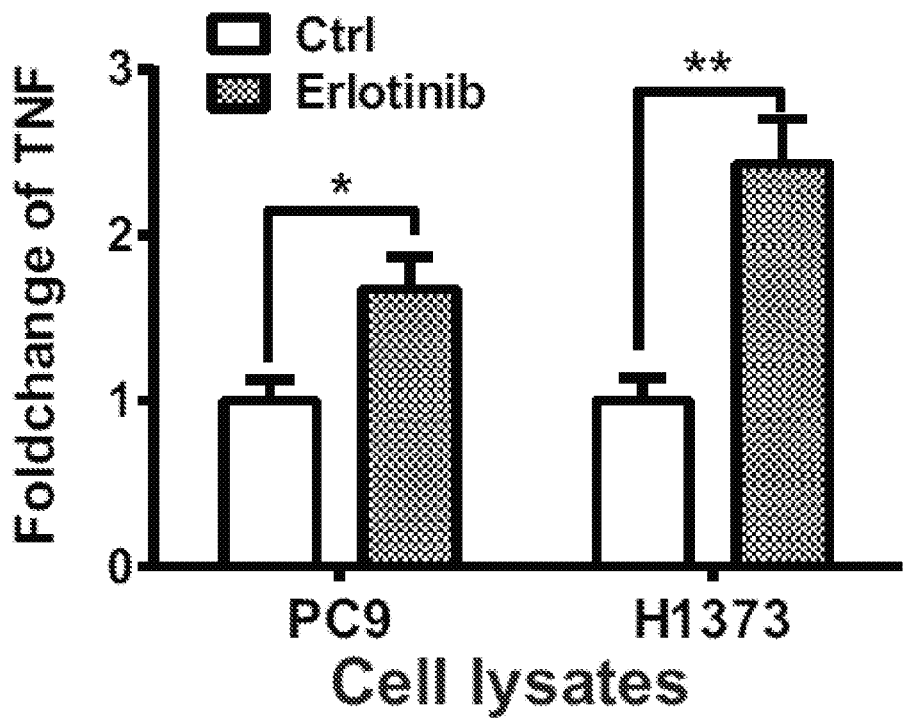
Figure 11D:
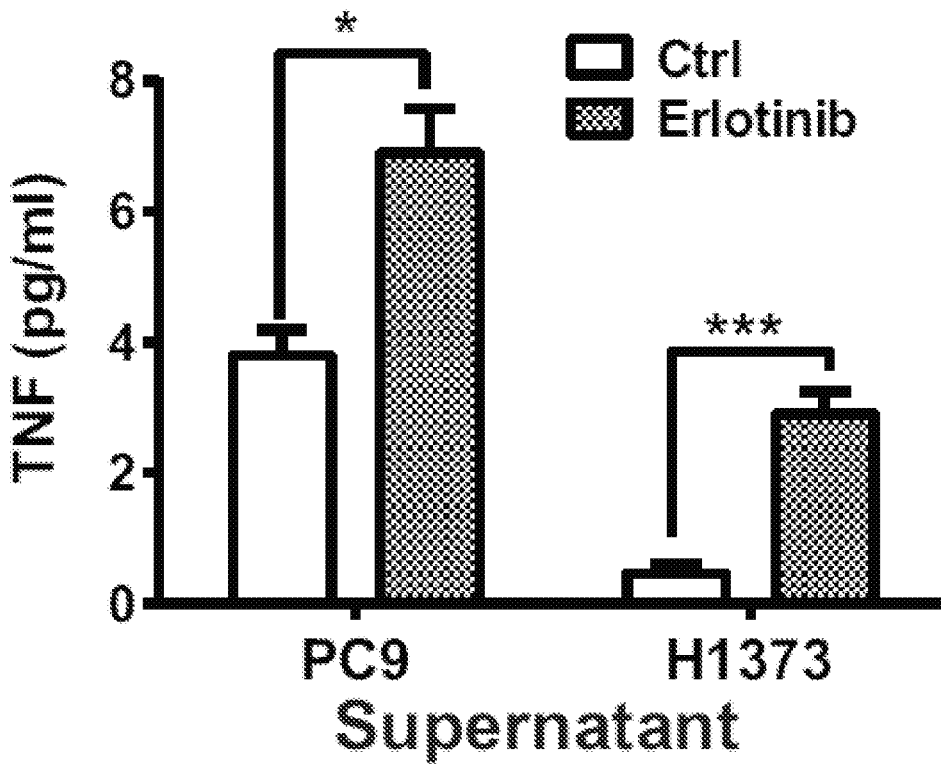
Figure 11E:
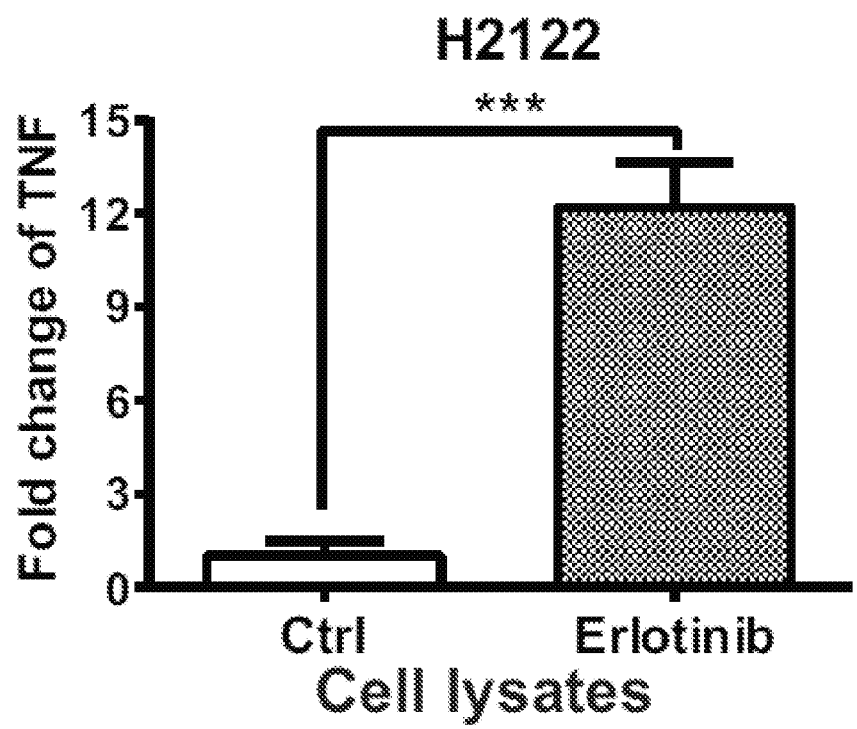
Figure 11F:
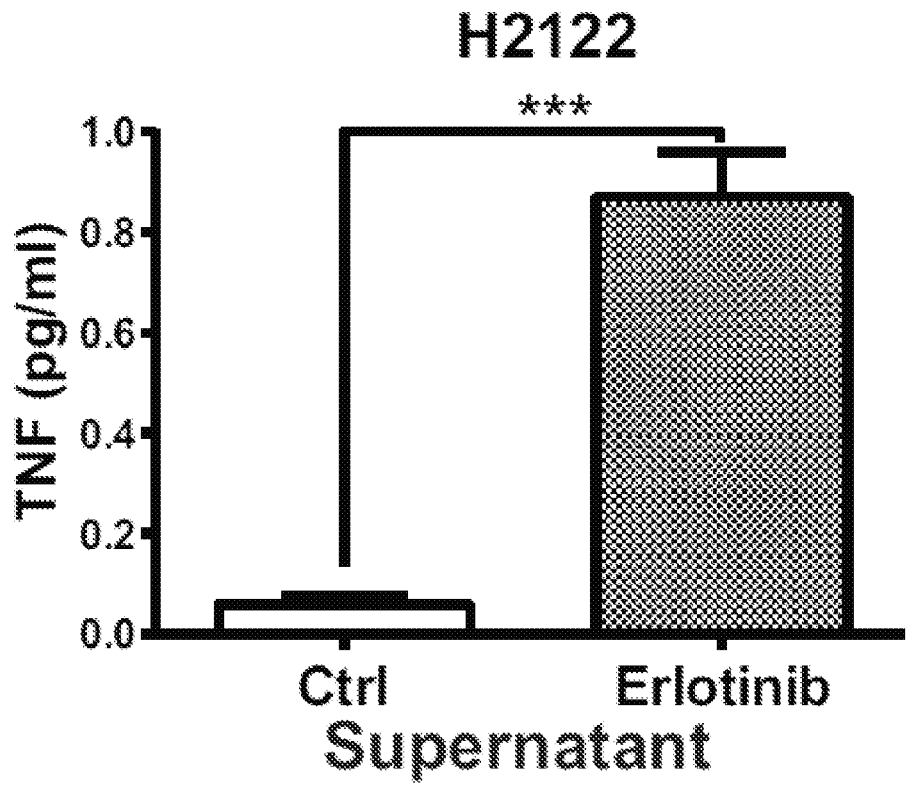
Figure 11G:
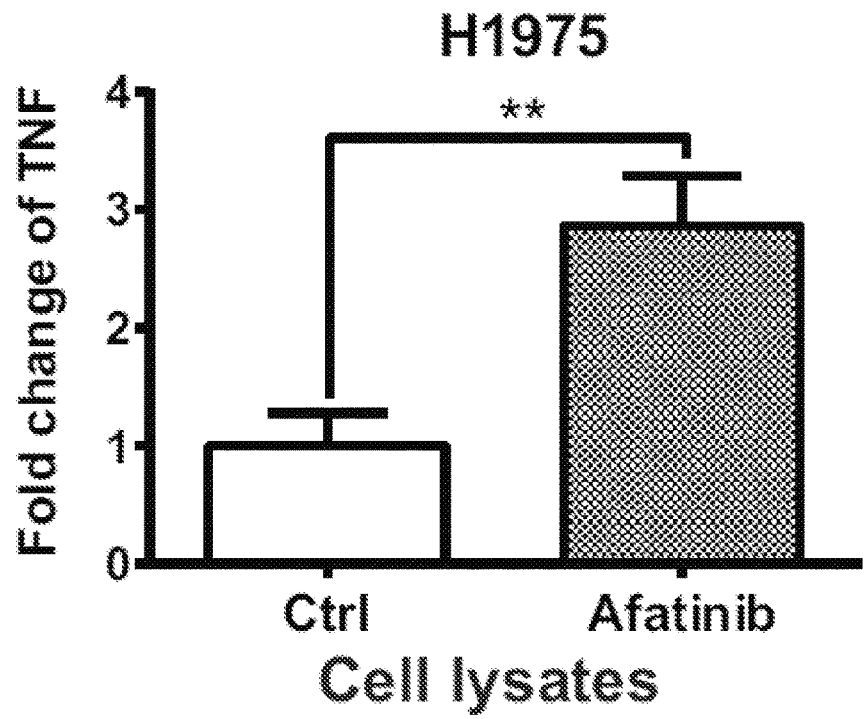
Figure 11H:
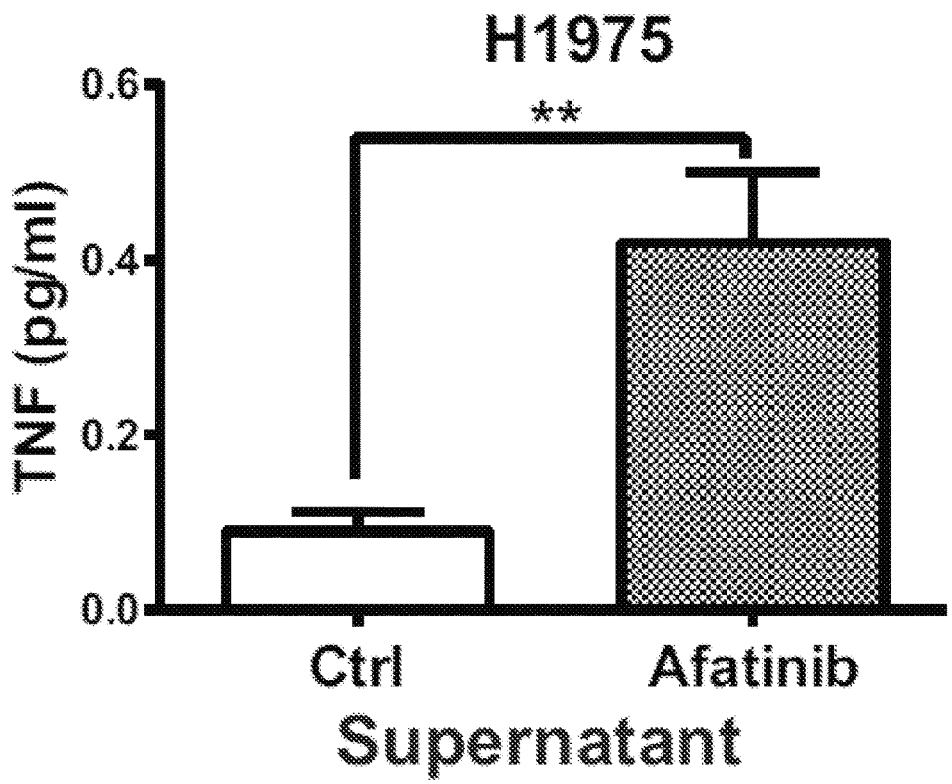
Figure 12A:
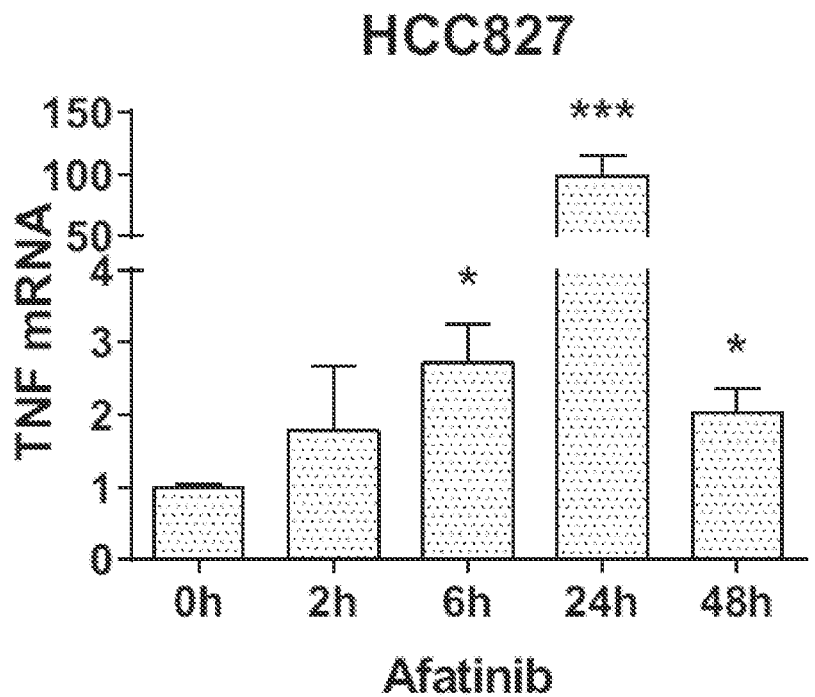
Figure 12B:
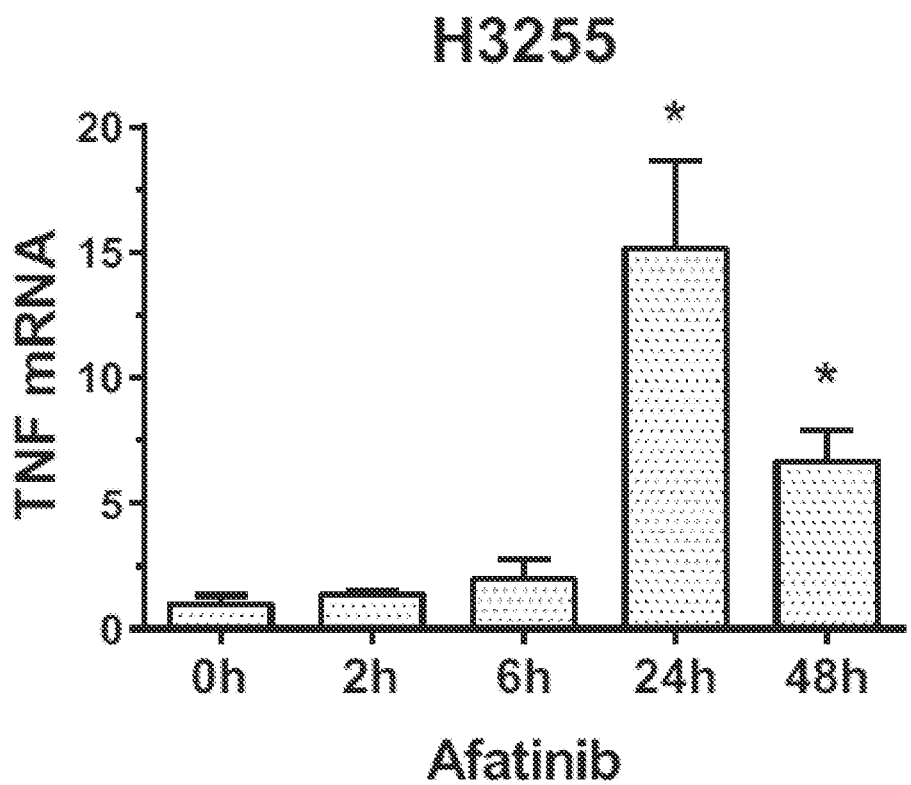
Figure 12C:
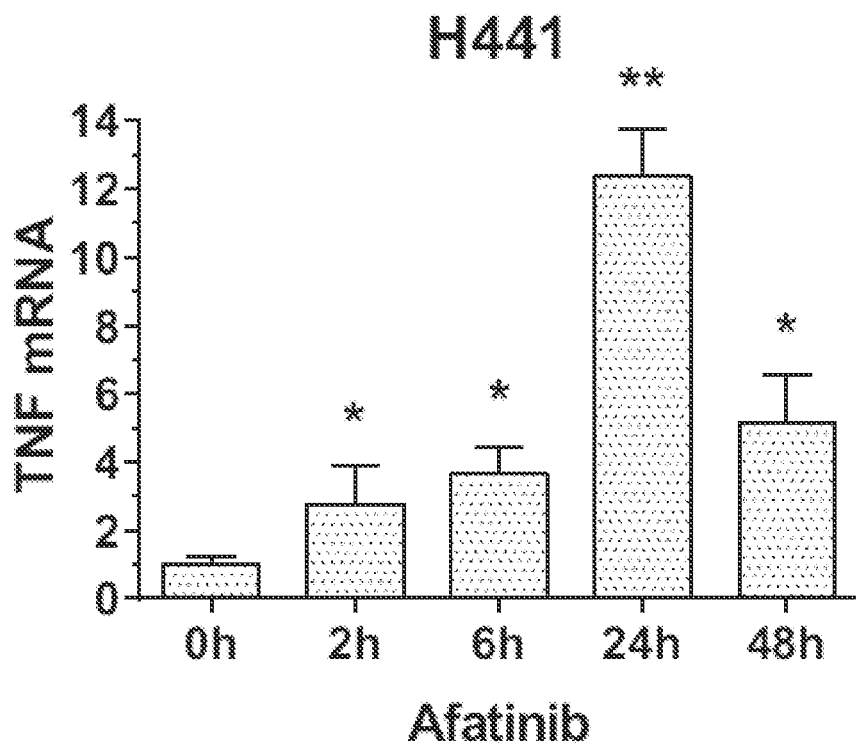
Figure 12D:
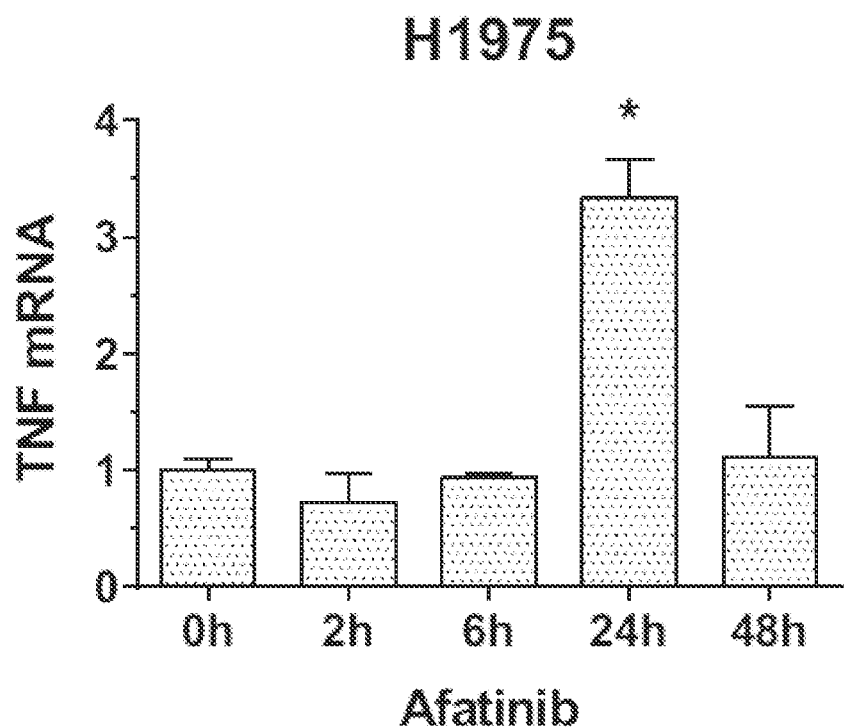
Figure 12E:
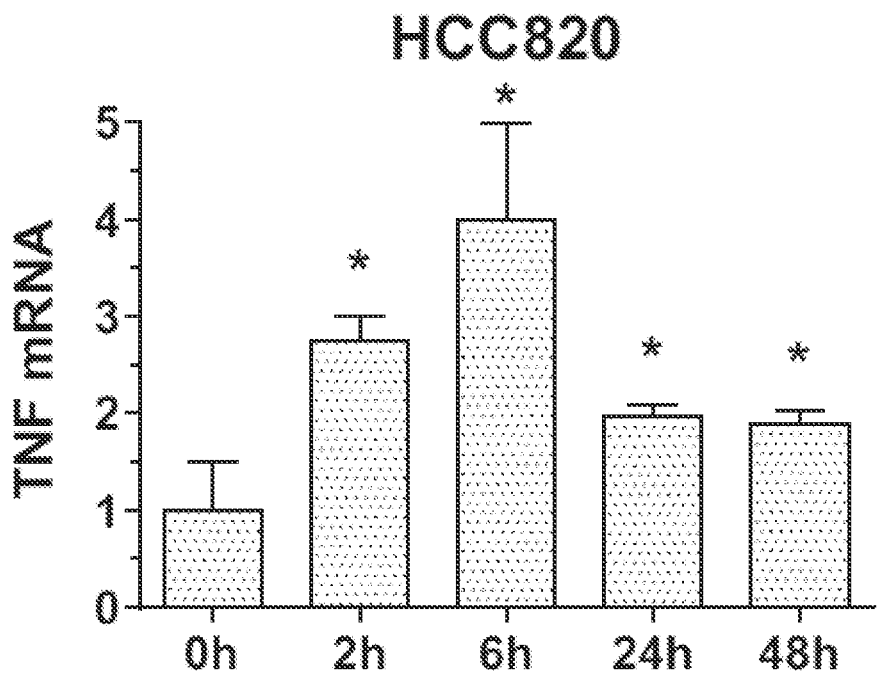
Figure 12F:
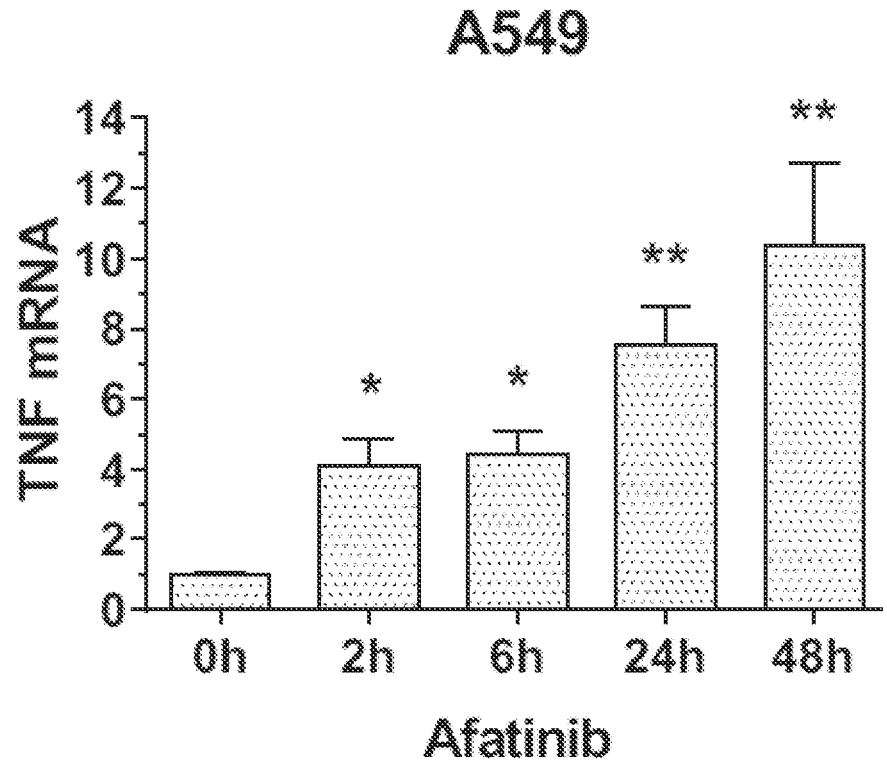
Figure 12G:
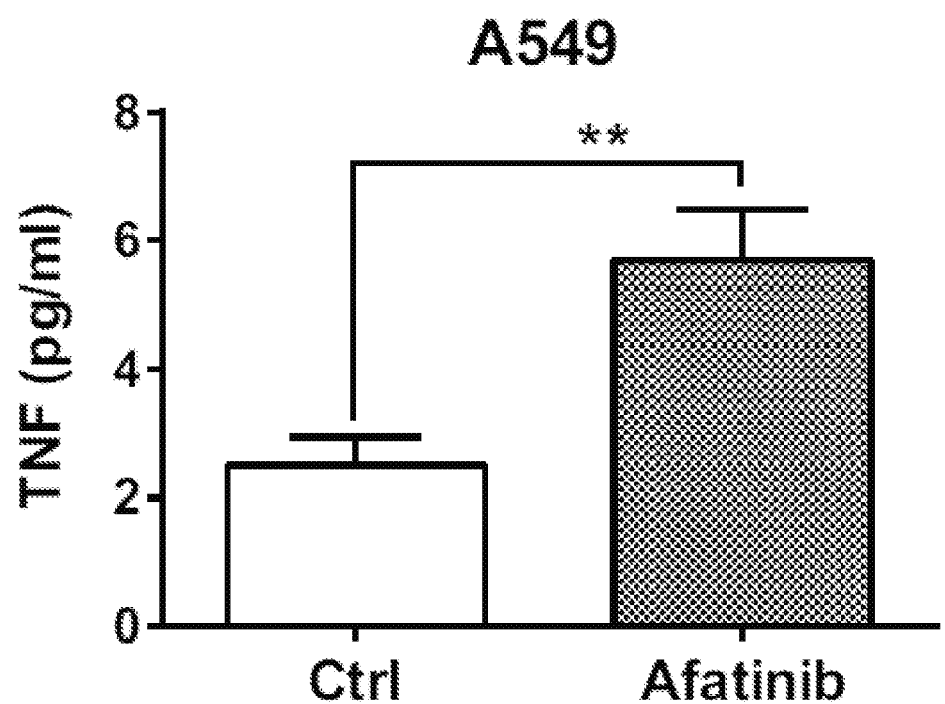
Figure 12H:
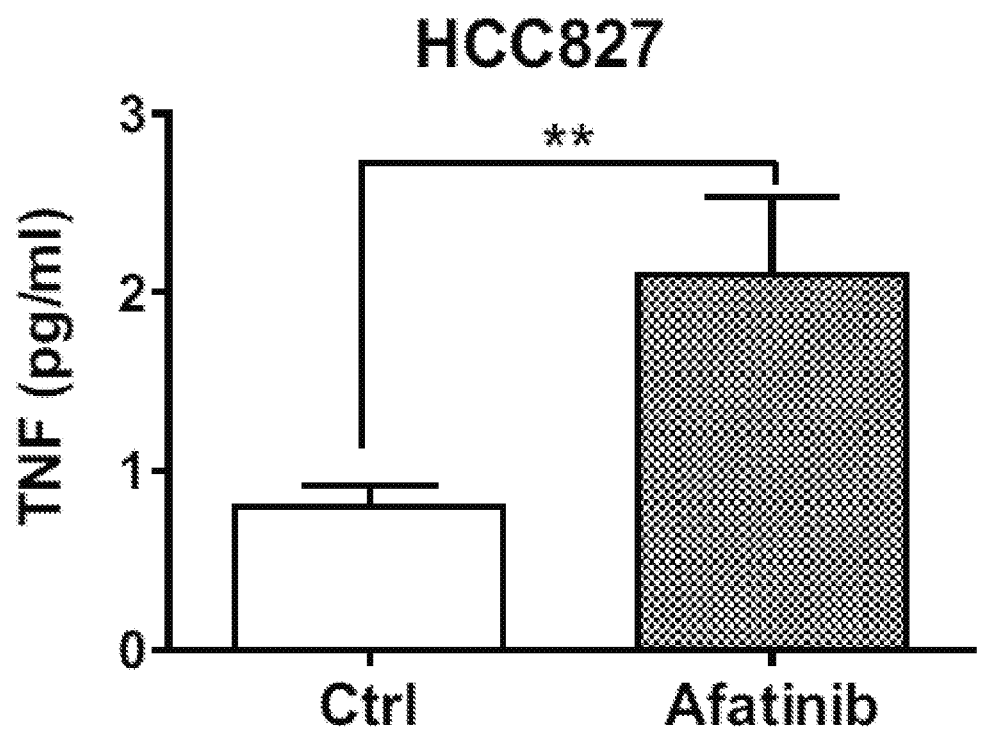

Remarkably, while the temporal profiles vary, the increase in TNF is detected in both EGFRwt and EGFR mutant cell lines. The increase in TNF levels upon EGFR inhibition was confirmed at a protein level by ELISA as shown in FIG. 1G-H and FIG. 11. A similar result was found with afatinib, an irreversible EGFR inhibitor in various cell lines (FIG. 12). Afatinib also induced upregulation of TNF in a resistant cell line H1975 that harbors the EGFR T790M mutation rendering it resistant to first generation TKIs like erlotinib (FIG. 11G-H and FIG. 12D).

Figure 1M:
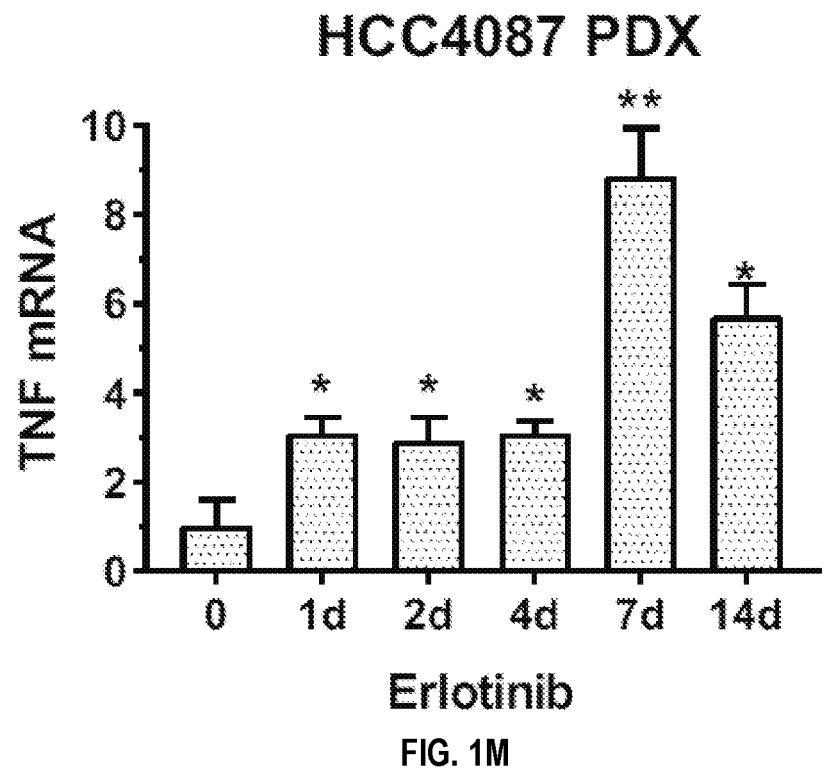
Figure 1N:
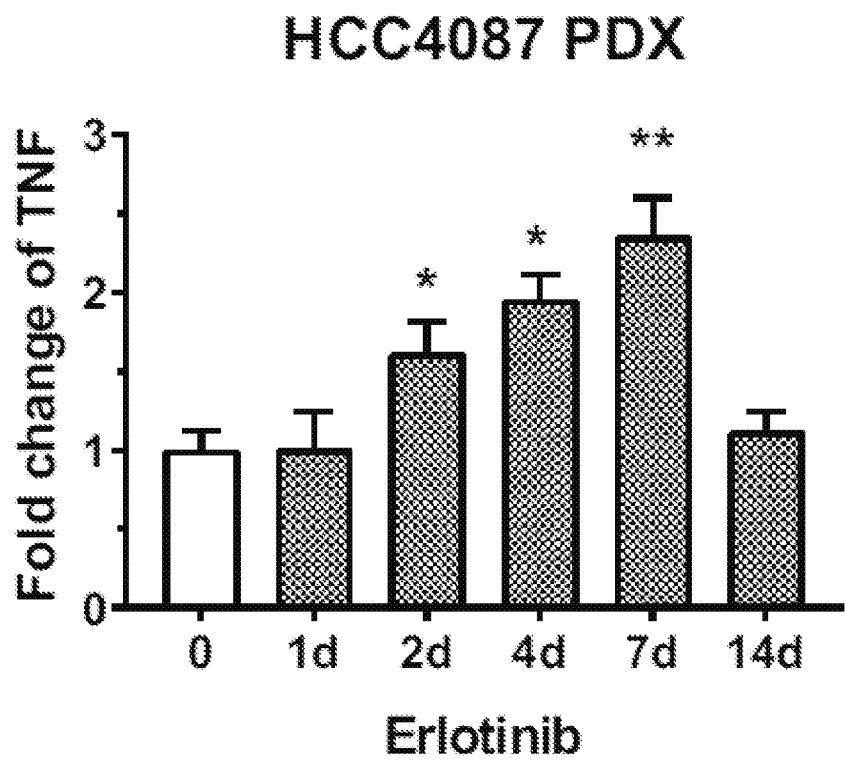
Figure 23A:
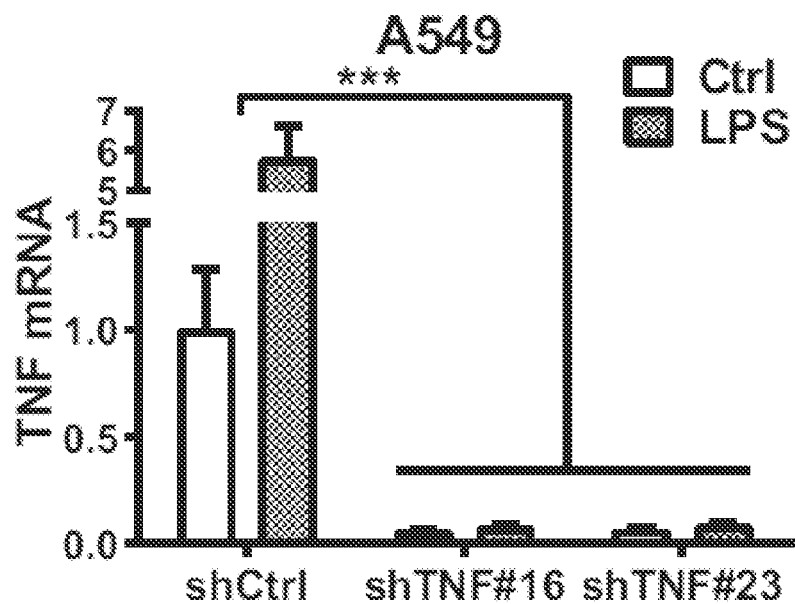
Figure 23B:
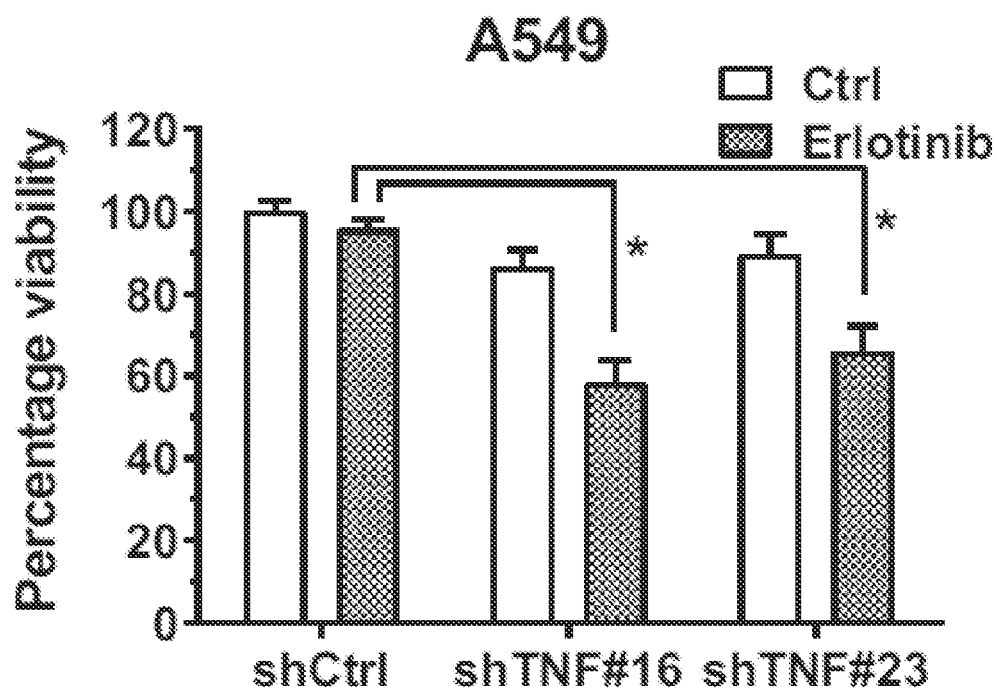
Figure 23C:
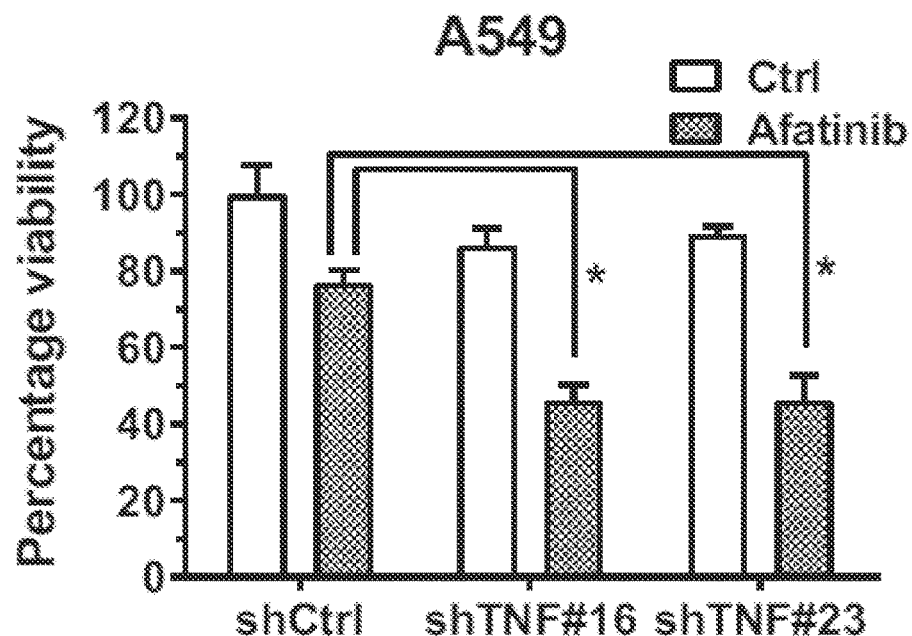
Figure 23D:
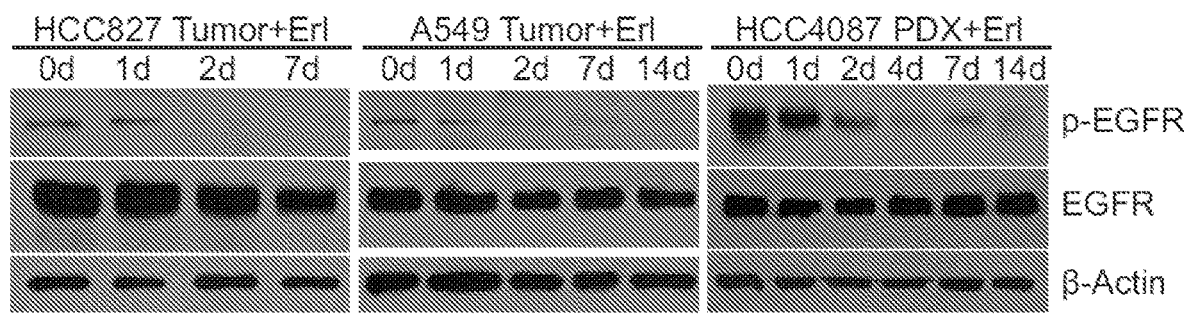

Erlotinib also induced upregulation of TNF in tumors growing in mice. Athymic mice were inoculated with EGFR mutant HCC827 or EGFRwt NSCLC A549 cells. Following formation of subcutaneous tumors, mice were treated with erlotinib for various time points. This was followed by removal of tumors. As is shown in FIG. 1I-L, TNF is increased in tumors generated with either EGFRwt expressing lung cancer cell line A549 or EGFR mutant expressing lung cancer cell lines (HCC827) upon treatment with erlotinib. Importantly, increased TNF was also detected in a NSCLC PDX derived from EGFR expressing NSCLC (HCC 4087) without EGFR activating mutations, growing in NOD-SCID mice and treated with erlotinib for the indicated time points (FIG. 1M-N and FIG. 23D).

EGFR Activation Leads to Decrease in TNF Mrna

Figure 13A:
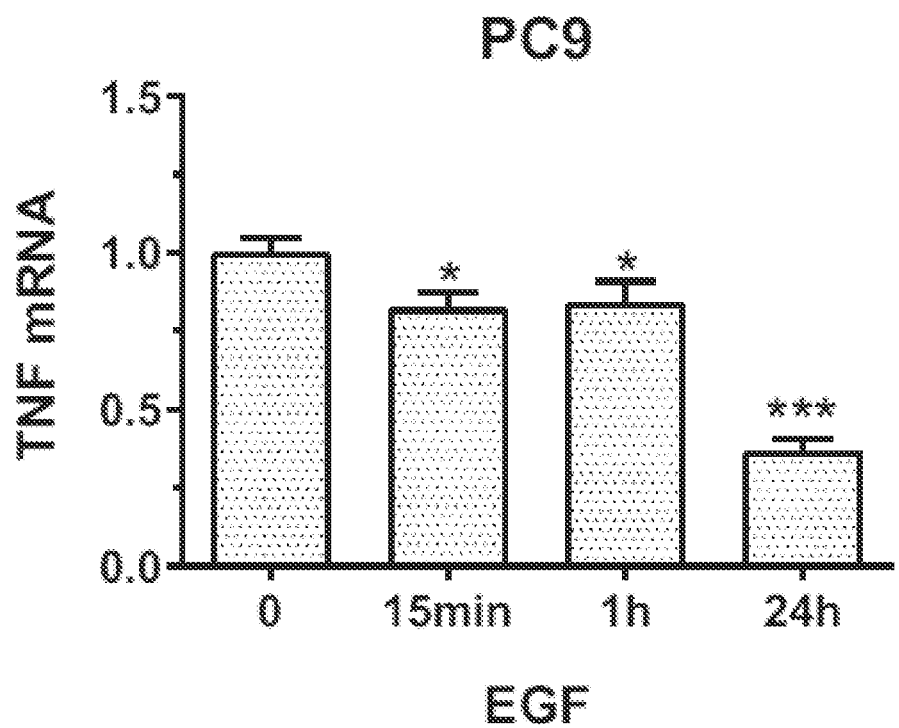
Figure 13B:
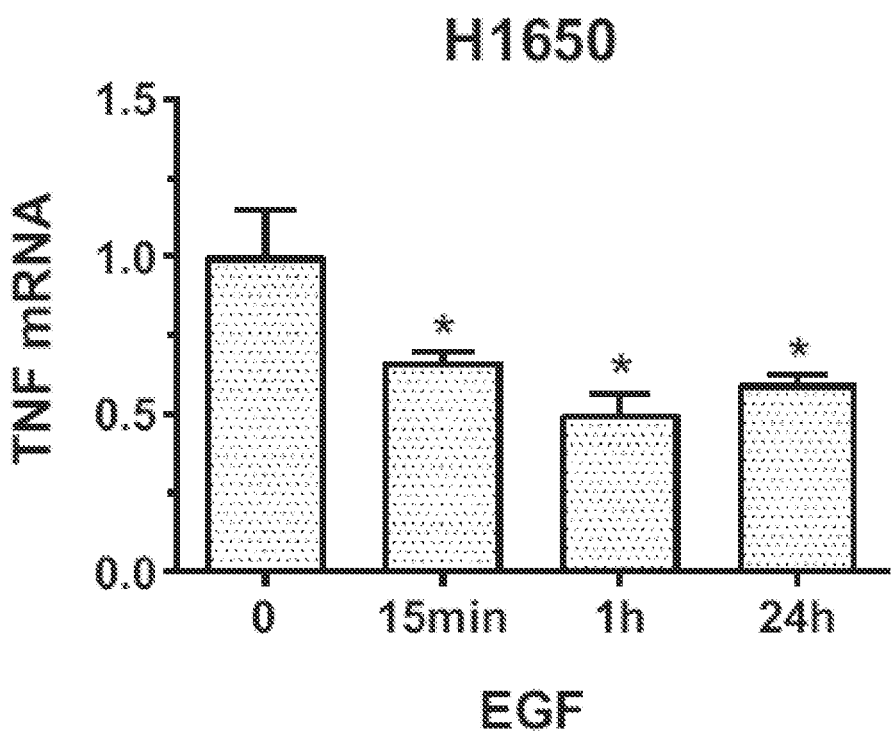
Figure 13C:
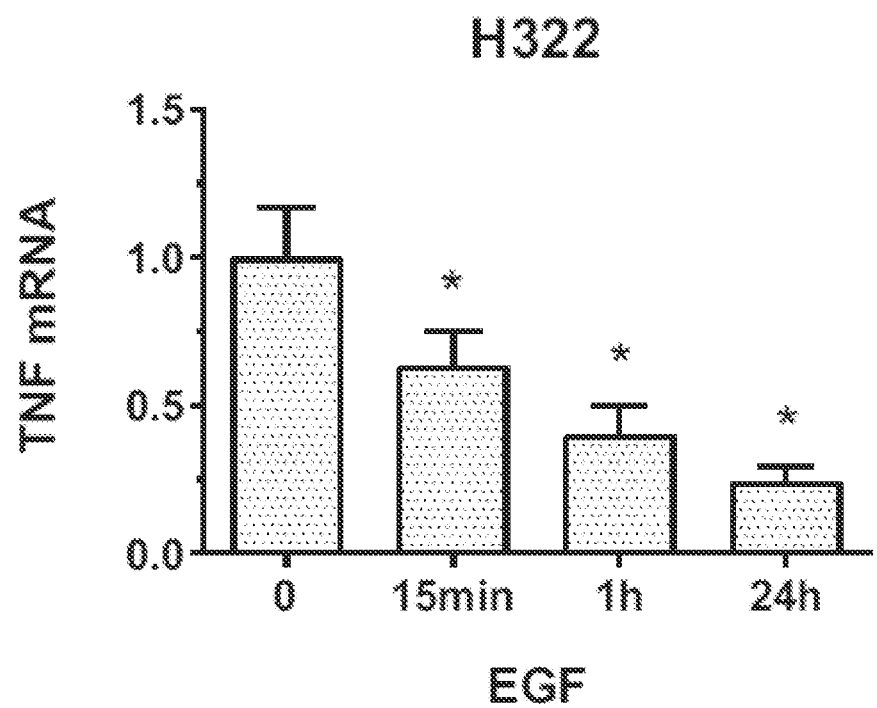
Figure 13D:
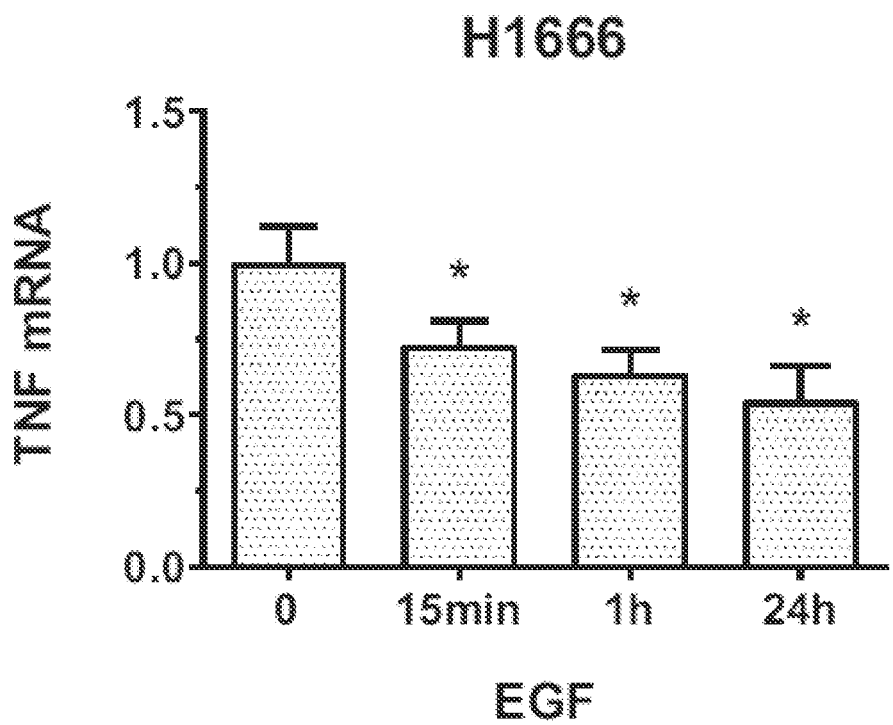
Figure 13E:
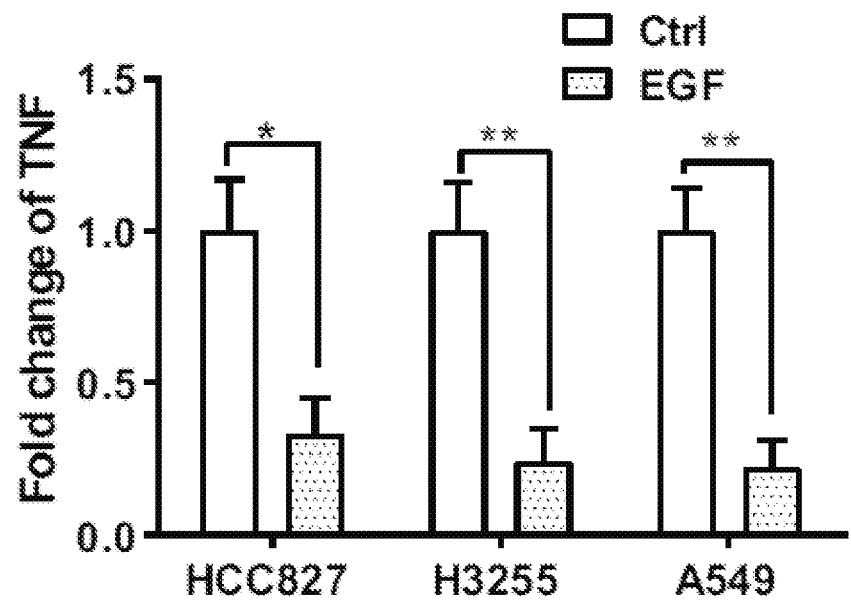
Figure 13F:
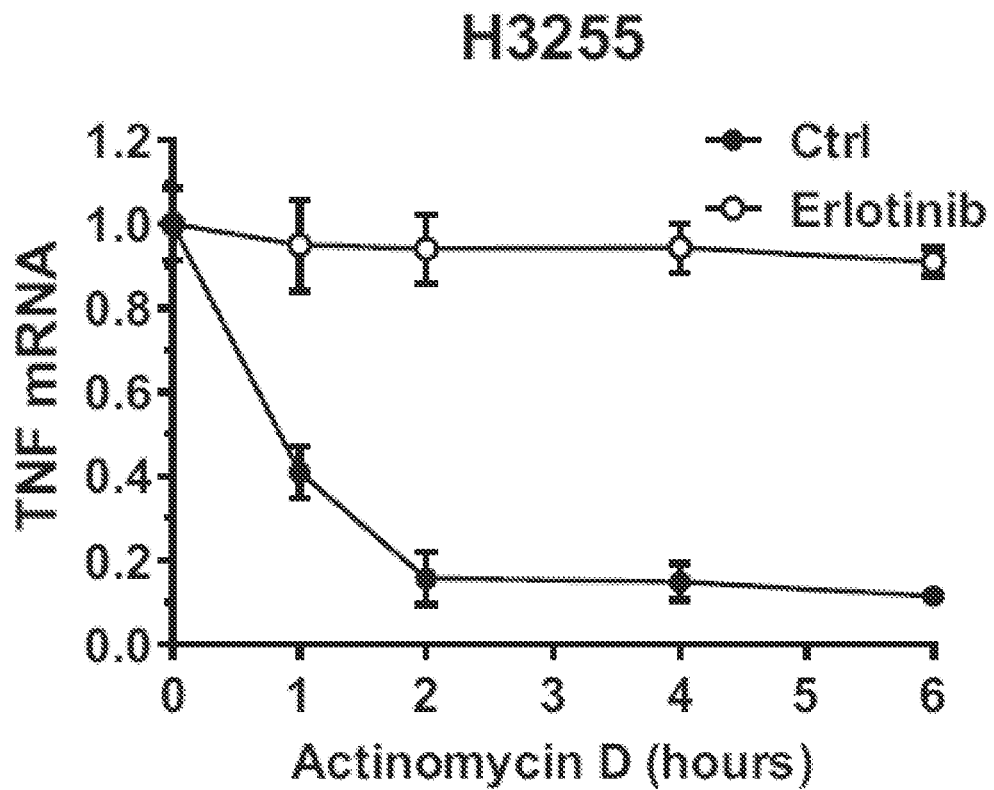
Figure 13G:
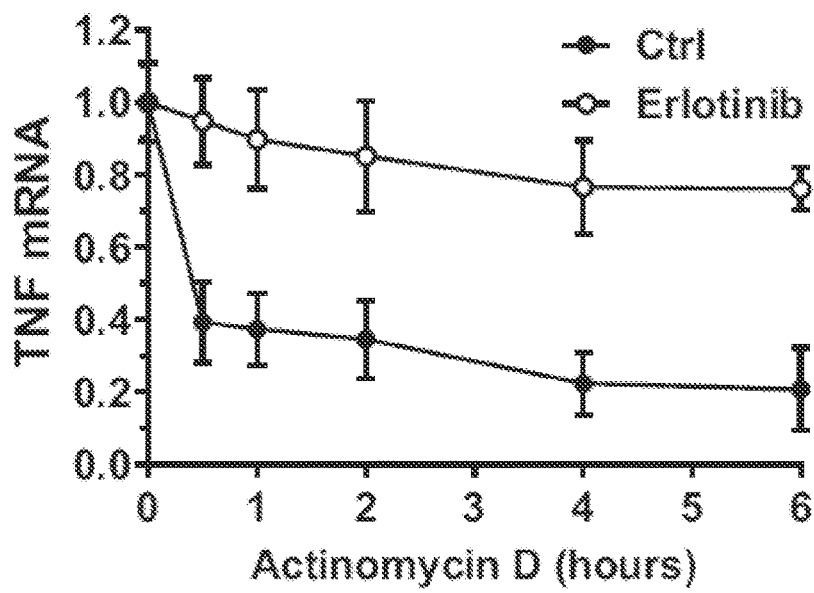
Figure 13H:
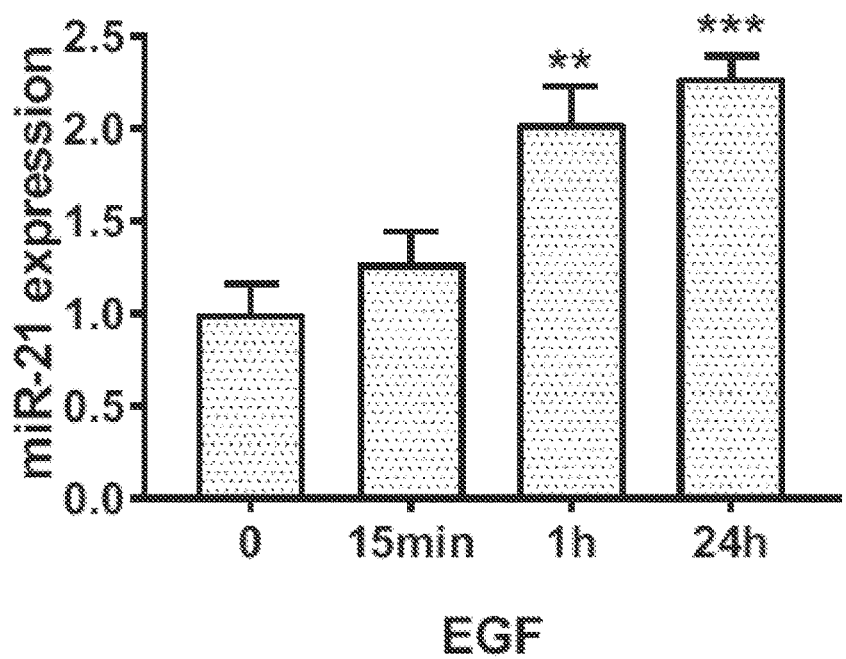
Figure 13I:
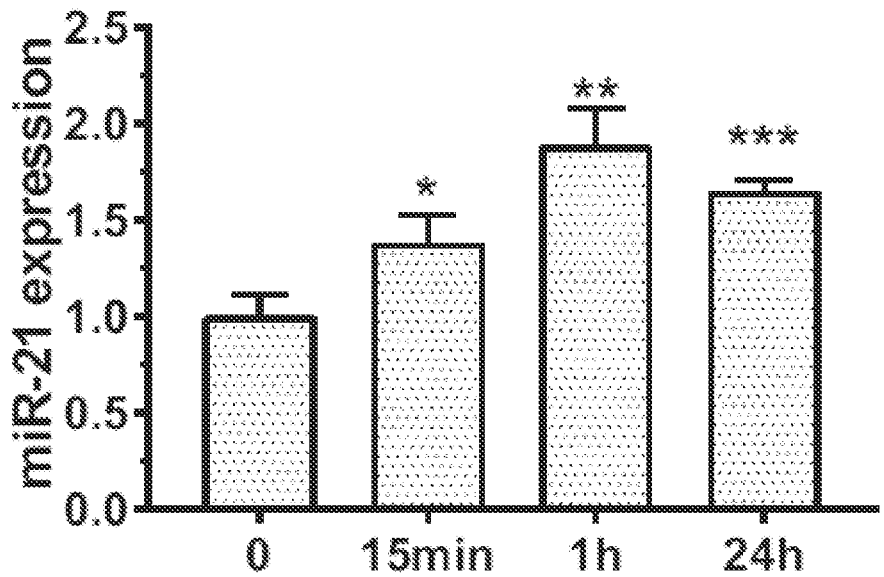
Figure 13J:
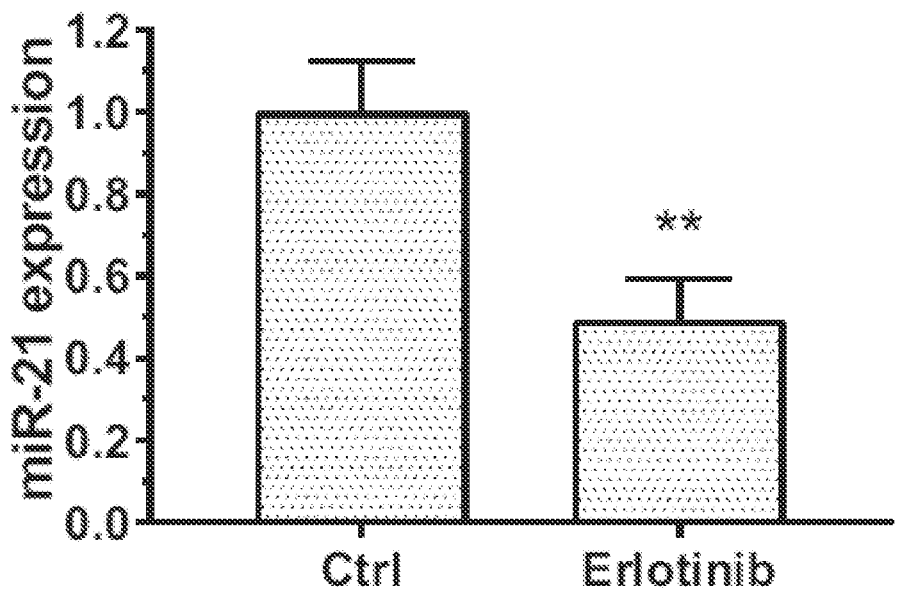
Figure 13K:
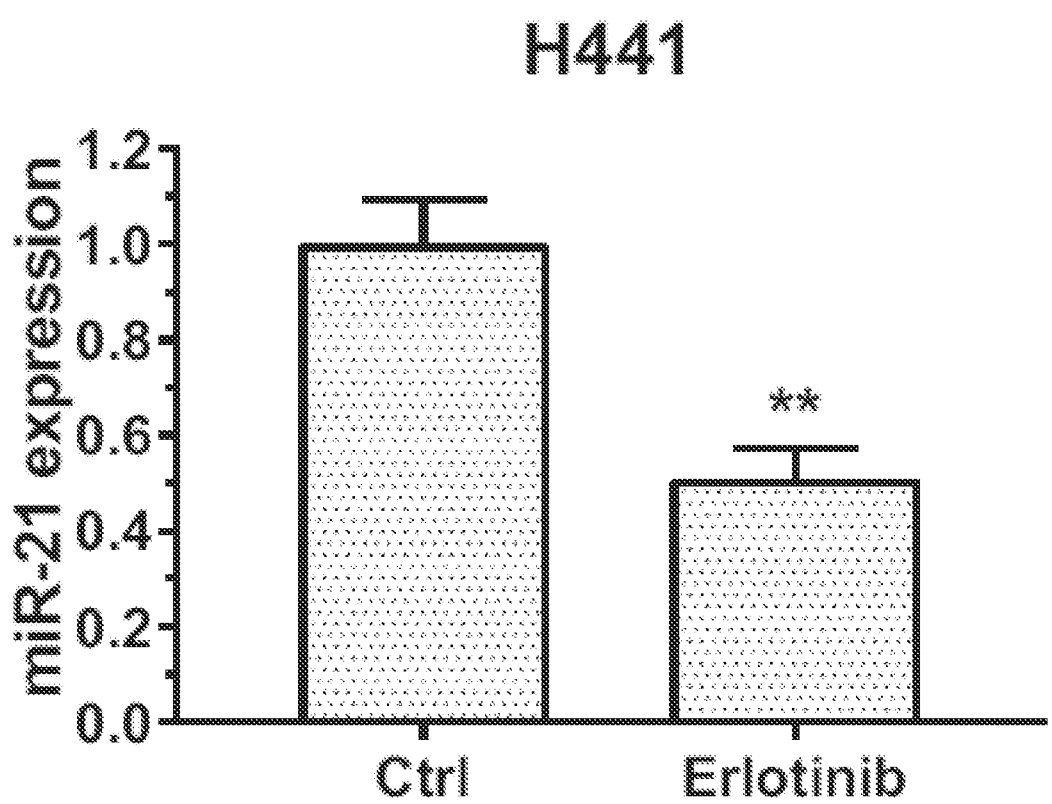
Figure 14A:
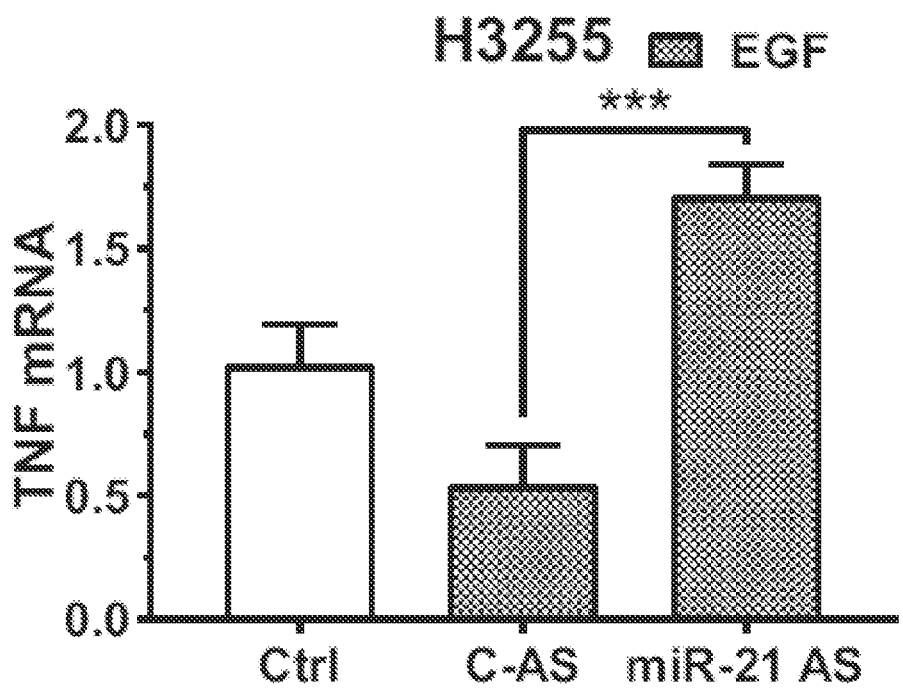
Figure 14B:
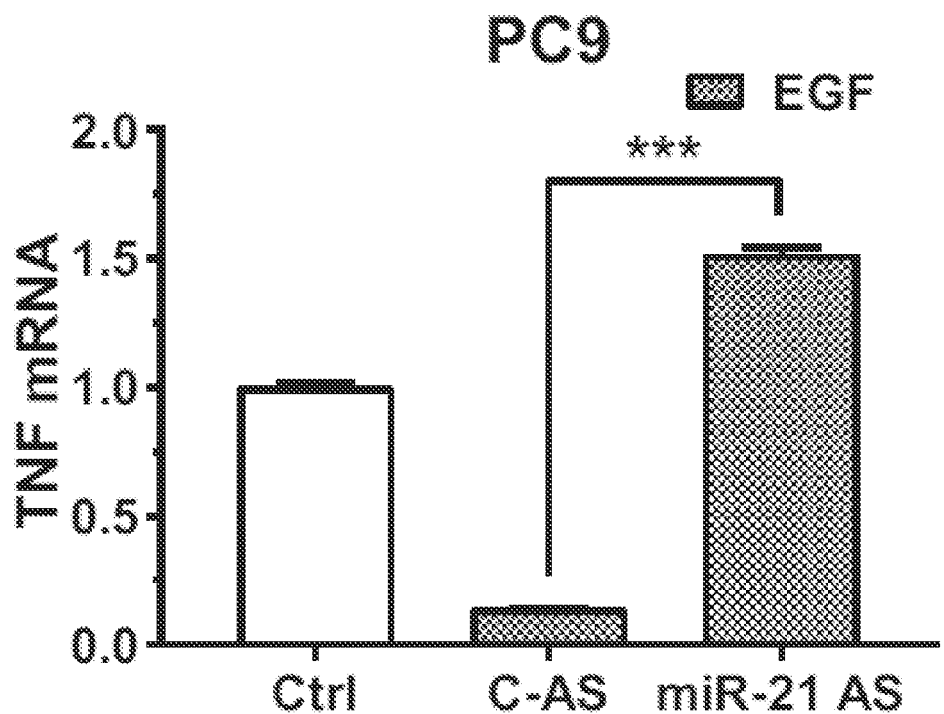
Figure 14C:
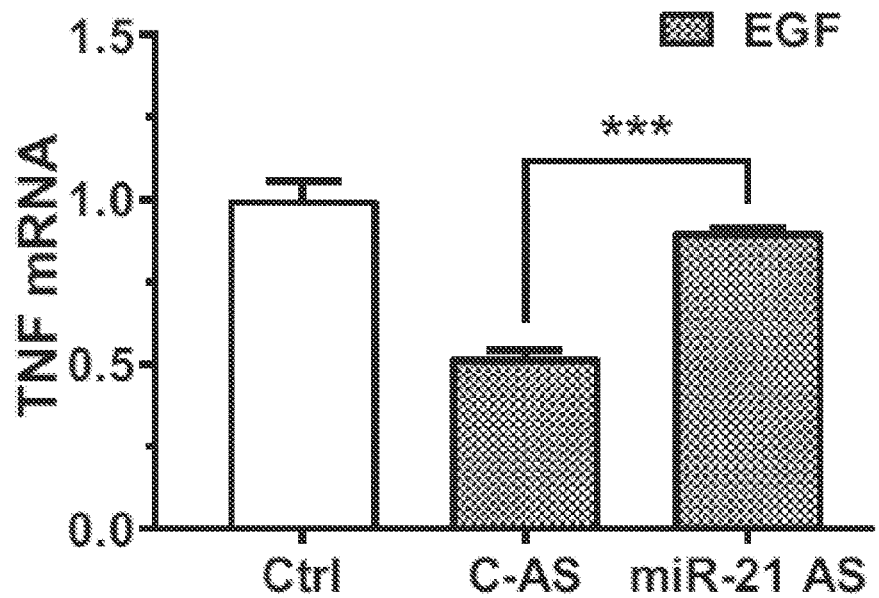
Figure 14D:
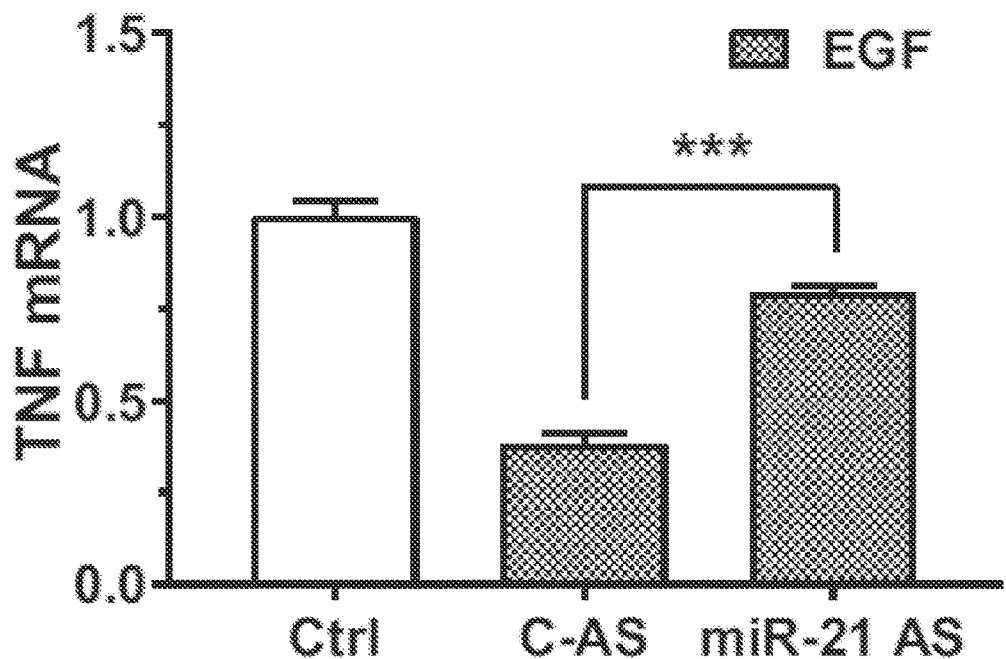
Figure 14E:
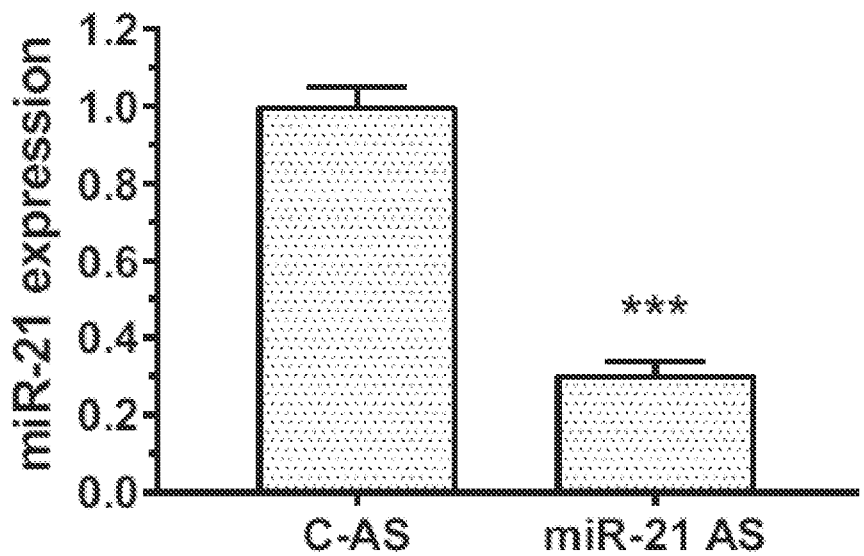
Figure 14F:
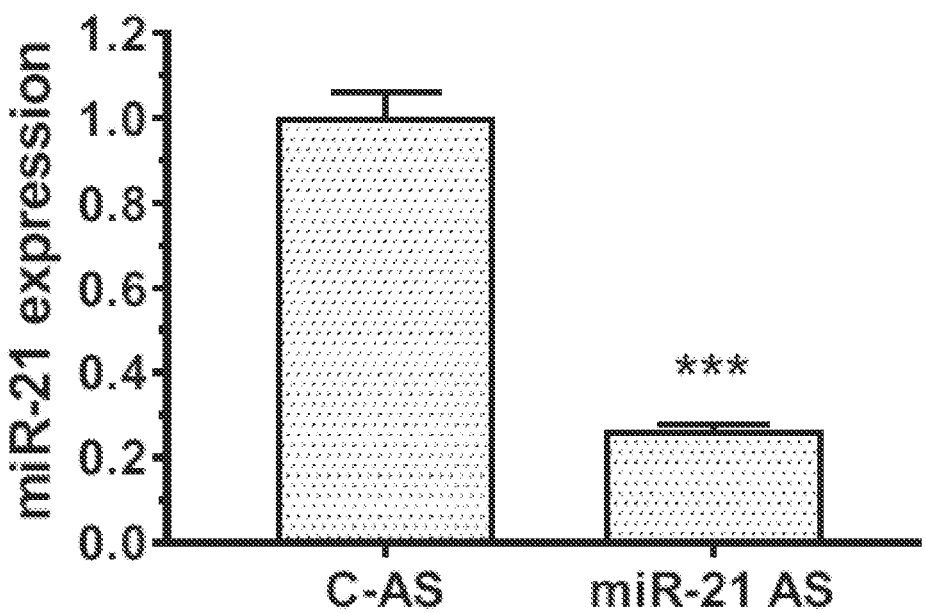
Figure 14G:
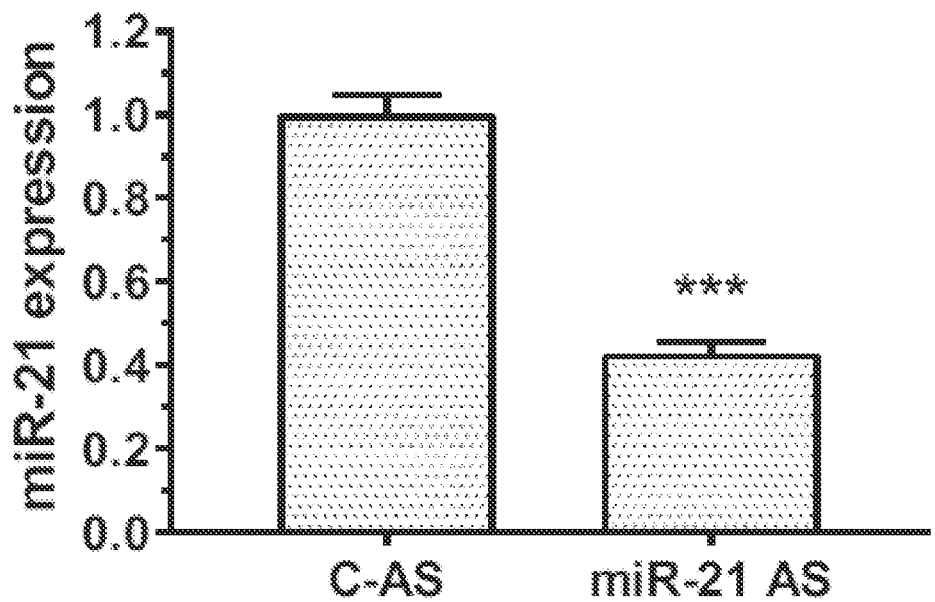
Figure 14H:
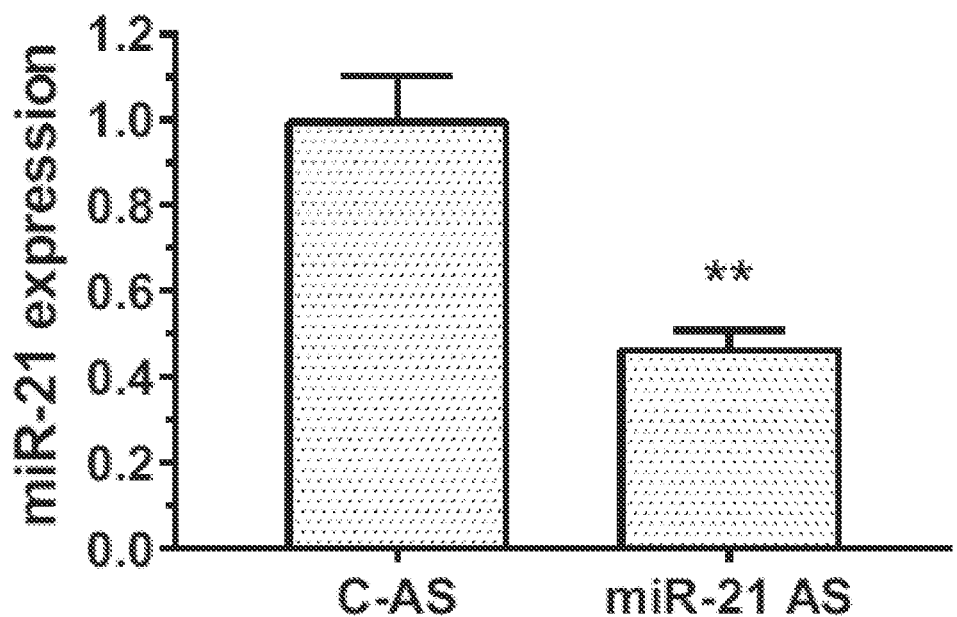

The increase in TNF mRNA following EGFR inhibition suggests that the EGFR is either actively suppressing TNF levels, or the rise in TNF could be secondary to a feedback mechanism. To examine a direct suppression, cells were treated with EGF to activate the EGFR and the TNF mRNA level was determined. As can be seen in FIG. 2A-D and FIG. 13A-D, EGF-mediated activation of the EGFR results in a rapid decrease in TNF mRNA levels in both EGFR mutant as well as EGFRwt cell lines. This decrease in TNF mRNA can be detected as early as 15 minutes after EGF exposure, suggesting an effect on TNF mRNA stability rather than transcription. This finding would suggest that EGFR signaling normally keeps the TNF level low and a loss of EGFR signaling results in increased TNF. The EGFR induced decrease in TNF at a protein level was confirmed by ELISA (FIG. 13E). Next, whether EGFR activity influences TNF mRNA stability was examined using Actinomycin D as an inhibitor of transcription. As can be seen in FIG. 2E-F and FIG. 13F-G, inhibition of the EGFR with erlotinib leads to an increase in TNF mRNA stability.

EGFR Regulates TNF mRNA via Expression of MicroRNA-21

Figure 2A:
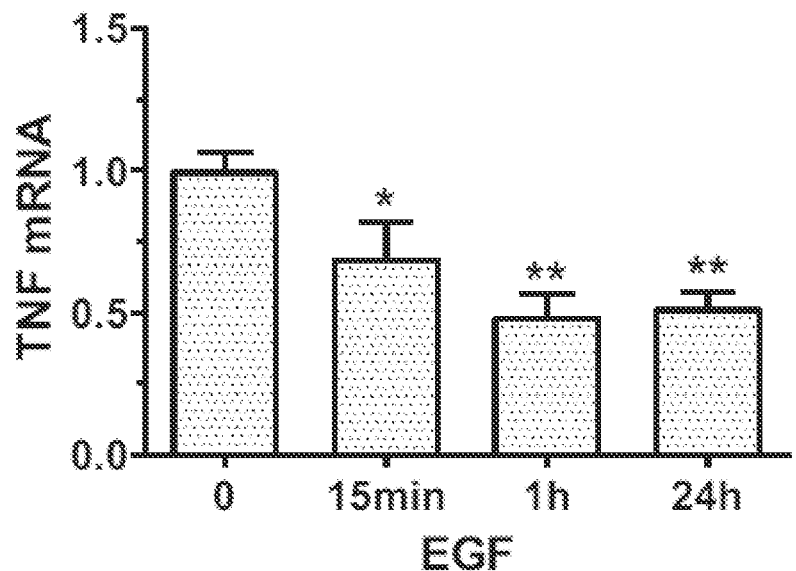
Figure 2B:
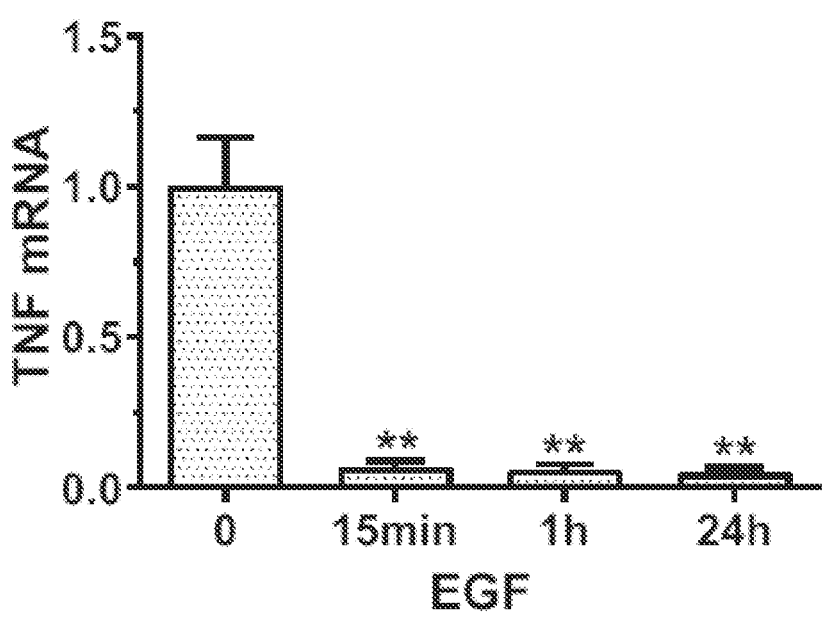
Figure 2C:
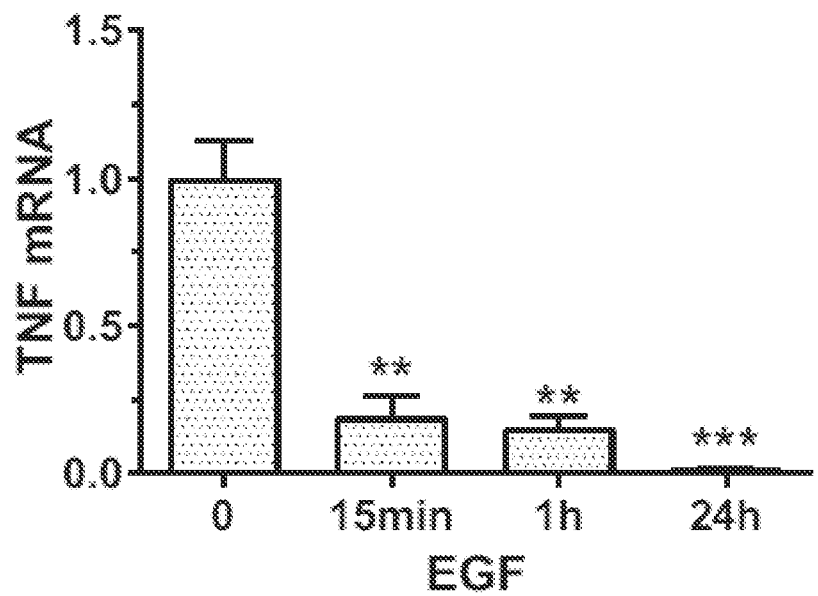
Figure 2D:
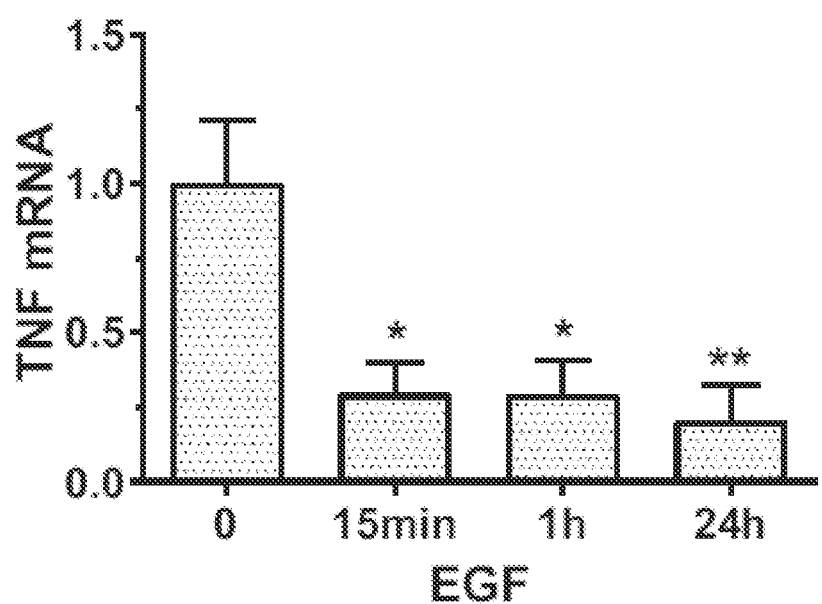
Figure 2E:
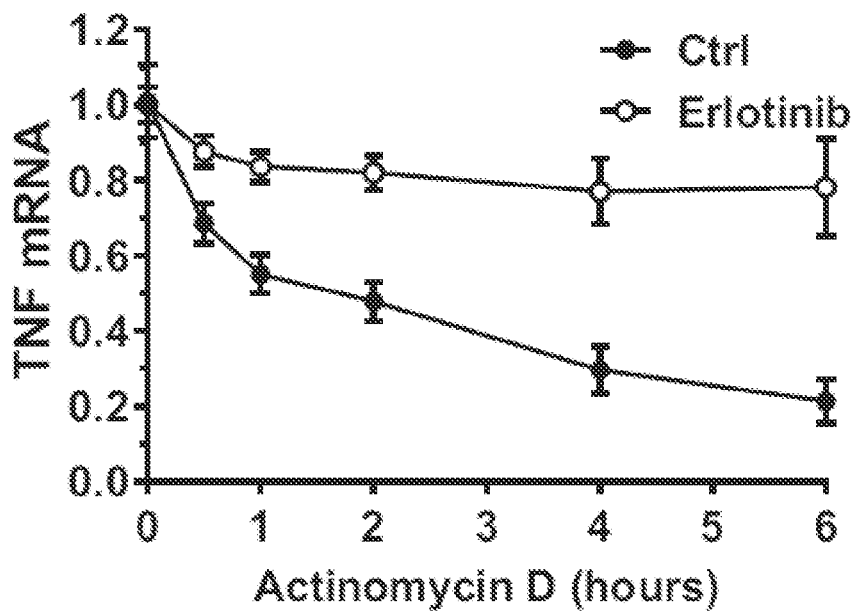
Figure 2F:
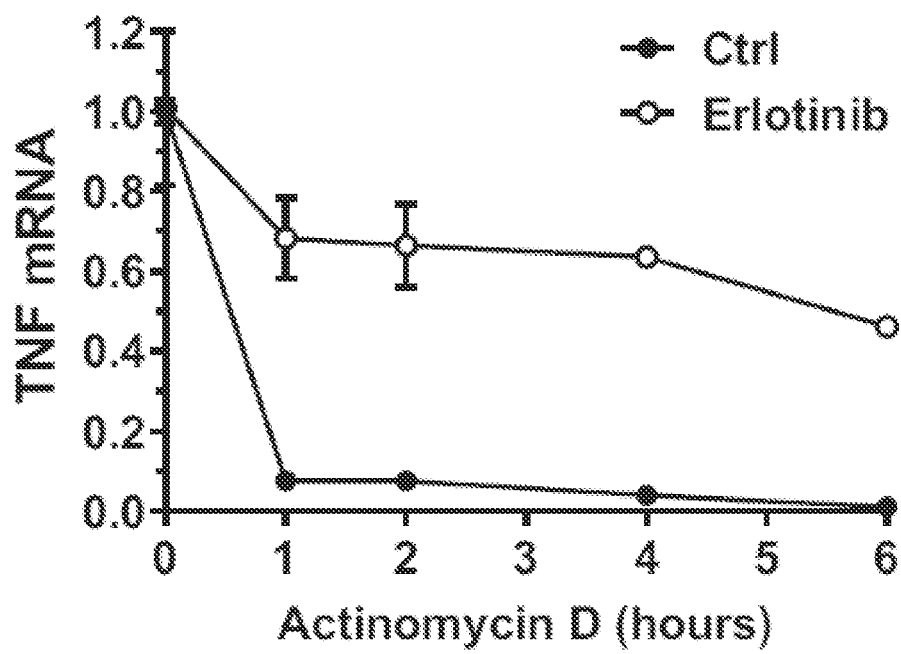
Figure 2G:
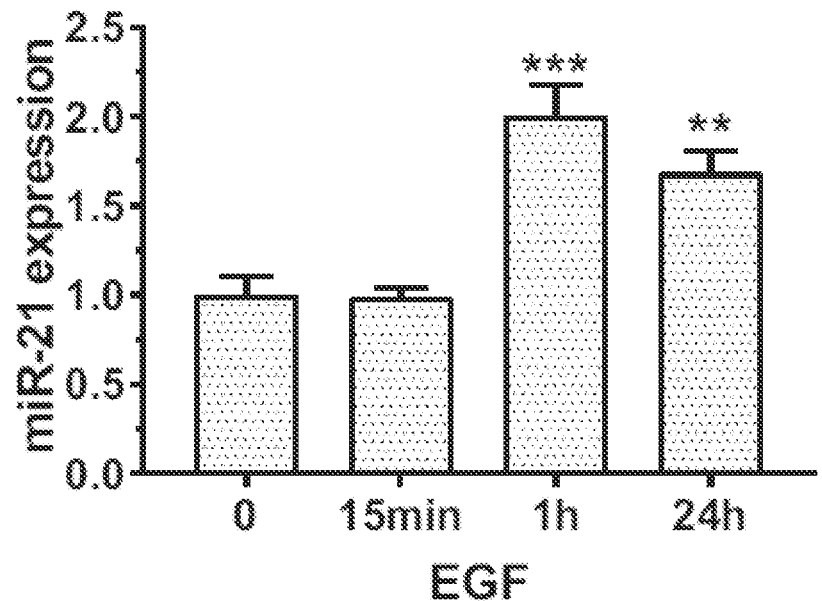
Figure 2H:
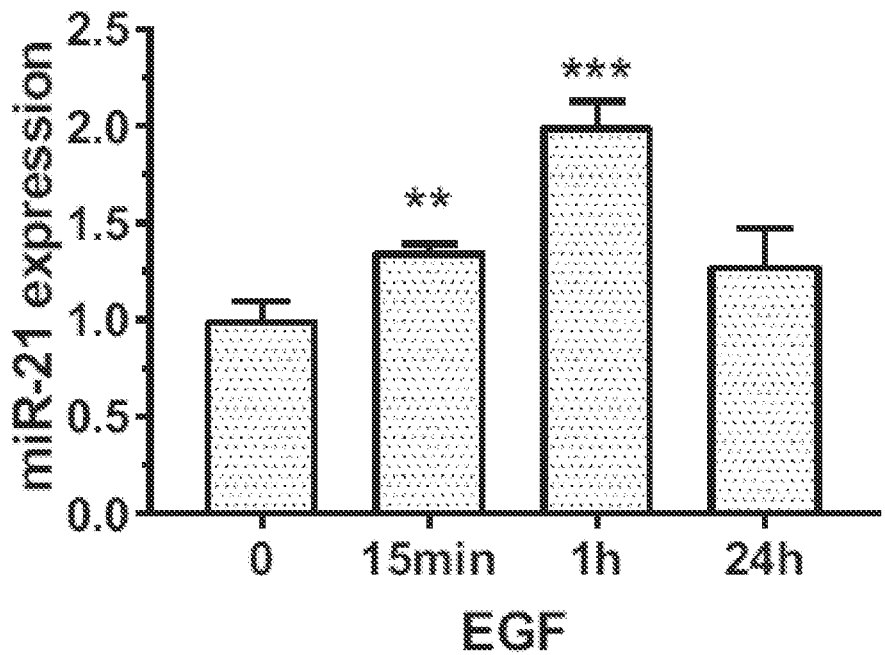
Figure 2I:
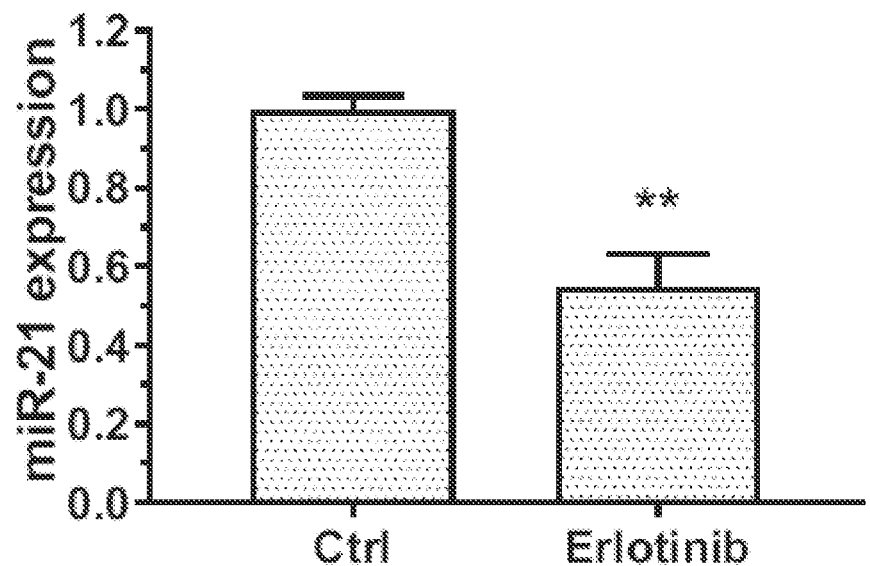
Figure 2J:
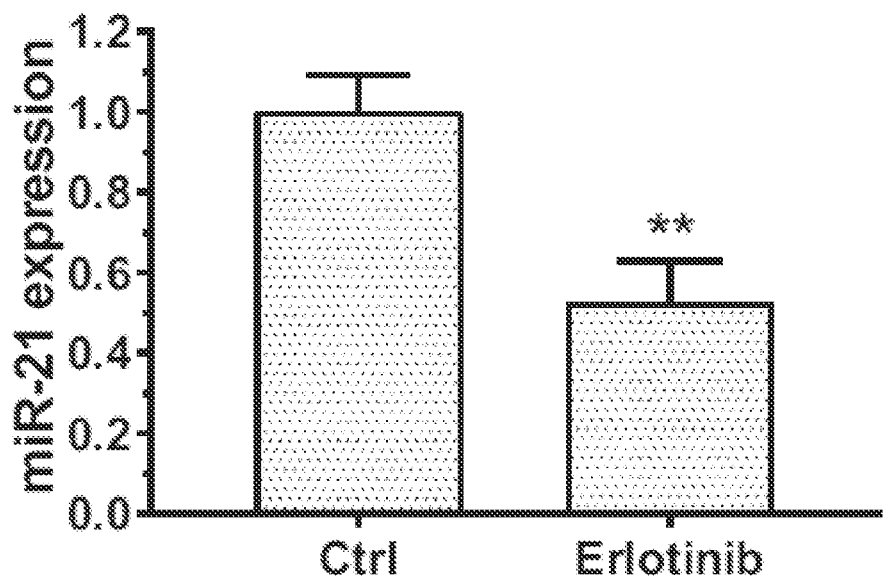
Figure 2K:
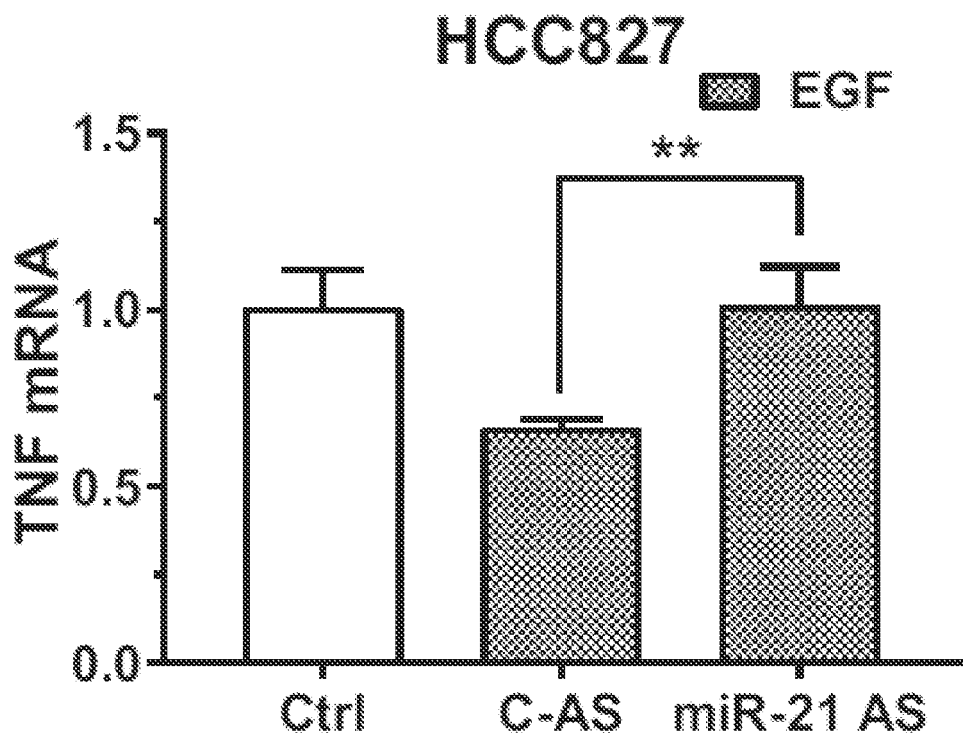
Figure 2L:
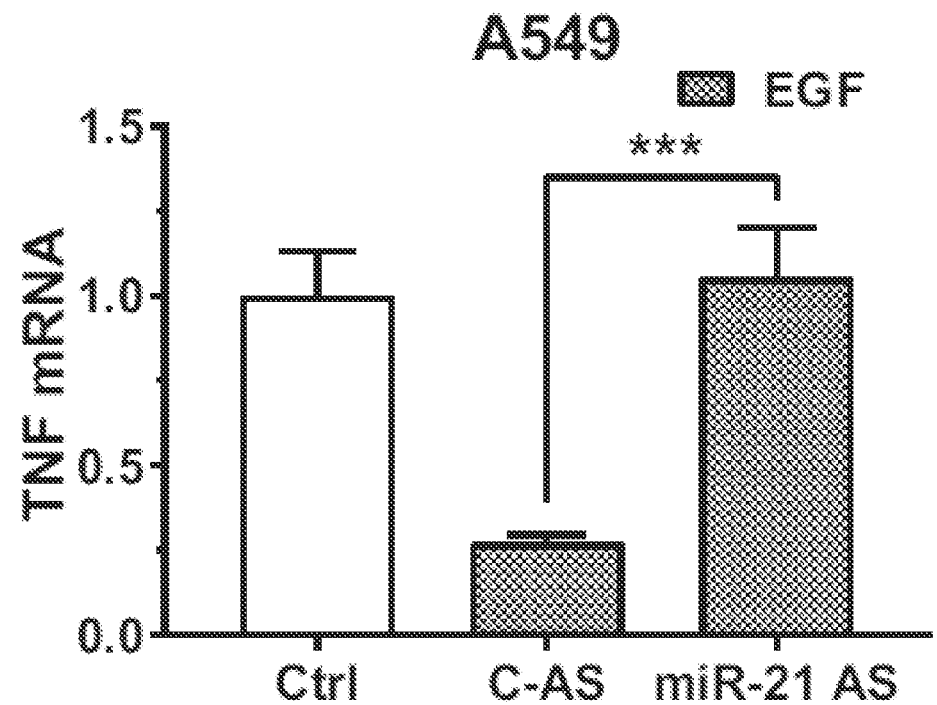
Figure 2M:
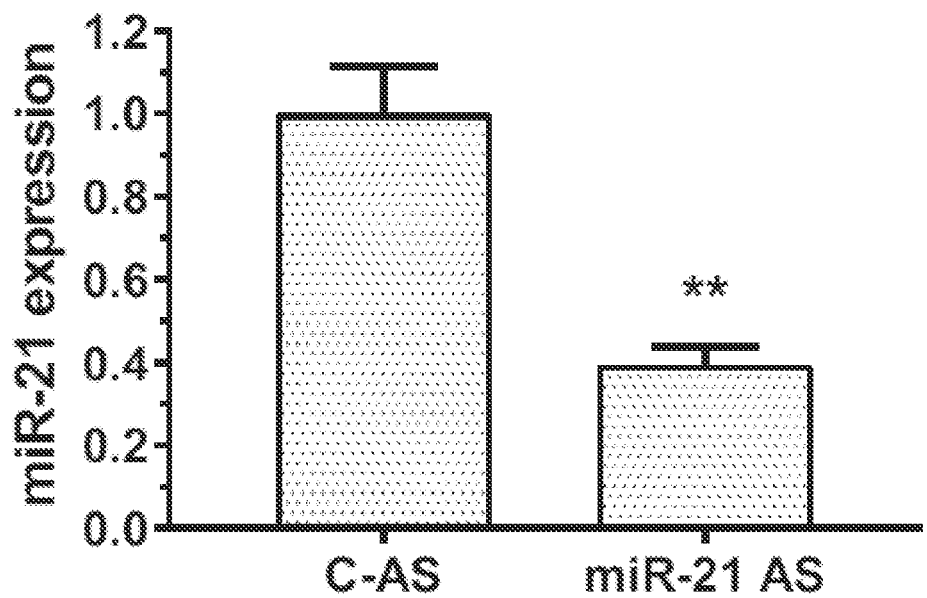
Figure 2N:
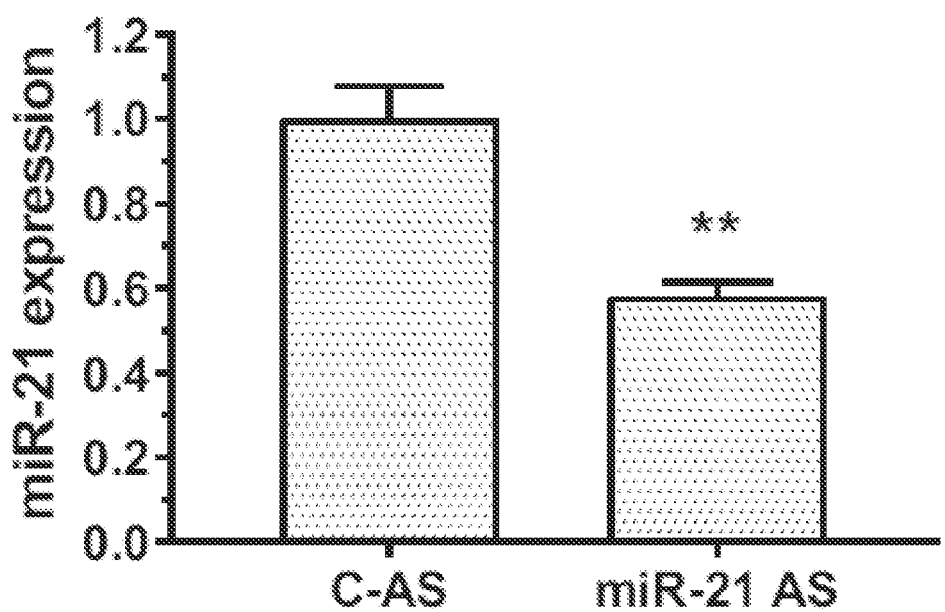

MicroRNAs represent an important and rapidly inducible mechanism of regulating mRNA stability and translation. Previous studies have demonstrated that EGFR regulates the expression of specific miRNAs in lung cancer cells. Importantly, studies have shown that EGFR regulates miRNA levels in lung cancer. We hypothesized that EGFR activity may regulate TNF mRNA stability by a mechanism involving expression of specific miRNA. Previous studies have also reported that miR-21, one of the microRNAs that is regulated by EGFR activity in lung cancer cells, is also known to negatively regulate TNF mRNA levels. Thus, microRNA mediated regulation of TNF mRNA seemed like a plausible mechanism of rapid regulation of TNF mRNA stability by EGFR signaling. We first confirmed the upregulation of miR-21 by EGFR activity and its downregulation by EGFR inhibition in multiple lung cancer cell lines as shown in FIG. 2G-J and FIG. 13H-K. Next, we examined the effect of antisense miR-21 on EGFR induced downregulation of TNF. Indeed, we find that inhibition of miR-21 results in a rescue of EGF-induced downregulation of TNF in multiple EGFR mutant and EGFRwt cell lines (FIG. 2K-L and FIG. 14A-D). We confirmed miR-21 inhibition by real time quantitative PCR (FIG. 2M-N and FIG. 14 E-H).

Erlotinib Induced NF-κB Activation is Mediated by TNF

Figure 3A:
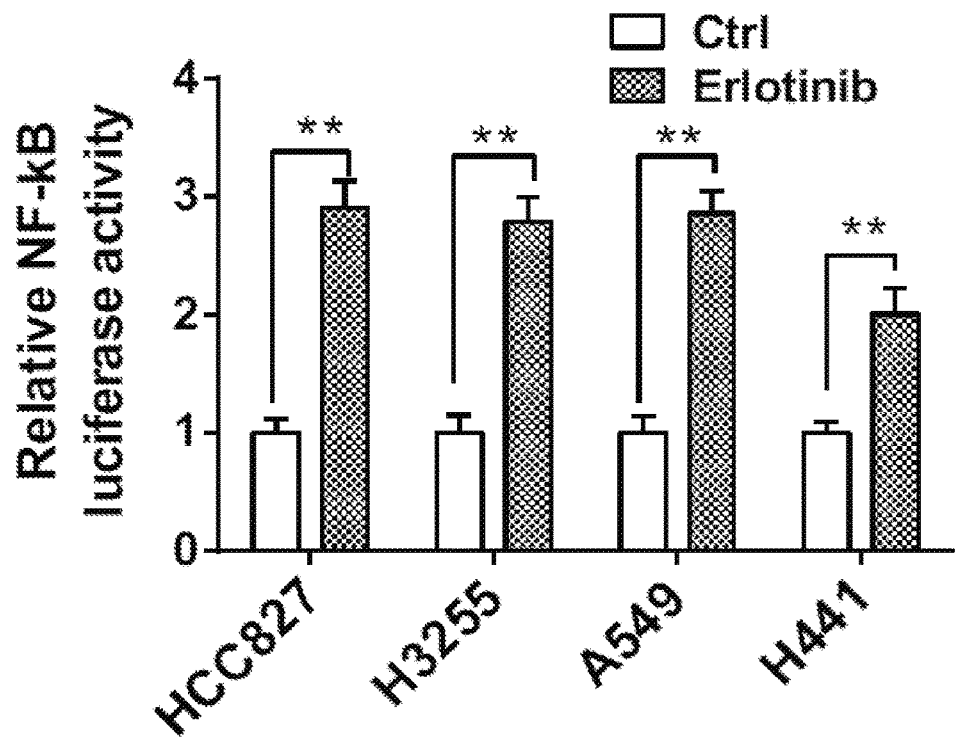
Figure 3B:
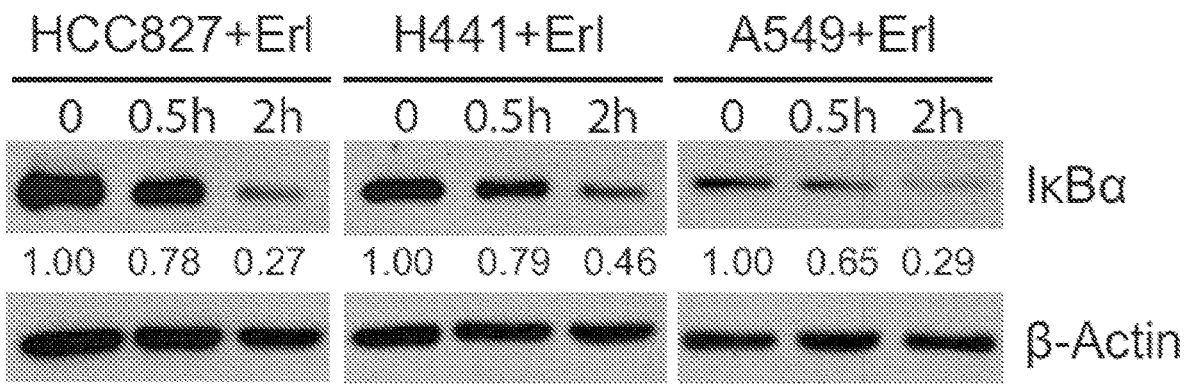
Figure 3C:
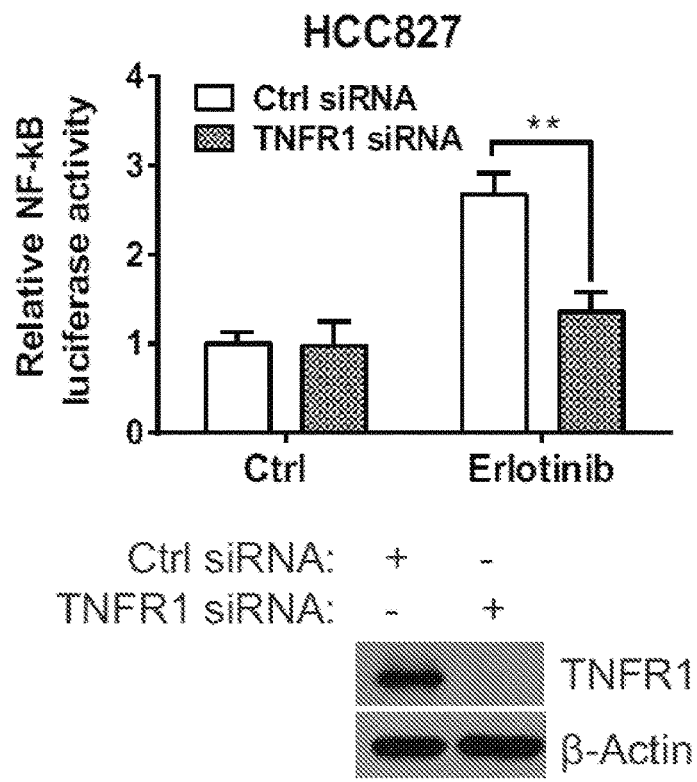
Figure 3D:
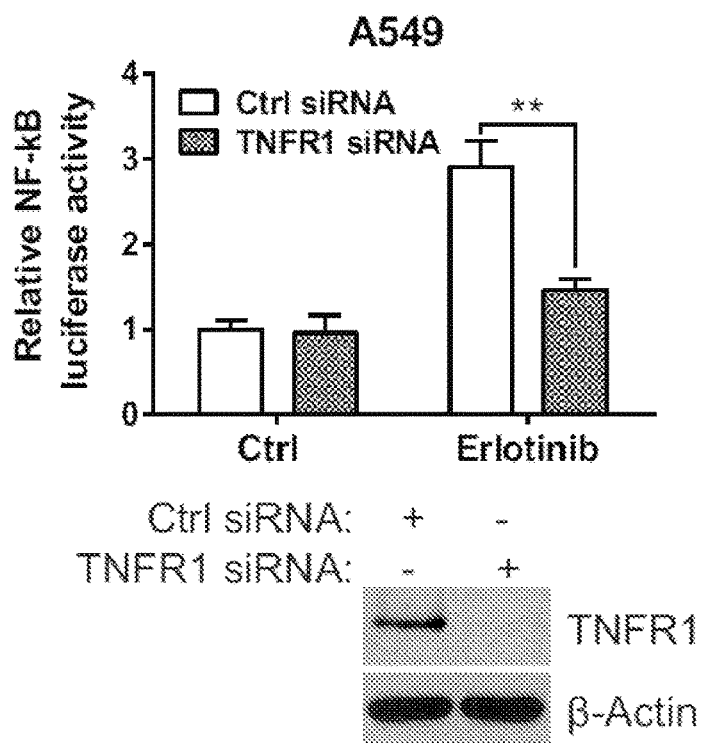
Figure 3E:
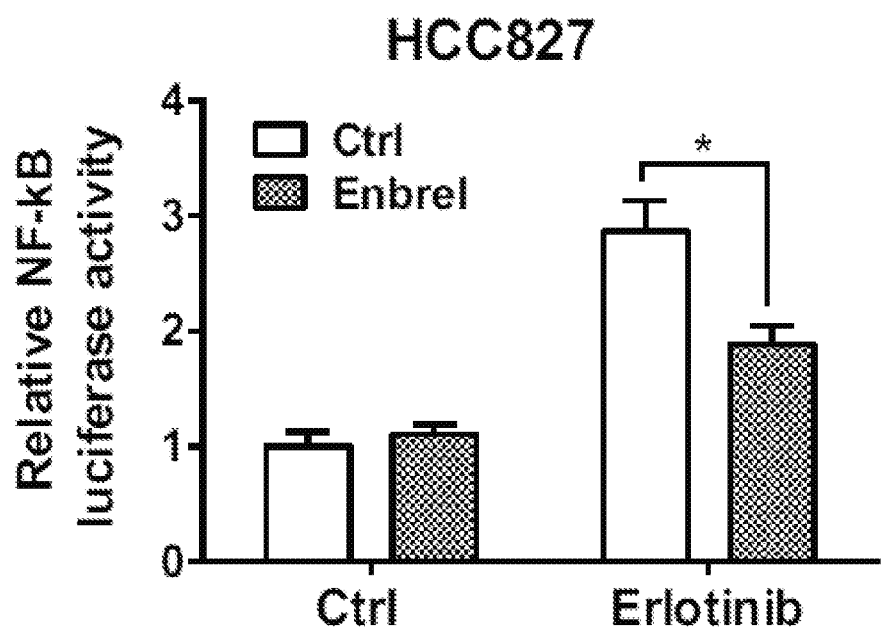
Figure 3F:
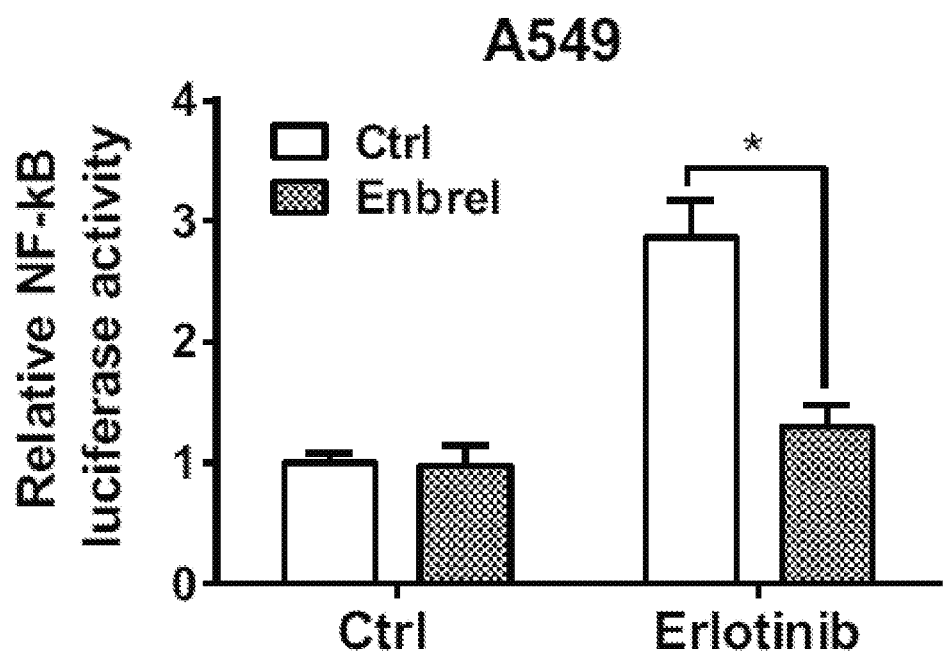
Figure 3G:
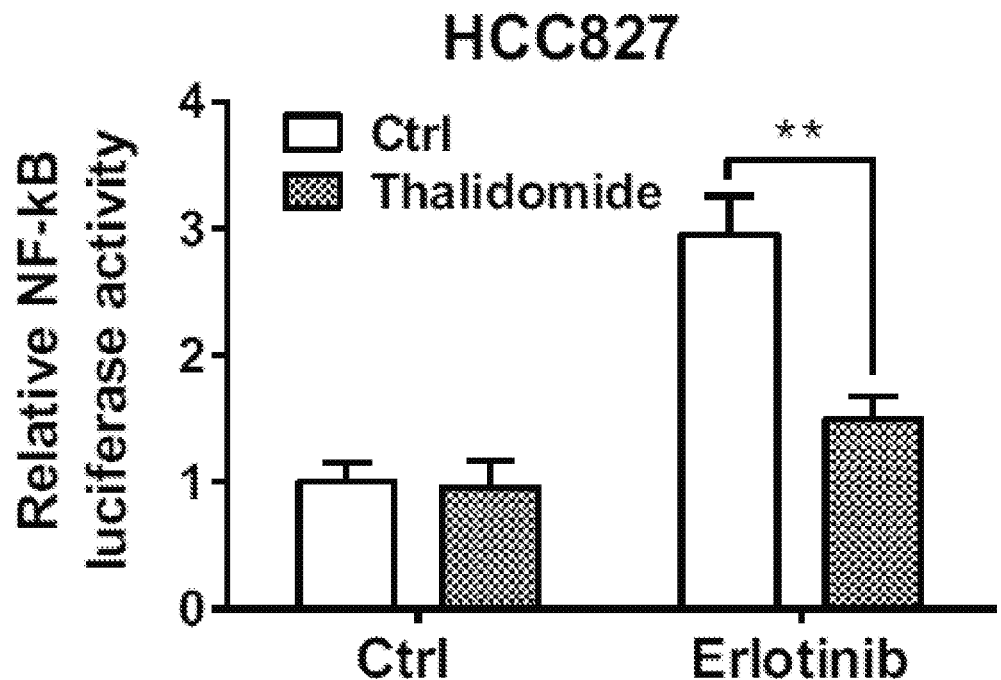
Figure 3H:
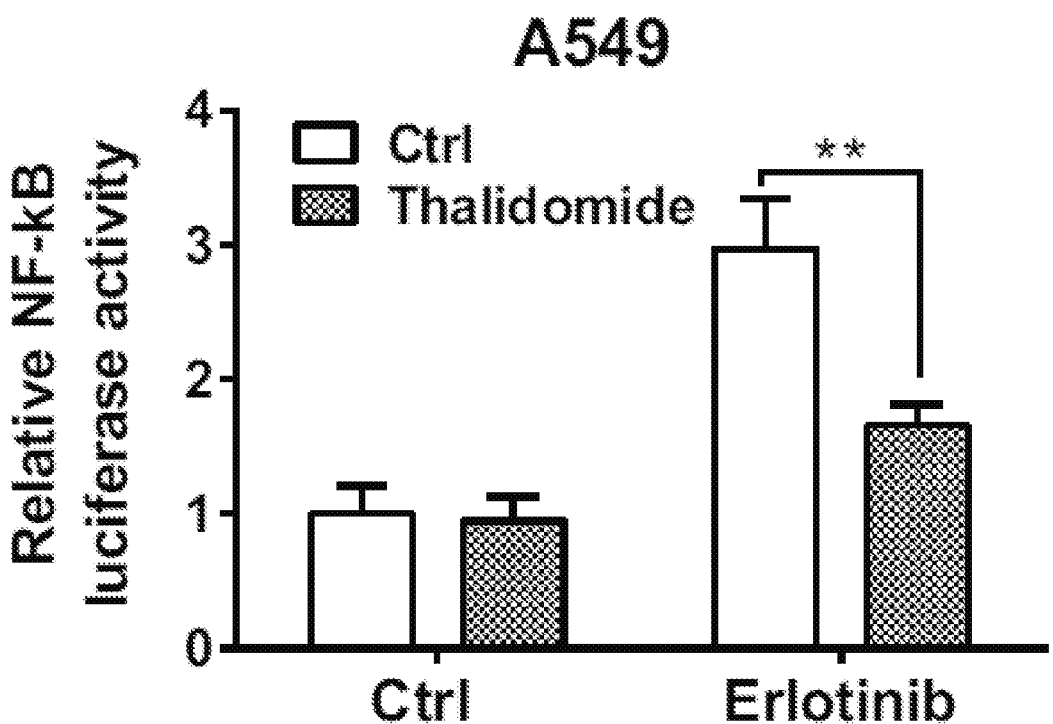
Figure 3I:
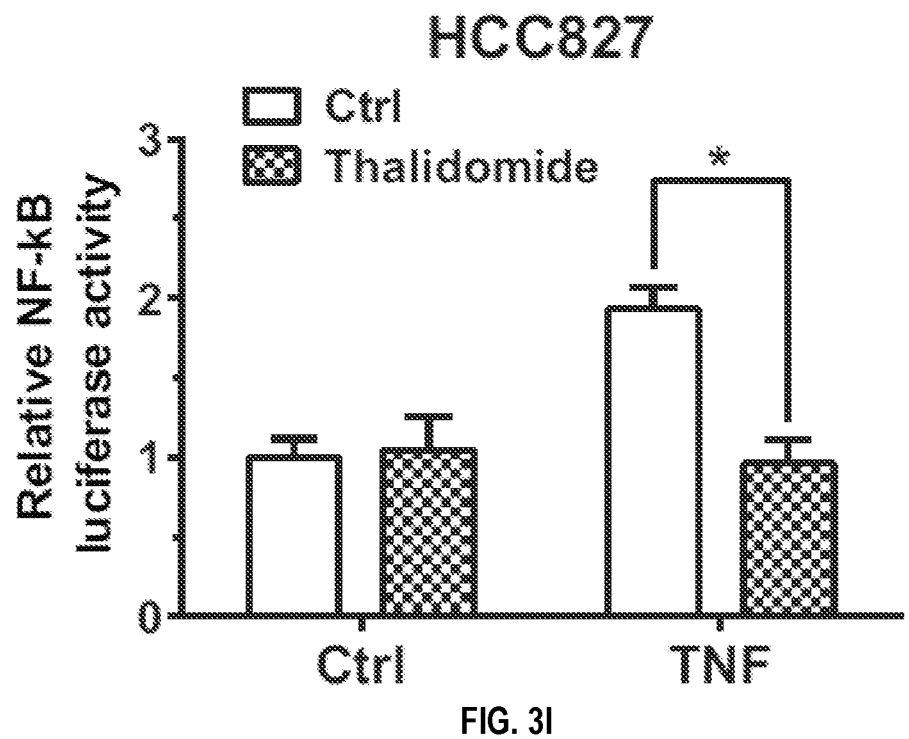
Figure 3J:
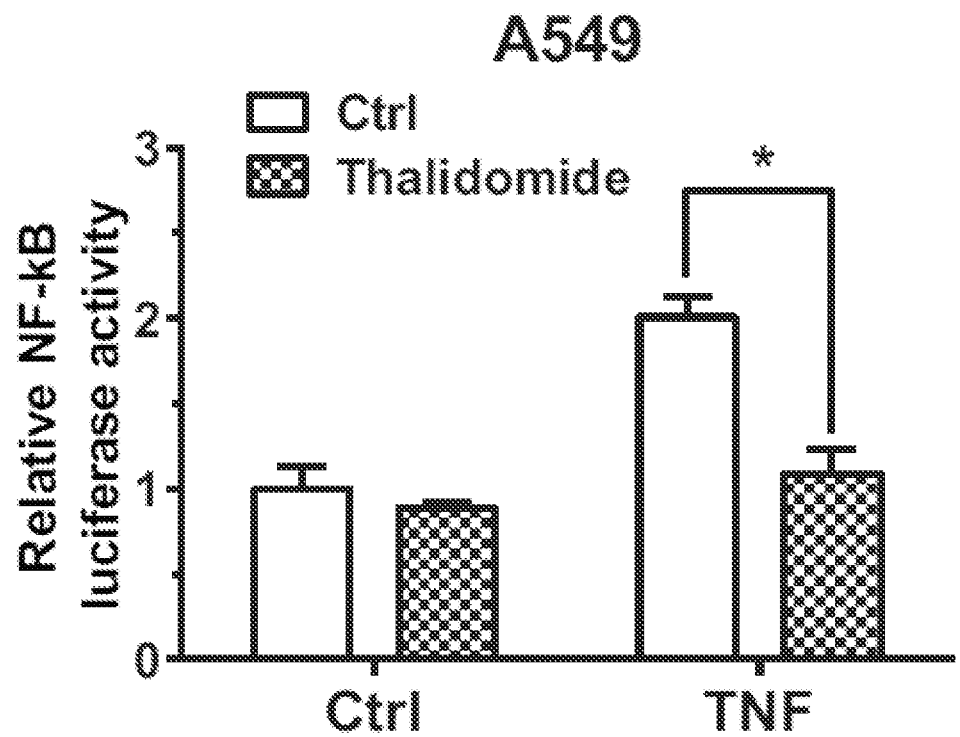
Figure 15A:
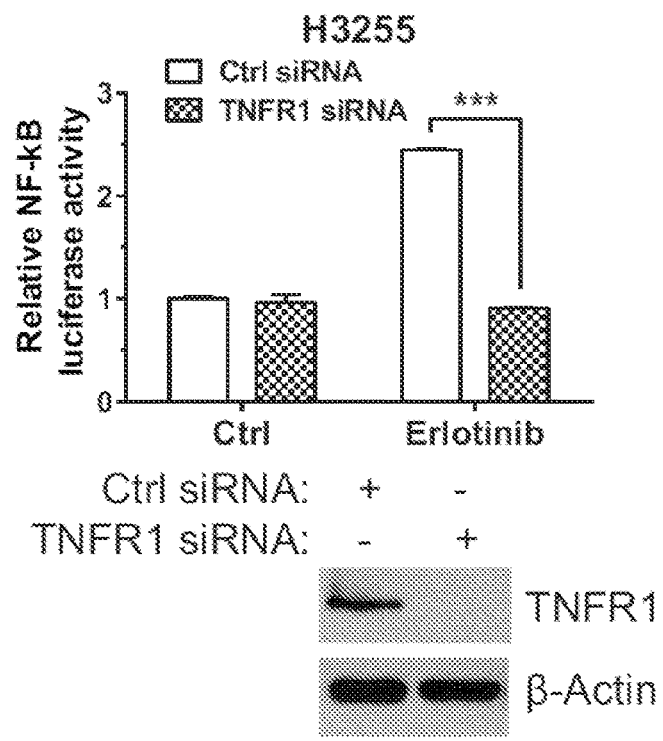
Figure 15B:
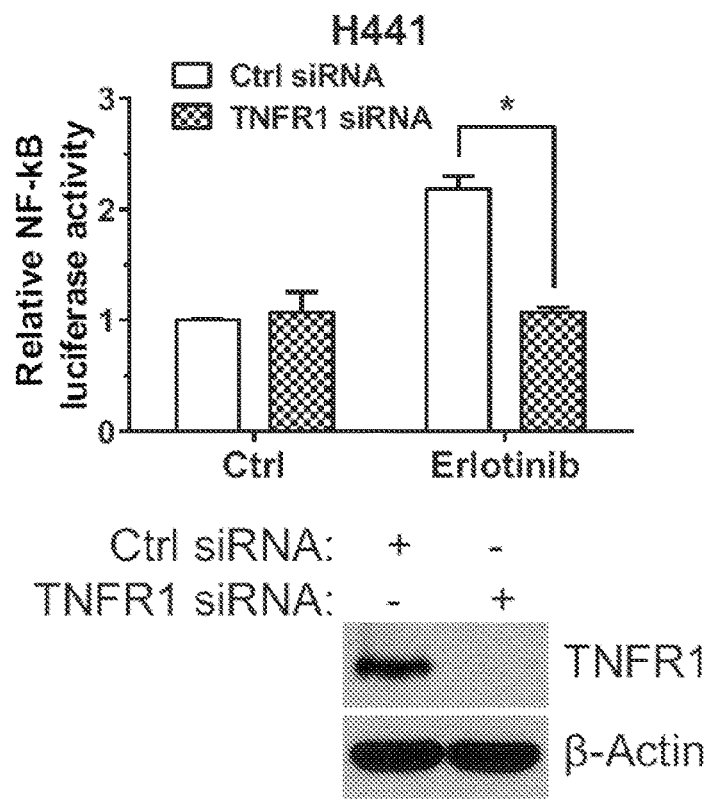
Figure 15C:
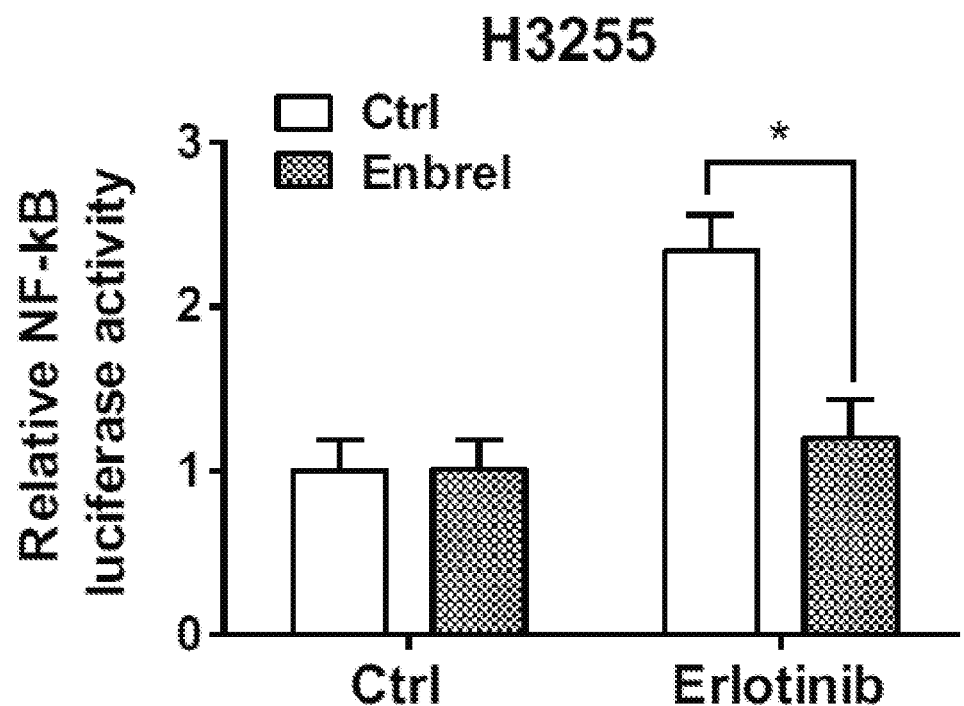
Figure 15D:
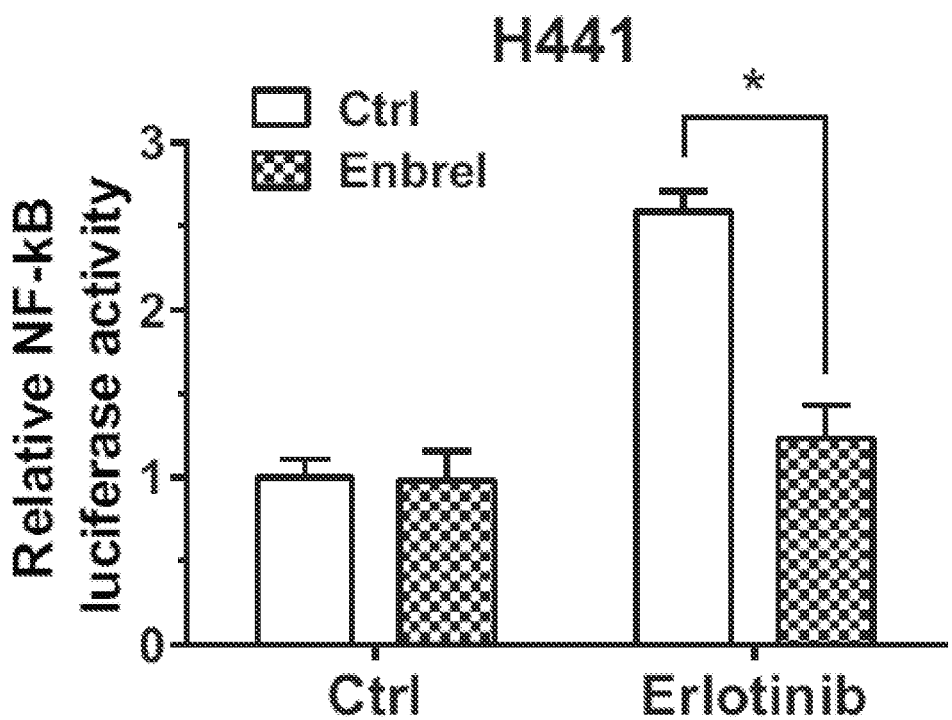
Figure 15E:
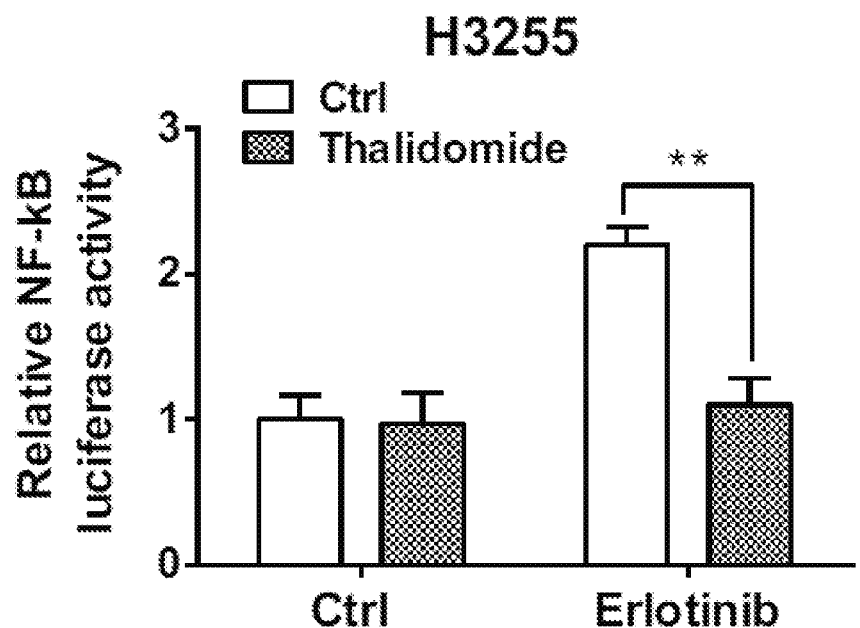
Figure 15F:
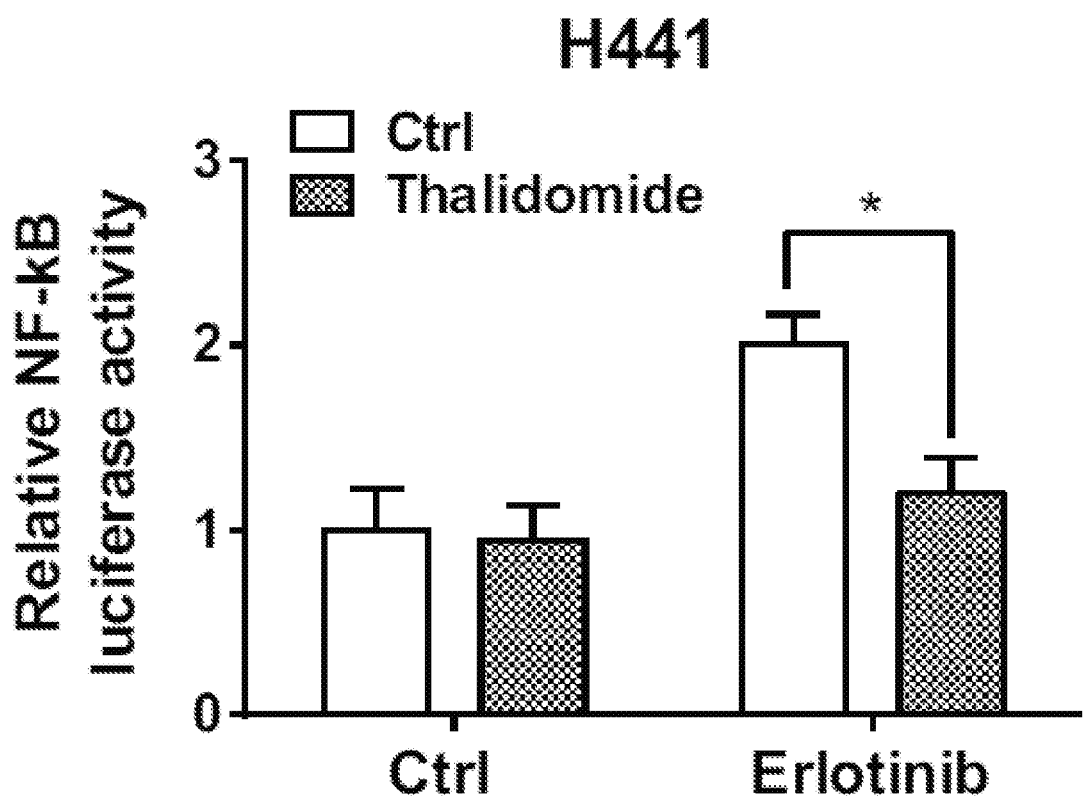
Figure 16A:
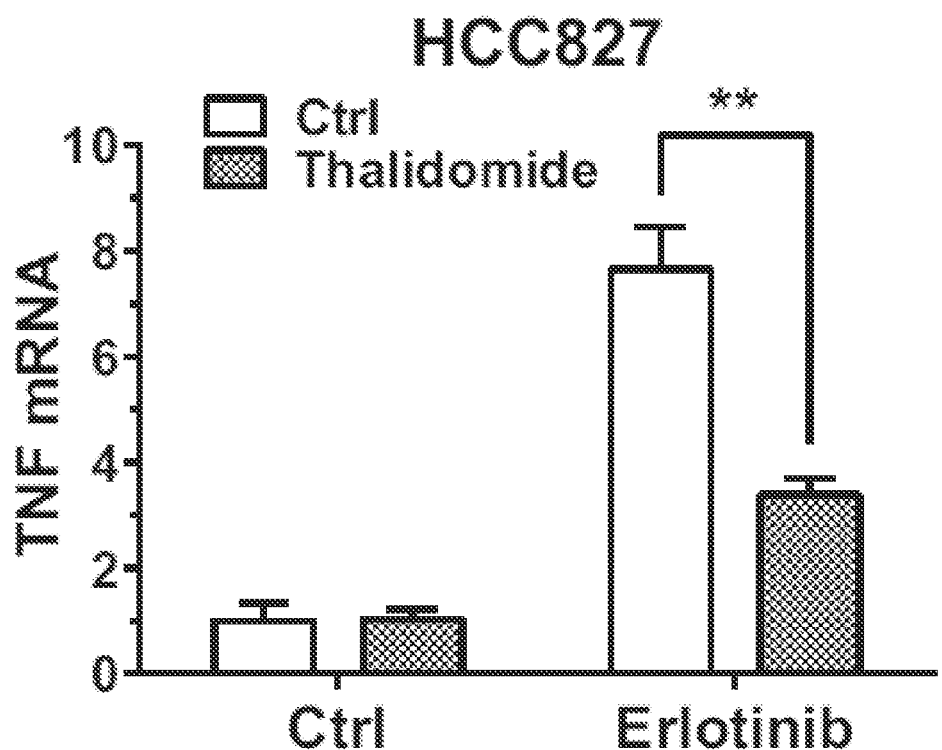
Figure 16B:
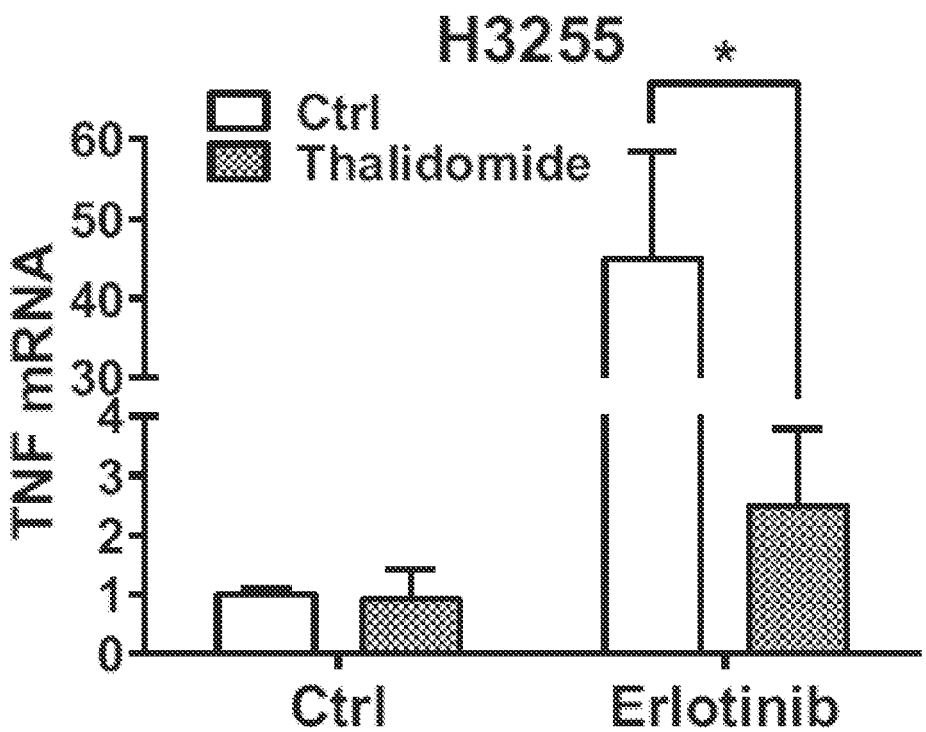
Figure 16C:
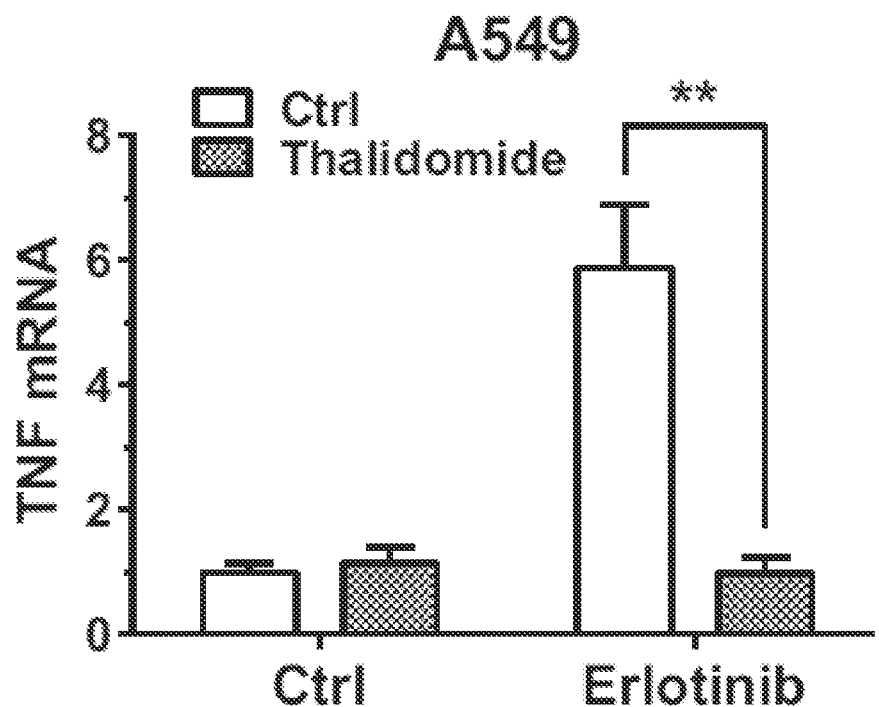
Figure 16D:
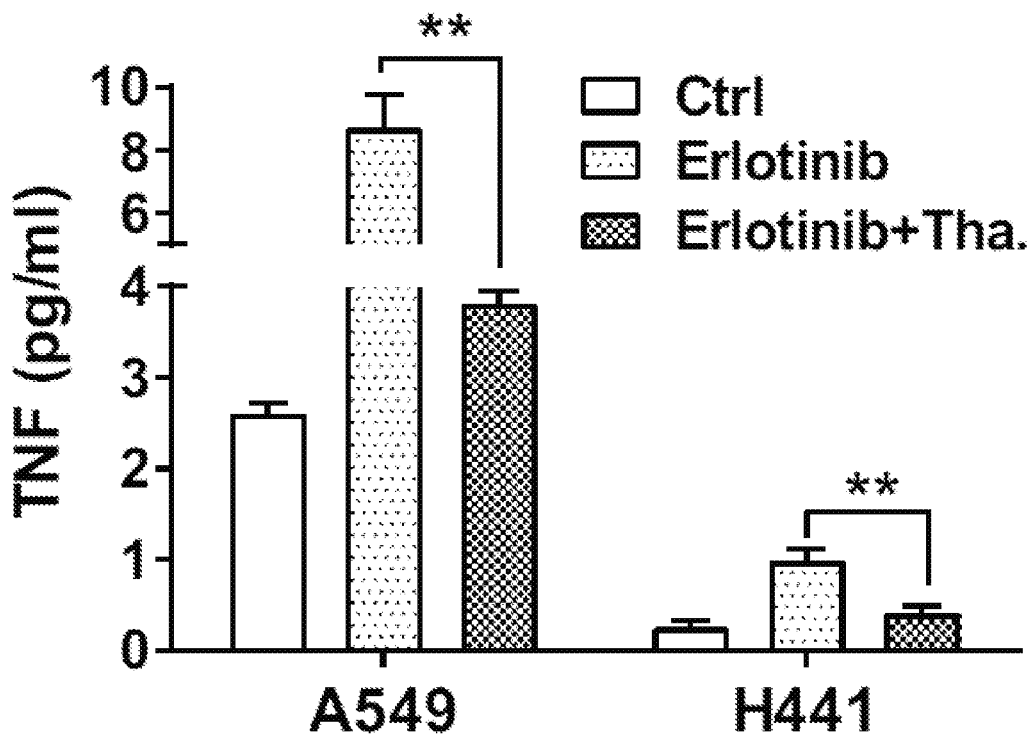
Figure 16E:
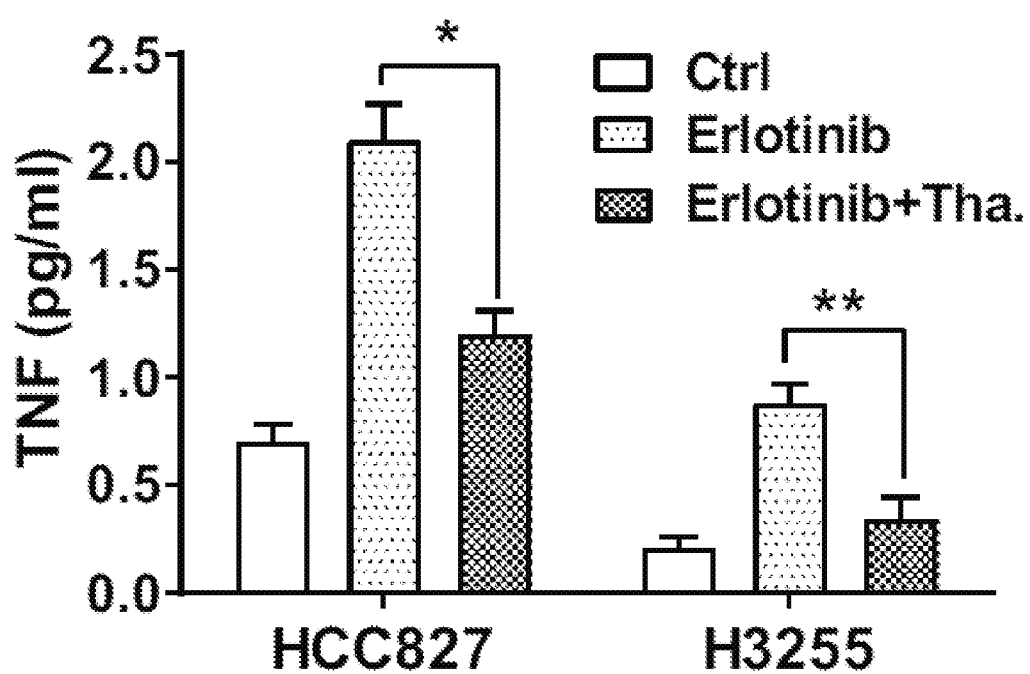

Next, we examined whether the increased TNF plays a role in erlotinib-induced NF-κB activation. A recent study has reported that NF-κB is rapidly activated in lung cancer cells expressing EGFR activating mutations. We confirmed that NF-κB was activated by erlotinib in EGFR mutant cell lines and found that NF-κB is also activated in cell lines that express EGFRwt using a reporter assay as shown in FIG. 3A. NF-κB activation was also confirmed by degradation of IKBα following erlotinib treatment (FIG. 3B). Thus, the activation of NF-κB is seen in both EGFRwt as well as EGFR mutant expressing cell lines. Since TNF is a major activator of NF-κB, we considered the possibility that erlotinib activated NF-κB via an increase in TNF level. TNFR1 is expressed widely, while TNFR2 expression is limited to immune cells and endothelial cells. We first examined the effect of siRNA knockdown of TNFR1 in lung cancer cell lines. siRNA knockdown of TNFR1 leads to inhibition of erlotinib induced NF-κB activation in both EGFR mutant and EGFRwt cells as shown in FIG. 3C-D and FIG. 15A-B. Etanercept (Enbrel) is a fusion protein of TNFR and IgG1 and is in clinical use as a stable and effective TNF blocking agent for autoimmune diseases. Enbrel also blocks erlotinib induced NF-κB activation in multiple cell lines FIG. 3E-F and FIG. 15C-D. We also used thalidomide, a drug that is known to reduce TNF levels. Thalidomide also inhibited erlotinib induced NF-κB activation in both EGFRwt and EGFR mutant cell lines (FIG. 3 G-H and FIG. 15E-F). We confirmed that thalidomide inhibits erlotinib induced TNF increase in lung cancer cells (FIG. 16). It should be noted that thalidomide is also reported to inhibit NF-κB activation independent of its effect on TNF. Consistent with this effect, we find that thalidomide can block NF-κB activation induced by exogenous TNF (FIG. 3 I-J). Thus, our studies indicate that erlotinib induces activation of NF-κB via increased TNF signaling.

Figure 17A:
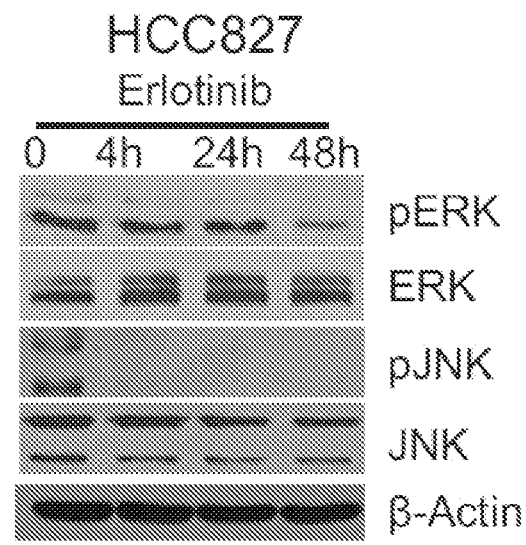
Figure 17B:
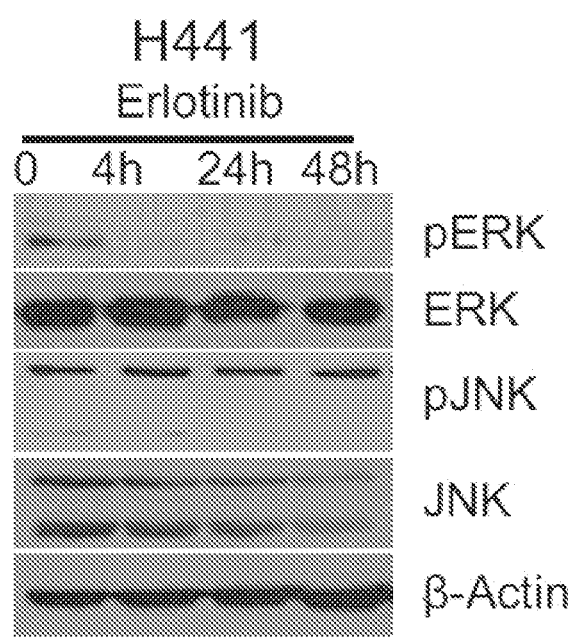

We recently found that EGFR inhibition results in activation of other signals such as JNK and ERK activation in glioma cells. However, in lung cancer cells, and consistent with what has been reported previously, although these signals are attenuated following EGFR inhibition, neither ERK nor JNK re-activation is detected. (FIG. 17A-B).

Erlotinib Induced TNF Expression is Regulated by NF-κB in Feedforward Loop

Figure 4A:
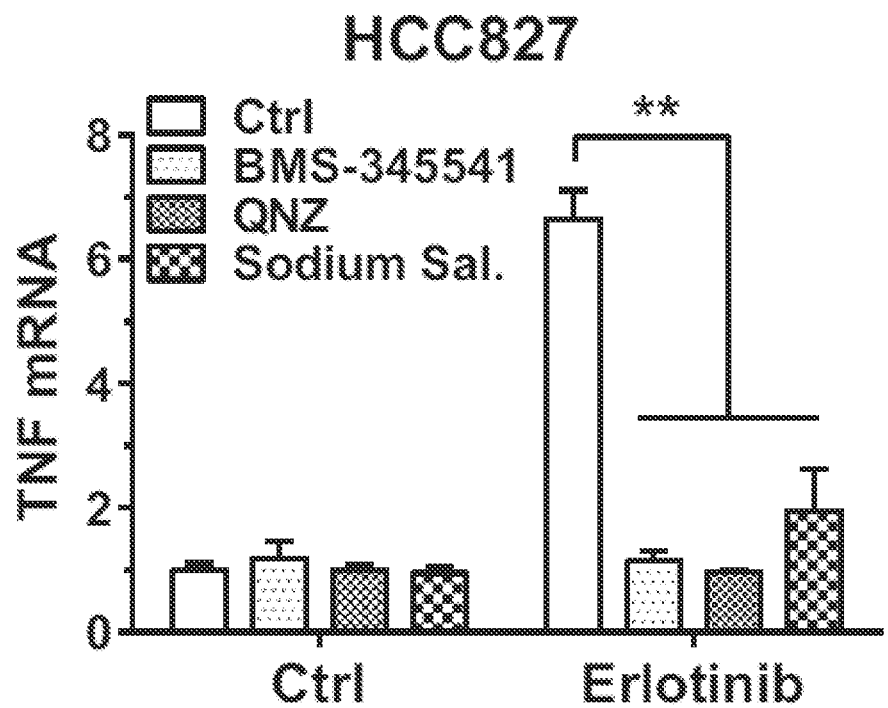
Figure 4B:
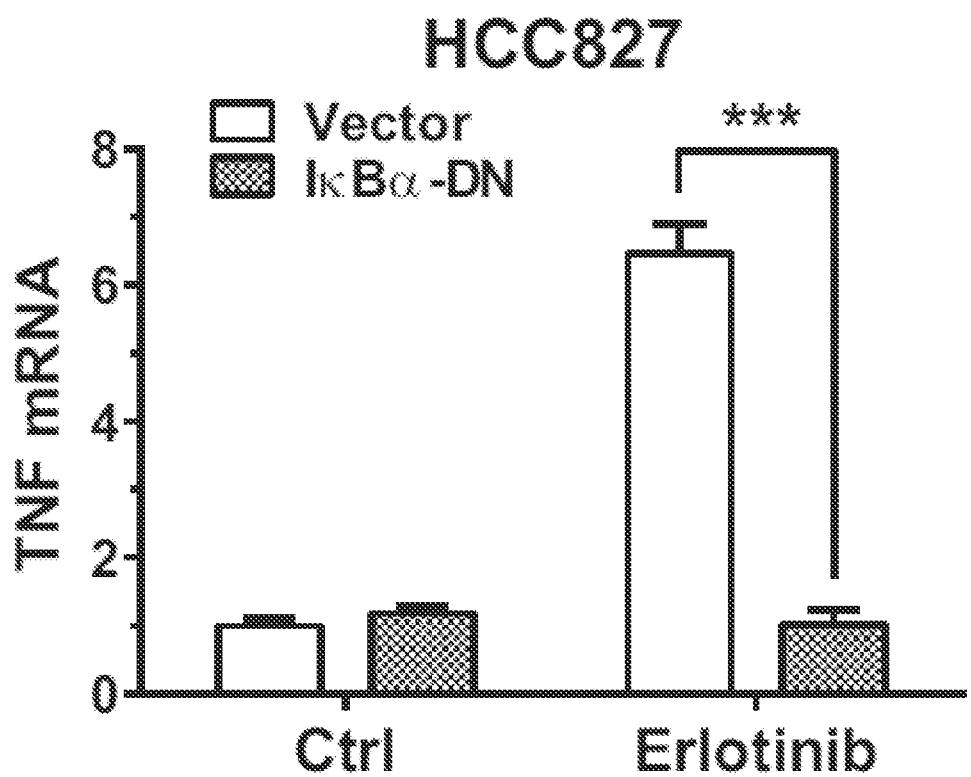
Figure 4C:
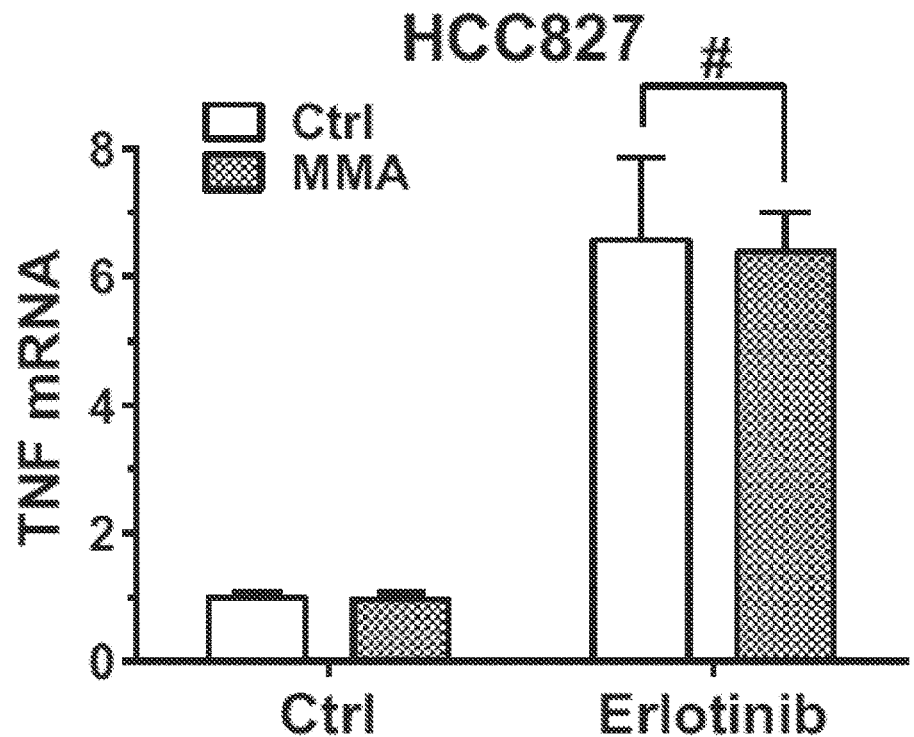
Figure 4D:
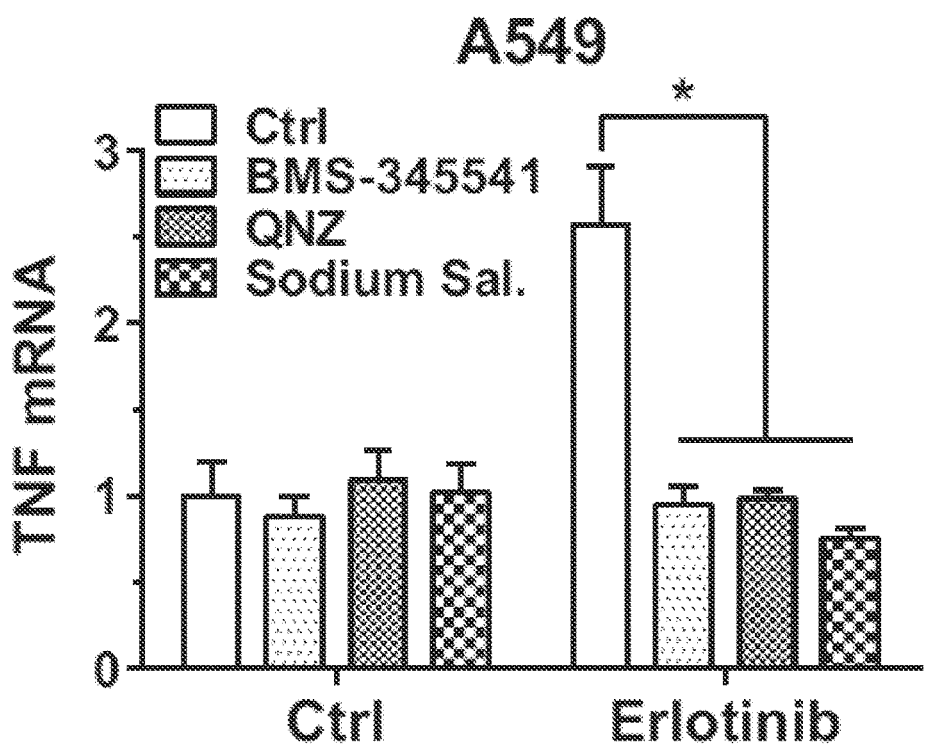
Figure 4E:
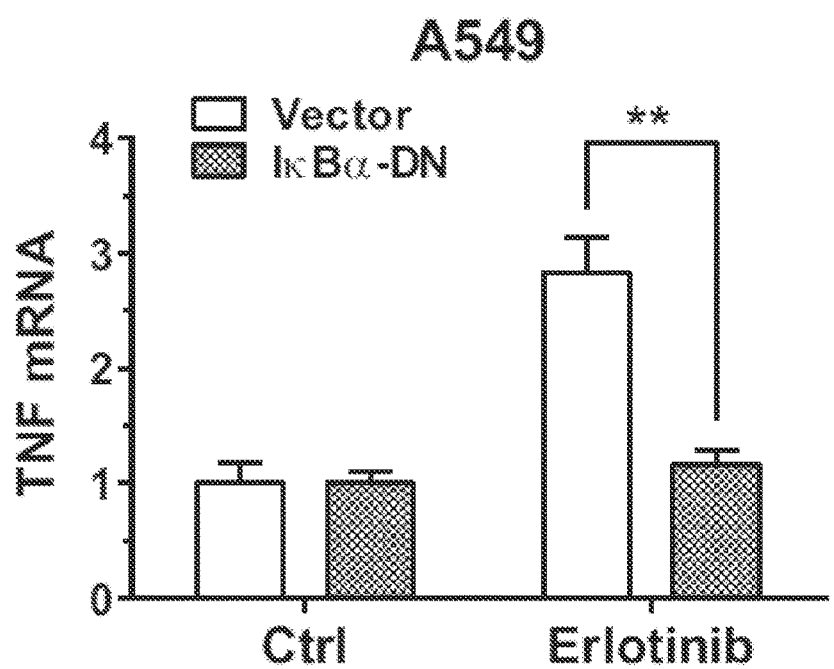
Figure 4F:
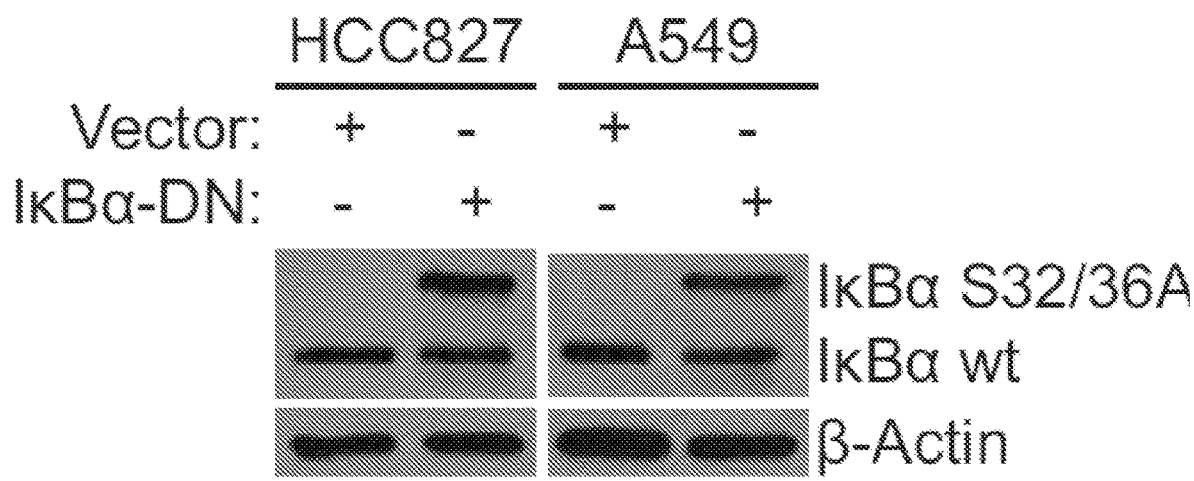
Figure 4G:
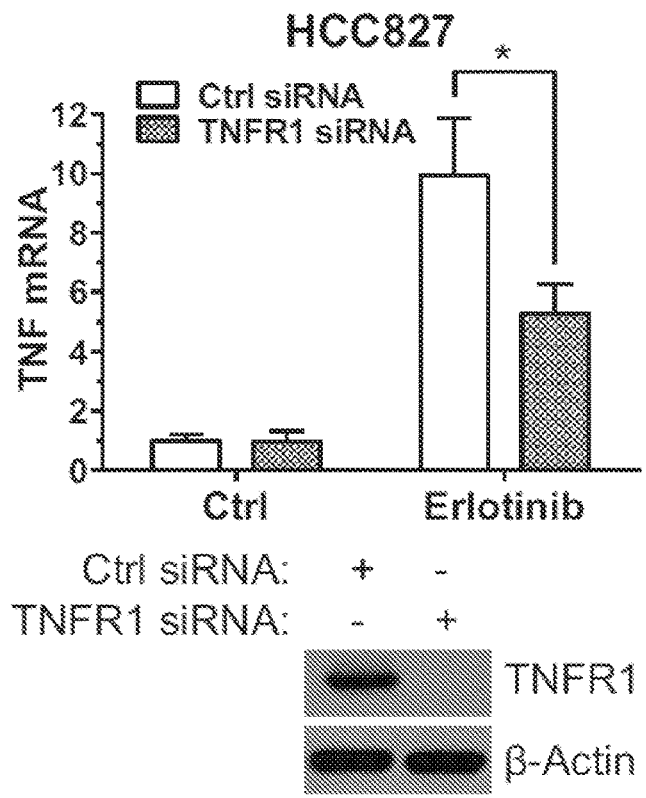
Figure 4H:
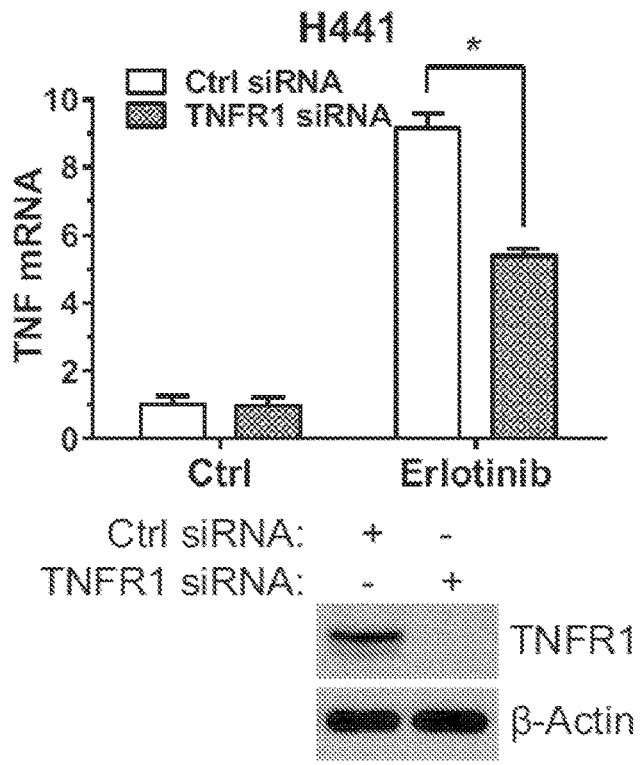
Figure 4I:
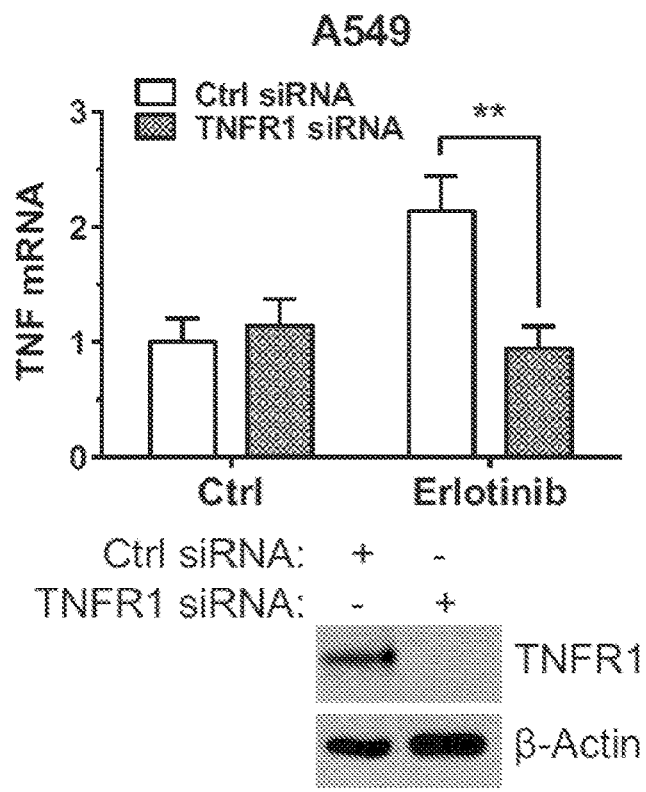
Figure 4J:
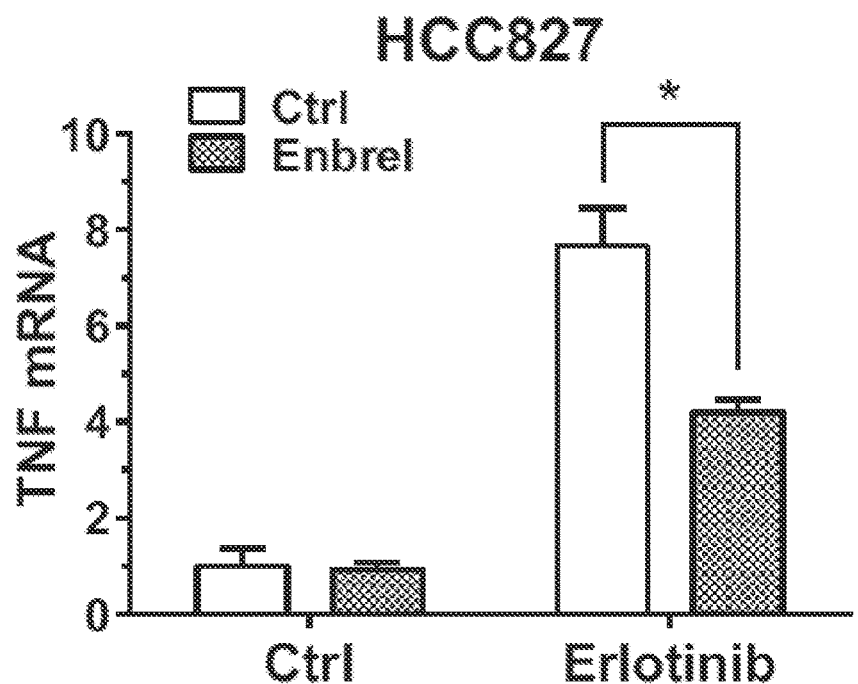
Figure 4K:
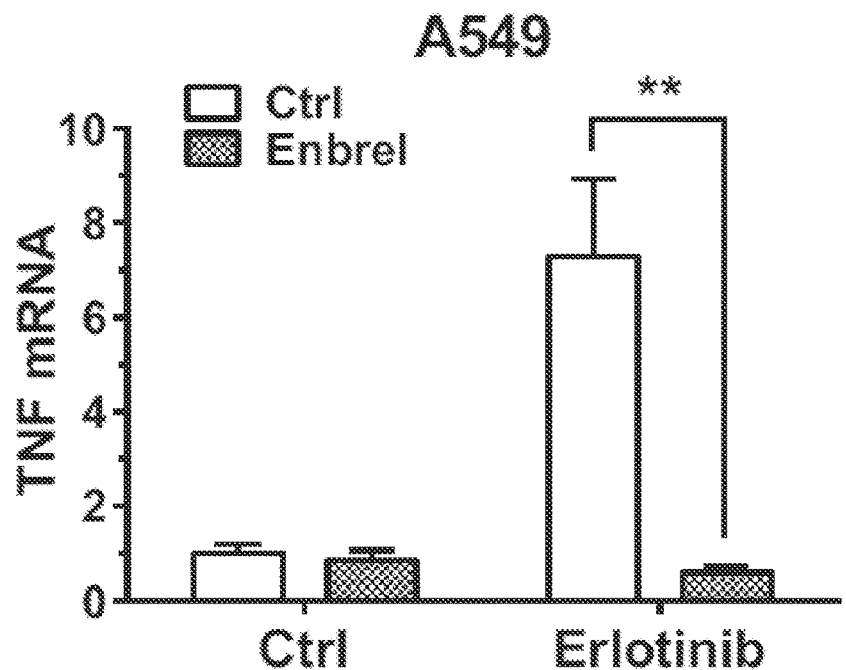

TNF is an inducible cytokine and is regulated at multiple levels including transcription. NF-κB is a key transcription factor involved in TNF transcription. We considered the possibility that erlotinib induced increase in TNF expression may also be mediated by NF-κB in a feedforward loop. We examined whether inhibition of NF-κB using a chemical inhibitor, or a dominant negative IkBα (super repressor) mutant would block the increase in TNF following exposure of cells to erlotinib (FIG. 4). Indeed we find that inhibition of NF-κB blocks the erlotinib induced increase in TNF mRNA as detected by quantitative real time PCR. NF-κB activity is essential for TNF upregulation in both EGFRwt as well as EGFR mutant cell lines (FIG. 4A-B, D-F). As an additional negative control, we used Mithramycin an inhibitor of Sp1. Although Sp1 binding sites are present in the TNF promoter (FIG. 18), there is no effect of Sp1 inhibition on erlotinib induced TNF upregulation (FIG. 4C and FIG. 19).

Next we examined whether NF-κB and TNF induce each other in a feedforward loop. If this is the case, then it should be possible to inhibit erlotinib induced TNF upregulation by an inhibition of the TNFR. Indeed, we find that blocking the TNFR1 using siRNA or Etanercept results in inhibition of erlotinib induced TNF upregulation (FIG. 4G-K). These data indicate that TNF is upregulated via a feedforward loop that includes activity of NF-κB and TNFR1 signaling.

Figure 4L:
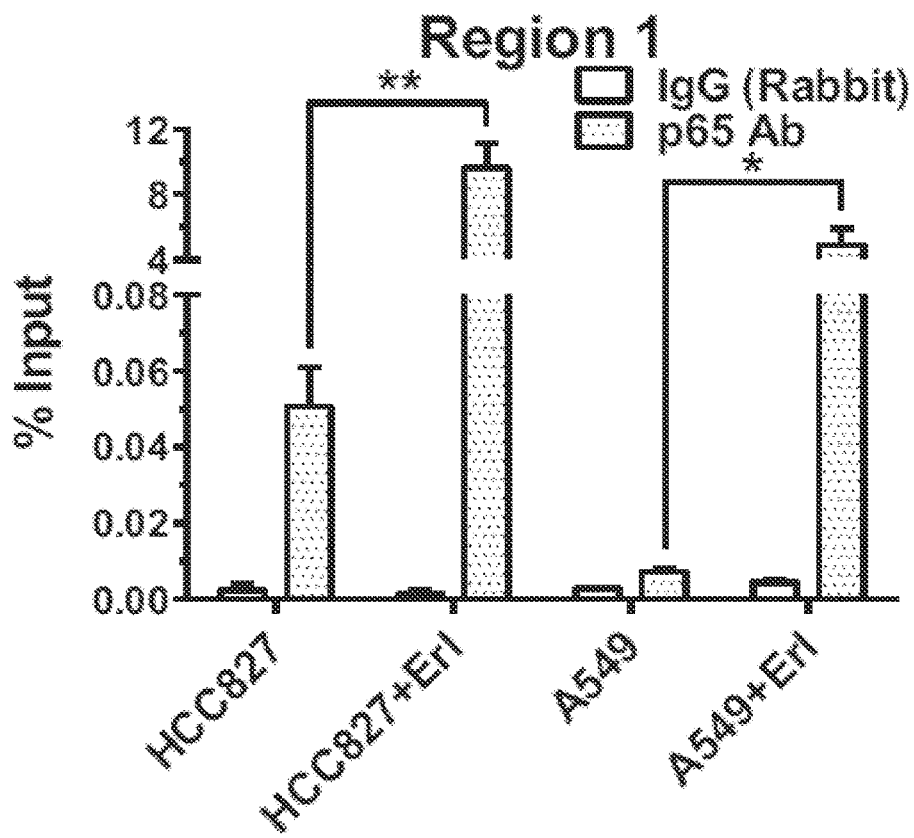

Finally, we find that NF-κB can bind to two putative sites (FIG. 18) on the TNF promotor by ChIP-qPCR assay. We show that NF-κB can be detected on the TNF promotor by ChIP in cells. While there is some binding of NF-κB to the TNF promoter even under basal conditions, when EGFR is inhibited there is increased presence of NF-κB on the TNF promoter in both EGFRwt and EGFR mutant cells (FIG. 4L and FIG. 20).

TNF Protects Lung Cancer Cells from EGFR Inhibition

Figure 5A:
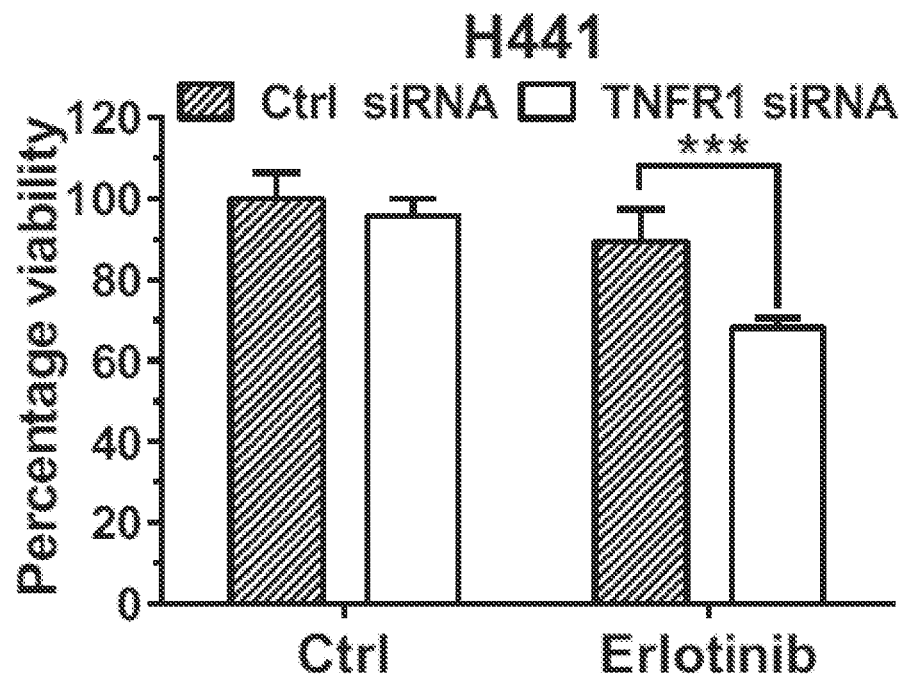
Figure 5B:
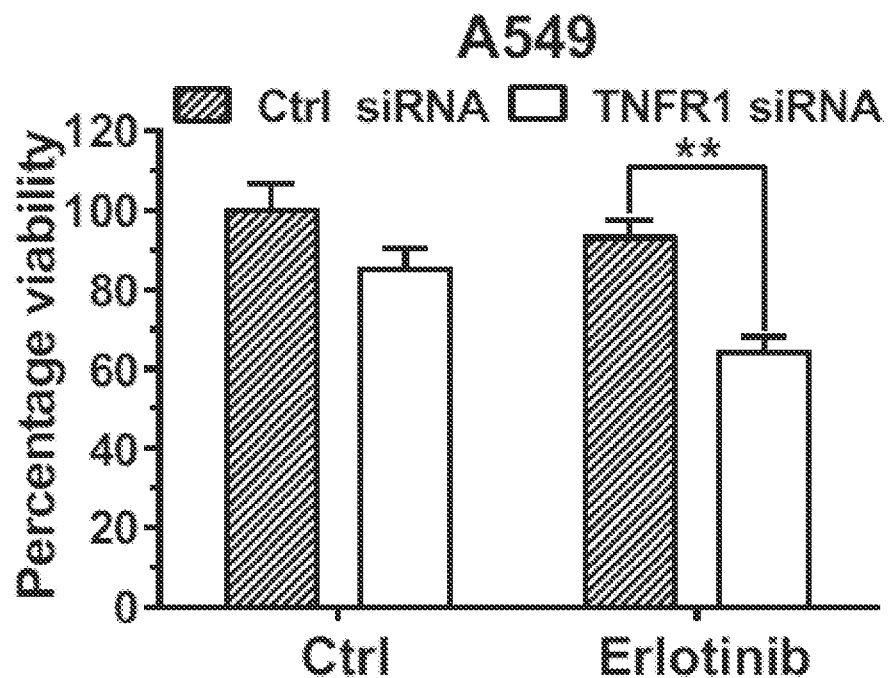
Figure 5C:
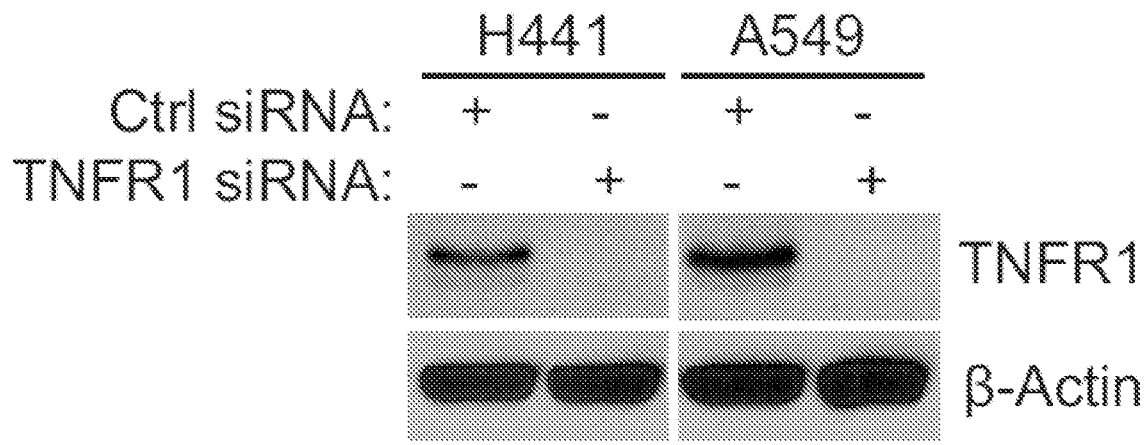
Figure 5D:
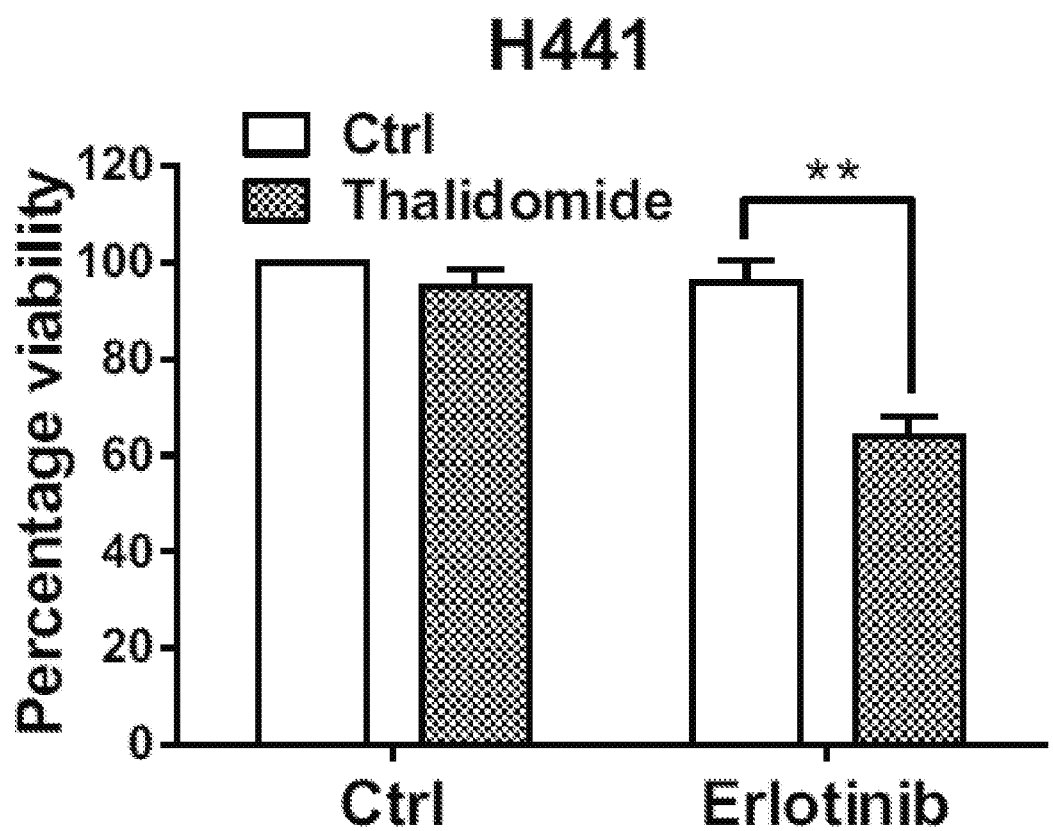
Figure 5E:
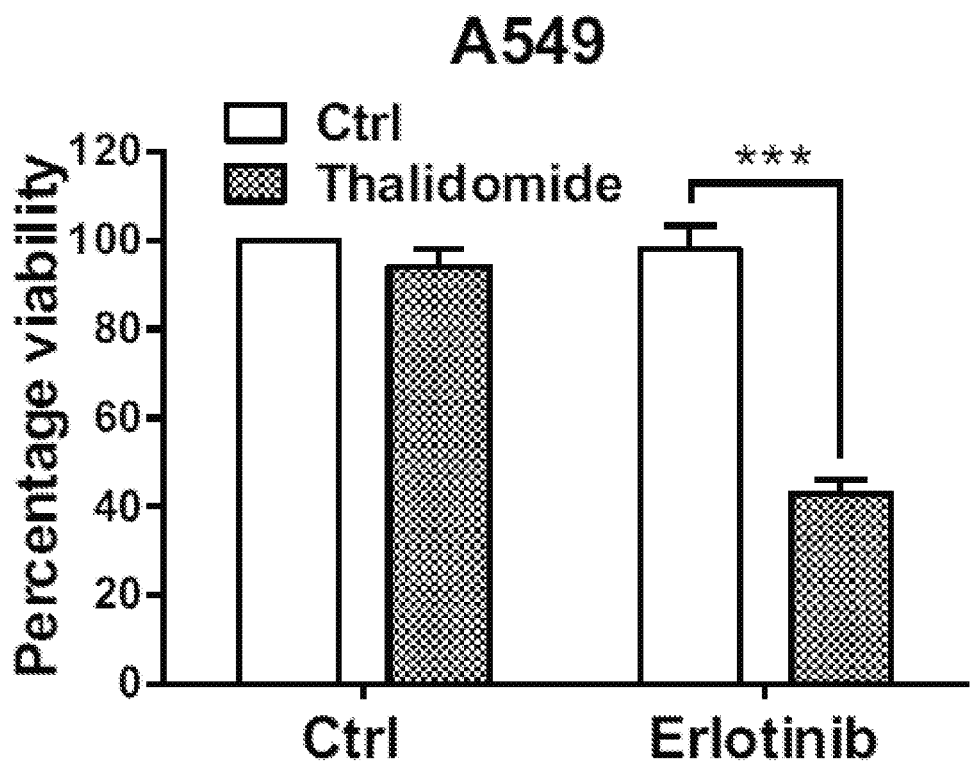
Figure 5F:
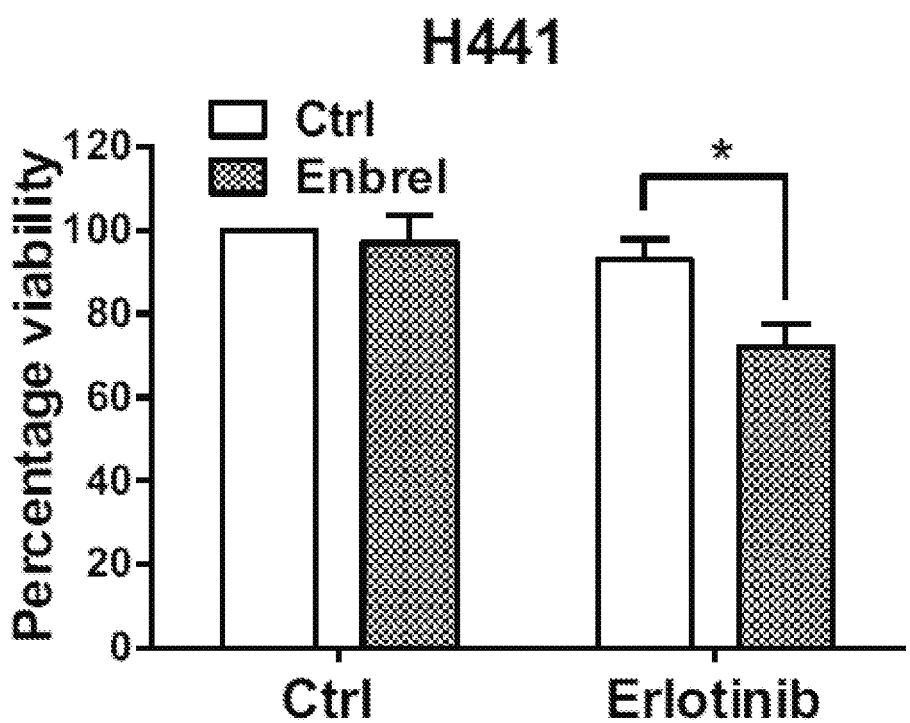
Figure 5G:
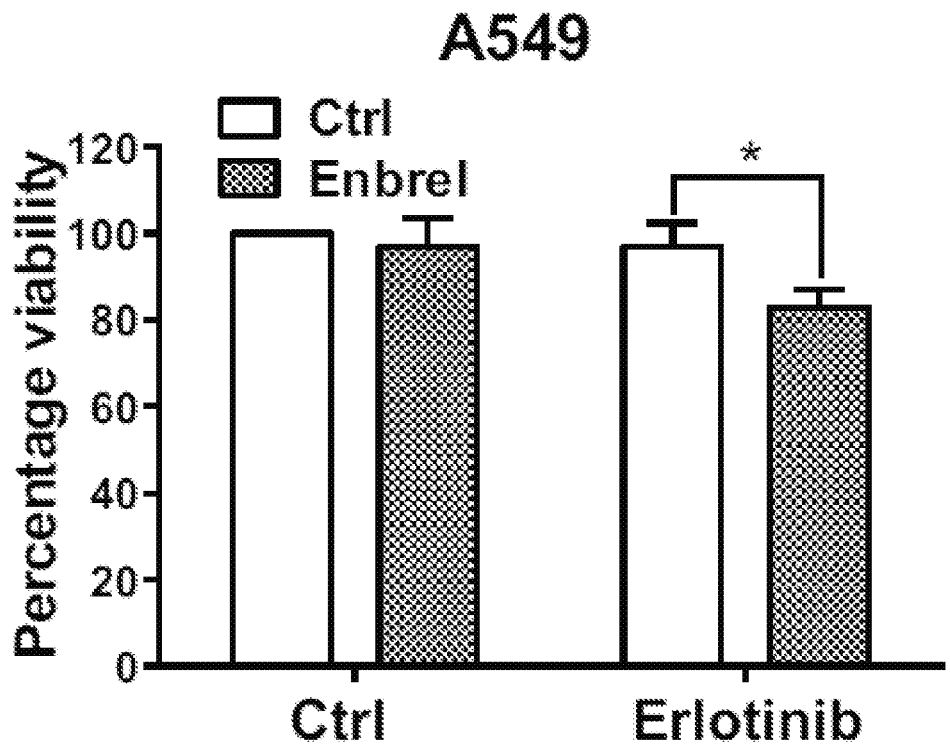
Figure 5H:
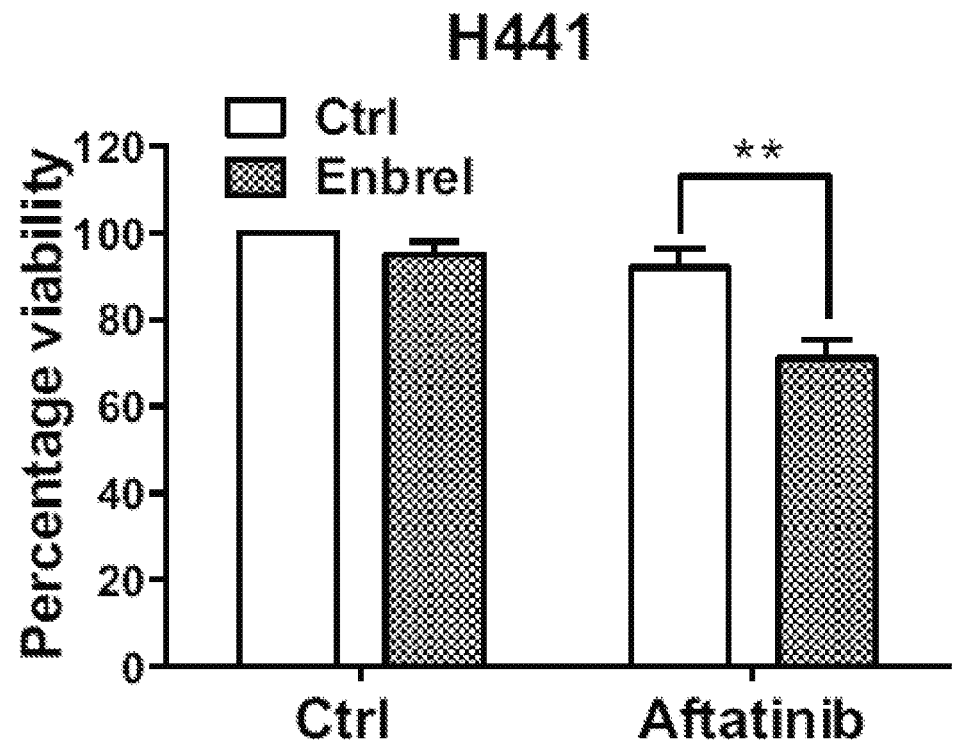
Figure 5I:
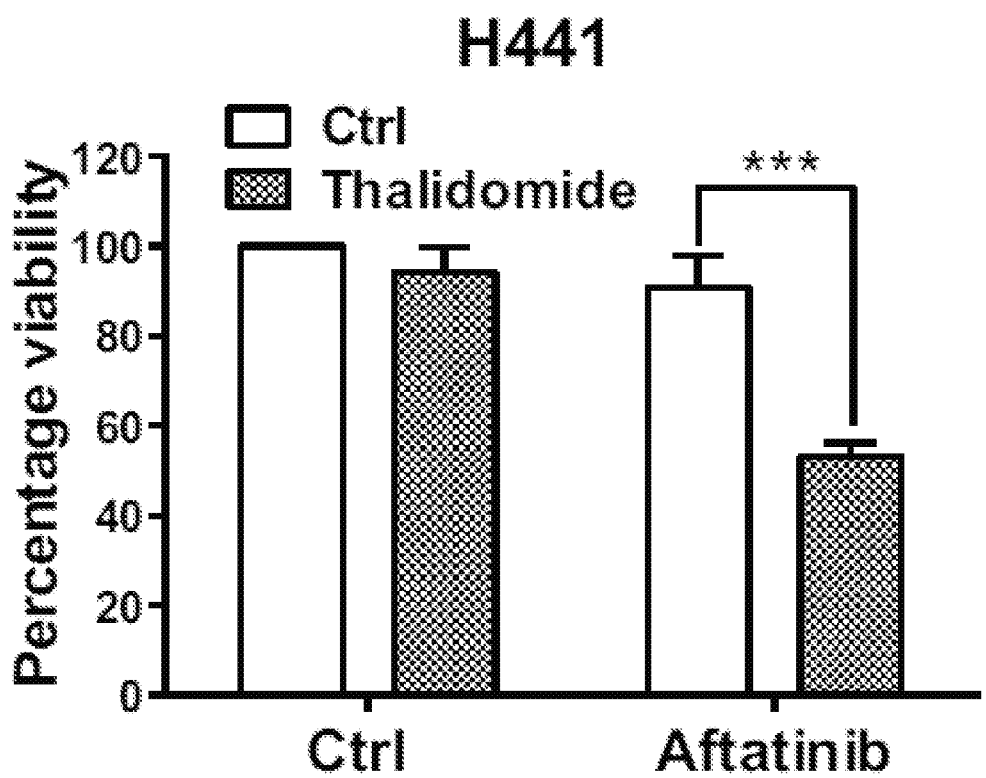
Figure 5J:
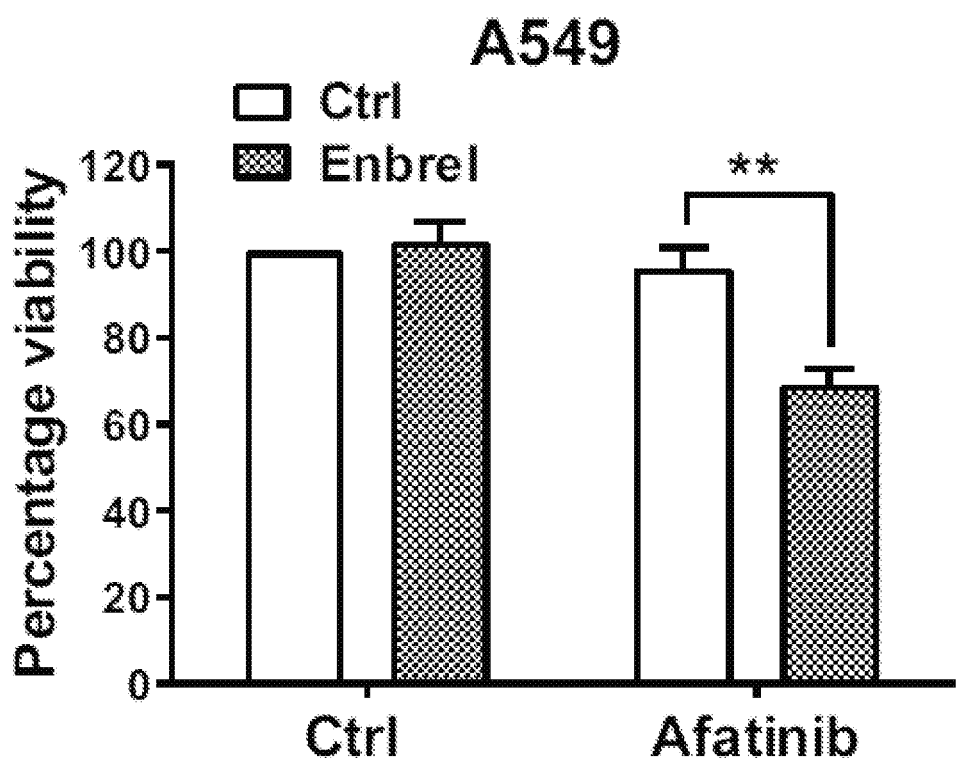
Figure 5K:
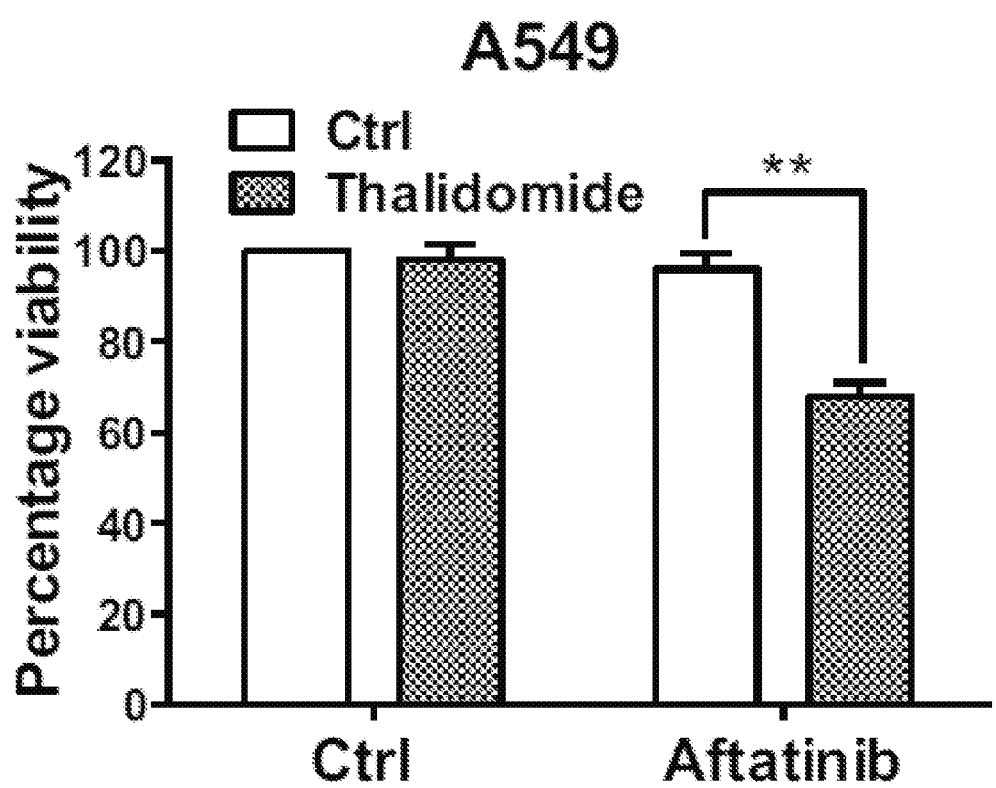

The TNF level is upregulated by EGFR inhibition using tyrosine kinase inhibitors in all 18 lung cancer cell lines and in the animal models that we tested. This led us to investigate whether the TNF upregulation has biological significance. In particular, we hypothesized that increased TNF secretion protects EGFR expressing lung cancer cells from cell death following the loss of EGFR signaling. We started with A549 and H441, two cell lines that express EGFRwt and are known to be resistant to EGFR TKIs. First we did siRNA knockdown of TNFR1 and found that this confers sensitivity to erlotinib in cell survival assays. Erlotinib alone or TNFR1 silencing alone has no effect on the viability of these cells (FIG. 5A-C). Next, we examined the effect of thalidomide, an inhibitor of TNF and of NF-κB activation. Thalidomide alone had no effect, but it rendered A549 and H441 cells sensitive to the effects of erlotinib, (FIG. 5D-E). Thus EGFR inhibition combined with either biological or chemical inhibition of TNF signaling renders EGFRwt expressing resistant cells sensitive to EGFR inhibition. Etanercept (Enbrel) also rendered both A549 and H441 cells sensitive to the effect of erlotinib (FIG. 5F-G), whereas Etanercept alone had no effect. We also examined found combining Etanercept or thalidomide with erlotinib or afatinib (1 uM each) to impact cell viability (FIG. 5H-K). In fact, we still saw, a statistically significant Enbrel or thalidomide sensitizing effect if the EGFR inhibitor concentration is decreased to 100 nM (FIG. 21).

Figure 6A:
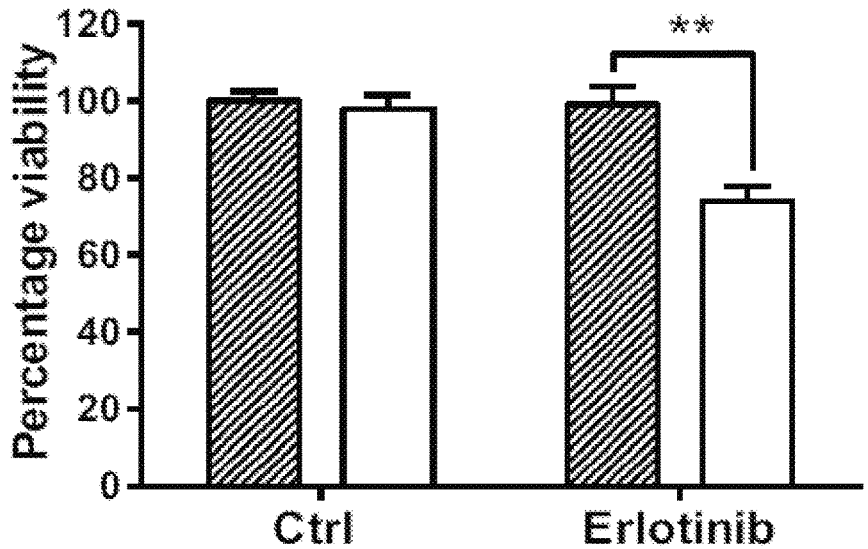
Figure 6B:
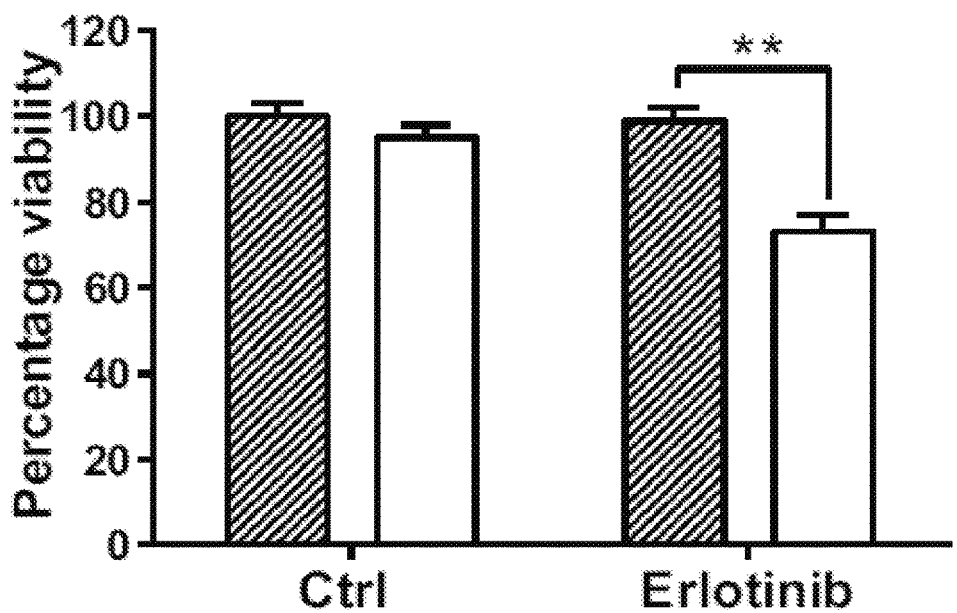
Figure 6C:
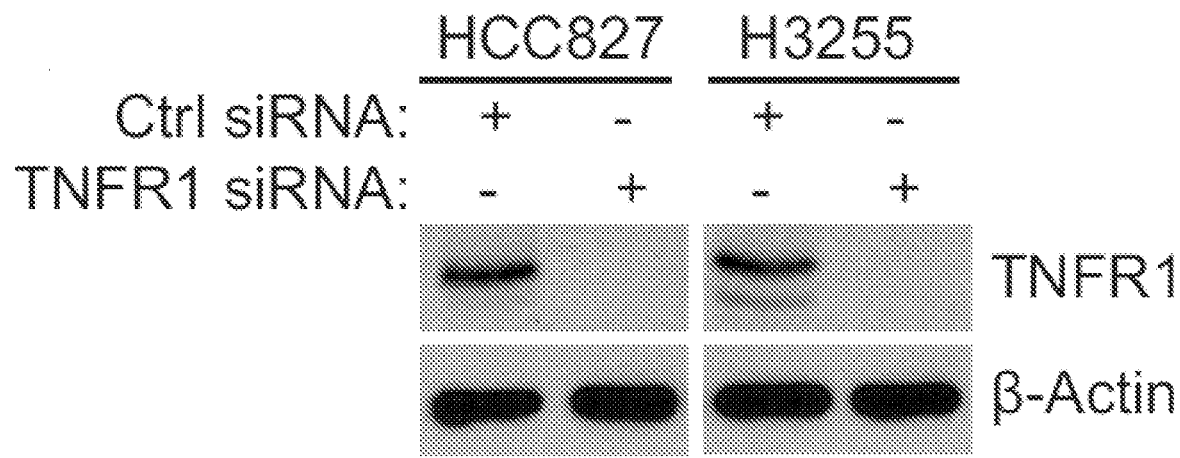
Figure 6D:
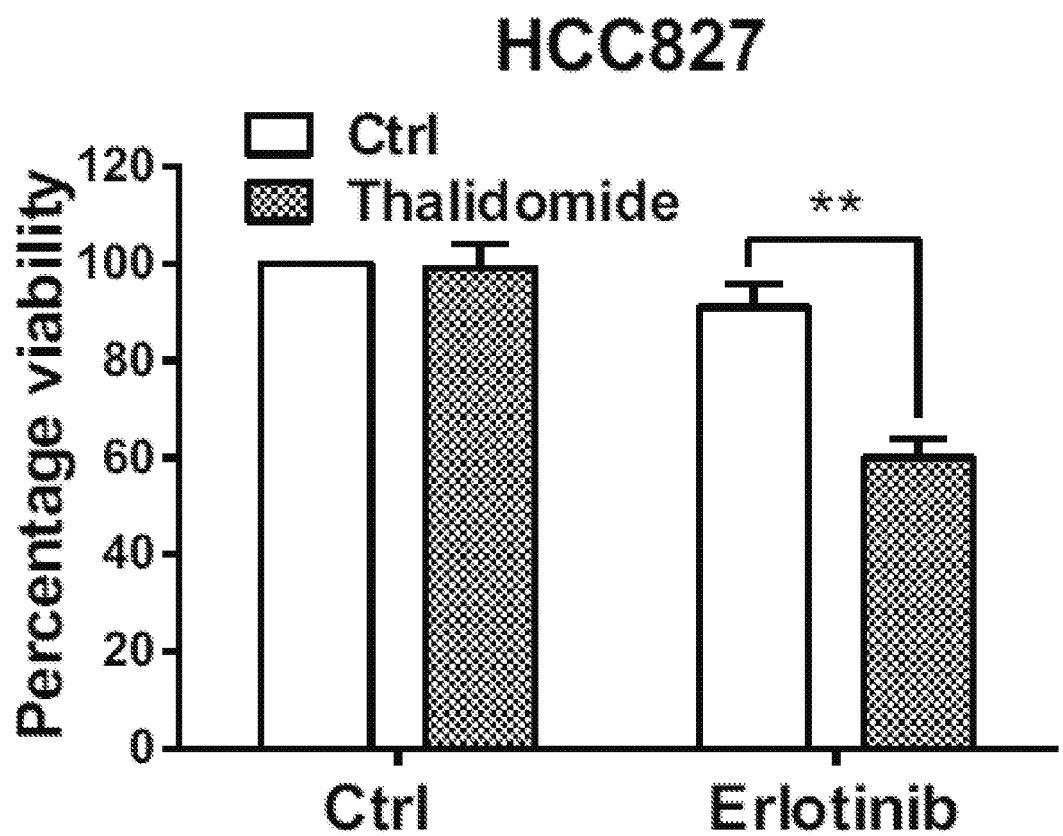
Figure 6E:
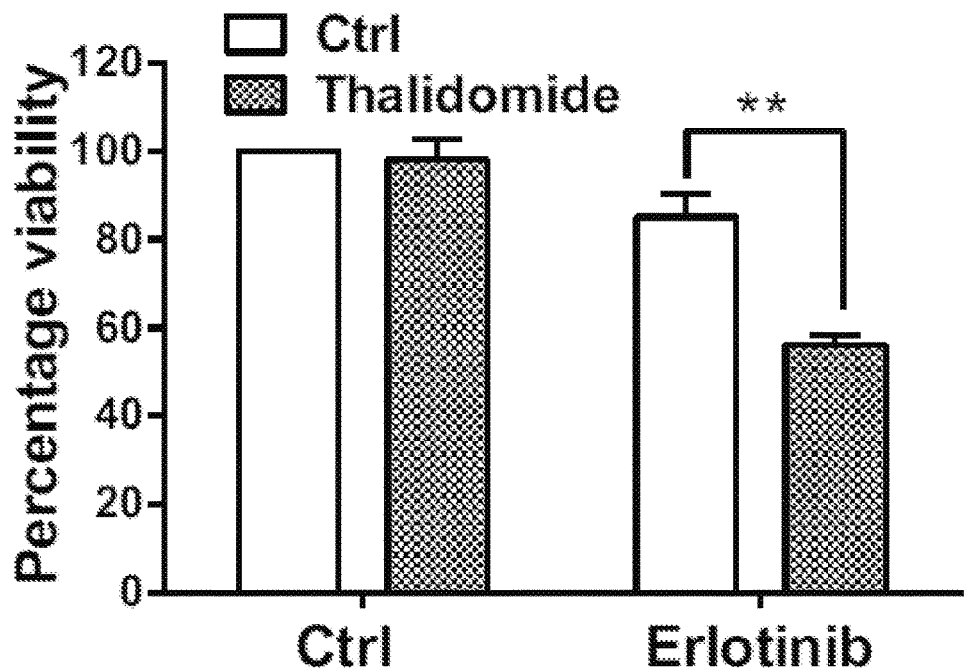
Figure 6F:
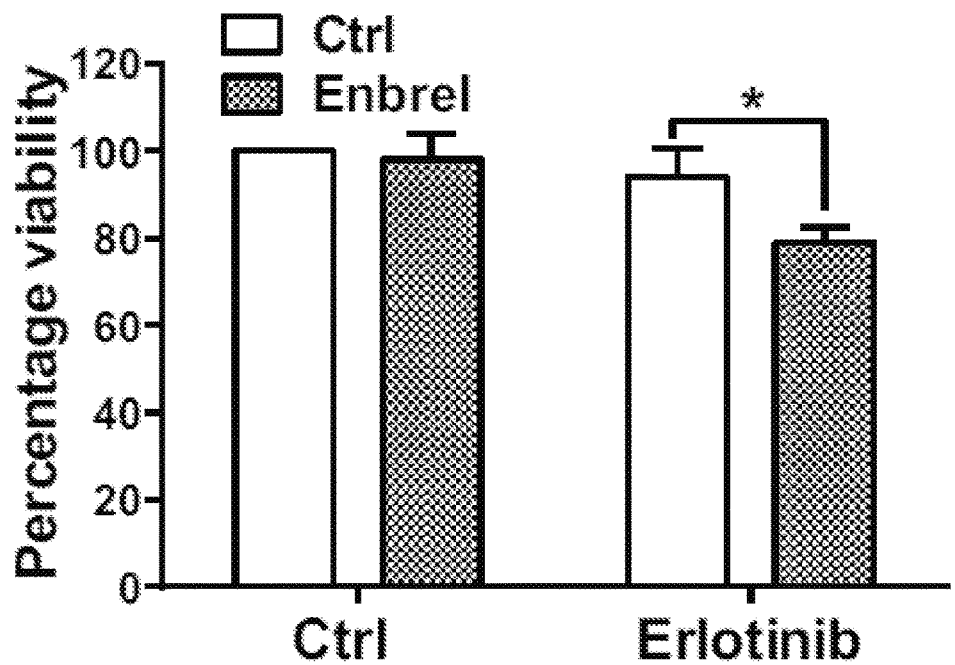
Figure 6G:
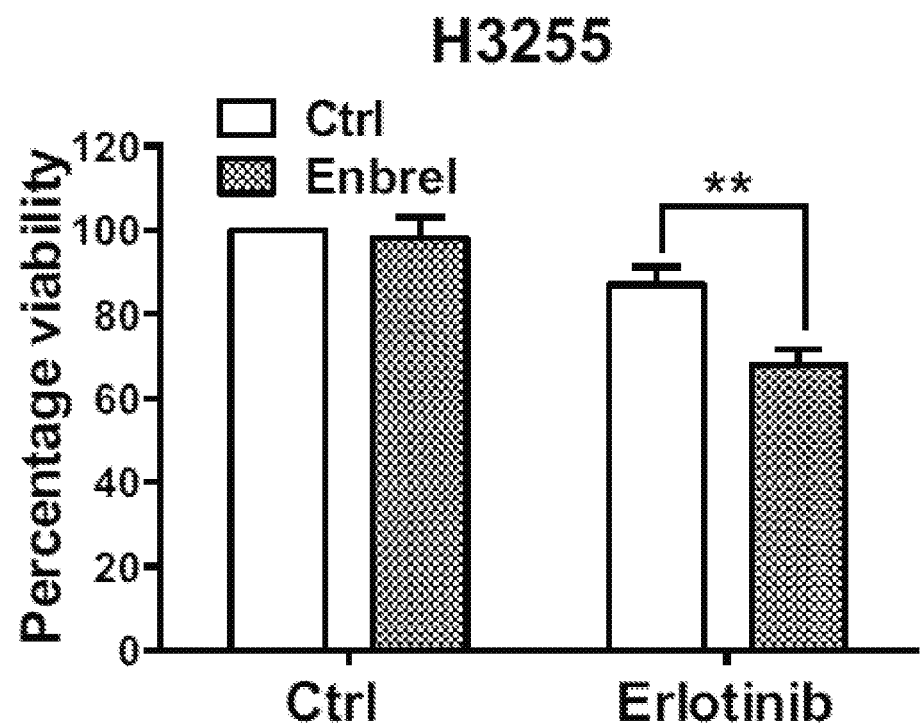
Figure 6H:
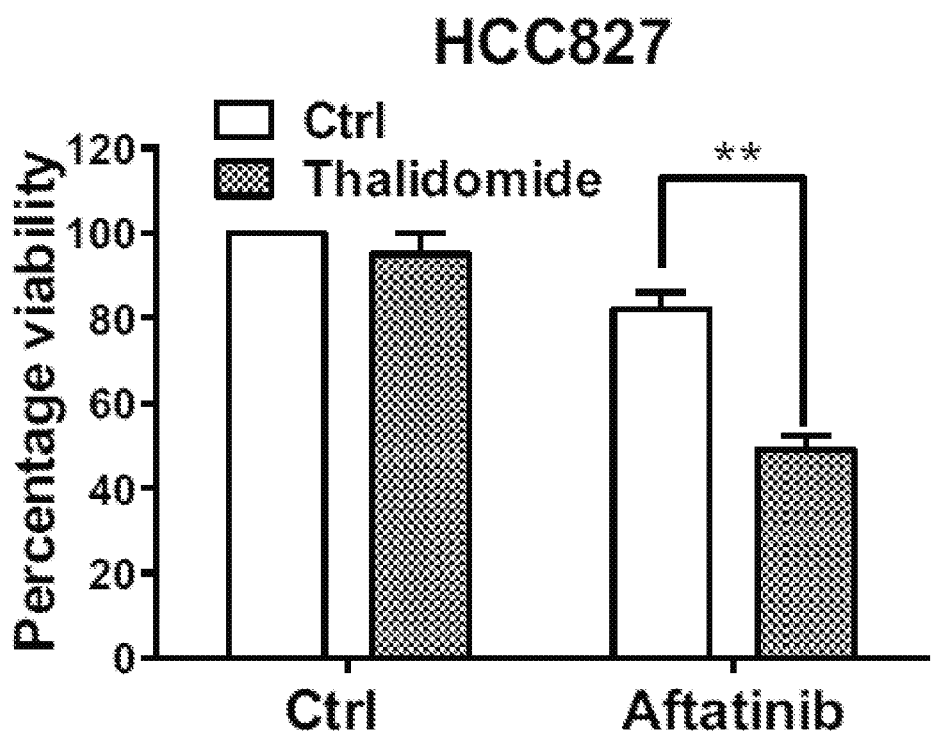
Figure 6I:
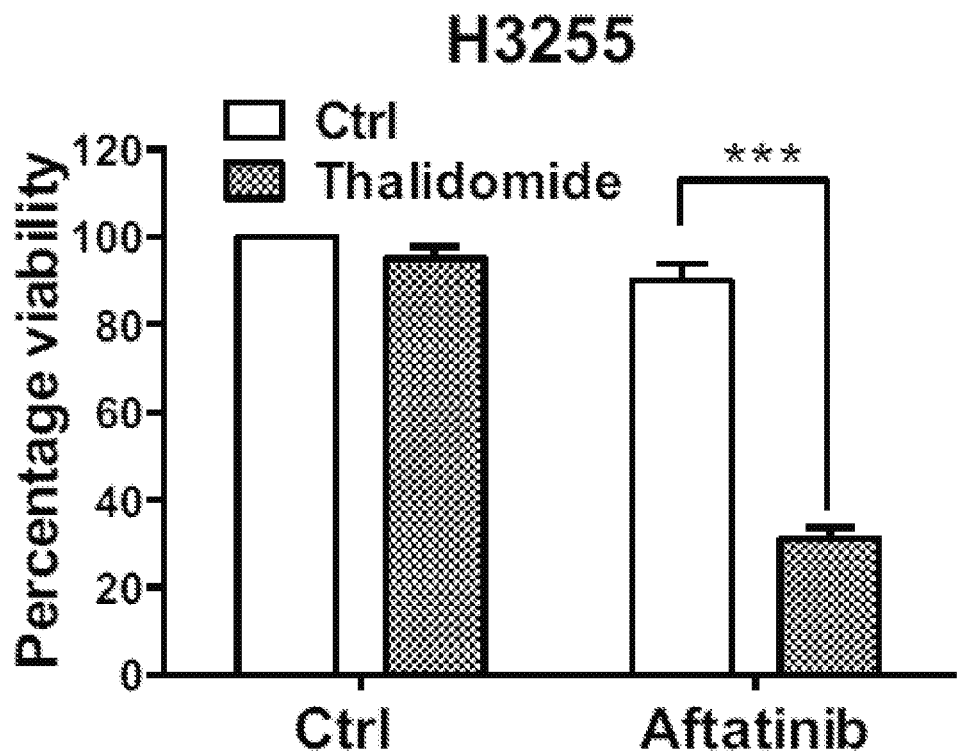
Figure 6J:
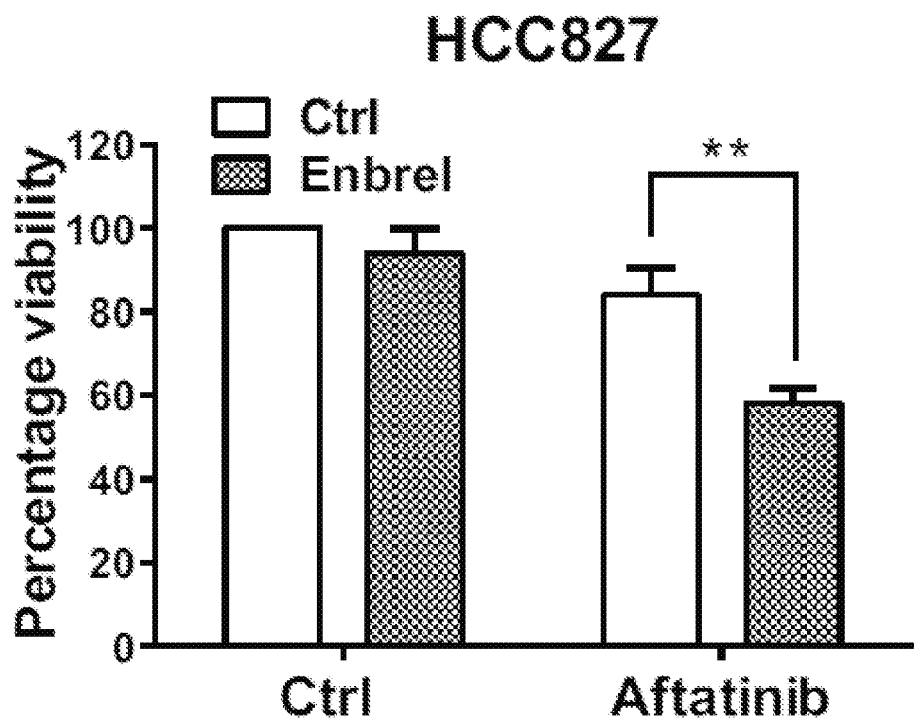
Figure 6K:
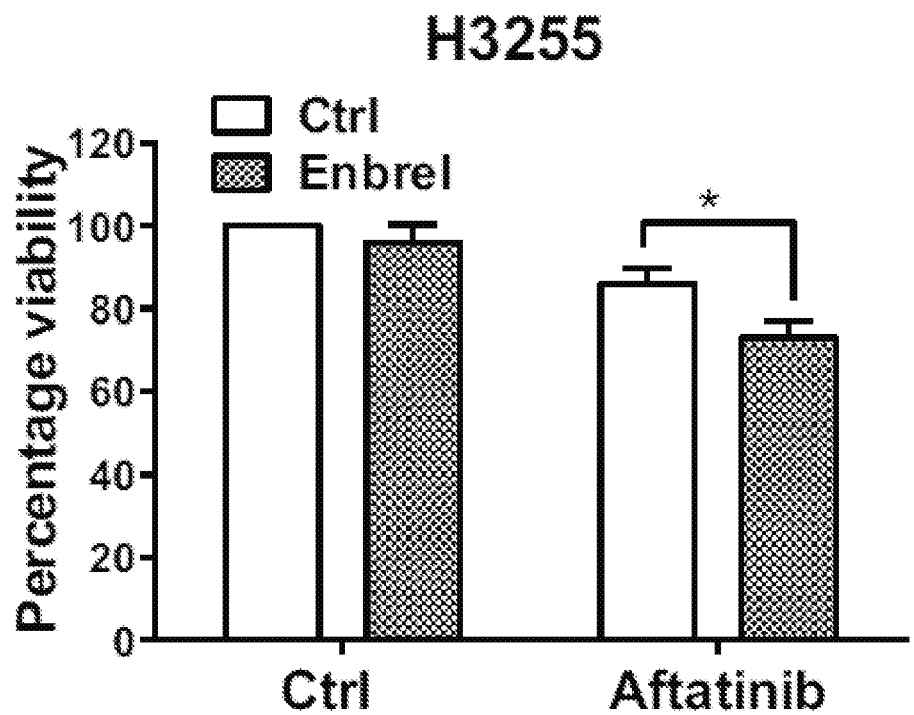

Next we examined the effect of combining TNF and EGFR inhibition in lung cancer cells (HCC827, EGFR exon 19 deletion, or H3255, EGFR L858R mutation) that are oncogene addicted and sensitive to EGFR inhibition. Experiments with low concentrations of erlotinib revealed a sensitizing effect of TNF inhibition obtained by TNFR1 gene silencing (FIG. 6A-C). A combination of erlotinib and thalidomide also enhanced the sensitivity of HCC827 and H3255 cells to EGFR inhibition (FIG. 6D-E). Similarly, a combination of erlotinib and Enbrel results in greater sensitivity to EGFR inhibition in HCC827 and H3255 cells (FIG. 6F-G). TNF inhibition alone had no effect on the viability of oncogene addicted cells. We also tested a combination of afatinib and thalidomide or Enbrel and found a greater sensitivity to EGFR inhibition (FIG. 6H-K).

Figure 22A:
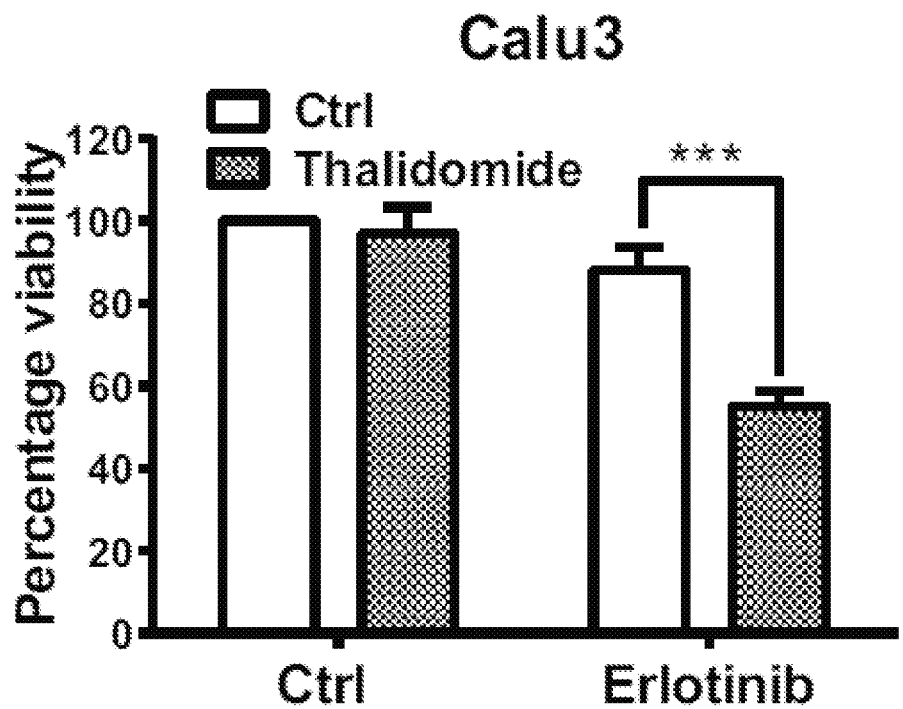
Figure 22B:
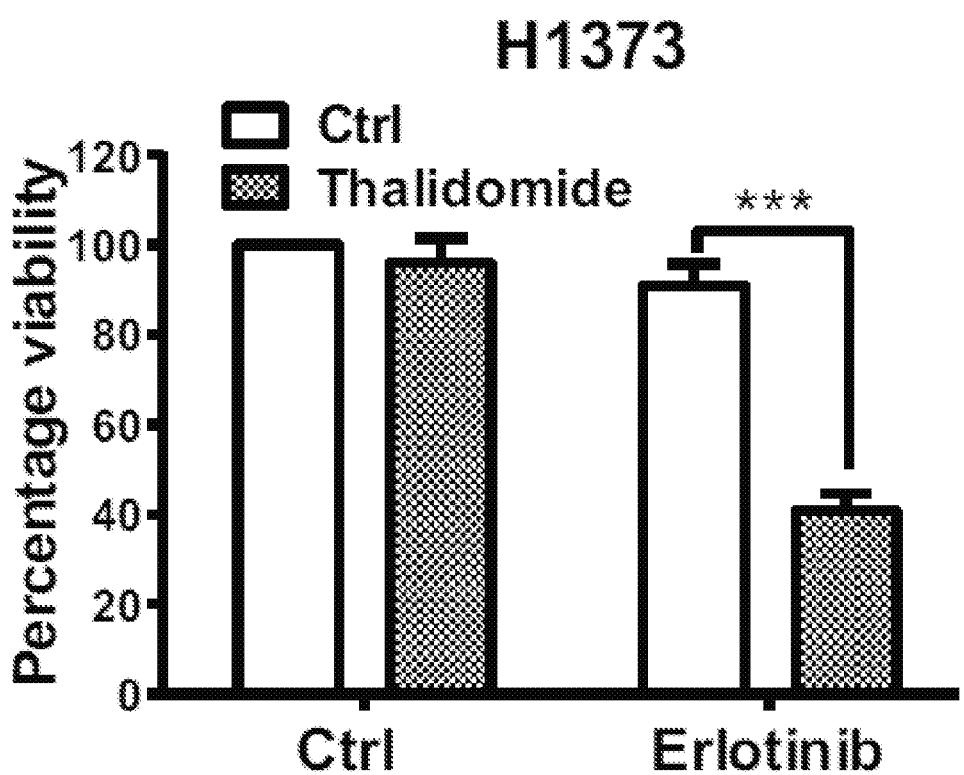
Figure 22C:
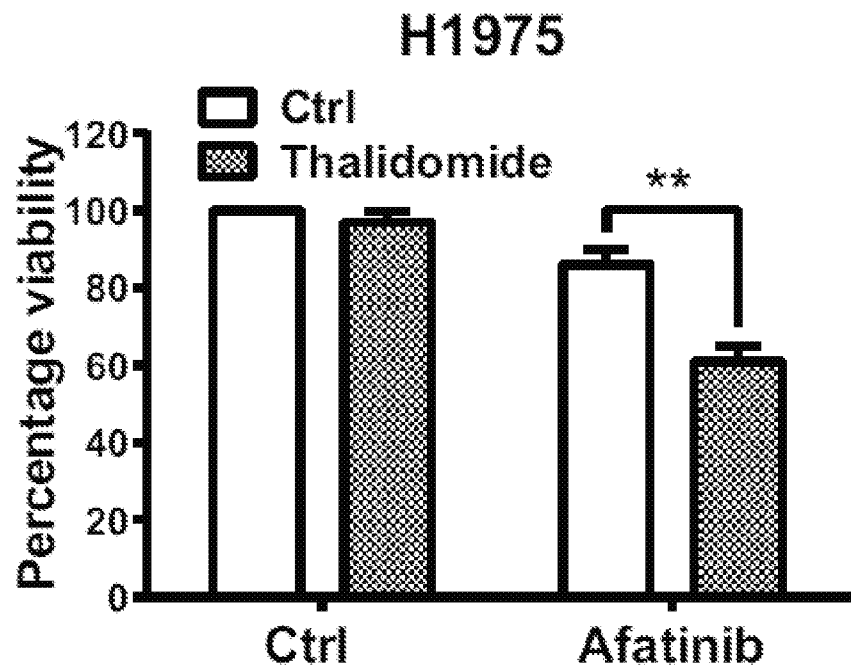
Figure 22D:
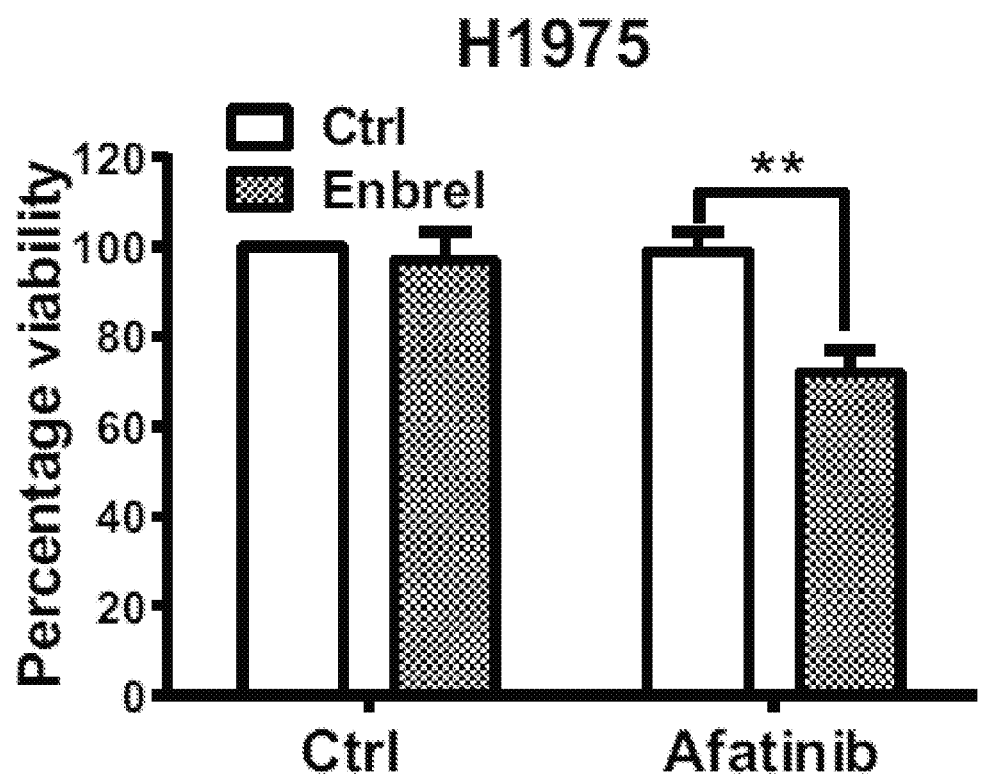
Figure 22E:
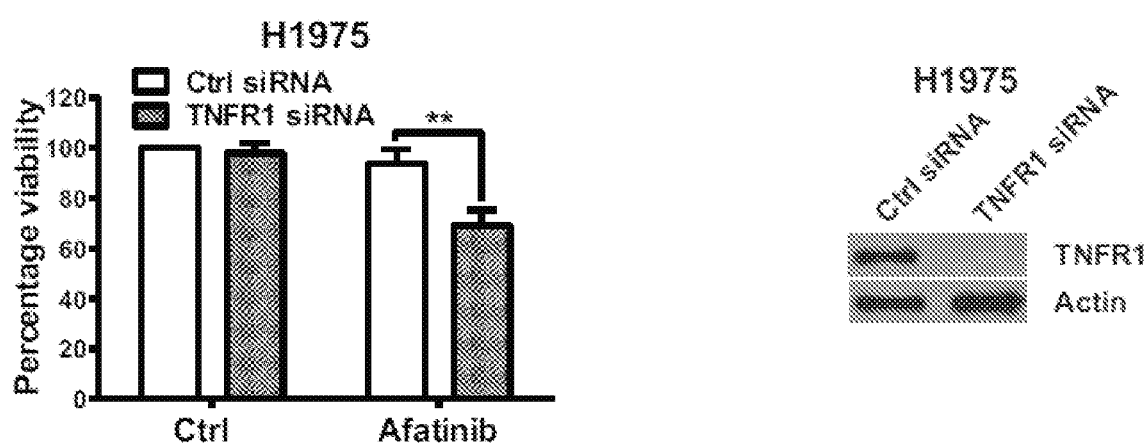

Additional NSCLC lines with EGFRwt (Calu-3 and H1373) exhibited similar results with combined inhibition (FIG. 22A-B). In addition, we tested H1975 cells (with a T790M mutation) using afatinib and found that these cells also can be rendered sensitive to EGFR inhibition if TNFR is inhibited (FIG. 22C-E).

Figure 6L:
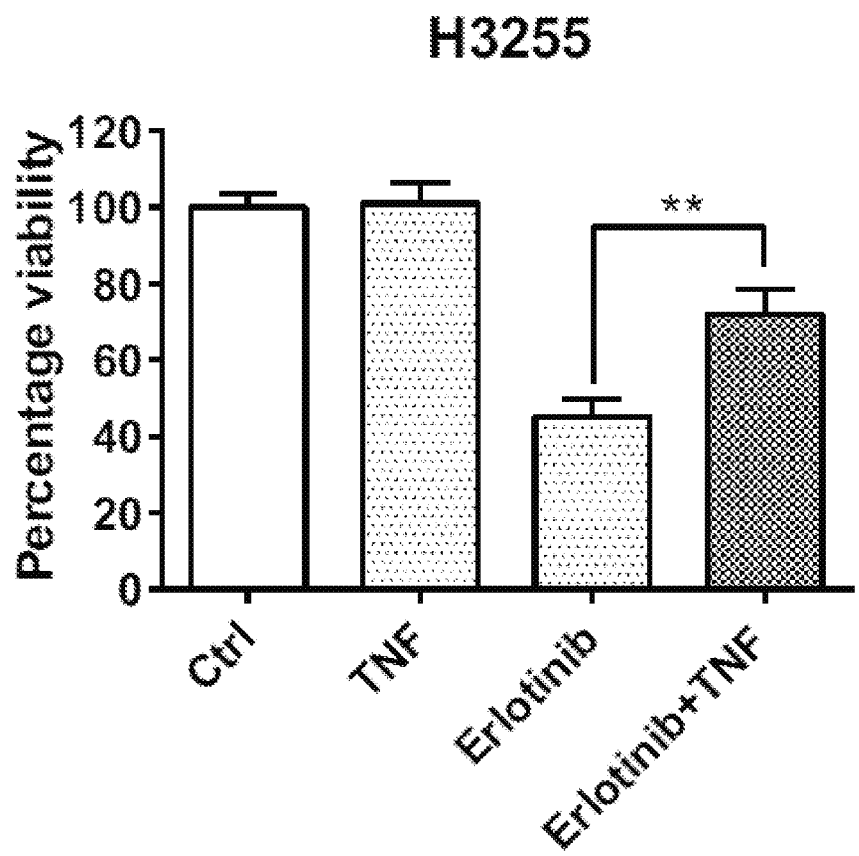
Figure 6M:
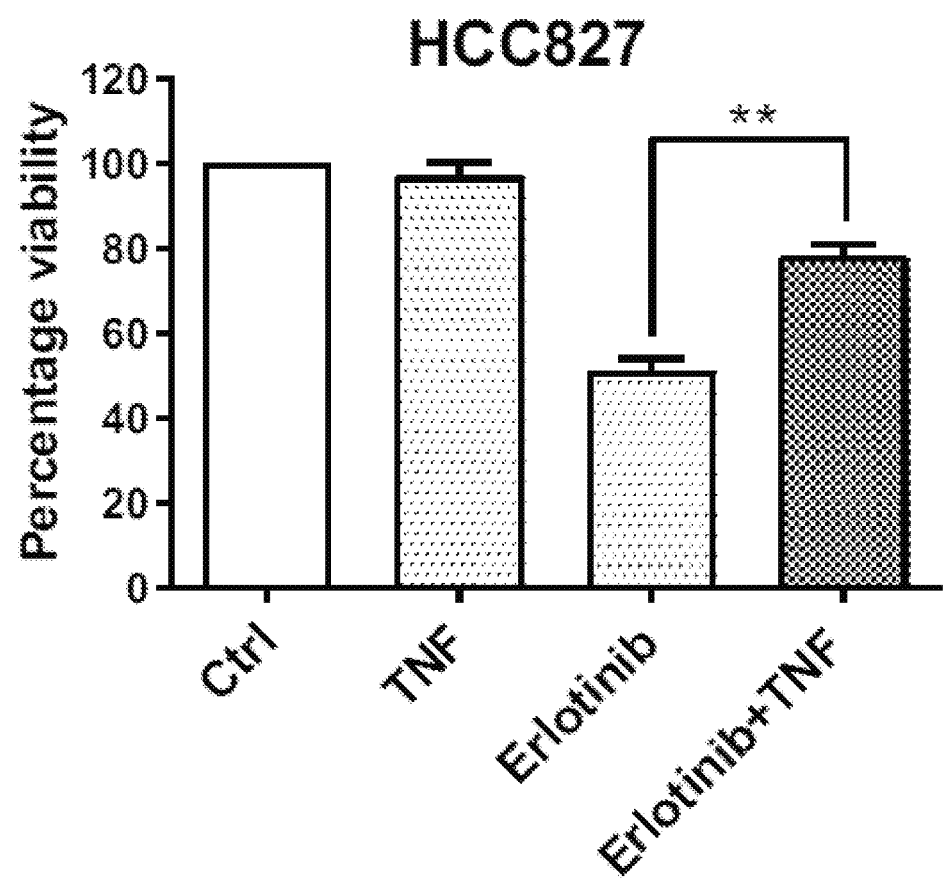

Since we hypothesize that erlotinib induced TNF expression mediates resistance to EGFR inhibition, we examined whether exogenous TNF would protect cells from erlotinib induced cell death. This experiment was conducted in EGFR oncogene addicted mutant cell lines, since EGFRwt cell lines are resistant to erlotinib alone. Indeed, we find that exogenous TNF protects HCC827 and H3255 cells from erlotinib induced cell death as shown in FIG. 6L-M.

Inhibition of NF-κB Results Enhances Sensitivity to EGFR Inhibition

Figure 7A:
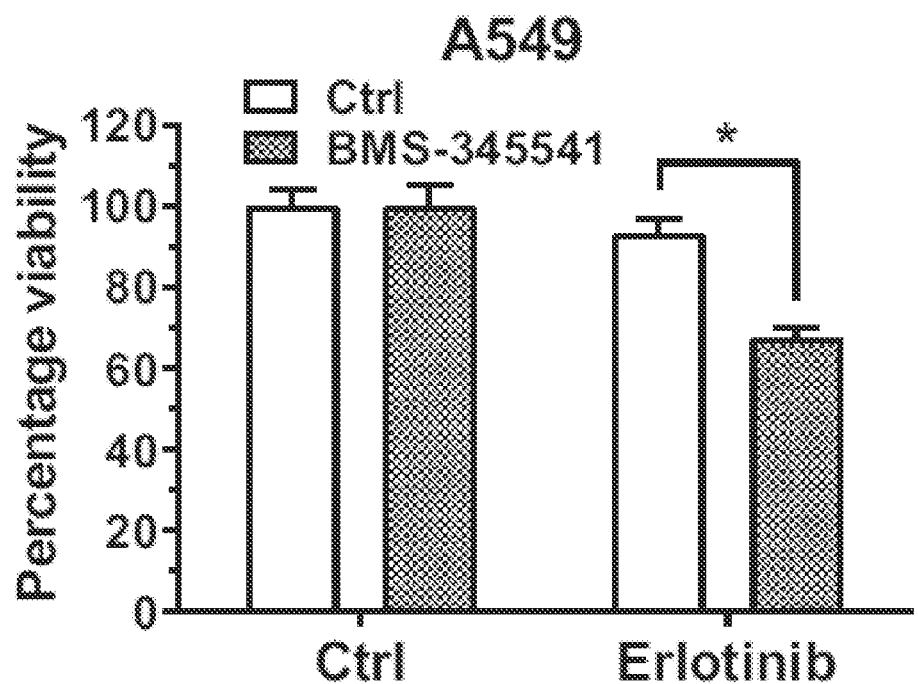
Figure 7B:
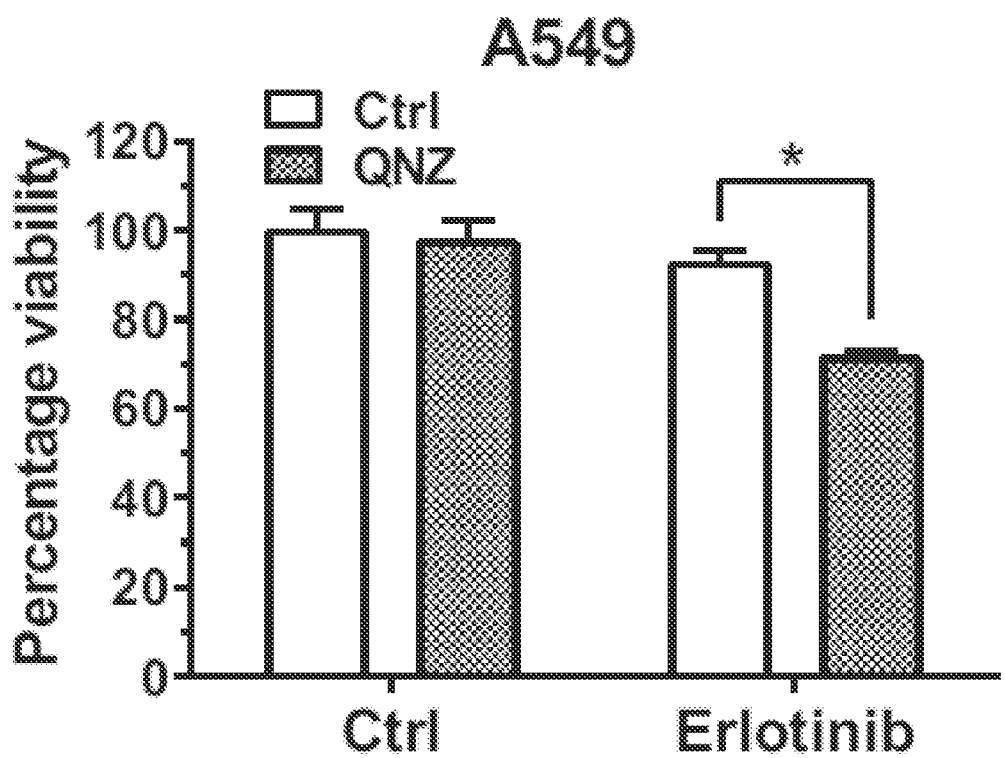
Figure 7C:
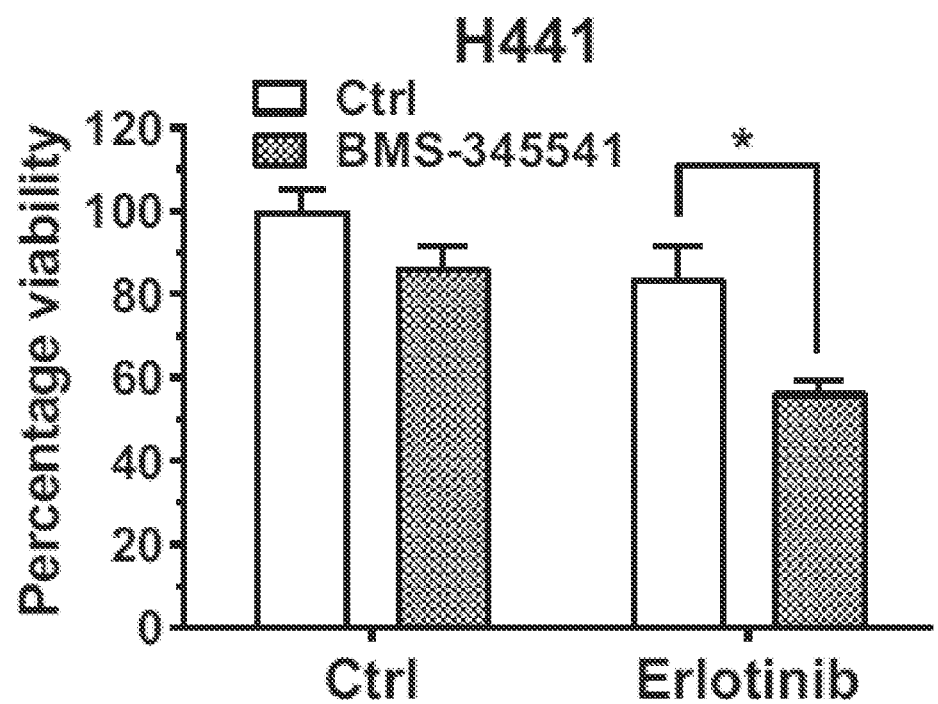
Figure 7D:
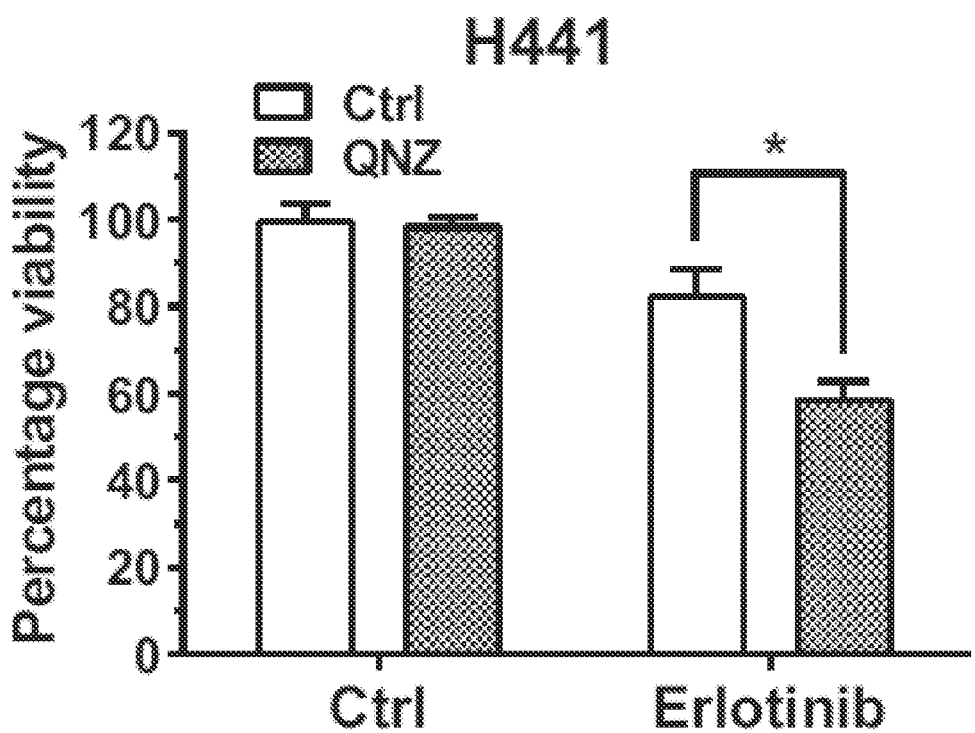
Figure 7E:
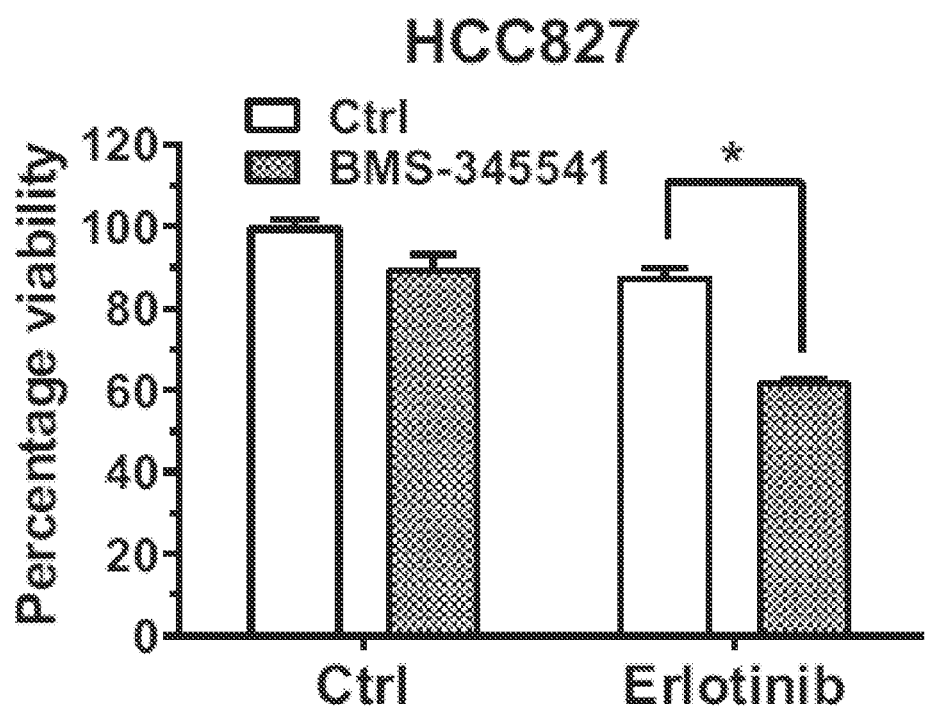
Figure 7F:
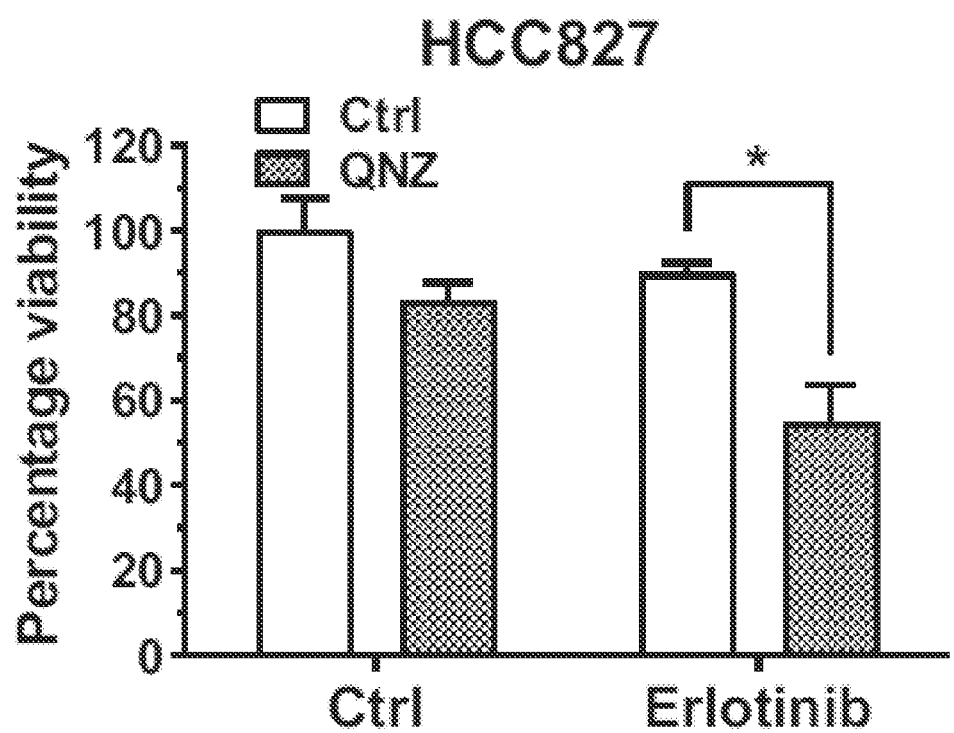
Figure 7G:
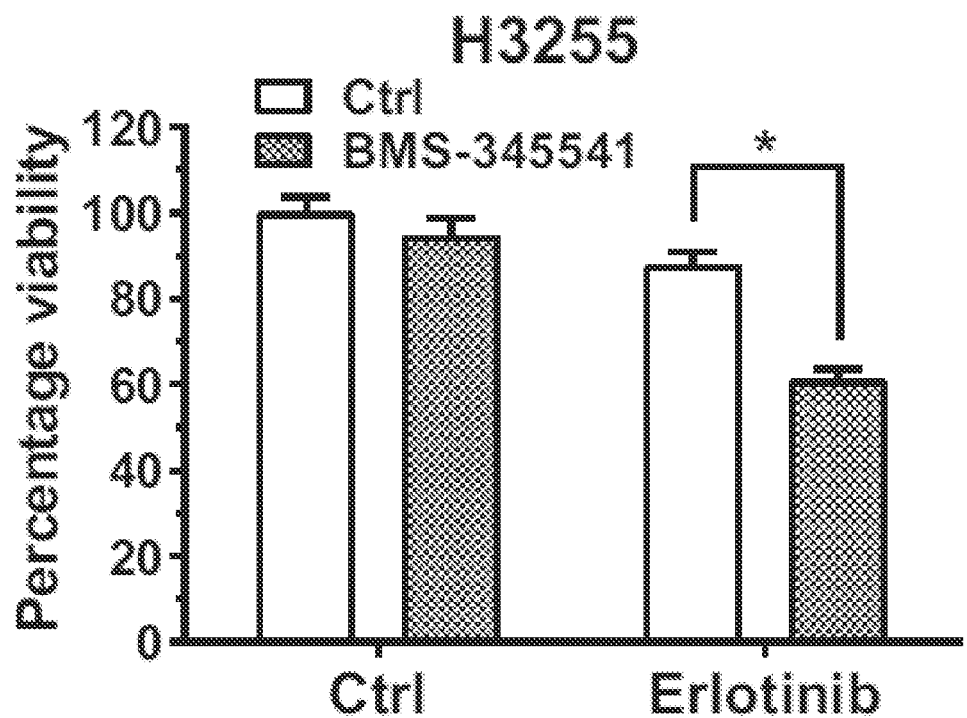
Figure 7H:
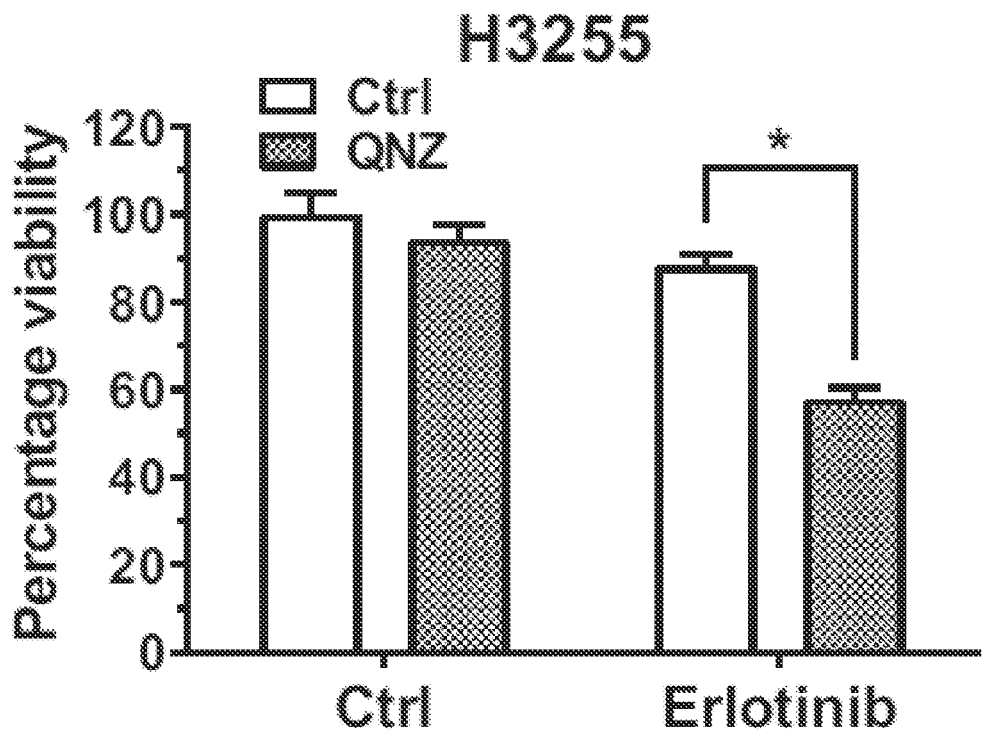
Figure 7I:
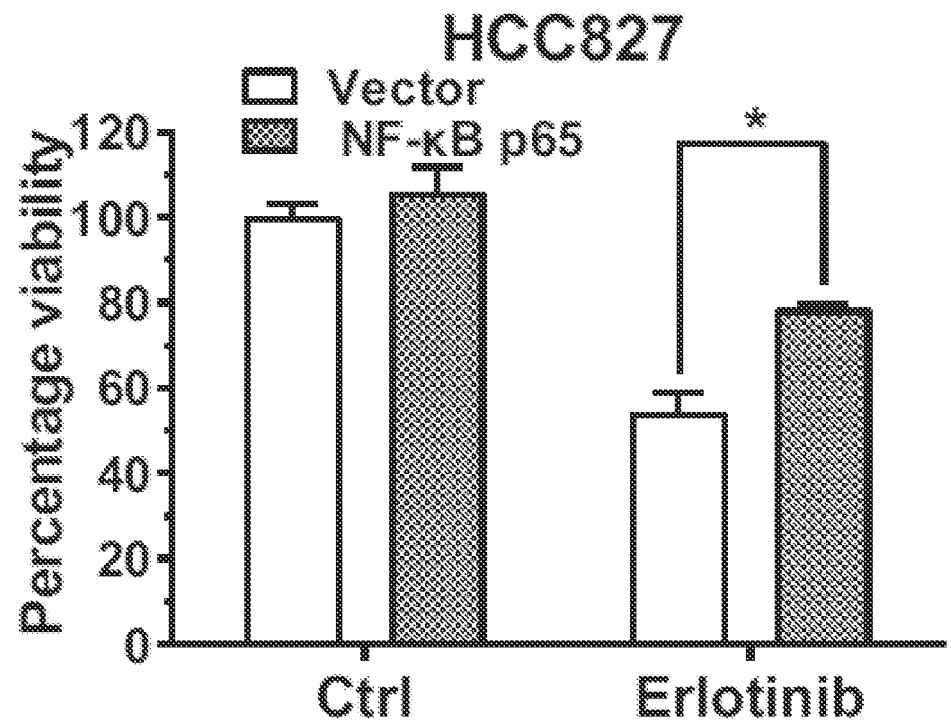
Figure 7J:
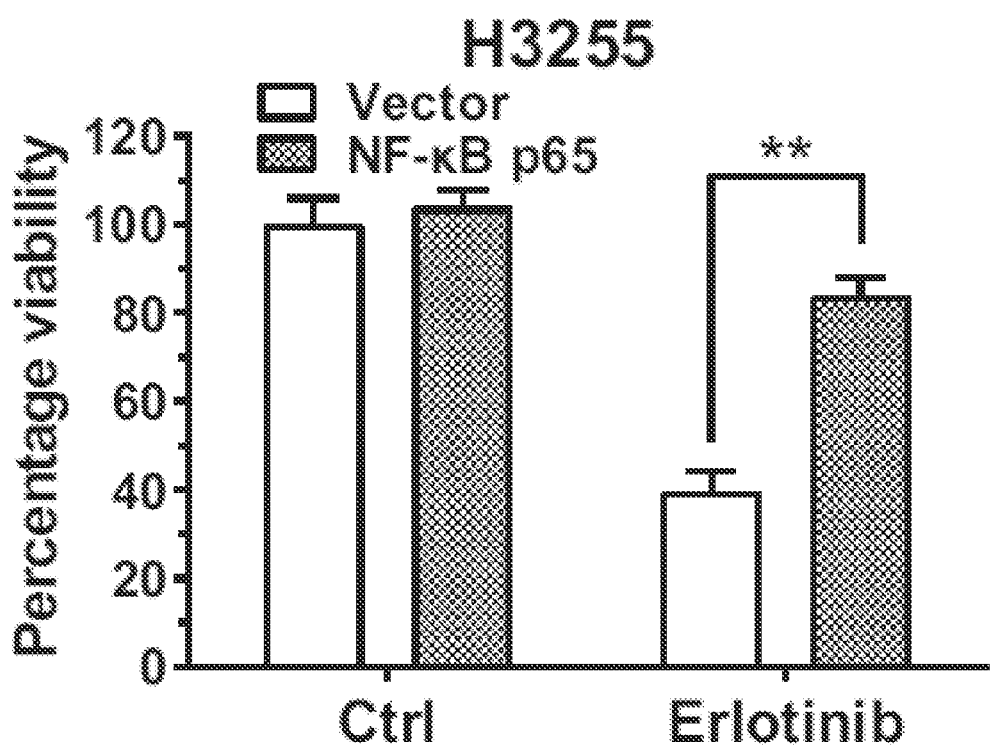
Figure 7K:
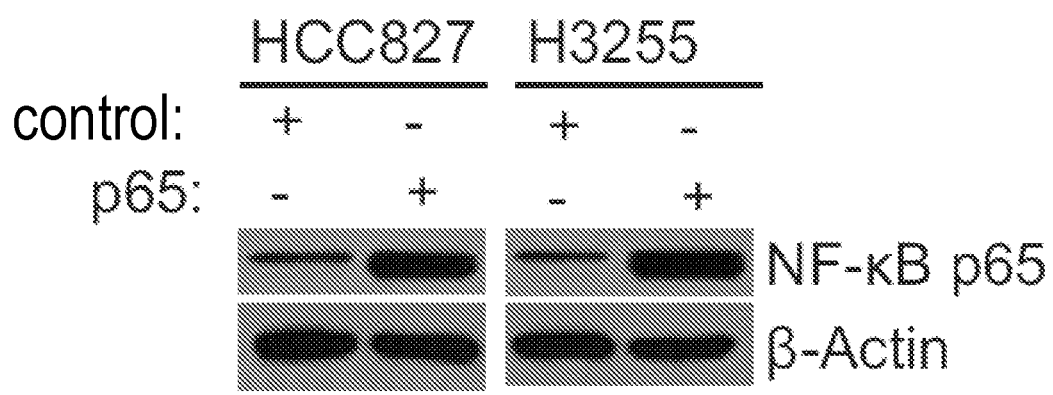

NF-κB is a key component of inflammation induced cancer. Previous studies have shown that NF-κB plays a role in resistance to EGFR inhibition in EGFR mutant cells. Our data indicate that the activation of NF-κB by EGFR inhibition is not limited to cells with EGFR activating mutations and is also detected in NSCLC cells with EGFRwt. We examined whether inhibition of NF-κB would sensitize lung cancer cells with EGFRwt to the effects of EGFR inhibition. Indeed, we find that inhibition of NF-κB using either two different inhibitors rendered two EGFRwt expressing cell lines sensitive to EGFR inhibition as shown in FIG. 7A-D. We also confirmed that inhibition of NF-κB enhanced sensitivity of oncogene addicted cells to EGFR inhibition (FIG. 7E-H), consistent with previous reports. Finally, we find that overexpressing the p65 subunit of NF-κB results in a resistance to combined exposure of lung cancer cells to EGFR and TNF inhibition as shown in FIG. 7I-K, suggesting that TNF induced sensitization to EGFR inhibition is mediated, at least in part, via NF-κB activation.

A Combined Inhibition of TNF and EGFR in an Animal Model of Lung Cancer

Figure 8A:
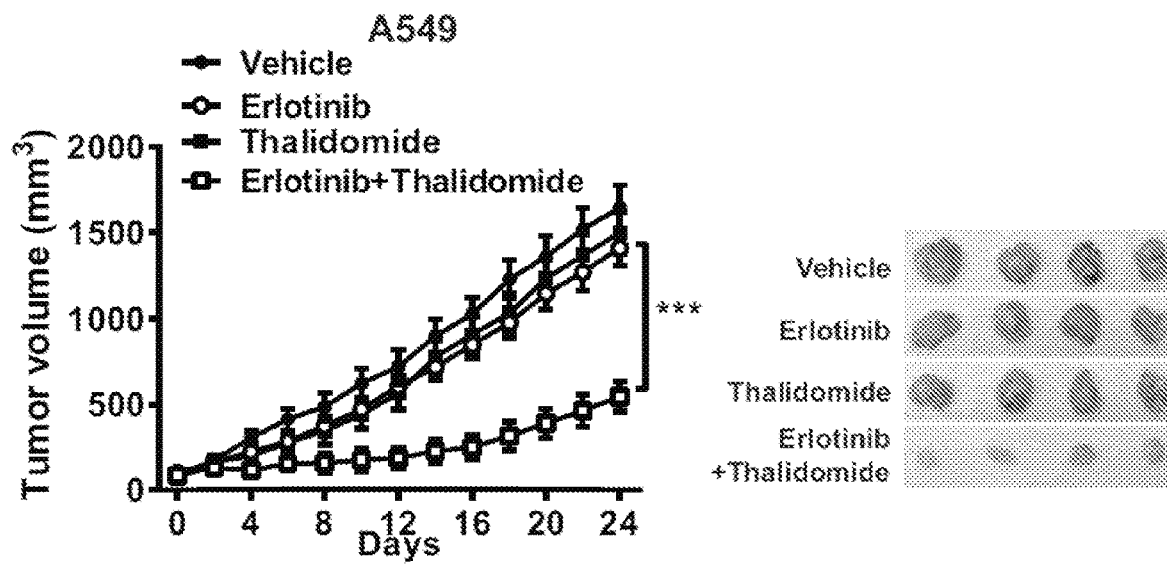
Figure 8B:
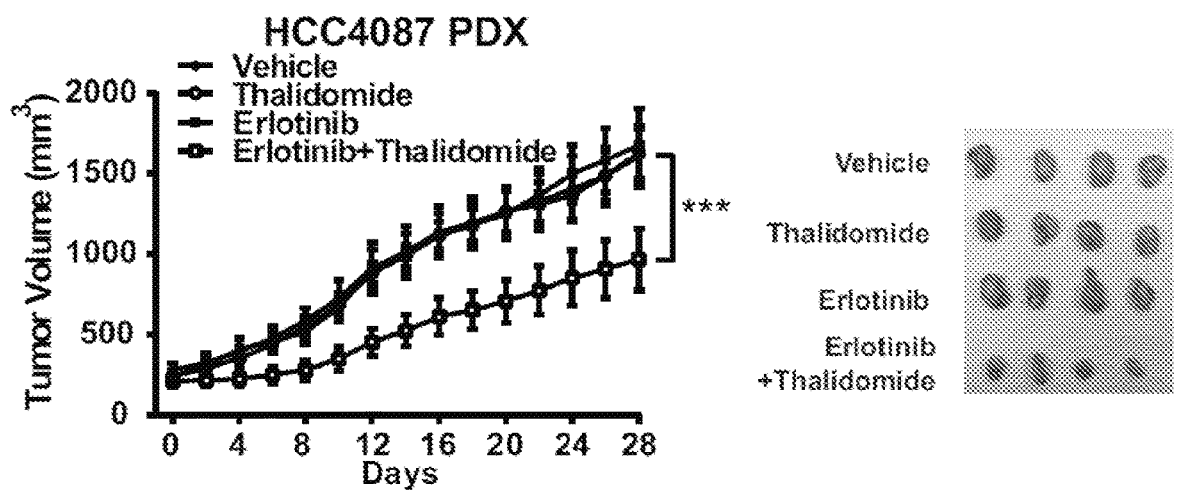
Figure 8C:
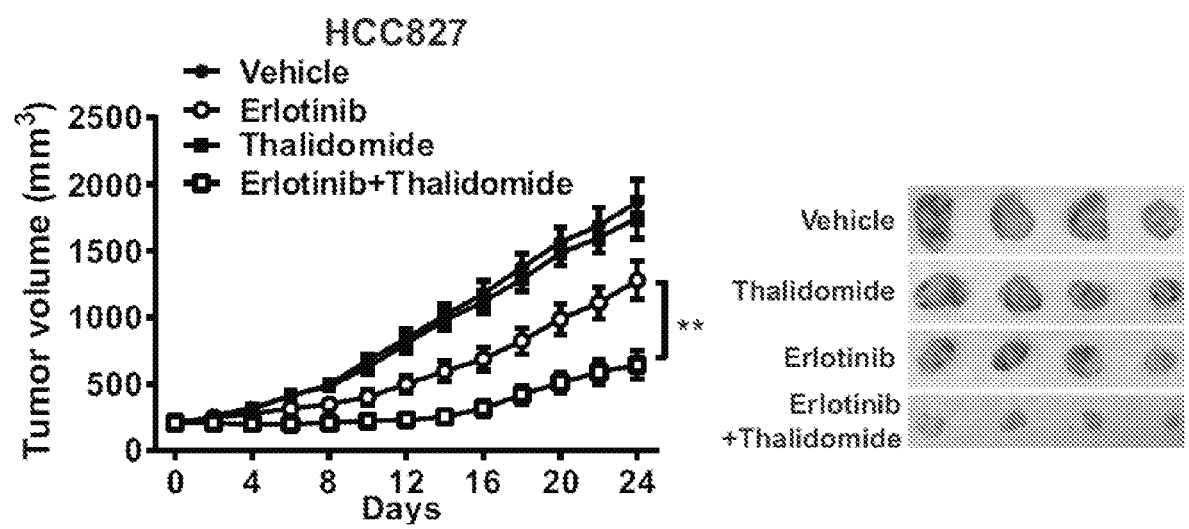
Figure 8D:
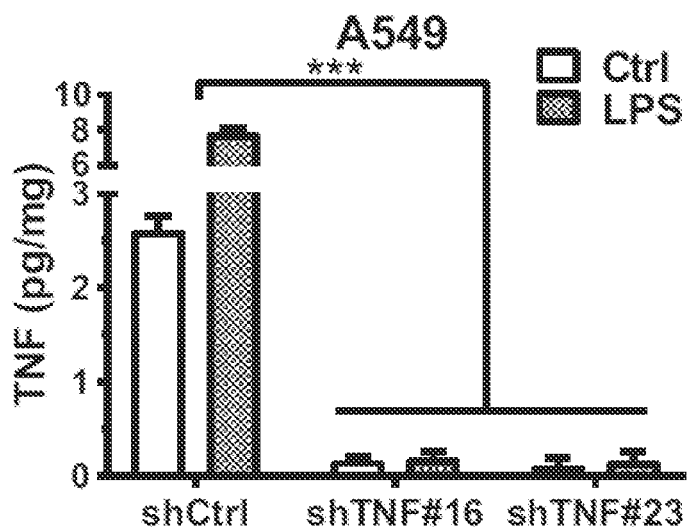
Figure 8E:
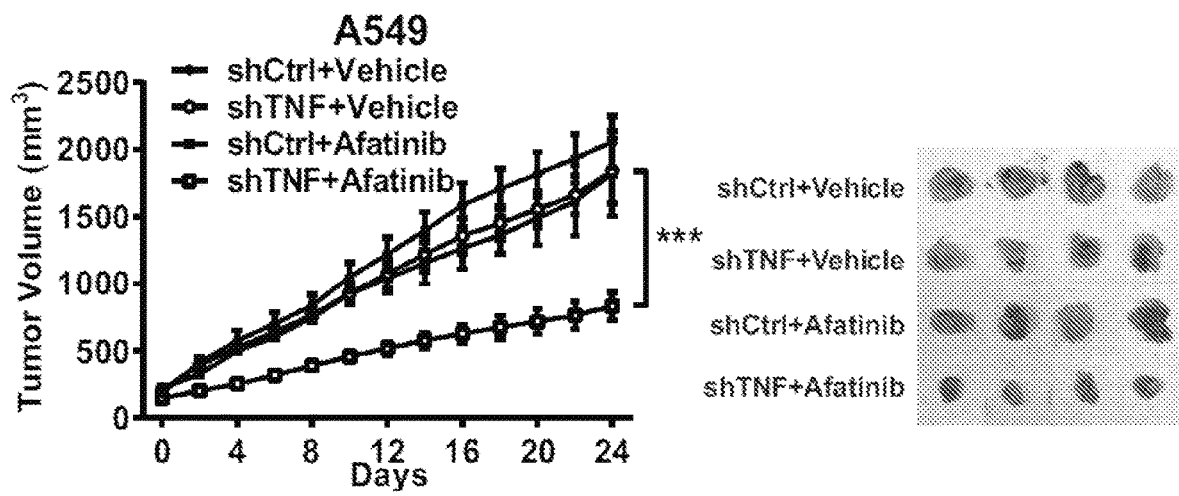
Figure 8F:
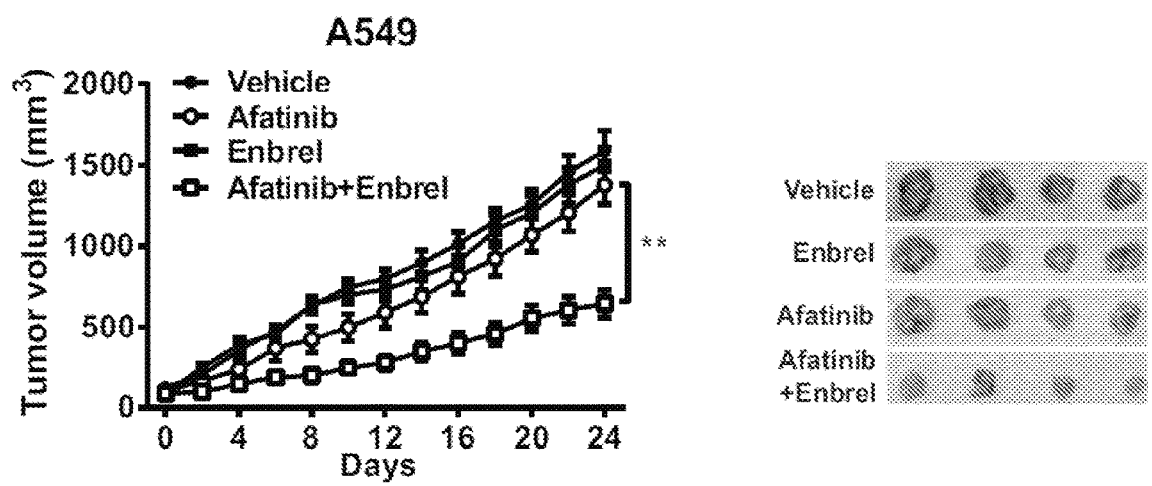

Next, we examined whether a combined inhibition of TNF and EGFR would influence sensitivity to erlotinib in a mouse xenograft model. We started our experiments with the A549 cell line that expresses EGFRwt and is resistant to EGFR inhibition. Since our studies indicated that a TNF-NF-κB loop was a key mediator of resistance to EGFR inhibition, we chose thalidomide for our initial studies. A number of studies have demonstrated that thalidomide downregulates TNF levels and also inhibits NF-κB activation directly. A549 cells were injected into the flanks of mice to form subcutaneous tumors. Once tumors became visible, treatment was started with control vehicle, erlotinib, thalidomide, or erlotinib plus thalidomide as indicated in FIG. 8. As expected, we found robust tumor growth in controls. The Erlotinib and thalidomide alone treated groups had a minor decrease in tumor growth that was not statistically significant. However, a combined inhibition of erlotinib and thalidomide resulted in a highly effective suppression of tumor growth (FIG. 8A). Next, we examined the effect of EGFR+TNF inhibition using thalidomide in an EGFRwt NSCLC patient derived xenograft tumor. The combination of erotinib+thalidomide was highly effective in inhibiting the growth of this PDX tumor (FIG. 8B). Additionally, we examined the effect of a combined TNF and EGFR inhibition in a mouse subcutaneous model using EGFR mutant erlotinib sensitive HCC827 cells and found that the combination of EGFR inhibition plus thalidomide results in a more effective inhibition of tumor growth than EGFR inhibition alone while thalidomide alone had no significant effect (FIG. 8C). Next, to definitively determine the role of TNF, we examined the effect of stably silencing TNF using shRNA. Effective silencing of TNF was determined by decreased basal level and a lack of TNF upregulation in response to LPS by qPCR and ELISA (FIG. 8D and FIG. 23A). We also confirmed that TNF silenced clones were more sensitive to EGFR inhibition in cell viability assays (FIG. 23B-C). Next, we determined the effect of EGFR inhibition in A549 cells with stably silenced TNF in a mouse subcutaneous model. As can be seen in FIG. 8E, stable silencing of TNF results in enhanced sensitivity of xenografted tumors to erlotinib. Next, we examined the effect of a specific TNF blocker Etanercept that is in clinical use. Again, we find that Etanercept rendered A549 cells sensitive to the effect of EGFR inhibition (FIG. 8F).

FIG. 24 shows that erlotinib in combination with either thalidomide or prednisone was effective to reduce tumor volume in an A549 EGRF wild type (EGFRwt) xenograft model relative to the use of these agents alone. In the left panel of FIG. 24, prednisone is shown to be more effective than thalidomide in combination with erlotinib for reducing tumor volume. The right panel indicates that the pharmaceutical composition combination of erlotinib and prednisone was more effective at reducing tumor volume than either of these agents used alone.

FIG. 25 shows that the pharmaceutical composition combination of erlotinib and prednisone is effective to shrink tumor volume beginning at day 32 in the A549 xenograft model.

FIG. 26 shows the effect of withdrawing treatment of the A549 xenograft model with the combination of erlotinib and prednisone at day 32 versus maintaining treatment with this combination. From FIG. 26, it is evident that tumor volume increases comparable to control with the combination therapy is withdrawn, whereas tumor volume shrinks if the combination therapy is continuously maintained.

FIG. 27 shows that afatinib in combination with either thalidomide or prednisone was effective to reduce tumor volume in an H441 EGRF wild type (EGFRwt) xenograft model relative to the use of these agents alone. In the left panel of FIG. 27, prednisone is shown to be more effective than thalidomide in combination with erlotinib for reducing tumor volume. The right panel indicates that the pharmaceutical composition combination of afatinib and prednisone was more effective at reducing tumor volume than either of these agents used alone.

FIG. 28 shows that afatinib in combination with either thalidomide or prednisone was effective to reduce tumor volume in an H1975 EGRF L858R/T790M xenograft model relative to the use of these agents alone. In the left panel of FIG. 28, both prednisone and thalidomide are shown to be relatively equally effective in combination with erlotinib for reducing tumor volume. The right panel indicates that the pharmaceutical composition combination of afatinib and prednisone was more effective at reducing tumor volume than either of these agents used alone.

FIG. 29 shows that prednisone is able to block the TNF upregulation that is induced by EGFR inhibition in both A549 and H441 cells.

EQUIVALENTS

Those skilled in the art will recognize, or be able to ascertain using no more than routine experimentation, numerous equivalents to the specific procedures described herein. Such equivalents are considered to be within the scope of the present invention and are covered by the following claims. The contents of all references, patents, and patent applications cited throughout this application are hereby incorporated by reference. The appropriate components, processes, and methods of those patents, applications and other documents may be selected for the present invention and embodiments thereof.

What is claimed is:

1. A method for treating non-small cell lung cancer in a patient in need thereof, said method comprising concurrently administering to said patient an effective amount of afatinib and prednisone, wherein the non-small cell lung cancer expresses EGFR having a T790M mutation.

2. The method of claim 1, wherein the non-small cell lung cancer further expresses EGFR having a L858R mutation.

3. The method of claim 1, wherein the non-small cell lung cancer further expresses EGFR having an exon 19 deletion.

4. The method of claim 1, wherein afatinib and prednisone are present in a pharmaceutical composition.

5. The method of claim 1, wherein the patient is a human patient.

6. A method for treating non-small cell lung cancer in a patient in need thereof, said method comprising administering to said patient an effective amount of afatinib and prednisone, wherein the non-small cell lung cancer expresses EGFR having a T790M mutation.

7. The method of claim 6, wherein the non-small cell lung cancer further expresses EGFR having a L858R mutation.

8. The method of claim 6, wherein the non-small cell lung cancer further expresses EGFR having an exon 19 deletion.

9. The method of claim 6, wherein the patient is a human patient.

* * * * *